US007256322B2

(12) United States Patent
Lowe et al.

(10) Patent No.: US 7,256,322 B2
(45) Date of Patent: Aug. 14, 2007

(54) WUSCHEL (WUS) GENE HOMOLOGS

(75) Inventors: Keith S. Lowe, Johnston, IA (US); Rebecca E. Cahoon, Webster Groves, MO (US); Christopher J. Scelonge, Ankeny, IA (US); Yumin Tao, Urbandale, IA (US); William J. Gordon-Kamm, Urbandale, IA (US); Wesley B. Bruce, Grimes, IA (US); Lisa J. Newman, Urbandale, IA (US)

(73) Assignees: Pioneer Hi-Bred International, Inc., Johnston, IA (US); E.I. du Pont de Nemours and Company, Wilmington, DE (US)

(*) Notice: Subject to any disclaimer, the term of this patent is extended or adjusted under 35 U.S.C. 154(b) by 231 days.

(21) Appl. No.: 10/744,572

(22) Filed: Dec. 23, 2003

(65) Prior Publication Data
US 2004/0166563 A1 Aug. 26, 2004

Related U.S. Application Data

(63) Continuation-in-part of application No. 09/807,946, filed on Apr. 20, 2001.

(60) Provisional application No. 60/157,216, filed on Oct. 1, 1999.

(51) Int. Cl.
C12N 15/29 (2006.01)
C12N 15/82 (2006.01)
C12N 5/04 (2006.01)
A01H 5/00 (2006.01)
A01H 5/10 (2006.01)

(52) U.S. Cl. ............ 800/278; 800/298; 800/290; 800/287; 536/23.6; 435/419

(58) Field of Classification Search .......... 536/23.1, 536/23.6; 800/298, 278, 290, 287; 435/410, 435/419, 468
See application file for complete search history.

(56) References Cited

U.S. PATENT DOCUMENTS 5,929,301 A 7/1999 Baszcynski et al.

FOREIGN PATENT DOCUMENTS

WO WO 01/23575 A2 4/2001
WO WO 03/037072 A2 5/2003

OTHER PUBLICATIONS

Kamiya et al (2003, The Plant Journal 35:429-441).*
Bowie et al, Science 247:1306-1310, 1990.*
McConnell et al, Nature 411 (6838):709-713, 2001.*
Endrizzi et al., The Shoot Meristemless gene is required for maintenance of undifferentiated cells in Arabidopsis shoot and floral meristems and acts at a different regulatory level than the meristem genes WUSHEL and ZWILLE, Plant J. 10(6):967-979 (1996).
Brand et al., Department of Stem Cell Fate in Arabidopsis on a Feedback Loop Regulated by CLV3 Activity, Science 289:617-619 (2000).
Schoof et al., The Stem Cell Population of Arabidopsis Shoot Meristems Is Maintained by a Regulatory Loop between the CLAVATA and WUSCHEL Genes, Cell 100:635-644 (2000).
Lin et al., Sequence and analysis of chromosome 2 of the plant Arabidopsis thaliana, NCBI General Identifier No. 3785979 (2000).
Lin et al., Sequence and analysis of chromosome 2 of the plant Arabidopsis Thaliana, Nature 402:761-768 (1999).
Laux et al., Role of WUSCHEL in regulating stem cell fate in the Arabidopsis shoot meristem, NCBI General Identifier No. 4090200 (1998).
Lin et al., Sequence and analysis of chromosome 2 of the plant Arabidopsis thaliana, NCBI General Identifier No. 4580396 (2000).
Sato et al., Structural analysis of Arabidopsis thaliana chromosome 3. I. Sequence features of the regions of 4,504,864 bp covered by sixty P1 and TAC clones, NCBI General Identifier No. 9294502 (2000).
Sato et al., Structural Analysis of Arabidopsis thaliana Chromosome 3. I. Sequence Features of the Regions of 4,504,864 bp Covered by Sixty P1 and TAC Clones, DNA Research 7:131-135 (2000).
Lin et al., Arabidopsis thaliana chromosome III BAC T12J13 genomic sequence, NCBI General Identifier No. 6091768 (2001).
Hsing et al., Oryza sativa PAC P0699E04 genomics sequence, complete sequence, NCBI General Identifier No. 8099120 (2000).
Bidney et al., Microprojectile bombardment of plant tissues increases transformation frequency by Agrobacterium tumefaciens, Plant Mol. Biol. 18:301-313 (1992).
Burrus et al., Regeneration of fertile plant from protoplasts of sunflower (Helianthus annuus L.), Plant Cell Reports 10:161-166 (1991).
Sugiura et al., Purification and Properties of Oxalate Oxidase from Barley Seedings, Chem. Pharm. Bull. 27(9):2003-2007 (1979).
Wohlleben et al., Nucleotides sequence of the phosphinothricin N-acetyltransferase gene from Streptomyces virido-chromogenes Tu494 and its expression in Nicotiana tabacum, Gene 70:25-37 (1988).
Lowe et al., Transformation of the Maize Apical Meristem: Transgenic Sector Reorganization and Germline Transmission, Genetics, Biotechnology and Breeding Maize and Sorghum pp. 94-97 (1997).
Mayer et al., Role of WUSCHEL in Regulating Stem Cell Fate in the Arabidopsis Shoot Meristem, Cell 95:805-815 (1998).

(Continued)

Primary Examiner—Stuart F. Baum

(57) ABSTRACT

This invention relates to isolated polynucleotides encoding WUS polypeptides. The invention further provides isolated WUS polypeptides. The invention also provides methods of using the polynucleotides to modulate the level of WUS, improve transformation efficiency, to stimulate plant cell growth, including stem cells, to stimulate organogenesis, to stimulate somatic embryogenesis, to induce apomixis, and to provide a positive selection for cells comprising the polynucleotide. The invention also relates to cells, plants and seeds comprising the polynucleotides of the invention or produced by the methods of the invention.

15 Claims, 3 Drawing Sheets

OTHER PUBLICATIONS

Figure 2:

Laux et al., The WUSCHEL gene is required for shoot and floral meristem integrity in Arabidopsis, Development 122:87-96 (1996).

De La Bastide et al., Thaliana BAC T13L16 from chromosome II, near 33cM, complete sequence, NCBI Database Accession No. AC003952 (1999).

De La Bastide et al., Wuschel protein—Arabidopsis thaliana, PIR2 Sequence Database Accession No. T00829 (1999).

Gallois et al., Combined Shoot Meristemless and WUSCHEL trigger ectopic organogenesis in *Arabidopsis*, Development 129:3207-3217 (2002).

Kamiya et al., Isolation and characterization of a rice WUSCHEL-type homeobox gene that is specifically expressed in the central cells of a quiescent center in the root apical meristem, Plant J. 35(4):429-441 (2003).

Nardmann et al., The maize duplicate genes *narrow sheath 1* and *narrow sheath2* encode a conserved homeobox gene function in a lateral domain of shoot apical meristems, Development 131(12):2827-2839 (2004).

Scanlon, Michael J., Narrow Sheath1 functions from two meristematic foci during founder-cell recruitment in maize leaf development, Development 127(21):4573-4585 (2000).

Zuo et al., The WUSCHEL gene promotes vegetative-to-embryonic transition in *Arabidopsis*, Plant J. 30(3):349-359 (2002).

Hsing et al., Database UniProt, Accession No. Q9LIX7 Abstract (2000).

* cited by examiner

FIGURE 1A

```
              *  *****  *********************  **             *      ********  ***
SEQ ID NO:04  MEALS---------------------------------------------------------------
SEQ ID NO:10  MEG-----------------------------------------------------------------
SEQ ID NO:20  MESHS---------------------------------------------------------------
SEQ ID NO:22  MKVHQFARGF-WEHEPSLTLGCKRLRPLAPKLSNTDTISPPHHPVTTFDLKSFIKPESAS
SEQ ID NO:24  MKVHQFTRGLIWEHEPFLTLGCKRLRPLAPKLPNTKTITTP------FDLKSFIRPESGP
SEQ ID NO:25  MEPPQHQH------------------------------------------HHH-------
              1                                                                 60

**                              *           *    **       *
SEQ ID NO:04  -------G-------RVGVKC------------GRWNPTAEQKVLTELF-RAGLRTPSTEQ
SEQ ID NO:10  ---------------------------------PVRSRWTPKPEQILILESIF-NSGMVNPPKDE
SEQ ID NO:20  -----SDAEAENVRTHSSV--------------SRWSPTKEQIDMLENLY-KQGIRTPSTEQ
SEQ ID NO:22  RKLGIGSSDDNTNKRDPSSPQGQAETHIPGGTRWNPTQEQIGILEMLY-RGGMRTPNAQQ
SEQ ID NO:24  RK------PVSSDDTKKDPPSPQGQIETH-PGGTRWNPTQEQIGILEMLY-KGGMRTPNAQQ
SEQ ID NO:25  -------QADQESGNNNNKSGSGGYTCR-QTSTRWTPTTEQIKILKELYYNNAIRSPTADQ
              61                                                                120

*           *   ********   *
SEQ ID NO:04  IQRISTHLSAFGKVESKNVFYWFQNHKARERHHHK-KRRRGASSSSPDSGSGRGSNNEED
SEQ ID NO:10  TVRIRKLLERFGAVGDANVFYWFQNRRSRSRRRQRLQAQAAASSSSSGSPPTSGLAPGH
SEQ ID NO:20  IQQITSRLRAYGHIEGKNVFYWFQNHKARQRQKLM-KQQTIAYSNR---FLRASHPICQ
SEQ ID NO:22  IEQITAQLSKYGKIEGKNVFYWFQNHKARERQKQ--KRNNLGLAHSPRTTLTTSPPFSC-
SEQ ID NO:24  IEQITVQLGKYGKIEGKNVFYWFQNHKARERQKQ--KRSSLASSHSPRTPTIHS------
SEQ ID NO:25  IQKITARLRQFGKIEGKNVFYWFQNHKARERQKKRFNGTNMTTPSSSPNSVMMAANDHYH
              121                                                                180
```

FIGURE 1B (CONTINUED from 1A)

```
SEQ ID NO:04   ---GRGAASQSHDAD-ADADLVLQPPESKREARS-YG--HHHRL---------------------
SEQ ID NO:10   ATASSTAGMFAHGATYGSSASASWPPPPSCEGMMGDLDYGGGDDLFAISRQMGYASGGGS
SEQ ID NO:20   ---NVACAPYCLQ----RSGFSFYPQQSKVLASGGIS--STGPL----------------
SEQ ID NO:22   -----CVITTMDTT-KRGEVV----ERE-EEDSPLK--K-CR------------------
SEQ ID NO:24   --------VVTLETT--RGEVV----ERDHEEDSPYK--KKCR-----------------
SEQ ID NO:25   PLLHHHHGVPMQRPA-NSVNVKLNQDHHLYHHNKPYPSFNNGNLNHASSGTECGVVNASN
                                                                        240
                                                          *  *
181

SEQ ID NO:04   --VTCYVRDVVEQQ-------EASPSWERPTRE---------VETLELFPLKSYGDLE--A
SEQ ID NO:10   GSASSAAVAHHEQQQQLYYSP-------CQPASMTVFINGVATEVPRGPIDLRSMF
SEQ ID NO:20   --G---MQRMFDGM-------QSS----EHPDCN--------REVLTLFPLHPTGILKEKT
SEQ ID NO:22   ------SWAFEYLEDQ--------R----EE--E--------HRTLELFPLHPEG------
SEQ ID NO:24   ------RWVFDCLEEQ-------NMSSPCEQE--E-------HRTLELFPLHPEG------
SEQ ID NO:25   GYMSSHVYGSMEQDCSMNYNNVGGWANMDHHYSSAPYNFFDRAKPLFGLEGHQDEEECG
                                                                        300
                      *                                       ****    *
241

SEQ ID NO:04   AEKVRSYVRGIA---ATS---EQCRELS---FFDVSAGRDPP---LELRLCSFGP
SEQ ID NO:10   GQDVMLVHSTAGLLPVNEYGVLTQSLQMGESYF----------------LVTRGY
SEQ ID NO:20   THQVPSLASTSV---VAV----DEDGHLGNQPFFNFFTTEPRS---RE---------
SEQ ID NO:22   ------------------------------------------------------R
SEQ ID NO:24   ------------------------------------------------------R
SEQ ID NO:25   GDAYLEHRRTLPLFPMHG-----EDHINGGSGAIWKYGQSEVRPCASLELRL----N
                        *  *                                            356
301
```

A. YFP Control (40X)     B. YFP + Ole:WUS2 (200X)

Effects of Ole:WUS2 expression on organogenic/embryogenic callus response from 18DAP 581 embryos

SEQUENCE LISTING

<160> NUMBER OF SEQ ID NOS: 91

<210> SEQ ID NO 1
<211> LENGTH: 462
<212> TYPE: DNA
<213> ORGANISM: Zea mays

<400> SEQUENCE: 1
gaggaagatc ccggaagcaa ccaaatcaga agcagaagct agagctacta gtttttgcat        60
tagcaagcag cagcgcagct atagcttctt gcactcgacc atcgatcgct acaaaccaca       120

| catatagctg aagcaaatat atccacttgc ttaactggcg gtgtagtgta gctgcgatcg | 180 |
| ctgcaaacta cagggtgtag tgatcgtcga tcggctacat atcatatacc atggaggcgc | 240 |
| tgagcgggcg gtaggcgtc aagtgcgggc ggtggaaccc tacggcggag caggtgaagg | 300 |
| tcctgacgga gctcttccgc gcggggctgc ggacgcccag cacggagcag attcagcgca | 360 |
| tctccaacca actcagcgcc tttgggaagg gggagaacaa aaacgtcctc ctaacgggtc | 420 |
| caaaacaaaa aggccgcgag cggcaacaac aaaagaagcg cc | 462 |

<210> SEQ ID NO 2
<211> LENGTH: 77
<212> TYPE: PRT
<213> ORGANISM: Zea mays

<400> SEQUENCE: 2

Met Glu Ala Leu Ser Gly Arg Val Gly Val Lys Cys Gly Arg Trp Asn
1               5                   10                  15
Pro Thr Ala Glu Gln Val Lys Val Leu Thr Glu Leu Phe Arg Ala Gly
            20                  25                  30
Leu Arg Thr Pro Ser Thr Glu Gln Ile Gln Arg Ile Ser Asn Gln Leu
        35                  40                  45
Ser Ala Phe Gly Lys Gly Glu Asn Lys Asn Val Leu Leu Thr Gly Pro
    50                  55                  60
Lys Gln Lys Gly Arg Glu Arg Gln Gln Gln Lys Lys Arg
65                  70                  75

<210> SEQ ID NO 3
<211> LENGTH: 1338
<212> TYPE: DNA
<213> ORGANISM: Zea mays

<400> SEQUENCE: 3

| gcacgaggag gaagatcccg gaagcaacca aatcagaagc agaagctaga gctactagtt | 60 |
| tttgcattag caagcagcag cgcagctata gcttcttgca ctcgaccatc gatcgctaca | 120 |
| aaccacacat atagctgaag caaatatatc cacttgctta actggcggtg tagtgtagct | 180 |
| gcgatcgctg caaactacag ggtgtagtga tcgtcgatcg gctacatatc ataccatg | 240 |
| aggcgctga gcgggcgggt aggcgtcaag tgcggcggt ggaaccctac ggcggagcag | 300 |
| gtgaaggtcc tgacggagct cttccgcgcg gggctgcgga cgcccagcac ggagcagatc | 360 |
| cagcgcatct ccacccacct cagcgccttc ggcaaggtgg agagcaagaa cgtcttctac | 420 |
| tggttccaga accacaaggc ccgcgagcgc caccaccaca agaagcgccg ccgcggcgcg | 480 |
| tcgtcgtcct ccccccgacag cggcagcggc aggggaagca caacgagga agacggccgt | 540 |
| ggtgccgcct cgcagtcgca cgacgccgac gccgacgccg acctcgtgct gcaaccgcca | 600 |
| gagagcaagc gggaggccag aagctatggc accatcacc ggctcgtgac atgctacgtc | 660 |
| agggacgtgg tggagcagca ggaggcgtcg ccgtcgtggg agcggccgac gagggaggtg | 720 |
| gagacgctag agctcttccc cctcaagtcg tacggcgacc tcgaggcggc ggagaaggtc | 780 |
| cggtcgtacg tcagaggcat cgccgccacc agcgagcagt gcaggagtt gtccttcttc | 840 |
| gacgtctccg ccggccggga tccgccgctc gagctcaggc tctgcagctt cggtccctag | 900 |
| cagtagcagc tgatcgaccg tcgacgcatg catgcacgta ctgcgtgctg ctgtgcagtg | 960 |
| gccttgtcga acgcatcatt gtgtagtcct tgggttctag ctaataccga catgaaagaa | 1020 |
| tgtgtgagat gtggaaatac gcatatatat aagctgtaga acgtacgtac gtacgcgcgt | 1080 |

-continued

```
agtatcgctg ccctaccaaa cgacgtacgt tgcataaaga atctgagagg gtcagggaat    1140
gagcatgcag ctgctgctga gatttcaact gcccttttcg ctgatctttt catcatgagg    1200
ccggatgcgc tgcgtgccac ttttttttc gttcatttat gctggtctgt gccctcatgc    1260
atggcatata cggaaattaa ttaacctttg tgctccctaa aaaaaaaaaa aaaaaaaaaa    1320
aaaaaaaaaa aaaaaaaa                                                 1338
```

<210> SEQ ID NO 4
<211> LENGTH: 219
<212> TYPE: PRT
<213> ORGANISM: Zea mays

<400> SEQUENCE: 4

```
Met Glu Ala Leu Ser Gly Arg Val Gly Val Lys Cys Gly Arg Trp Asn
 1               5                  10                  15

Pro Thr Ala Glu Gln Val Lys Val Leu Thr Glu Leu Phe Arg Ala Gly
             20                  25                  30

Leu Arg Thr Pro Ser Thr Glu Gln Ile Gln Arg Ile Ser Thr His Leu
         35                  40                  45

Ser Ala Phe Gly Lys Val Glu Ser Lys Asn Val Phe Tyr Trp Phe Gln
     50                  55                  60

Asn His Lys Ala Arg Glu Arg His His Lys Lys Arg Arg Arg Arg Gly
 65                  70                  75                  80

Ala Ser Ser Ser Pro Asp Ser Gly Ser Gly Arg Gly Ser Asn Asn
                 85                  90                  95

Glu Glu Asp Gly Arg Gly Ala Ala Ser Gln Ser His Asp Ala Asp
            100                 105                 110

Ala Asp Leu Val Leu Gln Pro Pro Glu Ser Lys Arg Glu Ala Arg Ser
        115                 120                 125

Tyr Gly His His His Arg Leu Val Thr Cys Tyr Val Arg Asp Val Val
    130                 135                 140

Glu Gln Gln Glu Ala Ser Pro Ser Trp Glu Arg Pro Thr Arg Glu Val
145                 150                 155                 160

Glu Thr Leu Glu Leu Phe Pro Leu Lys Ser Tyr Gly Asp Leu Glu Ala
                165                 170                 175

Ala Glu Lys Val Arg Ser Tyr Val Arg Gly Ile Ala Ala Thr Ser Glu
            180                 185                 190

Gln Cys Arg Glu Leu Ser Phe Phe Asp Val Ser Ala Gly Arg Asp Pro
        195                 200                 205

Pro Leu Glu Leu Arg Leu Cys Ser Phe Gly Pro
    210                 215
```

<210> SEQ ID NO 5
<211> LENGTH: 720
<212> TYPE: DNA
<213> ORGANISM: Zea mays

<400> SEQUENCE: 5

```
atggcggcca atgcgggcgg cggtggagcg ggaggaggca gcggcagcgg cagcgtggct      60
gcgccggcgg tgtgccgccc cagcggctcg cggtggacgc cgacgccgga gcagatcagg     120
atgctgaagg agctctacta cggctgcggc atccggtcgc ccagctcgga gcagatccag     180
cgcatcaccg ccatgctgcg gcagcacggc aagatcgagg caagaacgt cttctactgg     240 ttccagaacc acaaggcccg cgagcgccag aagcgccgcc tcaccagcct cgacgtcaac     300
```

```
gtgcccgccg ccggcgcggc ggacgccacc accagccaac tcggcgtcct ctcgctgtcg   360
tcgccgccgc cttcaggcgc ggcgcctccc tcgcccaccc tcggtttata cgccgccggc   420
aatggcggcg gatcggctgt gctgctggac acgagttccg actggggcag cagcggcgct   480
gccatggcca ccgagacatg cttcctgcag gtcggtgctg tagtacgttc tttttcttggg  540 cattgcgcgc agtttcacgt tcgtacgtac gagttgatcg ccgcgtcgtt ccatccaccg   600
gtatatataa ctgttaggta cggcggtgcg cgcccgcagg actacatggg cgtgacggac   660
acgggcagct cgtcgcagtg ccacgcttc tcgtcgtcgg acacgataat ggcggcggcc    720
```

<210> SEQ ID NO 6
<211> LENGTH: 238
<212> TYPE: PRT
<213> ORGANISM: Zea mays

<400> SEQUENCE: 6

```
Met Ala Ala Asn Ala Gly Gly Gly Ala Gly Gly Ser Gly Ser
 1               5                  10                  15

Gly Ser Val Ala Ala Pro Ala Val Cys Arg Pro Ser Gly Ser Arg Trp
                20                  25                  30

Thr Pro Thr Pro Glu Gln Ile Arg Met Leu Lys Glu Leu Tyr Tyr Gly
             35                  40                  45

Cys Gly Ile Arg Ser Pro Ser Ser Glu Gln Ile Gln Arg Ile Thr Ala
     50                  55                  60

Met Leu Arg Gln His Gly Lys Ile Glu Gly Lys Asn Val Phe Tyr Trp
 65                  70                  75                  80

Phe Gln Asn His Lys Ala Arg Glu Arg Gln Lys Arg Arg Leu Thr Ser
                 85                  90                  95

Leu Asp Val Asn Val Pro Ala Ala Gly Ala Ala Asp Ala Thr Thr Ser
            100                 105                 110

Gln Leu Gly Val Leu Ser Leu Ser Pro Pro Ser Gly Ala Ala
            115                 120                 125

Pro Pro Ser Pro Thr Leu Gly Leu Tyr Ala Ala Gly Asn Gly Gly Gly
        130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Val Gly Ala Val Val Arg
                165                 170                 175

Ser Phe Leu Gly His Cys Ala Gln Phe His Val Arg Thr Tyr Glu Leu
            180                 185                 190

Ile Ala Ala Ser Phe His Pro Pro Val Tyr Ile Thr Val Arg Tyr Gly
        195                 200                 205

Gly Ala Arg Pro Gln Asp Tyr Met Gly Val Thr Asp Thr Gly Ser Ser
    210                 215                 220

Ser Gln Trp Pro Arg Phe Ser Ser Ser Asp Thr Ile Met Ala
225                 230                 235
```

<210> SEQ ID NO 7
<211> LENGTH: 767
<212> TYPE: DNA
<213> ORGANISM: Zea mays

<400> SEQUENCE: 7

```
ccacgcgtcc gagctaggtc acagaagcgc tcaggaaggc cgctgagata gaggcatggc    60
ggccaatgcg ggcggcggtg gagcgggagg aggcagcggc agcggcagcg tggctgcgcc   120
```

```
ggcggtgtgc cgccccagcg gctcgcggtg gacgccgacg ccggagcaga tcaggatgct    180
gaaggagctc tactacggct gcggcatccg gtcgcccagc tcggagcaga tccagcgcat    240
caccgccatg ctgcggcagc acggcaagat cgagggcaag aacgtcttct actggttcca    300
gaaccacaag gcccgcgagc gccagaagcg ccgcctcacc agcctcgacg tcaacgtgcc    360
cgccgccggc gcggccgacg ccaccaccag ccaactcggc gtcctctcgc tgtcgtcgcc    420
gccgccttca ggcgcggcgc tccctcgcc caccctcggc ttctacgccg ccggcaatgg    480
cggcggatcg gctgtgctgc tggacacgag ttccgactgg ggcagcagcg cgctgccat    540 ggccaccgag acatgcttcc tgcaggtcgg tgctgtagta cgttcttttc ttgggcattg    600
cgcgcagttt cacgttcgta cgtacgagtt gatcgccgcg tcgttccatc caccggtata    660
tataactgtt aggtacggcg gtgcgcgccc gcaggactac atgggcgtga cggacacggg    720
cagctcgtcg cagtggccac gcttcgcgtc gtcggacacg ataatgg                  767
```

<210> SEQ ID NO 8
<211> LENGTH: 237
<212> TYPE: PRT
<213> ORGANISM: Zea mays

<400> SEQUENCE: 8

```
Met Ala Asn Ala Gly Gly Gly Ala Gly Gly Ser Gly Ser
  1               5                  10                  15

Gly Ser Val Ala Ala Pro Ala Val Cys Arg Pro Ser Gly Ser Arg Trp
                 20                  25                  30

Thr Pro Thr Pro Glu Gln Ile Arg Met Leu Lys Glu Leu Tyr Tyr Gly
             35                  40                  45

Cys Gly Ile Arg Ser Pro Ser Ser Glu Gln Ile Gln Arg Ile Thr Ala
         50                  55                  60

Met Leu Arg Gln His Gly Lys Ile Glu Gly Lys Asn Val Phe Tyr Trp
 65                  70                  75                  80

Phe Gln Asn His Lys Ala Arg Glu Arg Gln Lys Arg Arg Leu Thr Ser
                 85                  90                  95

Leu Asp Val Asn Val Pro Ala Ala Gly Ala Ala Asp Ala Thr Thr Ser
                100                 105                 110

Gln Leu Gly Val Leu Ser Leu Ser Ser Pro Pro Ser Gly Ala Ala
            115                 120                 125

Pro Pro Ser Pro Thr Leu Gly Phe Tyr Ala Ala Gly Asn Gly Gly
        130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Val Gly Ala Val Val Arg
                165                 170                 175

Ser Phe Leu Gly His Cys Ala Gln Phe His Val Arg Thr Tyr Glu Leu
            180                 185                 190

Ile Ala Ala Ser Phe His Pro Pro Val Tyr Ile Thr Val Arg Tyr Gly
        195                 200                 205

Gly Ala Arg Pro Gln Asp Tyr Met Gly Val Thr Asp Thr Gly Ser Ser
    210                 215                 220

Ser Gln Trp Pro Arg Phe Ala Ser Ser Asp Thr Ile Met
225                 230                 235
```

<210> SEQ ID NO 9
<211> LENGTH: 1367

```
<212> TYPE: DNA
<213> ORGANISM: Zea mays

<400> SEQUENCE: 9
ccacgcgtcc gcctcgatcc atcacctttg catagcatat atagcgcagc agctcgacga      60
aacaccatct catcacatca catcagagca gagcagagca gagcatcacc cgatcccgat     120
cccgctattc ccagccttca gtagcagcag cagtacgtcg cgccctgccc atcgatccat     180
ctggctatca tacctgtcga catggaaggc ggactgagcc cggagcggca cgcggcggcg     240
gagccggtgc ggtcgcggtg gacgcccaag ccggagcaga tactcatcct cgagtccatc     300
ttcaacagcg gcatggtgaa cccgcccaag gacgagacgg tccgcatccg caagctgctg     360
gagcgcttcg gcgccgtggg cgacgccaac gtcttctact ggttccagaa ccgccgctcc     420
cgctcccgcc ggcgccagcg ccagctgcag gcgcaggcgg cggcctcctc gtcctcgtcg     480
ggatcgcccc ccacgagcgg cctcgcaccg ggacacgcga cggcttcgtc gacggcgggg     540
atgttcgcgc acggcgccac ctacggctcg tccgcgtccg cgtcctggcc gccgccgccg     600
tcgtgcgagg ggatgatggg cgacctggac tacggcggcg cgacgacct gttcgccatc      660
tcgcggcaga tgggctacgc cagcggcggt ggctccggct ccgcgtcctc ggcggccgtc     720
gcccaccacg agcagcagca gcagctttac tactcgccgt gccagccagc gagcatgacg     780
gtgttcatca atggcgtggc gacggaggtg ccgcgggggc cgatcgacct gcggtccatg     840
ttcgggcagg acgtgatgct ggtgcactcc accgccggcc tcctcccgt caacgagtac      900
ggcgtgctca cgcagagcct gcagatgggc gagagctact tcctggtcac gagggctac      960
taggtagcta gctatagcac attgcattgc cgacatggag accccagagc tagctgatgc    1020
agtacacgta ctcctcctta ccatgcatgg aattggatgt tattcggatc gtcggagacg    1080
catgcatgca ttgcatgctg cagtacctag tatctctgtc tctgtgtacg tgttcttcag    1140
tgaatgtctg tcagctcttg ccgtccgtcc gtccgtccgg tgtagatcag aaaaaggagg    1200
caaagaattc gataccagca gtgtgtgtgt gtgtgtttac tatatataaa gagagagaca    1260
cacacaaaca aatagagtgt tgtacctacg acgcatccac atcgaacatc tatactaagt    1320
atgtatgtaa tgatgaatca aaaaaaaaaa aaaaaaaaa aaaaag                    1367

<210> SEQ ID NO 10
<211> LENGTH: 253
<212> TYPE: PRT
<213> ORGANISM: Zea mays

<400> SEQUENCE: 10

Met Glu Gly Gly Leu Ser Pro Glu Arg His Ala Ala Ala Glu Pro Val
 1               5                  10                  15

Arg Ser Arg Trp Thr Pro Lys Pro Glu Gln Ile Leu Ile Leu Glu Ser
            20                  25                  30

Ile Phe Asn Ser Gly Met Val Asn Pro Pro Lys Asp Glu Thr Val Arg
        35                  40                  45

Ile Arg Lys Leu Leu Glu Arg Phe Gly Ala Val Gly Asp Ala Asn Val
    50                  55                  60

Phe Tyr Trp Phe Gln Asn Arg Arg Ser Arg Ser Arg Arg Gln Arg
65                  70                  75                  80

Gln Leu Gln Ala Gln Ala Ala Ala Ser Ser Ser Ser Gly Ser Pro
                85                  90                  95

Pro Thr Ser Gly Leu Ala Pro Gly His Ala Thr Ala Ser Ser Thr Ala
            100                 105                 110
```

```
Gly Met Phe Ala His Gly Ala Thr Tyr Gly Ser Ser Ala Ser Ala Ser
            115                 120                 125

Trp Pro Pro Pro Ser Cys Glu Gly Met Met Gly Asp Leu Asp Tyr
130                 135                 140

Gly Gly Gly Asp Asp Leu Phe Ala Ile Ser Arg Gln Met Gly Tyr Ala
145                 150                 155                 160

Ser Gly Gly Gly Ser Gly Ser Ala Ser Ser Ala Val Ala His His
            165                 170                 175

Glu Gln Gln Gln Gln Leu Tyr Tyr Ser Pro Cys Gln Pro Ala Ser Met
            180                 185                 190

Thr Val Phe Ile Asn Gly Val Ala Thr Glu Val Pro Arg Gly Pro Ile
            195                 200                 205

Asp Leu Arg Ser Met Phe Gly Gln Asp Val Met Leu Val His Ser Thr
            210                 215                 220

Ala Gly Leu Leu Pro Val Asn Glu Tyr Gly Val Leu Thr Gln Ser Leu
225                 230                 235                 240

Gln Met Gly Glu Ser Tyr Phe Leu Val Thr Arg Gly Tyr
            245                 250
```

<210> SEQ ID NO 11
<211> LENGTH: 513
<212> TYPE: DNA
<213> ORGANISM: Zea mays
<220> FEATURE:
<221> NAME/KEY: misc_feature
<222> LOCATION: (1)...(513)
<223> OTHER INFORMATION: n = A, T, C, or G

<400> SEQUENCE: 11

```
gcggtacgcg tgggcgtacc aaggtagcag gtggccgtgc tggagggggct gtacgaacac    60
ggnctgcgca cccccagcgc ggagcagata cagcagatca cgggcaggct gcgggagcac   120
ggcgccatcg agggcaagaa cgtcttctac tggttccaga accacaaggc ccgccagcgc   180
cagangcagn aagcaggaca gcttcgccta cttcagcagg ctcctccgcc ggccccccgcc   240
gctgcccgtg ctctccatgc ccccgcgcc accgtaccat cacgcccgcg tcccggngcc   300
gcccgcgaat accgatgccg attggcgccg ccgccgcccg ctngcattgc aaacgaacaa   360
cnggggggnc gcgttttttat cttacangaa acccattcta ctttgctgcc ccgcaagggc   420
cccctgcaaa tgccgcctaa taantacccc aagcacagca caacaacaa caagnaggtn    480
aaagtcnttt tccattnccc aaaaatggaa gtt                                513
```

<210> SEQ ID NO 12
<211> LENGTH: 89
<212> TYPE: PRT
<213> ORGANISM: Zea mays
<220> FEATURE:
<221> NAME/KEY: VARIANT
<222> LOCATION: (1)...(89)
<223> OTHER INFORMATION: Xaa = any amino acid

<400> SEQUENCE: 12

```
Gln Val Ala Val Leu Glu Gly Leu Tyr Glu His Gly Leu Arg Thr Pro
1               5                   10                  15

Ser Ala Glu Gln Ile Gln Gln Ile Thr Gly Arg Leu Arg Glu His Gly
            20                  25                  30

Ala Ile Glu Gly Lys Asn Val Phe Tyr Trp Phe Gln Asn His Lys Ala
        35                  40                  45
```

-continued

Arg Gln Arg Gln Xaa Gln Xaa Ala Gly Gln Leu Arg Leu Leu Gln Gln
    50                  55                  60

Ala Pro Pro Ala Pro Ala Ala Arg Ala Leu His Ala Pro Arg
65                  70                  75                  80

Ala Thr Val Pro Ser Arg Pro Arg Pro
                85

<210> SEQ ID NO 13
<211> LENGTH: 1194
<212> TYPE: DNA
<213> ORGANISM: Zea mays

<400> SEQUENCE: 13
ccacgcgtcc gcggacgcgt gggcgaccaa ggagcaggtg gccgtgctgg aggggctgta      60
cgagcacggc ctgcgcaccc ccagcgcgga gcagatacag cagatcacgg gcaggctgcg     120
ggagcacggc gccatcgagg gcaagaacgt cttctactgg ttccagaacc acaaggcccg     180
ccagcgccag aggcagaagc aggacagctt cgcctacttc agcaggctcc tccgccggcc     240
cccgccgctg cccgtgctct ccatgccccc cgcgccaccg taccatcacg cccgcgtccc     300
ggcgccgccc gcgataccga tgccgatggc gccgccgccg cccgctgcat gcaacgacaa     360
cggcggcgcg cgtgtgatct acaggaaccc attctacgtg gctgcgccgc aggcgccccc     420
tgcaaatgcc gcctactact acccacagcc acagcagcag cagcagcagc aggtgacagt     480
catgtaccag tacccgagaa tggaggtagc cggccaggac aagatgatga ccagggccgc     540
ggcgcaccag cagcagcagc acaacggcgc cgggcaacaa ccgggacgcg ccggccaccc     600
cagccgcgag acgctccagc tgttcccgcc tccagcccac cttcgtgctg cggcacgaca     660
agggcgcgc cgccaacggc agtaataacg actccctgac gtcgacgtcg acggcgactg     720
cgacagcgac agcgacagcg acagcgtccg cttccatctc cgaggactcg gatggcctgg     780
agagcggcag ctccggcaag ggcgtcgagg aggcgcccgc gctgccgttc tatgacttct     840
tcgggctcca gtcctccgga ggccgctgat catgggactg aggtagagcg agctcgagtg     900
atgaaagccg agccagacgt tcgtgtgatc tcgagtcgtc gtcgatggac ccggttgccg     960
ttgccttttg ttgggttatt gcatgcatgg tgtgcttcat caactactgg aagaagcctg    1020
tgccgatcga accaaaacag tttgcattgt tgagttccgt accgtcctgt agcaacaatg    1080
tagcggagaa atgctactag tagcttcttt ttaaaaaaaa aaaaaaaaaa aaaaaaaaa     1140
aaaaaaaaaa aaaaaaaaaa aaaaaaaaaa aaaaaaaaa aaaaaaaaaa aaag           1194

<210> SEQ ID NO 14
<211> LENGTH: 221
<212> TYPE: PRT
<213> ORGANISM: Zea mays

<400> SEQUENCE: 14

Trp Ala Thr Lys Glu Gln Val Ala Val Leu Glu Gly Leu Tyr Glu His
1               5                   10                  15

Gly Leu Arg Thr Pro Ser Ala Glu Gln Ile Gln Gln Ile Thr Gly Arg
            20                  25                  30

Leu Arg Glu His Gly Ala Ile Glu Gly Lys Asn Val Phe Tyr Trp Phe
        35                  40                  45

Gln Asn His Lys Ala Arg Gln Arg Gln Arg Gln Lys Gln Asp Ser Phe
    50                  55                  60

Ala Tyr Phe Ser Arg Leu Leu Arg Arg Pro Pro Pro Leu Pro Val Leu

```
                65                  70                  75                  80
Ser Met Pro Pro Ala Pro Pro Tyr His His Ala Arg Val Pro Ala Pro
                    85                  90                  95

Pro Ala Ile Pro Met Pro Met Ala Pro Pro Pro Ala Ala Cys Asn
            100                 105                 110

Asp Asn Gly Gly Ala Arg Val Ile Tyr Arg Asn Pro Phe Tyr Val Ala
            115                 120                 125

Ala Pro Gln Ala Pro Pro Ala Asn Ala Ala Tyr Tyr Tyr Pro Gln Pro
        130                 135                 140

Gln Gln Gln Gln Gln Gln Val Thr Val Met Tyr Gln Tyr Pro Arg
145                 150                 155                 160

Met Glu Val Ala Gly Gln Asp Lys Met Met Thr Arg Ala Ala His
            165                 170                 175

Gln Gln Gln Gln His Asn Gly Ala Gly Gln Gln Pro Gly Arg Ala Gly
            180                 185                 190

His Pro Ser Arg Glu Thr Leu Gln Leu Phe Pro Pro Ala His Leu
        195                 200                 205

Arg Ala Ala Ala Arg Gln Gly Ala Arg Arg Gln Arg Gln
    210                 215                 220
```

<210> SEQ ID NO 15
<211> LENGTH: 506
<212> TYPE: DNA
<213> ORGANISM: Glycine max
<220> FEATURE:
<221> NAME/KEY: misc_feature
<222> LOCATION: (1)...(506)
<223> OTHER INFORMATION: n = A, T, C, or G

<400> SEQUENCE: 15

```
caacaagcta gtactagang atggagagta gtcacagtac tgcagaggat gagagtggat      60
ggaaaggatc aagtggtgct cattcatcag tttcacgatg gagtcctaca aaggagcaaa    120
tagacatgtt ggagaacttt tacaagcagg gaataaggac tcccagcact gagcaaatac    180
aacagattac ctctaggctt agggcttatg gttacatcga gggaaaaaat gtcttctact    240
ggtttcaaaa tcacaaagcg cgccaaagac agaagctcaa gcagaagcaa caaagcattg    300
catactgcaa ttgctttctt catgcctccc accccatttg ccaaaatgtt gtctgcgtcc    360
atattgtttg caaagagtg gattcagctt ttatcctcac caaccaaagg tgcttgcaag    420
tgtaggtatt agctcaaggg attgagactg ggtcctttgg catgctaaag aatatgtgat    480
ggcatgcann agtgaacacc cggatt                                          506
```

<210> SEQ ID NO 16
<211> LENGTH: 134
<212> TYPE: PRT
<213> ORGANISM: Glycine max

<400> SEQUENCE: 16

```
Met Glu Ser Ser His Ser Thr Ala Glu Asp Glu Ser Gly Trp Lys Gly
1               5                   10                  15

Ser Ser Gly Ala His Ser Ser Val Ser Arg Trp Ser Pro Thr Lys Glu
            20                  25                  30

Gln Ile Asp Met Leu Glu Asn Phe Tyr Lys Gln Gly Ile Arg Thr Pro
        35                  40                  45

Ser Thr Glu Gln Ile Gln Gln Ile Thr Ser Arg Leu Arg Ala Tyr Gly
    50                  55                  60
```

```
Tyr Ile Glu Gly Lys Asn Val Phe Tyr Trp Phe Gln Asn His Lys Ala
 65                  70                  75                  80

Arg Gln Arg Gln Lys Leu Lys Gln Lys Gln Gln Ser Ile Ala Tyr Cys
                 85                  90                  95

Asn Cys Phe Leu His Ala Ser His Pro Ile Cys Gln Asn Val Val Cys
            100                 105                 110

Val His Ile Val Cys Lys Arg Val Asp Ser Ala Phe Ile Leu Thr Asn
        115                 120                 125

Gln Arg Cys Leu Gln Val
        130
```

<210> SEQ ID NO 17
<211> LENGTH: 844
<212> TYPE: DNA
<213> ORGANISM: Glycine max

<400> SEQUENCE: 17

```
gcacgagagt cacagtactg cagaggatga gagtggatgg aaaggatcaa gtggtgctca      60
ttcatcagtt tcacgatgga gtcctacaaa ggagcaaata acatgttgg agaactttta     120
caagcaggga ataaggactc ccagcactga gcaaatacaa cagattacct ctaggcttag     180
ggcttatggt tacatcgagg gaaaaaatgt cttctactgg tttcaaaatc acaaagcgcg     240
ccaaagacag aagctcaagc agaagcaaca agcattgca tactgcaatt gctttcttca     300
tgcctcccac cccatttgcc aaaatgttgt ctgcgctcca tattgtttgc aaaagagtgg     360
attcagcttt tatcctcacc aaccaaaggt gcttgcaagt gtaggtatta gctcaaggat     420
tgagactggg tcctttggca tgctaagaat atgtgatggc atgcagagtg aacacccgga     480
ttataactat agcaccagta accgtgaagc cttaactcta tttcctcttc atccaaccgg     540
tattttggaa gaaaaacaa ctcatcactc tgttgatgtc accgacaaat cttttgtttc     600
tattgctgtt gacgaaaatg gtcatcttgg aaatcaaccc tgctttaatt ttcagtactg     660
aagaacgaag gtatcgagat agtgattaag tatcatcgac caaaactact aacactgtac     720
tactactttc tttgagtagc tcgttgttca tcttcgaaat gagttttatc taattggata     780
ttgagtttaa cgtagtaaaa aaaaaaaaaa aaaaaaaa aaaaaaaaaa aaaaaaaaaa     840
aaaa                                                                 844
```

<210> SEQ ID NO 18
<211> LENGTH: 217
<212> TYPE: PRT
<213> ORGANISM: Glycine max

<400> SEQUENCE: 18

```
Ser His Ser Thr Ala Glu Asp Glu Ser Gly Trp Lys Gly Ser Ser Gly
  1               5                  10                  15

Ala His Ser Ser Val Ser Arg Trp Ser Pro Thr Lys Glu Gln Ile Asp
                 20                  25                  30

Met Leu Glu Asn Phe Tyr Lys Gln Gly Ile Arg Thr Pro Ser Thr Glu
             35                  40                  45

Gln Ile Gln Gln Ile Thr Ser Arg Leu Arg Ala Tyr Gly Tyr Ile Glu
         50                  55                  60

Gly Lys Asn Val Phe Tyr Trp Phe Gln Asn His Lys Ala Arg Gln Arg
 65                  70                  75                  80

Gln Lys Leu Lys Gln Lys Gln Gln Ser Ile Ala Tyr Cys Asn Cys Phe
                 85                  90                  95
```

```
Leu His Ala Ser His Pro Ile Cys Gln Asn Val Val Cys Ala Pro Tyr
            100                 105                 110

Cys Leu Gln Lys Ser Gly Phe Ser Phe Tyr Pro His Gln Pro Lys Val
        115                 120                 125

Leu Ala Ser Val Gly Ile Ser Ser Arg Ile Glu Thr Gly Ser Phe Gly
    130                 135                 140

Met Leu Arg Ile Cys Asp Gly Met Gln Ser Glu His Pro Asp Tyr Asn
145                 150                 155                 160

Tyr Ser Thr Ser Asn Arg Glu Ala Leu Thr Leu Phe Pro Leu His Pro
                165                 170                 175

Thr Gly Ile Leu Glu Glu Lys Thr Thr His His Ser Val Asp Val Thr
            180                 185                 190

Asp Lys Ser Phe Val Ser Ile Ala Val Asp Glu Asn Gly His Leu Gly
        195                 200                 205

Asn Gln Pro Cys Phe Asn Phe Gln Tyr
    210                 215

<210> SEQ ID NO 19
<211> LENGTH: 741
<212> TYPE: DNA
<213> ORGANISM: Glycine max

<400> SEQUENCE: 19
gcacgagaac aagctagtac tagaagatgg agagtcacag tagtgatgct gaggcggaga      60
atgtaaggac tcattcatca gtttcacggt ggagtcctac aaaggagcaa atagacatgt     120
tagagaacct ttacaagcag ggaataagga ctcccagcac tgagcaaata aacagatta      180
cctctaggct cagggcttat ggtcacatcg agggaaagaa tgtcttctac tggtttcaaa     240
atcacaaagc tcgtcaaaga cagaagctga tgaagcaaca aaccattgca tattccaatc     300
gctttcttcg tgcctcccac cccatttgcc aaaatgttgc ctgcgctcca tattgtttgc     360
aacggagtgg attcagcttt tatcctcaac aatcgaaggt gcttgcaagt ggaggtataa     420
gttcaactgg gcctttaggc atgcaaagaa tgtttgatgg catgcagagt agtgaacacc     480
cggattgtaa ccgtgaagtc ttaactctct tcctcttca tccaaccggc attttgaaag      540
aaaaaacaac tcatcaagtg ccttcccttg cttcaacttc tgttgttgct gttgatgaag     600
atggtcatct tggaaatcag cccttcttta atttttcac tactgaacca aggtcgagag      660
agtgattagg tgttaattgt cattgaccaa aaaacaact aacatggcac tactttgagt      720
aaaaaaaaaa aaaaaaaaa a                                                741

<210> SEQ ID NO 20
<211> LENGTH: 212
<212> TYPE: PRT
<213> ORGANISM: Glycine max

<400> SEQUENCE: 20

Met Glu Ser His Ser Ser Asp Ala Glu Ala Glu Asn Val Arg Thr His
1               5                   10                  15

Ser Ser Val Ser Arg Trp Ser Pro Thr Lys Glu Gln Ile Asp Met Leu
            20                  25                  30

Glu Asn Leu Tyr Lys Gln Gly Ile Arg Thr Pro Ser Thr Glu Gln Ile
        35                  40                  45

Gln Gln Ile Thr Ser Arg Leu Arg Ala Tyr Gly His Ile Glu Gly Lys
    50                  55                  60

Asn Val Phe Tyr Trp Phe Gln Asn His Lys Ala Arg Gln Arg Gln Lys
```

```
                65                  70                  75                  80
Leu Met Lys Gln Gln Thr Ile Ala Tyr Ser Asn Arg Phe Leu Arg Ala
                    85                  90                  95

Ser His Pro Ile Cys Gln Asn Val Ala Cys Ala Pro Tyr Cys Leu Gln
                100                 105                 110

Arg Ser Gly Phe Ser Phe Tyr Pro Gln Gln Ser Lys Val Leu Ala Ser
                115                 120                 125

Gly Gly Ile Ser Ser Thr Gly Pro Leu Gly Met Gln Arg Met Phe Asp
        130                 135                 140

Gly Met Gln Ser Ser Glu His Pro Asp Cys Asn Arg Glu Val Leu Thr
145                 150                 155                 160

Leu Phe Pro Leu His Pro Thr Gly Ile Leu Lys Glu Lys Thr Thr His
                165                 170                 175

Gln Val Pro Ser Leu Ala Ser Thr Ser Val Val Ala Val Asp Glu Asp
                180                 185                 190

Gly His Leu Gly Asn Gln Pro Phe Phe Asn Phe Phe Thr Thr Glu Pro
            195                 200                 205

Arg Ser Arg Glu
        210

<210> SEQ ID NO 21
<211> LENGTH: 906
<212> TYPE: DNA
<213> ORGANISM: Glycine max

<400> SEQUENCE: 21
accagctaaa attaagcatg aaggtgcatc agttcgcacg tggattctgg gagcacgaac      60 cctcccctcac actcgggtgc aaacgcttac gcccccttgc ccccaagctt tccaacaccg    120
acaccatttc tccacctcat catcctgtta caaccttcga cctcaagagc ttcatcaaac    180
ctgaaagtgc ctccagaaaa cttggaattg atcctccga tgataatact aataagagag      240
acccatcttc accccagggc caggctgaaa cgcatattcc aggagggaca cggtggaatc    300
cgactcaaga acaaataggg atattggaga tgctgtacag aggagggatg cgaactccga    360
atgctcaaca atagagcag atcacagcac agcttagcaa gtacggcaag atcgaaggga    420
agaacgtgtt ctattggttc aaaaccaca agcacgcga gagacagaag cagaagcgta      480
acaacytagg ccttgctcat agtcctcgta ctactctcac cacttcaccc cccttagtt    540 gttgtgtaat taccactatg gacaccacaa acgggggga agtagtagaa agagaggagg    600
aagatagccc gttgaagaag tgtaggagct gggcgtttga gtacttggaa gaccaaagag    660
aggaggaaca tagaactctg gagctttcc cattgcaccc ggaaggcaga tgaagggggtt    720 tgttttaatt gtttgaccaa tttaacgaga atatttta gcttttaatt aattgtttct      780 gaaccttca ggctgattgg aatgtatgtg ctttaattag tttggtttag tttttcatca    840
ctttcttctt tggttgtgtt gggaaagaag aaaacacaaa gtcgtctaca aaaaaaaaa    900 aaaaaa                                                                906

<210> SEQ ID NO 22
<211> LENGTH: 231
<212> TYPE: PRT
<213> ORGANISM: Glycine max

<400> SEQUENCE: 22

Met Lys Val His Gln Phe Ala Arg Gly Phe Trp Glu His Glu Pro Ser
1               5                   10                  15
```

```
Leu Thr Leu Gly Cys Lys Arg Leu Arg Pro Leu Ala Pro Lys Leu Ser
            20                  25                  30

Asn Thr Asp Thr Ile Ser Pro Pro His His Pro Val Thr Thr Phe Asp
        35                  40                  45

Leu Lys Ser Phe Ile Lys Pro Glu Ser Ala Ser Arg Lys Leu Gly Ile
    50                  55                  60

Gly Ser Ser Asp Asp Asn Thr Asn Lys Arg Asp Pro Ser Ser Pro Gln
65                  70                  75                  80

Gly Gln Ala Glu Thr His Ile Pro Gly Gly Thr Arg Trp Asn Pro Thr
                85                  90                  95

Gln Glu Gln Ile Gly Ile Leu Glu Met Leu Tyr Arg Gly Gly Met Arg
            100                 105                 110

Thr Pro Asn Ala Gln Gln Ile Glu Gln Ile Thr Ala Gln Leu Ser Lys
        115                 120                 125

Tyr Gly Lys Ile Glu Gly Lys Asn Val Phe Tyr Trp Phe Gln Asn His
    130                 135                 140

Lys Ala Arg Glu Arg Gln Lys Gln Lys Arg Asn Asn Leu Gly Leu Ala
145                 150                 155                 160

His Ser Pro Arg Thr Thr Leu Thr Thr Ser Pro Pro Phe Ser Cys Cys
                165                 170                 175

Val Ile Thr Thr Met Asp Thr Thr Lys Arg Gly Glu Val Val Glu Arg
            180                 185                 190

Glu Glu Glu Asp Ser Pro Leu Lys Lys Cys Arg Ser Trp Ala Phe Glu
        195                 200                 205

Tyr Leu Glu Asp Gln Arg Glu Glu His Arg Thr Leu Glu Leu Phe
    210                 215                 220

Pro Leu His Pro Glu Gly Arg
225                 230

<210> SEQ ID NO 23
<211> LENGTH: 904
<212> TYPE: DNA
<213> ORGANISM: Glycine max

<400> SEQUENCE: 23
cagcatgaag gtgcatcagt tcacacgtgg attaatctgg gagcacgaac ctttcctcac      60
acttggctgc aagagattac gccctcttgc tcccaagctt cccaacacca aaactatcac    120
taccccttc gatctcaaga gcttcatcag gcccgaaagt ggccccagaa acccgtttc      180
ctctgacgac actaagaagg atccaccttc accccaaggc cagattgaaa cgcacccagg    240
agggacacgg tggaatccta cgcaagaaca gataggcata ttggagatgt tgtacaaagg    300
agggatgcga actccgaatg ctcaacagat agagcagatc actgtccagc ttggaaagta    360
cggcaagatc gaagggaaga acgtgttcta ttggtttcag aatcacaaag cacgcgagag    420
acaaaagcag aagcgcagca gccttgcatc ttctcatagt cctcgaactc ccacaattca    480
cagtgttgtt actttggaga caacaagggg ggaagtggta gagagagatc acgaggaaga    540
tagtccgtac aagaagaagt gcaggagatg ggtatttgac tgcttggaag aacaaaacat    600
gtcatcacct tgtgaacaag aggaacatag aactctggag cttttccat gcacccgga      660
aggcagatga aggggtttga gtttgattga ccatttatct atcatttttc actttgcttt    720
agttccgaat cgcagctgat tattgaatga atgtggttta attaatttgc tttacttttc    780
tttttctttt gtattgggaa agaagaaaga caaagttgtc tctgatctgt actcttccac    840
```

```
ttaatgctat tcctgacttt ggaaccaaaa aaaaaaaaaa aaaactcgga gagagcgaac    900
tagt                                                                 904
```

<210> SEQ ID NO 24
<211> LENGTH: 221
<212> TYPE: PRT
<213> ORGANISM: Glycine max

<400> SEQUENCE: 24

```
Met Lys Val His Gln Phe Thr Arg Gly Leu Ile Trp Glu His Glu Pro
 1               5                  10                  15
Phe Leu Thr Leu Gly Cys Lys Arg Leu Arg Pro Leu Ala Pro Lys Leu
             20                  25                  30
Pro Asn Thr Lys Thr Ile Thr Thr Pro Phe Asp Leu Lys Ser Phe Ile
         35                  40                  45
Arg Pro Glu Ser Gly Pro Arg Lys Pro Val Ser Ser Asp Asp Thr Lys
     50                  55                  60
Lys Asp Pro Pro Ser Pro Gln Gly Gln Ile Glu Thr His Pro Gly Gly
 65                  70                  75                  80
Thr Arg Trp Asn Pro Thr Gln Glu Gln Ile Gly Ile Leu Glu Met Leu
                 85                  90                  95
Tyr Lys Gly Gly Met Arg Thr Pro Asn Ala Gln Gln Ile Glu Gln Ile
            100                 105                 110
Thr Val Gln Leu Gly Lys Tyr Gly Lys Ile Glu Gly Lys Asn Val Phe
        115                 120                 125
Tyr Trp Phe Gln Asn His Lys Ala Arg Glu Arg Gln Lys Gln Lys Arg
    130                 135                 140
Ser Ser Leu Ala Ser Ser His Ser Pro Arg Thr Pro Thr Ile His Ser
145                 150                 155                 160
Val Val Thr Leu Glu Thr Thr Arg Gly Glu Val Val Glu Arg Asp His
                165                 170                 175
Glu Glu Asp Ser Pro Tyr Lys Lys Cys Arg Arg Trp Val Phe Asp
            180                 185                 190
Cys Leu Glu Glu Gln Asn Met Ser Ser Pro Cys Glu Gln Glu His
            195                 200                 205
Arg Thr Leu Glu Leu Phe Pro Leu His Pro Glu Gly Arg
    210                 215                 220
```

<210> SEQ ID NO 25
<211> LENGTH: 291
<212> TYPE: PRT
<213> ORGANISM: Arabidopsis thaliana
<220> FEATURE:
<223> OTHER INFORMATION: NCBI GI 4090200

<400> SEQUENCE: 25

```
Met Glu Pro Pro Gln His Gln His His His Gln Ala Asp Gln Glu
 1               5                  10                  15
Ser Gly Asn Asn Asn Lys Ser Gly Ser Gly Gly Tyr Thr Cys Arg
             20                  25                  30
Gln Thr Ser Thr Arg Trp Thr Pro Thr Thr Glu Gln Ile Lys Ile Leu
         35                  40                  45
Lys Glu Leu Tyr Tyr Asn Asn Ala Ile Arg Ser Pro Thr Ala Asp Gln
     50                  55                  60
Ile Gln Lys Ile Thr Ala Arg Leu Arg Gln Phe Gly Lys Ile Glu Gly
 65                  70                  75                  80
```

```
Lys Asn Val Phe Tyr Trp Phe Gln Asn His Lys Ala Arg Glu Arg Gln
                85                  90                  95
Lys Lys Arg Phe Asn Gly Thr Asn Met Thr Thr Pro Ser Ser Ser Pro
            100                 105                 110
Asn Ser Val Met Met Ala Ala Asn Asp His Tyr His Pro Leu Leu His
        115                 120                 125
His His His Gly Val Pro Met Gln Arg Pro Ala Asn Ser Val Asn Val
    130                 135                 140
Lys Leu Asn Gln Asp His His Leu Tyr His His Asn Lys Pro Tyr Pro
145                 150                 155                 160
Ser Phe Asn Asn Gly Asn Leu Asn His Ala Ser Ser Gly Thr Glu Cys
                165                 170                 175
Gly Val Val Asn Ala Ser Asn Gly Tyr Met Ser Ser His Val Tyr Gly
            180                 185                 190
Ser Met Glu Gln Asp Cys Ser Met Asn Tyr Asn Asn Val Gly Gly Gly
        195                 200                 205
Trp Ala Asn Met Asp His His Tyr Ser Ser Ala Pro Tyr Asn Phe Phe
    210                 215                 220
Asp Arg Ala Lys Pro Leu Phe Gly Leu Glu Gly His Gln Asp Glu Glu
225                 230                 235                 240
Glu Cys Gly Gly Asp Ala Tyr Leu Glu His Arg Arg Thr Leu Pro Leu
                245                 250                 255
Phe Pro Met His Gly Glu Asp His Ile Asn Gly Gly Ser Gly Ala Ile
            260                 265                 270
Trp Lys Tyr Gly Gln Ser Glu Val Arg Pro Cys Ala Ser Leu Glu Leu
        275                 280                 285
Arg Leu Asn
    290

<210> SEQ ID NO 26
<211> LENGTH: 1417
<212> TYPE: DNA
<213> ORGANISM: Zea mays

<400> SEQUENCE: 26
gtccgagcta ggtcacagaa gcgctcagga aggccgctga gatagaggca tggcggccaa    60
tgcgggcggc ggtggagcgg gaggaggcag cggcagcggc agcgtggctg cgccggcggt   120
gtgccgcccc agcggctcgc ggtggacgcc gacgccggag cagatcagga tgctgaagga   180
gctctactac ggctgcggca tccggtcgcc cagctcggag cagatccagc gcatcaccgc   240
catgctgcgg cagcacggca agatcgaggg caagaacgtc ttctactggt tccagaacca   300
caaggcccgc gagcgccaga gcgccgcct caccagcctc gacgtcaacg tgcccgccgc   360
cggcgcggcc gacgccacca ccagccaact cggcgtcctc tcgctgtcgt cgccgccgcc   420
ttcaggcgcg cgcctccct cgcccaccct cggcttctac gccgccggca atggcggcgg   480
atcggctgtg ctgctggaca cgagttccga ctggggcagc agcggcgctg ccatggccac   540
cgagacatgc ttcctgcagg tcggtgctgt agtacgttct tttcttggc attgcgcgca   600
gtttcacgtt cgtacgtacg agttgatcgc cgcgtcgttc catccaccgg tatatataac   660
tgttaggtac ggcggtgcgc gcccgcagga ctacatgggc gtgacggaca cgggcagctc   720
gtcgcagtgg ccatgcttct cgtcgtcgga cacgataatg gcggcggcgg cggccgcggc   780
gcgggtggcg acgacgcggg cgcccgagac actccctctc ttcccgacct gcggcgacga   840
cgacgacgac gacagccagc cccgccgcg gccgcggcac gcagtcccag tcccggcagg   900
```

-continued

```
cgagaccatc cgcggcggcg gcggcagcag cagcagctac ttgccgttct ggggtgccgg      960
tgccgcgtcc acaactgccg gcgccacttc ttccgttgcg atccagcagc aacaccagct     1020
gcaggagcag tacagctttt acagcaacag cacccagctg ccggcaccg gcagccaaga      1080 cgtatcggct tcagcggccg ccctggagct gagcctcagc tcatggtgct ccccttaccc    1140
tgctgcaggg agcatgtgag agcaacgcga gctaccactg ggacgtgcgt tgctgtcatt    1200
gtcctaggtt agtagctagt gccagttact agtaagcatc aggcatagga gtatgtagta    1260
gaagcatgtc tggagaaagg caatagctag cgtttgggag atctctggcg gtactattat    1320
tagatagcga atttgcatac tatgcagcat gcatgttgcc ggccgggcgg gctttagact    1380
ccagctactg catgcgtgca tgcggtggtc ctcatgt                              1417
```

<210> SEQ ID NO 27
<211> LENGTH: 369
<212> TYPE: PRT
<213> ORGANISM: Zea mays

<400> SEQUENCE: 27

```
Met Ala Ala Asn Ala Gly Gly Gly Gly Ala Gly Gly Ser Gly Ser
  1               5                  10                  15

Gly Ser Val Ala Ala Pro Ala Val Cys Arg Pro Ser Gly Ser Arg Trp
                 20                  25                  30

Thr Pro Thr Pro Glu Gln Ile Arg Met Leu Lys Glu Leu Tyr Tyr Gly
             35                  40                  45

Cys Gly Ile Arg Ser Pro Ser Ser Glu Gln Ile Gln Arg Ile Thr Ala
         50                  55                  60

Met Leu Arg Gln His Gly Lys Ile Glu Gly Lys Asn Val Phe Tyr Trp
 65                  70                  75                  80

Phe Gln Asn His Lys Ala Arg Glu Arg Gln Lys Arg Arg Leu Thr Ser
                 85                  90                  95

Leu Asp Val Asn Val Pro Ala Ala Gly Ala Ala Asp Ala Thr Thr Ser
            100                 105                 110

Gln Leu Gly Val Leu Ser Leu Ser Ser Pro Pro Ser Gly Ala Ala
            115                 120                 125

Pro Pro Ser Pro Thr Leu Gly Phe Tyr Ala Ala Gly Asn Gly Gly Gly
        130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Val Gly Ala Val Val Arg
                165                 170                 175

Ser Phe Leu Gly His Cys Ala Gln Phe His Val Arg Thr Tyr Glu Leu
            180                 185                 190

Ile Ala Ala Ser Phe His Pro Pro Val Tyr Ile Thr Val Arg Tyr Gly
        195                 200                 205

Gly Ala Arg Pro Gln Asp Tyr Met Gly Val Thr Asp Thr Gly Ser Ser
    210                 215                 220

Ser Gln Trp Pro Cys Phe Ser Ser Ser Asp Thr Ile Met Ala Ala Ala
225                 230                 235                 240

Ala Ala Ala Ala Arg Val Ala Thr Thr Arg Ala Pro Glu Thr Leu Pro
                245                 250                 255

Leu Phe Pro Thr Cys Gly Asp Asp Asp Asp Ser Gln Pro Pro
            260                 265                 270

Pro Arg Pro Arg His Ala Val Pro Val Pro Ala Gly Glu Thr Ile Arg
```

```
                275               280                285
Gly Gly Gly Gly Ser Ser Ser Tyr Leu Pro Phe Trp Gly Ala Gly
        290                 295                 300

Ala Ala Ser Thr Thr Ala Gly Ala Thr Ser Ser Val Ala Ile Gln Gln
305                 310                 315                 320

Gln His Gln Leu Gln Glu Gln Tyr Ser Phe Tyr Ser Asn Ser Thr Gln
                325                 330                 335

Leu Ala Gly Thr Gly Ser Gln Asp Val Ser Ala Ser Ala Ala Ala Leu
                340                 345                 350

Glu Leu Ser Leu Ser Ser Trp Cys Ser Pro Tyr Pro Ala Ala Gly Ser
                355                 360                 365

Met
```

<210> SEQ ID NO 28
<211> LENGTH: 1288
<212> TYPE: DNA
<213> ORGANISM: Zea mays

<400> SEQUENCE: 28

```
gtccgagcta ggtcacagaa gcgctcagga aggccgctga gatagaggca tggcggccaa      60
tgcgggcggc ggtggagcgg gaggaggcag cggcagcggc agcgtggctg cgccggcggt     120
gtgccgcccc agcggctcgc ggtggacgcc gacgccggag cagatcagga tgctgaagga     180
gctctactac ggctgcggca tccggtcgcc cagctcggag cagatccagc gcatcaccgc     240
catgctgcgg cagcacggca agatcgaggg caagaacgtc ttctactggt tccagaacca     300
caaggcccgc gagcgccaga gcgccgcct caccagcctc gacgtcaacg tgcccgccgc     360
cggcgcggcc gacgccacca ccagccaact cggcgtcctc tcgctgtcgt cgccgccgcc     420
ttcaggcgcg gcgcctccct cgcccaccct cggcttctac gccgccggca tggcggcgg     480
atcggctgtg ctgctggaca cgagttccga ctggggcagc agcggcgctg ccatggccac     540
cgagacatgc ttcctgcagg actacatggg cgtgacggac acgggcagct cgtcgcagtg     600
gccatgcttc tcgtcgtcgg acacgataat ggcggcggcg gcggccgcgg cgcgggtggc     660
gacgacgcgg gcgcccgaga cactccctct cttcccgacc tgcggcgacg acgacgacga     720
cgacagccag ccccgccgc ggccgcggca cgcagtccca gtcccggcag gcgagaccat     780
ccgcggcggc ggcggcagca gcagcagcta cttgccgttc tggggtgccg gtgccgcgtc     840
cacaactgcc ggcgccactt cttccgttgc gatccagcag caacaccagc tgcaggagca     900
gtacagcttt tacagcaaca gcacccagct ggccggcacc ggcagccaag acgtatcggc     960
ttcagcggcc gccctggagc tgagcctcag ctcatggtgc tcccttacc ctgctgcagg    1020
gagcatgtga gagcaacgcg agctaccact gggacgtgcg ttgctgtcat tgtcctaggt    1080
tagtagctag tgccagttac tagtaagcat caggcatagg agtatgtagt agaagcatgt    1140
ctggagaaag gcaatagcta gcgtttggga gatctctggc ggtactatta ttagatagcg    1200
aatttgcata ctatgcagca tgcatgttgc cggccgggcg ggctttagac tccagctact    1260
gcatgcgtgc atgcggtggt cctcatgt                                       1288
```

<210> SEQ ID NO 29
<211> LENGTH: 326
<212> TYPE: PRT
<213> ORGANISM: Zea mays

<400> SEQUENCE: 29

-continued

| | | | | | | | | | | | |
|---|---|---|---|---|---|---|---|---|---|---|---|
| Met<br>1 | Ala | Ala | Asn | Ala<br>5 | Gly | Gly | Gly | Ala | Gly<br>10 | Gly | Ser | Gly | Ser<br>15 |

Met Ala Ala Asn Ala Gly Gly Gly Ala Gly Gly Ser Gly Ser
 1               5                   10                  15

Gly Ser Val Ala Ala Pro Ala Val Cys Arg Pro Ser Gly Ser Arg Trp
            20                  25                  30

Thr Pro Thr Pro Glu Gln Ile Arg Met Leu Lys Glu Leu Tyr Tyr Gly
                35                  40                  45

Cys Gly Ile Arg Ser Pro Ser Ser Glu Gln Ile Gln Arg Ile Thr Ala
 50                      55                  60

Met Leu Arg Gln His Gly Lys Ile Glu Gly Lys Asn Val Phe Tyr Trp
 65                  70                  75                  80

Phe Gln Asn His Lys Ala Arg Glu Arg Gln Lys Arg Arg Leu Thr Ser
                85                  90                  95

Leu Asp Val Asn Val Pro Ala Ala Gly Ala Ala Asp Ala Thr Thr Ser
                100                 105                 110

Gln Leu Gly Val Leu Ser Leu Ser Pro Pro Ser Gly Ala Ala
            115                 120                 125

Pro Pro Ser Pro Thr Leu Gly Phe Tyr Ala Ala Gly Asn Gly Gly Gly
            130                 135                 140

Ser Ala Val Leu Leu Asp Thr Ser Ser Asp Trp Gly Ser Gly Ala
145                 150                 155                 160

Ala Met Ala Thr Glu Thr Cys Phe Leu Gln Asp Tyr Met Gly Val Thr
                165                 170                 175

Asp Thr Gly Ser Ser Ser Gln Trp Pro Cys Phe Ser Ser Asp Thr
            180                 185                 190

Ile Met Ala Ala Ala Ala Ala Ala Arg Val Ala Thr Thr Arg Ala
            195                 200                 205

Pro Glu Thr Leu Pro Leu Phe Pro Thr Cys Gly Asp Asp Asp Asp
 210                 215                 220

Asp Ser Gln Pro Pro Pro Arg Pro Arg His Ala Val Pro Val Pro Ala
225                 230                 235                 240

Gly Glu Thr Ile Arg Gly Gly Gly Ser Ser Ser Tyr Leu Pro
                245                 250                 255

Phe Trp Gly Ala Gly Ala Ala Ser Thr Thr Ala Gly Ala Thr Ser Ser
            260                 265                 270

Val Ala Ile Gln Gln Gln His Gln Leu Gln Glu Gln Tyr Ser Phe Tyr
            275                 280                 285

Ser Asn Ser Thr Gln Leu Ala Gly Thr Gly Ser Gln Asp Val Ser Ala
            290                 295                 300

Ser Ala Ala Leu Glu Leu Ser Leu Ser Ser Trp Cys Ser Pro Tyr
305                 310                 315                 320

Pro Ala Ala Gly Ser Met
            325

<210> SEQ ID NO 30
<211> LENGTH: 1310
<212> TYPE: DNA
<213> ORGANISM: Zea mays

<400> SEQUENCE: 30
gtccgagcta ggtcacagaa gcgctcagga aggccgctga gatagaggca tggcggccaa    60
tgcgggcggc ggtggagcgg gaggaggcag cggcagcggc agcgtggctg cgccggcggt   120
gtgccgcccc agcggctcgc ggtggacgcc gacgccggag cagatcagga tgctgaagga   180
gctctactac ggctgcggca tccggtcgcc cagctcggag cagatccagc gcatcaccgc   240

```
catgctgcgg cagcacggca agatcgaggg caagaacgtc ttctactggt tccagaacca      300
caaggcccgc gagcgccaga agcgccgcct caccagcctc gacgtcaacg tgcccgccgc      360
cggcgcggcc gacgccacca ccagccaact cggcgtcctc tcgctgtcgt cgccgccgcc      420
ttcaggcgcg gcgcctccct cgcccaccct cggcttctac gccgccggca atggcggcgg      480
atcggctgtg ctgctggaca cgagttccga ctggggcagc agcggcgctg ccatggccac      540
cgagacatgc ttcctgcagg tacggcggtg cgcgcccgca ggactacatg ggcgtgacgg      600
acacgggcag ctcgtcgcag tggccatgct tctcgtcgtc ggacacgata atggcggcgg      660
cggcggccgc ggcgcgggtg cgacgacgc gggcgcccga cactccct ctcttcccga       720 cctgcggcga cgacgacgac gacgacagcc agccccgcc gcggccgcgg cacgcagtcc      780
cagtcccggc aggcgagacc atccgcggcg gcggcggcag cagcagcagc tacttgccgt      840 tctgggtgc cggtgccgcg tccacaactg ccggcgccac ttcttccgtt gcgatccagc      900
agcaacacca gctgcaggag cagtacagct tttacagcaa cagcacccag ctggccggca      960
ccggcagcca agacgtatcg gcttcagcgg ccgccctgga gctgagcctc agctcatggt     1020 gctccccta ccctgctgca gggagcatgt gagagcaacg cgagctacca ctgggacgtg     1080
cgttgctgtc attgtcctag gttagtagct agtgccagtt actagtaagc atcaggcata     1140
ggagtatgta gtagaagcat gtctggagaa aggcaatagc tagcgtttgg gagatctctg     1200
gcggtactat tattagatag cgaatttgca tactatgcag catgcatgtt gccggccggg     1260
cgggctttag actccagcta ctgcatgcgt gcatgcggtg gtcctcatgt                1310
```

<210> SEQ ID NO 31
<211> LENGTH: 351
<212> TYPE: PRT
<213> ORGANISM: Zea mays

<400> SEQUENCE: 31

```
Met Ala Ala Asn Ala Gly Gly Gly Ala Gly Gly Ser Gly Ser
  1               5                  10                  15

Gly Ser Val Ala Ala Pro Ala Val Cys Arg Pro Ser Gly Ser Arg Trp
                 20                  25                  30

Thr Pro Thr Pro Glu Gln Ile Arg Met Leu Lys Glu Leu Tyr Tyr Gly
             35                  40                  45

Cys Gly Ile Arg Ser Pro Ser Ser Glu Gln Ile Gln Arg Ile Thr Ala
         50                  55                  60

Met Leu Arg Gln His Gly Lys Ile Glu Gly Lys Asn Val Phe Tyr Trp
 65                  70                  75                  80

Phe Gln Asn His Lys Ala Arg Glu Arg Gln Lys Arg Arg Leu Thr Ser
                 85                  90                  95

Leu Asp Val Asn Val Pro Ala Ala Gly Ala Ala Asp Ala Thr Thr Ser
            100                 105                 110

Gln Leu Gly Val Leu Ser Leu Ser Ser Pro Pro Ser Gly Ala Ala
        115                 120                 125

Pro Pro Ser Pro Thr Leu Gly Phe Tyr Ala Ala Gly Asn Gly Gly
    130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Val Arg Cys Ala Pro
                165                 170                 175

Ala Gly Leu His Gly Arg Asp Gly His Gly Gln Leu Val Ala Val Ala
            180                 185                 190
```

```
Met Leu Leu Val Val Gly His Asp Asn Gly Gly Gly Gly Arg Gly
            195                 200                 205

Ala Gly Gly Asp Asp Ala Gly Ala Arg Asp Thr Pro Ser Leu Pro Asp
            210                 215                 220

Leu Arg Arg Arg Arg Arg Arg Gln Pro Ala Pro Ala Ala Ala Ala
225                 230                 235                 240

Ala Arg Ser Pro Ser Pro Gly Arg Arg Asp His Pro Arg Arg Arg
            245                 250                 255

Gln Gln Gln Gln Leu Leu Ala Val Leu Gly Cys Arg Cys Arg Val His
            260                 265                 270

Asn Cys Arg Arg His Phe Phe Arg Cys Asp Pro Ala Ala Thr Pro Ala
            275                 280                 285

Ala Gly Ala Val Gln Leu Leu Gln Gln His Pro Ala Gly Arg His
            290                 295                 300

Arg Gln Pro Arg Arg Ile Gly Phe Ser Gly Arg Pro Gly Ala Glu Pro
305                 310                 315                 320

Gln Leu Met Val Leu Pro Leu Pro Cys Cys Arg Glu His Val Arg Ala
            325                 330                 335

Thr Arg Ala Thr Thr Gly Thr Cys Val Ala Val Ile Val Leu Gly
            340                 345                 350

<210> SEQ ID NO 32
<211> LENGTH: 1357
<212> TYPE: DNA
<213> ORGANISM: Zea mays

<400> SEQUENCE: 32
cacctcctct ttaaaacccc gcacgccccc acgccgcgcg cacacacaca catcgcctcc    60
ctcctcctcc ccaagagccg gcacagaggc aaaggccagc cctccagtga caggcagatc   120
gaggccacat ggagacgcca cagcagcaat ccgccgccgc cgccgccgcc gccgccacg    180
ggcaggacga cggcgggtcg ccgccgatgt cgccggcctc cgccgcggcg gcggcgctgg   240
cgaacgcgcg gtggaacccg accaaggagc aggtggccgt gctggagggg ctgtacgagc   300
acggcctgcg cacccccagc gcggagcaga tacagcagat cacgggcagg ctgcgggagc   360
acggcgccat cgagggcaag aacgtcttct actggttcca gaaccacaag gcccgccagc   420
gccagaggca gaagcaggac agcttcgcct acttcagcag gctcctccgc cggccccgc   480
cgctgcccgt gctctccatg ccccccgcgc accgtaccca tcacgcccgc gtcccggcgc   540
cgcccgcgat accgatgccg atggcgccgc cgccgcccgc tgcatgcaac gacaacggcg   600
gcgcgcgtgt gatctacagg aacccattct acgtggctgc gccgcaggcg cccctgcaa   660
atgccgccta ctactaccca cagccacagc agcagcagca gcagcaggtg acagtcatgt   720
accagtaccc gagaatggag gtagccggcc aggacaagat gatgaccagg gccgcggcgc   780
accagcagca gcagcacaac ggcgccgggc aacaaccggg acgcgccggc cacccccagcc   840
gcgagacgct ccagctgttc ccgctccagc ccaccttcgt gctgcggcac gacaaggggc   900
gcgccgccaa cggcagtaat aacgactccc tgacgtcgac gtcgacggcg actgcgacag   960
cgacagcgac agcgacagcg tccgcttcca tctccgagga ctcggatggc ctggagagcg  1020
gcagctccgg caagggcgtc gaggaggcgc ccgcgctgcc gttctatgac ttcttcgggc  1080
tccagtcctc cggaggccgc tgatcatggg actgaggtag agcgagctcg agtgatgaaa  1140
gccgagccag acgttcgtgt gatctcgagt cgtcgtcgat ggaccggtt gccgttgcct  1200
```

```
tttgttgggt tattgcatgc atggtgtgct tcatcaacta ctggaagaag cctgtgccga    1260
tcgaaccaaa acagtttgca ttgttgagtt ccgtaccgtc ctgtagcaac aatgtagcgg    1320
agaaatgcta ctagtagctt cttttaaaa aaaaaaa                              1357

<210> SEQ ID NO 33
<211> LENGTH: 324
<212> TYPE: PRT
<213> ORGANISM: Zea mays

<400> SEQUENCE: 33

Met Glu Thr Pro Gln Gln Gln Ser Ala Ala Ala Ala Ala Ala Ala Ala
 1               5                  10                  15

His Gly Gln Asp Asp Gly Gly Ser Pro Pro Met Ser Pro Ala Ser Ala
                20                  25                  30

Ala Ala Ala Ala Leu Ala Asn Ala Arg Trp Asn Pro Thr Lys Glu Gln
            35                  40                  45

Val Ala Val Leu Glu Gly Leu Tyr Glu His Gly Leu Arg Thr Pro Ser
        50                  55                  60

Ala Glu Gln Ile Gln Gln Ile Thr Gly Arg Leu Arg Glu His Gly Ala
65                  70                  75                  80

Ile Glu Gly Lys Asn Val Phe Tyr Trp Phe Gln Asn His Lys Ala Arg
                85                  90                  95

Gln Arg Gln Arg Gln Lys Gln Asp Ser Phe Ala Tyr Phe Ser Arg Leu
               100                 105                 110

Leu Arg Arg Pro Pro Pro Leu Pro Val Leu Ser Met Pro Pro Ala Pro
           115                 120                 125

Pro Tyr His His Ala Arg Val Pro Ala Pro Ala Ile Pro Met Pro
       130                 135                 140

Met Ala Pro Pro Pro Ala Ala Cys Asn Asp Asn Gly Gly Ala Arg
145                 150                 155                 160

Val Ile Tyr Arg Asn Pro Phe Tyr Val Ala Ala Pro Gln Ala Pro Pro
               165                 170                 175

Ala Asn Ala Ala Tyr Tyr Tyr Pro Gln Pro Gln Gln Gln Gln Gln Gln
           180                 185                 190

Gln Val Thr Val Met Tyr Gln Tyr Pro Arg Met Glu Val Ala Gly Gln
       195                 200                 205

Asp Lys Met Met Thr Arg Ala Ala His Gln Gln Gln Gln His Asn
210                 215                 220

Gly Ala Gly Gln Gln Pro Gly Arg Ala Gly His Pro Ser Arg Glu Thr
225                 230                 235                 240

Leu Gln Leu Phe Pro Leu Gln Pro Thr Phe Val Leu Arg His Asp Lys
               245                 250                 255

Gly Arg Ala Ala Asn Gly Ser Asn Asn Asp Ser Leu Thr Ser Thr Ser
           260                 265                 270

Thr Ala Thr Ala Thr Ala Thr Ala Thr Ala Ser Ala Ser Ile
       275                 280                 285

Ser Glu Asp Ser Asp Gly Leu Glu Ser Gly Ser Gly Lys Gly Val
290                 295                 300

Glu Glu Ala Pro Ala Leu Pro Phe Tyr Asp Phe Phe Gly Leu Gln Ser
305                 310                 315                 320

Ser Gly Gly Arg

<210> SEQ ID NO 34
<211> LENGTH: 1537
```

```
<212> TYPE: DNA
<213> ORGANISM: Zea mays

<400> SEQUENCE: 34
gtccgagcta ggtcacagaa gcgctcagga aggccgctga gatagaggca tggcggccaa     60
tgcgggcggc ggtggagcgg gaggaggcag cggcagcgtg gctgcgccgg cggtgtgctg    120
ccccagcggc tcgcggtgga cgccgacgcc ggagcagatc aggatgctga aggagctcta    180
ctacggctgc ggcatccggt cgcccagctc ggagcagatc cagcgcatca ccgccatgct    240
gcggcagcac ggcaagatcg agggcaagaa cgtcttctac tggttccaga ccacgaggc    300
ccgcgagcgc cagaagcgcc gcctcaccag cctcgacgtc aacgtgcccg ccgccggcgc    360
ggccgacgcc accaccagcc aactcggcgt cctctcgctg tcgtcgccgc cgccttcagg    420
tacgtgcgtc agtgcgtgtg gtgtgtgggt agtatatatg gtctctcctt gcattggcac    480
gccaatcggc catcgatcca atcatatcat cgtccaaacg tatatagtac atgtgactgc    540
aaactgatgt gcaccgtcgt catcactgat caggcgcggc gcctccctcg cccaccctcg    600
gcttctacgc cgccggcaat ggcggcggat cggctgtgct gctggacacg agttccgact    660
ggggcagcag cggcgctgcc atggccaccg agacatgctt cctgcaggtc ggtgctgtag    720
tacgttcttt tcttgggcat tgcgcgcagt ttcacgttcg tacgtacgag ttgatcgccg    780
cgtcgttcca tccaccggta tataactg ttaggtacgg cggtgcgcgc ccgcaggact    840
acatgggcgt gacggacacg ggcagctcgt cgcagtggcc atgcttgtcg tcgtcagaca    900
cgataatggc ggcggccgcg gcgcgggcgc cgacgacgac gcggccgccc gagaccctcc    960
ctctcttccc gacctgcggc gacgacgacg acgacgacaa ccagcccccg tcgcggccgc   1020
ggcacgcagt cccagtcccg gcaggcgagc ccatccgcgt cggcggtggc ggcagcagca   1080
gctacttgcc gttctggggt gccgcgtcca caactgccgg cgccacttct tccgttgcga   1140
tccagcagca acaccagcag caggagcagt acatctttta cagcaacagc acccagctgg   1200
ccggcaccgg cagccaagac gtatcggctt cagcagcagc agccgccgcc ctggagctga   1260
gcctcagctc atggtgctcc ccttaccctg ctgcagggag catgtgacca tagcgttggt   1320
gcgttgctgt cattgtccta ggttagtagc tagtgccagt tactagtaag catcaggcat   1380
aggagtatgt agaagcatgt ctggagaaag gcaatagcgt ttgggagatc tatggtggag   1440
tggtggtatg gtactattat tagatagcga atttgcacac tatgcagcat gcatgttgcc   1500
ggccgggcgg gctttagact ccagctactg catgcgt                            1537

<210> SEQ ID NO 35
<211> LENGTH: 1383
<212> TYPE: DNA
<213> ORGANISM: Zea mays

<400> SEQUENCE: 35
gtccgagcta ggtcacagaa gcgctcagga aggccgctga gatagaggca tggcggccaa     60
tgcgggcggc ggtggagcgg gaggaggcag cggcagcgtg gctgcgccgg cggtgtgctg    120
ccccagcggc tcgcggtgga cgccgacgcc ggagcagatc aggatgctga aggagctcta    180
ctacggctgc ggcatccggt cgcccagctc ggagcagatc cagcgcatca ccgccatgct    240
gcggcagcac ggcaagatcg agggcaagaa cgtcttctac tggttccaga ccacgaggc    300
ccgcgagcgc cagaagcgcc gcctcaccag cctcgacgtc aacgtgcccg ccgccggcgc    360
ggccgacgcc accaccagcc aactcggcgt cctctcgctg tcgtcgccgc cgccttcagg    420
```

```
cgcggcgcct ccctcgccca ccctcggctt ctacgccgcc ggcaatggcg gcggatcggc      480
tgtgctgctg gacacgagtt ccgactgggg cagcagcggc gctgccatgg ccaccgagac      540
atgcttcctg caggtcggtg ctgtagtacg ttcttttctt gggcattgcg cgcagtttca      600
cgttcgtacg tacgagttga tcgccgcgtc gttccatcca ccggtatata taactgttag      660
gtacggcggt gcgcgcccgc aggactacat gggcgtgacg gacacgggca gctcgtcgca      720
gtggccatgc ttgtcgtcgt cagacacgat aatggcggcg gccgcggcgc gggcgccgac      780
gacgacgcgg ccgcccgaga ccctcccctct cttcccgacc tgcggcgacg acgacgacga      840
cgacaaccag ccccgtcgc ggccgcggca cgcagtccca gtcccggcag gcgagcccat      900
ccgcgtcggc ggtggcggca gcagcagcta cttgccgttc tggggtgccg cgtccacaac      960
tgccggcgcc acttcttccg ttgcgatcca gcagcaacac cagcagcagg agcagtacat     1020
cttttacagc aacagcaccc agctggccgg caccggcagc caagacgtat cggcttcagc     1080
agcagcagcc gccgccctgg agctgagcct cagctcatgg tgctccctt accctgctgc     1140 agggagcatg tgaccatagc gttggtgcgt tgctgtcatt gtcctaggtt agtagctagt     1200
gccagttact agtaagcatc aggcatagga gtatgtagaa gcatgtctgg agaaaggcaa     1260
tagcgtttgg gagatctatg gtggagtggt ggtatggtac tattattaga tagcgaattt     1320
gcacactatg cagcatgcat gttgccggcc gggcgggctt tagactccag ctactgcatg     1380
cgt                                                                   1383

<210> SEQ ID NO 36
<211> LENGTH: 367
<212> TYPE: PRT
<213> ORGANISM: Zea mays

<400> SEQUENCE: 36

Met Ala Ala Asn Ala Gly Gly Gly Ala Gly Gly Gly Ser Gly Ser
  1               5                  10                  15

Val Ala Ala Pro Ala Val Cys Cys Pro Ser Gly Ser Arg Trp Thr Pro
                 20                  25                  30

Thr Pro Glu Gln Ile Arg Met Leu Lys Glu Leu Tyr Tyr Gly Cys Gly
             35                  40                  45

Ile Arg Ser Pro Ser Ser Glu Gln Ile Gln Arg Ile Thr Ala Met Leu
 50                  55                  60

Arg Gln His Gly Lys Ile Glu Gly Lys Asn Val Phe Tyr Trp Phe Gln
 65                  70                  75                  80

Asn His Glu Ala Arg Glu Arg Gln Lys Arg Arg Leu Thr Ser Leu Asp
                 85                  90                  95

Val Asn Val Pro Ala Ala Gly Ala Ala Asp Ala Thr Thr Ser Gln Leu
            100                 105                 110

Gly Val Leu Ser Leu Ser Ser Pro Pro Ser Gly Ala Ala Pro Pro
            115                 120                 125

Ser Pro Thr Leu Gly Phe Tyr Ala Ala Gly Asn Gly Gly Ser Ala
            130                 135                 140

Val Leu Leu Asp Thr Ser Ser Asp Trp Gly Ser Gly Ala Ala Met
145                 150                 155                 160

Ala Thr Glu Thr Cys Phe Leu Gln Val Gly Ala Val Arg Ser Phe
                165                 170                 175

Leu Gly His Cys Ala Gln Phe His Val Arg Thr Tyr Glu Leu Ile Ala
                180                 185                 190

Ala Ser Phe His Pro Pro Val Tyr Ile Thr Val Arg Tyr Gly Gly Ala
```

```
            195                 200                 205
Arg Pro Gln Asp Tyr Met Gly Val Thr Asp Thr Gly Ser Ser Gln
    210                 215                 220

Trp Pro Cys Leu Ser Ser Asp Thr Ile Met Ala Ala Ala Ala
225                 230                 235                 240

Arg Ala Pro Thr Thr Thr Arg Pro Pro Glu Thr Leu Pro Leu Phe Pro
                245                 250                 255

Thr Cys Gly Asp Asp Asp Asp Asp Asn Gln Pro Pro Ser Arg Pro
                260                 265                 270

Arg His Ala Val Pro Val Pro Ala Gly Glu Pro Ile Arg Val Gly Gly
            275                 280                 285

Gly Gly Ser Ser Tyr Leu Pro Phe Trp Gly Ala Ala Ser Thr Thr
    290                 295                 300

Ala Gly Ala Thr Ser Ser Val Ala Ile Gln Gln Gln His Gln Gln Gln
305                 310                 315                 320

Glu Gln Tyr Ile Phe Tyr Ser Asn Ser Thr Gln Leu Ala Gly Thr Gly
                325                 330                 335

Ser Gln Asp Val Ser Ala Ser Ala Ala Ala Ala Ala Leu Glu Leu
            340                 345                 350

Ser Leu Ser Ser Trp Cys Ser Pro Tyr Pro Ala Ala Gly Ser Met
        355                 360                 365

<210> SEQ ID NO 37
<211> LENGTH: 1254
<212> TYPE: DNA
<213> ORGANISM: Zea mays

<400> SEQUENCE: 37
gtccgagcta ggtcacagaa gcgctcagga aggccgctga gatagaggca tggcggccaa        60
tgcgggcggc ggtggagcgg gaggaggcag cggcagcgtg gctgcgccgg cggtgtgctg       120
ccccagcggc tcgcggtgga cgccgacgcc ggagcagatc aggatgctga aggagctcta       180
ctacggctgc ggcatccggt cgcccagctc ggagcagatc cagcgcatca ccgccatgct       240
gcggcagcac ggcaagatcg agggcaagaa cgtcttctac tggttccaga ccacgaggc       300
ccgcgagcgc cagaagcgcc gcctcaccag cctcgacgtc aacgtgcccg ccgccggcgc       360
ggccgacgcc accaccagcc aactcggcgt cctctcgctg tcgtcgccgc cgccttcagg       420
cgcggcgcct ccctcgccca ccctcggctt ctacgccgcc ggcaatggcg gcggatcggc       480
tgtgctgctg gacacgagtt ccgactgggg cagcagcggc gctgccatgg ccaccgagac       540
atgcttcctg caggactaca tgggcgtgac ggacacgggc agctcgtcgc agtggccatg       600
cttgtcgtcg tcagacacga taatggcggc ggccgcggcg cgggcgccga cgacgacgcg       660
gccgccgag acccctcccctc tcttcccgac ctgcggcgac gacgacgacg acgacaacca       720
gccccgtcg cggccgcggc acgcagtccc agtcccggca ggcgagccca tccgcgtcgg       780
cggtggcggc agcagcagct acttgccgtt ctgggtgcc gcgtccacaa ctgccggcgc       840
cacttcttcc gttgcgatcc agcagcaaca ccagcagcag gagcagtaca tcttttacag       900
caacagcacc cagctggccg gcaccggcag ccaagacgta tcggcttcag cagcagcagc       960
cgccgccctg gagctgagcc tcagctcatg gtgctcccct tacccctgctg cagggagcat      1020
gtgaccatag cgttggtgcg ttgctgtcat tgtcctaggt tagtagctag tgccagttac      1080
tagtaagcat caggcatagg agtatgtaga agcatgtctg gagaaaggca atagcgtttg      1140
ggagatctat ggtggagtgg tggtatggta ctattattag atagcgaatt tgcacactat      1200
```
gcagcatgca tgttgccggc cgggcgggct ttagactcca gctactgcat gcgt    1254

<210> SEQ ID NO 38
<211> LENGTH: 324
<212> TYPE: PRT
<213> ORGANISM: Zea mays

<400> SEQUENCE: 38

Met Ala Ala Asn Ala Gly Gly Gly Ala Gly Gly Ser Gly Ser
1               5                   10                  15

Val Ala Ala Pro Ala Val Cys Cys Pro Ser Gly Ser Arg Trp Thr Pro
            20                  25                  30

Thr Pro Glu Gln Ile Arg Met Leu Lys Glu Leu Tyr Tyr Gly Cys Gly
        35                  40                  45

Ile Arg Ser Pro Ser Ser Glu Gln Ile Gln Arg Ile Thr Ala Met Leu
    50                  55                  60

Arg Gln His Gly Lys Ile Glu Gly Lys Asn Val Phe Tyr Trp Phe Gln
65                  70                  75                  80

Asn His Glu Ala Arg Glu Arg Gln Lys Arg Arg Leu Thr Ser Leu Asp
                85                  90                  95

Val Asn Val Pro Ala Ala Gly Ala Ala Asp Ala Thr Thr Ser Gln Leu
            100                 105                 110

Gly Val Leu Ser Leu Ser Ser Pro Pro Ser Gly Ala Ala Pro Pro
        115                 120                 125

Ser Pro Thr Leu Gly Phe Tyr Ala Ala Gly Asn Gly Gly Ser Ala
    130                 135                 140

Val Leu Leu Asp Thr Ser Ser Asp Trp Gly Ser Gly Ala Ala Met
145                 150                 155                 160

Ala Thr Glu Thr Cys Phe Leu Gln Asp Tyr Met Gly Val Thr Asp Thr
                165                 170                 175

Gly Ser Ser Ser Gln Trp Pro Cys Leu Ser Ser Ser Asp Thr Ile Met
            180                 185                 190

Ala Ala Ala Ala Ala Arg Ala Pro Thr Thr Thr Arg Pro Pro Glu Thr
        195                 200                 205

Leu Pro Leu Phe Pro Thr Cys Gly Asp Asp Asp Asp Asp Asn Gln
    210                 215                 220

Pro Pro Ser Arg Pro Arg His Ala Val Pro Val Pro Ala Gly Glu Pro
225                 230                 235                 240

Ile Arg Val Gly Gly Gly Ser Ser Tyr Leu Pro Phe Trp Gly
                245                 250                 255

Ala Ala Ser Thr Thr Ala Gly Ala Thr Ser Ser Val Ala Ile Gln Gln
            260                 265                 270

Gln His Gln Gln Gln Glu Gln Tyr Ile Phe Tyr Ser Asn Ser Thr Gln
        275                 280                 285

Leu Ala Gly Thr Gly Ser Gln Asp Val Ser Ala Ser Ala Ala Ala
    290                 295                 300

Ala Ala Leu Glu Leu Ser Leu Ser Ser Trp Cys Ser Pro Tyr Pro Ala
305                 310                 315                 320

Ala Gly Ser Met

<210> SEQ ID NO 39
<211> LENGTH: 1276
<212> TYPE: DNA
<213> ORGANISM: Zea mays

-continued

```
<400> SEQUENCE: 39
gtccgagcta ggtcacagaa gcgctcagga aggccgctga gatagaggca tggcggccaa      60
tgcgggcggc ggtggagcgg gaggaggcag cggcagcgtg gctgcgccgg cggtgtgctg     120
ccccagcggc tcgcggtgga cgccgacgcc ggagcagatc aggatgctga aggagctcta     180
ctacggctgc ggcatccggt cgcccagctc ggagcagatc cagcgcatca ccgccatgct     240
gcggcagcac ggcaagatcg agggcaagaa cgtcttctac tggttccaga accacgaggc     300
ccgcgagcgc cagaagcgcc gcctcaccag cctcgacgtc aacgtgcccg ccgccggcgc     360
ggccgacgcc accaccagcc aactcggcgt cctctcgctg tcgtcgccgc cgccttcagg     420
cgcggcgcct ccctcgccca ccctcggctt ctacgccgcc ggcaatggcg gcggatcggc     480
tgtgctgctg gacacgagtt ccgactgggg cagcagcggc gctgccatgg ccaccgagac     540
atgcttcctg caggtacggc ggtgcgcgcc cgcaggacta catgggcgtg acggacacgg     600
gcagctcgtc gcagtggcca tgcttgtcgt cgtcagacac gataatggcg gcggccgcgg     660
cgcgggcgcc gacgacgacg cggccgcccg agaccctccc tctcttcccg acctgcggcg     720
acgacgacga cgacgacaac cagcccccgt cgcggccgcg gcacgcagtc ccagtcccgg     780
caggcgagcc catccgcgtc ggcggtggcg gcagcagcag ctacttgccg ttctggggtg     840
ccgcgtccac aactgccggc gccacttctt ccgttgcgat ccagcagcaa caccagcagc     900
aggagcagta catcttttac agcaacagca cccagctggc cggcaccggc agccaagacg     960
tatcggcttc agcagcagca gccgccgccc tggagctgag cctcagctca tggtgctccc    1020
cttaccctgc tgcagggagc atgtgaccat agcgttggtg cgttgctgtc attgtcctag    1080
gttagtagct agtgccagtt actagtaagc atcaggcata ggagtatgta aagcatgtc    1140 tggagaaagg caatagcgtt tgggagatct atggtggagt ggtggtatgg tactattatt    1200
agatagcgaa tttgcacact atgcagcatg catgttgccg gccgggcggg cttagactc    1260 cagctactgc atgcgt                                                    1276

<210> SEQ ID NO 40
<211> LENGTH: 351
<212> TYPE: PRT
<213> ORGANISM: Zea mays

<400> SEQUENCE: 40

Met Ala Ala Asn Ala Gly Gly Gly Ala Gly Gly Gly Ser Gly Ser
 1               5                  10                  15

Val Ala Ala Pro Ala Val Cys Cys Pro Ser Gly Ser Arg Trp Thr Pro
                20                  25                  30

Thr Pro Glu Gln Ile Arg Met Leu Lys Glu Leu Tyr Tyr Gly Cys Gly
            35                  40                  45

Ile Arg Ser Pro Ser Ser Glu Gln Ile Gln Arg Ile Thr Ala Met Leu
        50                  55                  60

Arg Gln His Gly Lys Ile Glu Gly Lys Asn Val Phe Tyr Trp Phe Gln
65                  70                  75                  80

Asn His Glu Ala Arg Glu Arg Gln Lys Arg Arg Leu Thr Ser Leu Asp
                85                  90                  95

Val Asn Val Pro Ala Ala Gly Ala Ala Asp Ala Thr Thr Ser Gln Leu
            100                 105                 110

Gly Val Leu Ser Leu Ser Ser Pro Pro Ser Gly Ala Ala Pro Pro
        115                 120                 125

Ser Pro Thr Leu Gly Phe Tyr Ala Ala Gly Asn Gly Gly Gly Ser Ala
```

```
                130             135             140
Val Leu Leu Asp Thr Ser Ser Asp Trp Gly Ser Gly Ala Ala Met
145                 150                 155                 160

Ala Thr Glu Thr Cys Phe Leu Gln Val Arg Arg Cys Ala Pro Ala Gly
                165                 170                 175

Leu His Gly Arg Asp Gly His Gly Gln Leu Val Ala Val Ala Met Leu
            180                 185                 190

Val Val Val Arg His Asp Asn Gly Gly Arg Gly Ala Gly Ala Asp
        195                 200                 205

Asp Asp Ala Ala Ala Arg Asp Pro Pro Ser Leu Pro Asp Leu Arg Arg
210                 215                 220

Arg Arg Arg Arg Arg Gln Pro Ala Pro Val Ala Ala Ala Arg Ser
225                 230                 235                 240

Pro Ser Pro Gly Arg Arg Ala His Pro Arg Arg Trp Arg Gln Gln
                245                 250                 255

Gln Leu Leu Ala Val Leu Gly Cys Arg Val His Asn Cys Arg Arg His
                260                 265                 270

Phe Phe Arg Cys Asp Pro Ala Ala Thr Pro Ala Gly Ala Val His
            275                 280                 285

Leu Leu Gln Gln Gln His Pro Ala Gly Arg His Arg Gln Pro Arg Arg
290                 295                 300

Ile Gly Phe Ser Ser Ser Arg Arg Pro Gly Ala Glu Pro Gln Leu
305                 310                 315                 320

Met Val Leu Pro Leu Pro Cys Cys Arg Glu His Val Thr Ile Ala Leu
                325                 330                 335

Val Arg Cys Cys His Cys Pro Arg Leu Val Ala Ser Ala Ser Tyr
            340                 345                 350

<210> SEQ ID NO 41
<211> LENGTH: 1537
<212> TYPE: DNA
<213> ORGANISM: Zea mays

<400> SEQUENCE: 41
gtccgagcta ggtcacagaa gcgctcagga aggccgctga gatagaggca tggcggccaa      60
tgcgggcggc ggtggagcgg gaggaggcag cggcagcgtg gctgcgccgg cggtgtgccg     120
ccccagcggc tcgcggtgga cgccgacgcc ggagcagatc aggatgctga aggagctcta     180
ctacggctgc ggcatccggt cgcccagctc ggagcagatc cagcgcatca ccgccatgct     240
gcggcagcac ggcaagatcg agggcaagaa cgtcttctac tggttccaga accacaaggc     300
ccgcgagcgc cagaagcgcc gcctcaccag cctcgacgtc aacgtgcccg ccgccggcgc     360
ggccgacgcc accaccagcc aactcggcgt cctctcgctg tcgtcgccgc cgccttcagg     420
tacgtgcgtc agtgcgtgtg gtgtgtgggt agtatatatg gtctctcctt gcattggcac     480
gccaatcggc catcgatcca atcatatcat cgtccaaacg tatatagtac atgtgactgc     540
aaactgatgt gcaccgtcgt catcactgat caggcgcggc gcctccctcg cccacccctcg     600
gcttctacgc cgccggcaat ggcggcggat cggctgtgct gctggacacg agttccgact     660
ggggcagcag cggcgctgcc atggccaccg agacatgctt cctgcaggtc ggtgctgtag     720
tacgttcttt tcttgggcat tgcgcgcagt ttcacgttcg tacgtacgag ttgatcgccg     780
cgtcgttcca tccaccggta tataaactg ttaggtacgg cggtgcgcgc ccgcaggact     840
acatgggcgt gacggacacg ggcagctcgt cgcagtggcc atgcttgtcg tcgtcagaca     900
```

```
cgataatggc ggcggccgcg gcgcgggcgc cgacgacgac gcggccgccc gagacgctcc      960
ctctcttccc gacctgcggc gacgacgacg acgacgacaa ccagccccg ccgcggccgc      1020 ggcacgcagt cccagtcccg gcaggcgagc ccatccgcgt cggcggtggc ggcagcagca      1080
gctacttgcc gttctggggt gccgcgtcca caactgccgg cgccacttct tccgttgcga      1140
tccagcagca acaccagctg caggagcagt acatctttta cagcaacagc acccagctgg      1200
ccggcaccgg cagccaagac gtatcggctt cagcagcagc agccgccgcc ctggagctga      1260
gcctcagctc atggtgctcc ccttaccctg ctgcagggag catgtgacca tagcgttggt      1320
gcgttgctgt cattgtccta ggttagtagc tagtgccagt tactagtaag catcaggcat      1380
aggagtatgt agaagcatgt ctggagaaag gcaatagcgt ttgggagatc tatggtggag      1440
tggtggtatg gtactattat tagatagcga atttgcacac tatgcagcat gcatgttgcc      1500
ggccgggcgg gctttagact ccagctactg catgcgt                              1537

<210> SEQ ID NO 42
<211> LENGTH: 1383
<212> TYPE: DNA
<213> ORGANISM: Zea mays

<400> SEQUENCE: 42
gtccgagcta ggtcacagaa gcgctcagga aggccgctga gatagaggca tggcggccaa       60
tgcgggcggc ggtggagcgg gaggaggcag cggcagcgtg gctgcgccgg cggtgtgccg      120
ccccagcggg tcgcggtgga cgccgacgcc ggagcagatc aggatgctga aggagctcta      180
ctacggctgc ggcatccggt cgcccagctc ggagcagatc cagcgcatca ccgccatgct      240
gcggcagcac ggcaagatcg agggcaagaa cgtcttctac tggttccaga accacaaggc      300
ccgcgagcgc cagaagcgcc gcctcaccag cctcgacgtc aacgtgcccg ccgccggcgc      360
ggccgacgcc accaccagcc aactcggcgt cctctcgctg tcgtcgccgc cgccttcagg      420
cgcggcgcct ccctcgccca cctcggctt ctacgccgcc ggcaatggcg gcggatcggc      480
tgtgctgctg gacacgagtt ccgactgggg cagcagcggc gctgccatgg ccaccgagac      540
atgcttcctg caggtcggtg ctgtagtacg ttctttttctt gggcattgcg cgcagtttca      600
cgttcgtacg tacgagttga tcgccgcgtc gttccatcca ccggtatata taactgttag      660
gtacggcggt gcgcgcccgc aggactacat gggcgtgacg gacacgggca gctcgtcgca      720
gtggccatgc ttgtcgtcgt cagacacgat aatggcggcg gccgcggcgc gggcgccgac      780
gacgacgcgg ccgcccgaga cgctccctct cttcccgacc tgcggcgacg acgacgacga      840
cgacaaccag cccccgccgc ggccgcggca gcagtcccca gtcccggcag gcgagcccat      900
ccgcgtcggc ggtggcggca gcagcagcta cttgccgttc tggggtgccg cgtccacaac      960
tgccggcgcc acttcttccg ttgcgatcca gcagcaacac cagctgcagg agcagtacat     1020
cttttacagc aacagcaccc agctggccgg caccggcagc caagacgtat cggcttcagc     1080
agcagcagcc gccgccctgg agctgagcct cagctcatgg tgctcccctt accctgctgc     1140
agggagcatg tgaccatagc gttggtgcgt tgctgtcatt gtcctaggtt agtagctagt     1200
gccagttact agtaagcatc aggcataggg gtatgtagaa gcatgtctgg agaaaggcaa     1260
tagcgtttgg gagatctatg gtggagtggt ggtatggtac tattattaga tagcgaatttt    1320 gcacactatg cagcatgcat gttgccggcc gggcgggctt tagactccag ctactgcatg     1380
cgt                                                                   1383
```

<210> SEQ ID NO 43
<211> LENGTH: 367
<212> TYPE: PRT
<213> ORGANISM: Zea mays

<400> SEQUENCE: 43

```
Met Ala Asn Ala Gly Gly Gly Ala Gly Gly Ser Gly Ser
1               5                   10              15

Val Ala Ala Pro Ala Val Cys Arg Pro Ser Gly Arg Trp Thr Pro
            20                  25                  30

Thr Pro Glu Gln Ile Arg Met Leu Lys Glu Leu Tyr Tyr Gly Cys Gly
                35                  40                  45

Ile Arg Ser Pro Ser Ser Glu Gln Ile Gln Arg Ile Thr Ala Met Leu
    50                  55                  60

Arg Gln His Gly Lys Ile Glu Gly Lys Asn Val Phe Tyr Trp Phe Gln
65                  70                  75                  80

Asn His Lys Ala Arg Glu Arg Gln Lys Arg Arg Leu Thr Ser Leu Asp
                85                  90                  95

Val Asn Val Pro Ala Ala Gly Ala Ala Asp Ala Thr Thr Ser Gln Leu
            100                 105                 110

Gly Val Leu Ser Leu Ser Ser Pro Pro Ser Gly Ala Ala Pro Pro
        115                 120                 125

Ser Pro Thr Leu Gly Phe Tyr Ala Ala Gly Asn Gly Gly Ser Ala
    130                 135                 140

Val Leu Leu Asp Thr Ser Ser Asp Trp Gly Ser Ser Gly Ala Ala Met
145                 150                 155                 160

Ala Thr Glu Thr Cys Phe Leu Gln Val Gly Ala Val Val Arg Ser Phe
                165                 170                 175

Leu Gly His Cys Ala Gln Phe His Val Arg Thr Tyr Glu Leu Ile Ala
            180                 185                 190

Ala Ser Phe His Pro Pro Val Tyr Ile Thr Val Arg Tyr Gly Gly Ala
        195                 200                 205

Arg Pro Gln Asp Tyr Met Gly Val Thr Asp Thr Gly Ser Ser Ser Gln
    210                 215                 220

Trp Pro Cys Leu Ser Ser Ser Asp Thr Ile Met Ala Ala Ala Ala
225                 230                 235                 240

Arg Ala Pro Thr Thr Thr Arg Pro Pro Glu Thr Leu Pro Leu Phe Pro
                245                 250                 255

Thr Cys Gly Asp Asp Asp Asp Asp Asn Gln Pro Pro Arg Pro
            260                 265                 270

Arg His Ala Val Pro Val Pro Ala Gly Glu Pro Ile Arg Val Gly Gly
        275                 280                 285

Gly Gly Ser Ser Ser Tyr Leu Pro Phe Trp Gly Ala Ala Ser Thr Thr
    290                 295                 300

Ala Gly Ala Thr Ser Ser Val Ala Ile Gln Gln Gln His Gln Leu Gln
305                 310                 315                 320

Glu Gln Tyr Ile Phe Tyr Ser Asn Ser Thr Gln Leu Ala Gly Thr Gly
                325                 330                 335

Ser Gln Asp Val Ser Ala Ser Ala Ala Ala Ala Ala Leu Glu Leu
            340                 345                 350

Ser Leu Ser Ser Trp Cys Ser Pro Tyr Pro Ala Ala Gly Ser Met
        355                 360                 365
```

<210> SEQ ID NO 44
<211> LENGTH: 1254

<212> TYPE: DNA
<213> ORGANISM: Zea mays

<400> SEQUENCE: 44

```
gtccgagcta ggtcacagaa gcgctcagga aggccgctga gatagaggca tggcggccaa      60
tgcgggcggc ggtggagcgg gaggaggcag cggcagcgtg gctgcgccgg cggtgtgccg     120
ccccagcggc tcgcggtgga cgccgacgcc ggagcagatc aggatgctga aggagctcta     180
ctacggctgc ggcatccggt cgcccagctc ggagcagatc cagcgcatca ccgccatgct     240
gcggcagcac ggcaagatcg agggcaagaa cgtcttctac tggttccaga accacaaggc     300
ccgcgagcgc cagaagcgcc gcctcaccag cctcgacgtc aacgtgcccg ccgccggcgc     360
ggccgacgcc accaccagcc aactcggcgt cctctcgctg tcgtcgccgc cgccttcagg     420
cgcggcgcct ccctcgccca ccctcggctt ctacgccgcc ggcaatggcg gcggatcggc     480
tgtgctgctg gacacgagtt ccgactgggg cagcagcggc gctgccatgg ccaccgagac     540
atgcttcctg caggactaca tgggcgtgac ggacacgggc agctcgtcgc agtggccatg     600
cttgtcgtcg tcagacacga taatggcggc ggccgcggcg cgggcgccga cgacgacgcg     660
gccgcccgag acgctccctc tcttcccgac ctgcggcgac gacgacgacg acgacaacca     720
gccccccgcc gcggccgcggc acgcagtccc agtcccggca ggcgagccca tccgcgtcgg     780
cggtggcggc agcagcagct acttgccgtt ctggggtgcc gcgtccacaa ctgccggcgc     840
cacttcttcc gttgcgatcc agcagcaaca ccagctgcag gagcagtaca tcttttacag     900
caacagcacc cagctggccg gcaccggcag ccaagacgta tcggcttcag cagcagcagc     960
cgccgccctg gagctgagcc tcagctcatg gtgctcccct taccctgctg cagggagcat    1020
gtgaccatag cgttggtgcg ttgctgtcat tgtcctaggt tagtagctag tgccagttac    1080
tagtaagcat caggcatagg agtatgtaga agcatgtctg gagaaaggca atagcgtttg    1140
ggagatctat ggtggagtgg tggtatggta ctattattag atagcgaatt tgcacactat    1200
gcagcatgca tgttgccggc cgggcgggct ttagactcca gctactgcat gcgt          1254
```

<210> SEQ ID NO 45
<211> LENGTH: 324
<212> TYPE: PRT
<213> ORGANISM: Zea mays

<400> SEQUENCE: 45

```
Met Ala Ala Asn Ala Gly Gly Gly Ala Gly Gly Ser Gly Ser
  1               5                  10                  15

Val Ala Ala Pro Ala Val Cys Arg Pro Ser Gly Ser Arg Trp Thr Pro
                 20                  25                  30

Thr Pro Glu Gln Ile Arg Met Leu Lys Glu Leu Tyr Tyr Gly Cys Gly
             35                  40                  45

Ile Arg Ser Pro Ser Ser Glu Gln Ile Gln Arg Ile Thr Ala Met Leu
         50                  55                  60

Arg Gln His Gly Lys Ile Glu Gly Lys Asn Val Phe Tyr Trp Phe Gln
 65                  70                  75                  80

Asn His Lys Ala Arg Glu Arg Gln Lys Arg Arg Leu Thr Ser Leu Asp
                 85                  90                  95

Val Asn Val Pro Ala Ala Gly Ala Ala Asp Ala Thr Thr Ser Gln Leu
            100                 105                 110

Gly Val Leu Ser Leu Ser Ser Pro Pro Ser Gly Ala Ala Pro Pro
            115                 120                 125
```

-continued

```
Ser Pro Thr Leu Gly Phe Tyr Ala Ala Gly Asn Gly Gly Ser Ala
    130                 135                 140

Val Leu Leu Asp Thr Ser Ser Asp Trp Gly Ser Gly Ala Ala Met
145                 150                 155                 160

Ala Thr Glu Thr Cys Phe Leu Gln Asp Tyr Met Gly Val Thr Asp Thr
                165                 170                 175

Gly Ser Ser Ser Gln Trp Pro Cys Leu Ser Ser Ser Asp Thr Ile Met
                180                 185                 190

Ala Ala Ala Ala Ala Arg Ala Pro Thr Thr Thr Arg Pro Pro Glu Thr
                195                 200                 205

Leu Pro Leu Phe Pro Thr Cys Gly Asp Asp Asp Asp Asp Asn Gln
    210                 215                 220

Pro Pro Pro Arg Pro Arg His Ala Val Pro Val Pro Ala Gly Glu Pro
225                 230                 235                 240

Ile Arg Val Gly Gly Gly Ser Ser Tyr Leu Pro Phe Trp Gly
                    245                 250                 255

Ala Ala Ser Thr Thr Ala Gly Ala Thr Ser Ser Val Ala Ile Gln Gln
                260                 265                 270

Gln His Gln Leu Gln Glu Gln Tyr Ile Phe Tyr Ser Asn Ser Thr Gln
            275                 280                 285

Leu Ala Gly Thr Gly Ser Gln Asp Val Ser Ala Ser Ala Ala Ala
    290                 295                 300

Ala Ala Leu Glu Leu Ser Leu Ser Ser Trp Cys Ser Pro Tyr Pro Ala
305                 310                 315                 320

Ala Gly Ser Met

<210> SEQ ID NO 46
<211> LENGTH: 1276
<212> TYPE: DNA
<213> ORGANISM: Zea mays

<400> SEQUENCE: 46
gtccgagcta ggtcacagaa gcgctcagga aggccgctga gatagaggca tggcggccaa      60
tgcgggcggc ggtggagcgg gaggaggcag cggcagcgtg gctgcgccgg cggtgtgccg     120
ccccagcggc tcgcggtgga cgccgacgcc ggagcagatc aggatgctga aggagctcta     180
ctacggctgc ggcatccggt cgcccagctc ggagcagatc cagcgcatca ccgccatgct     240
gcggcagcac ggcaagatcg agggcaagaa cgtcttctac tggttccaga accacaaggc     300
ccgcgagcgc cagaagcgcc gcctcaccag cctcgacgtc aacgtgcccg ccgccggcgc     360
ggccgacgcc accaccagcc aactcggcgt cctctcgctg tcgtcgccgc cgccttcagg     420
cgcggcgcct ccctcgccca ccctcggctt ctacgccgcc ggcaatggcg gcggatcggc     480
tgtgctgctg gacacgagtt ccgactgggg cagcagcggc gctgccatgg ccaccgagac     540
atgcttcctg caggtacggc ggtgcgcgcc gcaggactca tgggcgtga  cggacacgg     600 gcagctcgtc gcagtggcca tgcttgtcgt cgtcagacac gataatggcg gcggccgcgg     660
cgcgggcgcc gacgacgacg cggccgcccg agacgctccc tctcttcccg acctgcggcg     720
acgacgacga cgacgacaac cagcccccgc cgcggccgcg gcacgcagtc ccagtcccgg     780
caggcgagcc catccgcgtc ggcggtggcg gcagcagcag ctacttgccg ttctggggtg     840
ccgcgtccac aactgccggc gccacttctt ccgttgcgat ccagcagcaa caccagctgc     900
aggagcagta catcttttac agcaacagca cccagctggc cggcaccggc agccaagacg     960
tatcggcttc agcagcagca gccgccgccc tggagctgag cctcagctca tggtgctccc    1020
```

```
cttaccctgc tgcagggagc atgtgaccat agcgttggtg cgttgctgtc attgtcctag    1080
gttagtagct agtgccagtt actagtaagc atcaggcata ggagtatgta gaagcatgtc    1140
tggagaaagg caatagcgtt tgggagatct atggtggagt ggtggtatgg tactattatt    1200
agatagcgaa tttgcacact atgcagcatg catgttgccg gccgggcggg ctttagactc    1260
cagctactgc atgcgt                                                    1276
```

<210> SEQ ID NO 47
<211> LENGTH: 351
<212> TYPE: PRT
<213> ORGANISM: Zea mays

<400> SEQUENCE: 47

```
Met Ala Ala Asn Ala Gly Gly Gly Ala Gly Gly Ser Gly Ser
 1               5                  10                  15

Val Ala Ala Pro Ala Val Cys Arg Pro Ser Gly Ser Arg Trp Thr Pro
             20                  25                  30

Thr Pro Glu Gln Ile Arg Met Leu Lys Glu Leu Tyr Tyr Gly Cys Gly
         35                  40                  45

Ile Arg Ser Pro Ser Ser Glu Gln Ile Gln Arg Ile Thr Ala Met Leu
     50                  55                  60

Arg Gln His Gly Lys Ile Glu Gly Lys Asn Val Phe Tyr Trp Phe Gln
 65                  70                  75                  80

Asn His Lys Ala Arg Glu Arg Gln Lys Arg Arg Leu Thr Ser Leu Asp
                 85                  90                  95

Val Asn Val Pro Ala Ala Gly Ala Ala Asp Ala Thr Thr Ser Gln Leu
            100                 105                 110

Gly Val Leu Ser Leu Ser Ser Pro Pro Ser Gly Ala Ala Pro Pro
        115                 120                 125

Ser Pro Thr Leu Gly Phe Tyr Ala Ala Gly Asn Gly Gly Ser Ala
    130                 135                 140

Val Leu Leu Asp Thr Ser Ser Asp Trp Gly Ser Ser Gly Ala Ala Met
145                 150                 155                 160

Ala Thr Glu Thr Cys Phe Leu Gln Val Arg Arg Cys Ala Pro Ala Gly
                165                 170                 175

Leu His Gly Arg Asp Gly His Gly Gln Leu Val Ala Val Ala Met Leu
            180                 185                 190

Val Val Val Arg His Asp Asn Gly Gly Arg Gly Ala Gly Ala Asp
        195                 200                 205

Asp Asp Ala Ala Ala Arg Asp Ala Pro Ser Leu Pro Asp Leu Arg Arg
210                 215                 220

Arg Arg Arg Arg Gln Pro Ala Pro Ala Ala Ala Ala Arg Ser
225                 230                 235                 240

Pro Ser Pro Gly Arg Arg Ala His Pro Arg Arg Trp Arg Gln Gln
                245                 250                 255

Gln Leu Leu Ala Val Leu Gly Cys Arg Val His Asn Cys Arg His
            260                 265                 270

Phe Phe Arg Cys Asp Pro Ala Ala Thr Pro Ala Ala Gly Ala Val His
        275                 280                 285

Leu Leu Gln Gln Gln His Pro Ala Gly Arg His Arg Gln Pro Arg Arg
    290                 295                 300

Ile Gly Phe Ser Ser Ser Ser Arg Arg Pro Gly Ala Glu Pro Gln Leu
305                 310                 315                 320
```

```
Met Val Leu Pro Leu Pro Cys Cys Arg Glu His Val Thr Ile Ala Leu
            325                 330                 335

Val Arg Cys Cys His Cys Pro Arg Leu Val Ala Ser Ala Ser Tyr
            340                 345                 350

<210> SEQ ID NO 48
<211> LENGTH: 1630
<212> TYPE: DNA
<213> ORGANISM: Zea mays

<400> SEQUENCE: 48
gtccgagcta ggtcacagaa gcgctcagga aggccgctga gatagaggca tggcggccaa      60
tgcgggcggc ggtggagcgg gaggaggcag cggcagcgtg gctgcgccgg cggtgtgccg     120
ccccagcggc tcgcggtgga cgccgacgcc ggagcagatc aggatgctga aggagctcta     180
ctacggctgc ggcatccggt cgcccagctc ggagcagatc cagcgcatca ccgccatgct     240
gcggcagcac ggcaagatcg agggcaagaa cgtcttctac tggttccaga accacaaggc     300
ccgcgagcgc cagaagcgcc gcctcaccag cctcgacgtc aacgtgcccg ccgccggcgc     360
ggccgacgcc accaccagcc aactcggcgt cctctcgctg tcgtcgccgc cgccttcagg     420
tacgtgcgtc agtgcgtgtg gtgtgtgggt agtatatatg gtctctcctt gcattggcac     480
gccaatcggc catcgatcca atcatatcat cgtccaaacg tatatagtac atgtgactgc     540
aaactgatgt gcaccgtcgt catcactgat caggcgcggc gcctccctcg cccacccccg     600
gcttctacgc cgccggcaat ggcggcggat cggctgtgct gctggacacg agttccgact     660
ggggcagcag cggcgctgcc atggccaccg agacatgctt cctgcaggtc ggtgctgtag     720
tacgttcttt tcttgggcat tgcgcgcagt ttcacgttcg tacgtacgag ttgatcgccg     780
cgtcgttcca tccaccggta tatataactg ttaggtacgg cggtgcgcgc ccgcaggact     840
acatgggcgt gacggacacg ggcagctcgt cgcagtggcc acgcttctcg tcgtcggaca     900
cgataatggc ggcggccgcg gcgcgggcgg cgacgacgcg ggcgcccgag acgctccctc     960
tcttcccgac ctgcggcgac gacggcggca gcggtagcag cagctacttg ccgttctggg    1020
gtgccgcgtc cacaactgcc ggcgccactt cttccgttgc gatccagcag caacaccagc    1080
tgcaggagca gtacagcttt tacagcaaca gcaacagcac ccagctggcc ggcaccggca    1140
accaagacgt atcggcaaca gcagcagcag ccgccgccct ggagctgagc ctcagctcat    1200
ggtgctcccc ttaccctgct gcagggagta tgtgagagca acgcgagctg ccactgctct    1260
tcacttatgt ctctggaatg gaaggaggag gaagtgagca tagcgttggt gcgttgctg     1320 cattgtccta ggttagtagc tagtgccagt tactagtaag catcaggcat aggagtatg     1380 agtagaagca tgcacgttgc cggccagcca ggctttagac gggaaaagaa tttggtgca     1440 ccggctgcaa acaggatgt ttacagcccc cacacaaaaa aaaagattg accctacct     1500 taacaataat aacacaacta aaatgttatt tgatggacct acaagtggga taaatccttt    1560
tttttgtgag gtgctgcaaa cattctggtt catcaattt tttcctttag actccagct     1620 ctgcatgcgt                                                             1630

<210> SEQ ID NO 49
<211> LENGTH: 1476
<212> TYPE: DNA
<213> ORGANISM: Zea mays

<400> SEQUENCE: 49
gtccgagcta ggtcacagaa gcgctcagga aggccgctga gatagaggca tggcggccaa      60
```

-continued

| | |
|---|---|
| tgcgggcggc ggtggagcgg gaggaggcag cggcagcgtg gctgcgccgg cggtgtgccg | 120 |
| ccccagcggc tcgcggtgga cgccgacgcc ggagcagatc aggatgctga aggagctcta | 180 |
| ctacggctgc ggcatccggt cgcccagctc ggagcagatc cagcgcatca ccgccatgct | 240 |
| gcggcagcac ggcaagatcg agggcaagaa cgtcttctac tggttccaga accacaaggc | 300 |
| ccgcgagcgc cagaagcgcc gcctcaccag cctcgacgtc aacgtgcccg ccgcggcgc | 360 |
| ggccgacgcc accaccagcc aactcggcgt cctctcgctg tcgtcgccgc cgccttcagg | 420 |
| cgcggcgcct ccctcgccca ccctcggctt ctacgccgcc ggcaatggcg gcggatcggc | 480 |
| tgtgctgctg gacacgagtt ccgactgggg cagcagcggc gctgccatgg ccaccgagac | 540 |
| atgcttcctg caggtcggtg ctgtagtacg ttcttttctt gggcattgcg cgcagtttca | 600 |
| cgttcgtacg tacgagttga tcgccgcgtc gttccatcca ccggtatata aactgttag | 660 |
| gtacggcggt gcgcgcccgc aggactacat gggcgtgacg gacacgggca gctcgtcgca | 720 |
| gtggccacgc ttctcgtcgt cggacacgat aatggcggcg gccgcggcgc gggcggcgac | 780 |
| gacgcgggcg cccgagacgc tccctctctt cccgacctgc ggcgacgacg gcggcagcgg | 840 |
| tagcagcagc tacttgccgt tctggggtgc cgcgtccaca actgccggcg ccacttcttc | 900 |
| cgttgcgatc cagcagcaac accagctgca ggagcagtac agcttttaca gcaacagcaa | 960 |
| cagcacccag ctggccggca ccggcaacca agacgtatcg gcaacagcag cagcagccgc | 1020 |
| cgccctggag ctgagcctca gctcatggtg ctccccttac cctgctgcag ggagtatgtg | 1080 |
| agagcaacgc gagctgccac tgctcttcac ttatgtctct ggaatggaag gaggaggaag | 1140 |
| tgagcatagc gttggtgcgt tgctgtcatt gtcctaggtt agtagctagt gccagttact | 1200 |
| agtaagcatc aggcatagga gtatgtagta gaagcatgca cgttgccggc cagccaggct | 1260 |
| ttagacggga aaagaatttg gtgcagccgg ctgcaaaaca ggatgtttac agcccccaca | 1320 |
| caaaaaaaaa agattgaccc tacctgtaac aataataaca caactaaaat gttatttgat | 1380 |
| ggacctacaa gtgggataaa tccttctttt tgtgaggtgc tgcaaacatt ctggttcatc | 1440 |
| aattttttc ctttagactc cagctactgc atgcgt | 1476 |

<210> SEQ ID NO 50
<211> LENGTH: 343
<212> TYPE: PRT
<213> ORGANISM: Zea mays

<400> SEQUENCE: 50

Met Ala Ala Asn Ala Gly Gly Gly Gly Ala Gly Gly Gly Ser Gly Ser
1               5                   10                  15

Val Ala Ala Pro Ala Val Cys Arg Pro Ser Gly Ser Arg Trp Thr Pro
            20                  25                  30

Thr Pro Glu Gln Ile Arg Met Leu Lys Glu Leu Tyr Tyr Gly Cys Gly
        35                  40                  45

Ile Arg Ser Pro Ser Ser Glu Gln Ile Gln Arg Ile Thr Ala Met Leu
    50                  55                  60

Arg Gln His Gly Lys Ile Glu Gly Lys Asn Val Phe Tyr Trp Phe Gln
65                  70                  75                  80

Asn His Lys Ala Arg Glu Arg Gln Lys Arg Arg Leu Thr Ser Leu Asp
                85                  90                  95

Val Asn Val Pro Ala Ala Gly Ala Ala Asp Ala Thr Thr Ser Gln Leu
            100                 105                 110

Gly Val Leu Ser Leu Ser Ser Pro Pro Ser Gly Ala Ala Pro Pro

```
                115                 120                 125
Ser Pro Thr Leu Gly Phe Tyr Ala Ala Gly Asn Gly Gly Ser Ala
        130                 135                 140

Val Leu Leu Asp Thr Ser Ser Asp Trp Gly Ser Gly Ala Ala Met
145                 150                 155                 160

Ala Thr Glu Thr Cys Phe Leu Gln Val Gly Ala Val Arg Ser Phe
                165                 170                 175

Leu Gly His Cys Ala Gln Phe His Val Arg Thr Tyr Glu Leu Ile Ala
                180                 185                 190

Ala Ser Phe His Pro Pro Val Tyr Ile Thr Val Arg Tyr Gly Gly Ala
                195                 200                 205

Arg Pro Gln Asp Tyr Met Gly Val Thr Asp Thr Gly Ser Ser Ser Gln
        210                 215                 220

Trp Pro Arg Phe Ser Ser Ser Asp Thr Ile Met Ala Ala Ala Ala
225                 230                 235                 240

Arg Ala Ala Thr Thr Arg Ala Pro Glu Thr Leu Pro Leu Phe Pro Thr
                245                 250                 255

Cys Gly Asp Asp Gly Gly Ser Gly Ser Ser Ser Tyr Leu Pro Phe Trp
                260                 265                 270

Gly Ala Ala Ser Thr Thr Ala Gly Ala Thr Ser Ser Val Ala Ile Gln
            275                 280                 285

Gln Gln His Gln Leu Gln Glu Gln Tyr Ser Phe Tyr Ser Asn Ser Asn
        290                 295                 300

Ser Thr Gln Leu Ala Gly Thr Gly Asn Gln Asp Val Ser Ala Thr Ala
305                 310                 315                 320

Ala Ala Ala Ala Ala Leu Glu Leu Ser Leu Ser Ser Trp Cys Ser Pro
                325                 330                 335

Tyr Pro Ala Ala Gly Ser Met
                340

<210> SEQ ID NO 51
<211> LENGTH: 1347
<212> TYPE: DNA
<213> ORGANISM: Zea mays

<400> SEQUENCE: 51
gtccgagcta ggtcacagaa gcgctcagga aggccgctga gatagaggca tggcggccaa    60
tgcgggcggc ggtggagcgg gaggaggcag cggcagcgtg gctgcgccgg cggtgtgccg   120
ccccagcggc tcgcggtgga cgccgacgcc ggagcagatc aggatgctga aggagctcta   180
ctacggctgc ggcatccggt cgcccagctc ggagcagatc cagcgcatca ccgccatgct   240
gcggcagcac ggcaagatcg agggcaagaa cgtcttctac tggttccaga accacaaggc   300
ccgcgagcgc cagaagcgcc gcctcaccag cctcgacgtc aacgtgcccg ccgccggcgc   360
ggccgacgcc accaccagcc aactcggcgt cctctcgctg tcgtcgccgc cgccttcagg   420
cgcggcgcct ccctcgccca ccctcggctt ctacgccgcc ggcaatggcg gcggatcggc   480
tgtgctgctg gacacgagtt ccgactgggg cagcagcggc gctgccatgg ccaccgagac   540
atgcttcctg caggactaca tgggcgtgac ggacacgggc agctcgtcgc agtggccacg   600
cttctcgtcg tcggacacga taatggcggc ggccgcggcg cgggcggcga cgacgcgggc   660
gcccgagacg ctccctctct tcccgacctg cggcgacgac ggcggcagcg gtagcagcag   720
ctacttgccg ttctggggtg ccgcgtccac aactgccggc gccacttctt ccgttgcgat   780
ccagcagcaa caccagctgc aggagcagta cagcttttac agcaacagca acagcaccca   840
```

-continued

```
gctggccggc accggcaacc aagacgtatc ggcaacagca gcagcagccg ccgccctgga    900
gctgagcctc agctcatggt gctcccctta ccctgctgca gggagtatgt gagagcaacg    960
cgagctgcca ctgctcttca cttatgtctc tggaatggaa ggaggaggaa gtgagcatag   1020
cgttggtgcg ttgctgtcat tgtcctaggt tagtagctag tgccagttac tagtaagcat   1080
caggcatagg agtatgtagt agaagcatgc acgttgccgg ccagccaggc tttagacggg   1140
aaaagaattt ggtgcagccg gctgcaaaac aggatgttta cagcccccac acaaaaaaaa   1200
aagattgacc ctacctgtaa caataataac acaactaaaa tgttatttga tggacctaca   1260
agtgggataa atccttcttt ttgtgaggtg ctgcaaacat tctggttcat caattttttt   1320
cctttagact ccagctactg catgcgt                                      1347
```

<210> SEQ ID NO 52
<211> LENGTH: 300
<212> TYPE: PRT
<213> ORGANISM: Zea mays

<400> SEQUENCE: 52

```
Met Ala Asn Ala Gly Gly Gly Ala Gly Gly Ser Gly Ser
  1               5                  10                  15

Val Ala Ala Pro Ala Val Cys Arg Pro Ser Gly Ser Arg Trp Thr Pro
             20                  25                  30

Thr Pro Glu Gln Ile Arg Met Leu Lys Glu Leu Tyr Tyr Gly Cys Gly
         35                  40                  45

Ile Arg Ser Pro Ser Ser Glu Gln Ile Gln Arg Ile Thr Ala Met Leu
     50                  55                  60

Arg Gln His Gly Lys Ile Glu Gly Lys Asn Val Phe Tyr Trp Phe Gln
 65                  70                  75                  80

Asn His Lys Ala Arg Glu Arg Gln Lys Arg Arg Leu Thr Ser Leu Asp
                 85                  90                  95

Val Asn Val Pro Ala Ala Gly Ala Ala Asp Ala Thr Thr Ser Gln Leu
            100                 105                 110

Gly Val Leu Ser Leu Ser Pro Pro Ser Gly Ala Ala Pro Pro
        115                 120                 125

Ser Pro Thr Leu Gly Phe Tyr Ala Ala Gly Asn Gly Gly Ser Ala
    130                 135                 140

Val Leu Leu Asp Thr Ser Ser Asp Trp Gly Ser Gly Ala Ala Met
145                 150                 155                 160

Ala Thr Glu Thr Cys Phe Leu Gln Asp Tyr Met Gly Val Thr Asp Thr
                165                 170                 175

Gly Ser Ser Ser Gln Trp Pro Arg Phe Ser Ser Ser Asp Thr Ile Met
            180                 185                 190

Ala Ala Ala Ala Arg Ala Ala Thr Thr Arg Ala Pro Glu Thr Leu
        195                 200                 205

Pro Leu Phe Pro Thr Cys Gly Asp Asp Gly Ser Gly Ser Ser Ser
    210                 215                 220

Tyr Leu Pro Phe Trp Gly Ala Ala Ser Thr Thr Ala Gly Ala Thr Ser
225                 230                 235                 240

Ser Val Ala Ile Gln Gln Gln His Gln Leu Gln Glu Gln Tyr Ser Phe
                245                 250                 255

Tyr Ser Asn Ser Asn Ser Thr Gln Leu Ala Gly Thr Gly Asn Gln Asp
            260                 265                 270

Val Ser Ala Thr Ala Ala Ala Ala Ala Leu Glu Leu Ser Leu Ser
```

```
                 275                 280                 285
Ser Trp Cys Ser Pro Tyr Pro Ala Ala Gly Ser Met
    290                 295                 300
```

<210> SEQ ID NO 53
<211> LENGTH: 1369
<212> TYPE: DNA
<213> ORGANISM: Zea mays

<400> SEQUENCE: 53

```
gtccgagcta ggtcacagaa gcgctcagga aggccgctga gatagaggca tggcggccaa    60
tgcgggcggc ggtggagcgg gaggaggcag cggcagcgtg gctgcgccgg cggtgtgccg   120
ccccagcggc tcgcggtgga cgccgacgcc ggagcagatc aggatgctga aggagctcta   180
ctacggctgc ggcatccggt cgcccagctc ggagcagatc cagcgcatca ccgccatgct   240
gcggcagcac ggcaagatcg agggcaagaa cgtcttctac tggttccaga ccacaaggc   300
ccgcgagcgc cagaagcgcc gcctcaccag cctcgacgtc aacgtgcccg ccgccggcgc   360
ggccgacgcc accaccagcc aactcggcgt cctctcgctg tcgtcgccgc cgccttcagg   420
cgcggcgcct ccctcgccca ccctcggctt ctacgccgcc ggcaatggcg gcggatcggc   480
tgtgctgctg gacacgagtt ccgactgggg cagcagcggc gctgccatgg ccaccgagac   540
atgcttcctg caggtacggc ggtgcgcgcc cgcaggacta catgggcgtg acggacacgg   600
gcagctcgtc gcagtggcca cgcttctcgt cgtcggacac gataatggcg gcggccgcgg   660
cgcgggcggc gacgacgcgg gcgcccgaga cgctccctct cttcccgacc tgcggcgacg   720
acggcggcag cggtagcagc agctacttgc cgttctgggg tgccgcgtcc acaactgccg   780
gcgccacttc ttccgttgcg atccagcagc aacaccagct gcaggagcag tacagctttt   840
acagcaacag caacagcacc cagctggccg gcaccggcaa ccaagacgta tcggcaacag   900
cagcagcagc cgccgccctg gagctgagcc tcagctcatg gtgctcccct accctgctg    960
cagggagtat gtgagagcaa cgcgagctgc cactgctctt cacttatgtc tctggaatgg  1020
aaggaggagg aagtgagcat agcgttggtg cgttgctgtc attgtcctag gttagtagct  1080
agtgccagtt actagtaagc atcaggcata ggagtatgta gtagaagcat gcacgttgcc  1140
ggccagccag gctttagacg ggaaaagaat ttggtcagc cggctgcaaa acaggatgtt  1200
tacagccccc acacaaaaaa aaagattga ccctacctgt aacaataata acacaactaa  1260
aatgttattt gatggaccta caagtgggat aaatccttct ttttgtgagg tgctgcaaac  1320
attctggttc atcaattttt ttcctttaga ctccagctac tgcatgcgt              1369
```

<210> SEQ ID NO 54
<211> LENGTH: 228
<212> TYPE: PRT
<213> ORGANISM: Zea mays

<400> SEQUENCE: 54

```
Met Ala Ala Asn Ala Gly Gly Gly Ala Gly Gly Gly Ser Gly Ser
  1               5                  10                  15

Val Ala Ala Pro Ala Val Cys Arg Pro Ser Gly Ser Arg Trp Thr Pro
             20                  25                  30

Thr Pro Glu Gln Ile Arg Met Leu Lys Glu Leu Tyr Tyr Gly Cys Gly
         35                  40                  45

Ile Arg Ser Pro Ser Ser Glu Gln Ile Gln Arg Ile Thr Ala Met Leu
     50                  55                  60
```

```
Arg Gln His Gly Lys Ile Glu Gly Lys Asn Val Phe Tyr Trp Phe Gln
 65                  70                  75                  80

Asn His Lys Ala Arg Glu Arg Gln Lys Arg Arg Leu Thr Ser Leu Asp
             85                  90                  95

Val Asn Val Pro Ala Ala Gly Ala Ala Asp Ala Thr Thr Ser Gln Leu
            100                 105                 110

Gly Val Leu Ser Leu Ser Ser Pro Pro Ser Gly Ala Ala Pro Pro
        115                 120                 125

Ser Pro Thr Leu Gly Phe Tyr Ala Ala Gly Asn Gly Gly Ser Ala
    130                 135                 140

Val Leu Leu Asp Thr Ser Ser Asp Trp Gly Ser Ser Gly Ala Ala Met
145                 150                 155                 160

Ala Thr Glu Thr Cys Phe Leu Gln Val Arg Arg Cys Ala Pro Ala Gly
                165                 170                 175

Leu His Gly Arg Asp Gly His Gly Gln Leu Val Ala Val Ala Thr Leu
            180                 185                 190

Leu Val Val Gly His Asp Asn Gly Gly Gly Arg Gly Ala Gly Gly Asp
        195                 200                 205

Asp Ala Gly Ala Arg Asp Ala Pro Ser Leu Pro Asp Leu Arg Arg Arg
    210                 215                 220

Arg Arg Gln Arg
225

<210> SEQ ID NO 55
<211> LENGTH: 1629
<212> TYPE: DNA
<213> ORGANISM: Zea mays

<400> SEQUENCE: 55
gtccgagcta ggtcacagaa gcgctcagga aggccgctga gatagaggca tggcggccaa      60
tgcgggcggc ggtggagcgg gaggaggcag cggcagcgtg gctgcgccgg cggtgtgccg     120
ccccagcggc tcgcggtgga cgccgacgcc ggagcagatc aggatgctga aggagctcta     180
ctacggctgc ggcatccggt cgcccagctc ggagcagatc agcgcatca ccgccatgct      240
gcggcagcac ggcaagatcg agggcaagaa cgtcttctac tggttccaga accacaaggc     300
ccgcgagcgc cagaagcgcc gcctcaccag cctcgacgtc aacgtgcccg ccgccggcgc     360
cggccgacgcc accaccagcc aactcggcgt cctctcgctg tcgtcgccgc cgccttcagg    420
tacgtgcgtc agtgcgtgtg gtgtgtgggt agtatatatg gtctctcctt gcattggcac    480
gccaatcggc catcgatcca atcatatcat cgtccaaacg tatatagtac atgtgactgc    540
aaactgatgt gcaccgtcgt catcactgat caggcgcggc gcctccctcg cccaccctcg    600
gcttctacgc cgccggcaat ggcggcggat cggctgtgct gctggacacg agttccgact    660
ggggcagcag cggcgctgcc atggccaccg agacatgctt cctgcaggtc ggtgctgtag    720
tacgttcttt tcttgggcat tgcgcgcagt ttcacgttcg tacgtacgag ttgatcgccg    780
cgtcgttcca tccaccggta tatataactg ttaggtacgg cggtgcgcgc ccgcaggact    840
acatgggcgt gacggacacg ggcagctcgt cgcagtggcc acgcttctcg tcgtcggaca    900
cgataatggc ggcggccgcg gcgcgggcgg cgacgacgcg ggcgcccgag acgctccctc    960
tcttcccgac ctgcggcgac gacggcggca gcggtagcag cagctacttg ccgttctggg   1020
gtgccgcgtc cacaactgcc ggcgccactt cttccgttgc gatccagcag caacaccagc   1080
tgcaggagca gtacagcttt tacagcaaca gcaacagcac ccagctggcc ggcaccggca   1140
```

| accaagacgt atcggcaaca gcagcagcag ccgccgccct ggagctgagc ctcagctcat | 1200 |
| ggtgctcccc ttaccctgct gcagggagta tgtgagagca cgcgagctg ccactgctct | 1260 |
| tcacttatgt ctctggaatg gaaggaggag gaagtgagca tagcgttggt gcgttgctgt | 1320 |
| cattgtccta ggttagtagc tagtgccagt tactagtaag catcaggcat aggagtatgt | 1380 |
| agtagaagca tgcacgttgc cggccagcca ggctttagac gggaaaagaa tttggtgcag | 1440 |
| ccggctgcaa acaggatgt ttacagcccc cacacaaaaa aaaagattg accctacctg | 1500 |
| taacaataat aacacaacta aaatgttatt tgatggacct acaagtggga taaatccttc | 1560 |
| tttttgtgag gtgctgcaaa cattctggtt catcaatttt tttcctttag actccagcta | 1620 |
| ctgcatgcg | 1629 |

<210> SEQ ID NO 56
<211> LENGTH: 1475
<212> TYPE: DNA
<213> ORGANISM: Zea mays

<400> SEQUENCE: 56

| gtccgagcta ggtcacagaa gcgctcagga aggccgctga gatagaggca tggcggccaa | 60 |
| tgcgggcggc ggtggagcgg gaggaggcag cggcagcgtg gctgcgccgg cggtgtgccg | 120 |
| ccccagcggc tcgcggtgga cgccgacgcc ggagcagatc aggatgctga aggagctcta | 180 |
| ctacggctgc ggcatccggt cgcccagctc ggagcagatc cagcgcatca ccgccatgct | 240 |
| gcggcagcac ggcaagatcg agggcaagaa cgtcttctac tggttccaga ccacaaggc | 300 |
| ccgcgagcgc cagaagcgcc gcctcaccag cctcgacgtc aacgtgcccg ccgccggcgc | 360 |
| ggccgacgcc accaccagcc aactcggcgt cctctcgctg tcgtcgccgc cgccttcagg | 420 |
| cgcggcgcct ccctcgccca cctcggctt ctacgccgcc ggcaatggcg gcggatcggc | 480 |
| tgtgctgctg gacacgagtt ccgactgggg cagcagcggc gctgccatgg ccaccgagac | 540 |
| atgcttcctg caggtcggtg ctgtagtacg ttctttctt gggcattgcg cgcagtttca | 600 |
| cgttcgtacg tacgagttga tcgccgcgtc gttccatcca ccgtatata taactgttag | 660 |
| gtacggcggt gcgcgcccgc aggactacat gggcgtgacg gacacgggca gctcgtcgca | 720 |
| gtggccacgc ttctcgtcgt cggacacgat aatggcggcg gccgcggcgc gggcggcgac | 780 |
| gacgcgggcg cccgagacgc tccctctctt cccgacctgc ggcgacgacg gcggcagcgg | 840 |
| tagcagcagc tacttgccgt tctggggtgc cgcgtccaca actgccggcg ccacttcttc | 900 |
| cgttgcgatc cagcagcaac accagctgca ggagcagtac agcttttaca gcaacagcaa | 960 |
| cagcacccag ctggccggca ccggcaacca agacgtatcg gcaacagcag cagcagccgc | 1020 |
| cgccctggag ctgagcctca gctcatggtg ctcccttac cctgctgcag ggagtatgtg | 1080 |
| agagcaacgc gagctgccac tgctcttcac ttatgtctct ggaatggaag gaggaggaag | 1140 |
| tgagcatagc gttggtgcgt tgctgtcatt gtcctaggtt agtagctagt gccagttact | 1200 |
| agtaagcatc aggcatagga gtatgtagta gaagcatgca cgttgccggc cagccaggct | 1260 |
| ttagacggga aaagaaattg gtgcagccgg ctgcaaaaca ggatgtttac agcccccaca | 1320 |
| caaaaaaaa agattgaccc tacctgtaac aataataaca caactaaaat gttatttgat | 1380 |
| ggacctacaa gtgggataaa tccttctttt tgtgaggtgc tgcaaacatt ctggttcatc | 1440 |
| aattttttc ctttagactc cagctactgc atgcg | 1475 |

<210> SEQ ID NO 57
<211> LENGTH: 343

```
<212> TYPE: PRT
<213> ORGANISM: Zea mays

<400> SEQUENCE: 57

Met Ala Asn Ala Gly Gly Gly Ala Gly Gly Ser Gly Ser
 1               5                  10                 15

Val Ala Ala Pro Ala Val Cys Arg Pro Ser Gly Ser Arg Trp Thr Pro
            20                  25                  30

Thr Pro Glu Gln Ile Arg Met Leu Lys Glu Leu Tyr Tyr Gly Cys Gly
            35                  40                  45

Ile Arg Ser Pro Ser Ser Glu Gln Ile Gln Arg Ile Thr Ala Met Leu
 50                  55                  60

Arg Gln His Gly Lys Ile Glu Gly Lys Asn Val Phe Tyr Trp Phe Gln
 65                  70                  75                  80

Asn His Lys Ala Arg Glu Arg Gln Lys Arg Arg Leu Thr Ser Leu Asp
                85                  90                  95

Val Asn Val Pro Ala Ala Gly Ala Ala Asp Ala Thr Thr Ser Gln Leu
            100                 105                 110

Gly Val Leu Ser Leu Ser Ser Pro Pro Ser Gly Ala Ala Pro Pro
        115                 120                 125

Ser Pro Thr Leu Gly Phe Tyr Ala Ala Gly Asn Gly Gly Ser Ala
130                 135                 140

Val Leu Leu Asp Thr Ser Ser Asp Trp Gly Ser Gly Ala Ala Met
145                 150                 155                 160

Ala Thr Glu Thr Cys Phe Leu Gln Val Gly Ala Val Arg Ser Phe
                165                 170                 175

Leu Gly His Cys Ala Gln Phe His Val Arg Thr Tyr Glu Leu Ile Ala
                180                 185                 190

Ala Ser Phe His Pro Pro Val Tyr Ile Thr Val Arg Tyr Gly Gly Ala
            195                 200                 205

Arg Pro Gln Asp Tyr Met Gly Val Thr Asp Thr Gly Ser Ser Ser Gln
            210                 215                 220

Trp Pro Arg Phe Ser Ser Ser Asp Thr Ile Met Ala Ala Ala Ala
225                 230                 235                 240

Arg Ala Ala Thr Thr Arg Ala Pro Glu Thr Leu Pro Leu Phe Pro Thr
                245                 250                 255

Cys Gly Asp Asp Gly Gly Ser Gly Ser Ser Tyr Leu Pro Phe Trp
            260                 265                 270

Gly Ala Ala Ser Thr Thr Ala Gly Ala Thr Ser Ser Val Ala Ile Gln
            275                 280                 285

Gln Gln His Gln Leu Gln Glu Gln Tyr Ser Phe Tyr Ser Asn Ser Asn
        290                 295                 300

Ser Thr Gln Leu Ala Gly Thr Gly Asn Gln Asp Val Ser Ala Thr Ala
305                 310                 315                 320

Ala Ala Ala Ala Leu Glu Leu Ser Leu Ser Trp Cys Ser Pro
                325                 330                 335

Tyr Pro Ala Ala Gly Ser Met
            340

<210> SEQ ID NO 58
<211> LENGTH: 1346
<212> TYPE: DNA
<213> ORGANISM: Zea mays

<400> SEQUENCE: 58
```

-continued

```
gtccgagcta ggtcacagaa gcgctcagga aggccgctga gatagaggca tggcggccaa    60
tgcgggcggc ggtggagcgg gaggaggcag cggcagcgtg gctgcgccgg cggtgtgccg   120
ccccagcggc tcgcggtgga cgccgacgcc ggagcagatc aggatgctga aggagctcta   180
ctacggctgc ggcatccggt cgcccagctc ggagcagatc cagcgcatca ccgccatgct   240
gcggcagcac ggcaagatcg agggcaagaa cgtcttctac tggttccaga accacaaggc   300
ccgcgagcgc cagaagcgcc gcctcaccag cctcgacgtc aacgtgcccg ccgccggcgc   360
ggccgacgcc accaccagcc aactcggcgt cctctcgctg tcgtcgccgc cgccttcagg   420
cgcggcgcct ccctcgccca ccctcggctt ctacgccgcc ggcaatggcg gcggatcggc   480
tgtgctgctg gacacgagtt ccgactgggg cagcagcggc gctgccatgg ccaccgagac   540
atgcttcctg caggactaca tgggcgtgac ggacacgggc agctcgtcgc agtggccacg   600
cttctcgtcg tcggacacga taatggcggc ggccgcggcg cgggcggcga cgacgcgggc   660
gcccgagacg ctccctctct tcccgacctg cggcgacgac ggcggcagcg gtagcagcag   720
ctacttgccg ttctggggtg ccgcgtccac aactgccggc gccacttctt ccgttgcgat   780
ccagcagcaa caccagctgc aggagcagta cagcttttac agcaacagca acagcaccca   840
gctggccggc accggcaacc aagacgtatc ggcaacagca gcagcagccg ccgccctgga   900
gctgagcctc agctcatggt gctcccctta ccctgctgca gggagtatgt gagagcaacg   960
cgagctgcca ctgctcttca cttatgtctc tggaatggaa ggaggaggaa gtgagcatag  1020
cgttggtgcg ttgctgtcat tgtcctaggt tagtagctag tgccagttac tagtaagcat  1080
caggcatagg agtatgtagt agaagcatgc acgttgccgg ccagccaggc tttagacggg  1140
aaaagaattt ggtgcagccg gctgcaaaac aggatgttta cagcccccac acaaaaaaaa  1200
aagattgacc ctacctgtaa caataataac acaactaaaa tgttatttga tggacctaca  1260
agtgggataa atccttcttt ttgtgaggtg ctgcaaacat tctggttcat caatttttt   1320
cctttagact ccagctactg catgcg                                        1346
```

<210> SEQ ID NO 59
<211> LENGTH: 300
<212> TYPE: PRT
<213> ORGANISM: Zea mays

<400> SEQUENCE: 59

```
Met Ala Ala Asn Ala Gly Gly Gly Ala Gly Gly Ser Gly Ser
  1               5                  10                  15

Val Ala Ala Pro Ala Val Cys Arg Pro Ser Gly Ser Arg Trp Thr Pro
             20                  25                  30

Thr Pro Glu Gln Ile Arg Met Leu Lys Glu Leu Tyr Tyr Gly Cys Gly
         35                  40                  45

Ile Arg Ser Pro Ser Ser Glu Gln Ile Gln Arg Ile Thr Ala Met Leu
     50                  55                  60

Arg Gln His Gly Lys Ile Glu Gly Lys Asn Val Phe Tyr Trp Phe Gln
 65                  70                  75                  80

Asn His Lys Ala Arg Glu Arg Gln Lys Arg Arg Leu Thr Ser Leu Asp
                 85                  90                  95

Val Asn Val Pro Ala Ala Gly Ala Ala Asp Ala Thr Thr Ser Gln Leu
            100                 105                 110

Gly Val Leu Ser Leu Ser Ser Pro Pro Ser Gly Ala Ala Pro
        115                 120                 125

Ser Pro Thr Leu Gly Phe Tyr Ala Ala Gly Asn Gly Gly Gly Ser Ala
```

```
            130                 135                 140
Val Leu Leu Asp Thr Ser Ser Asp Trp Gly Ser Gly Ala Ala Met
145                 150                 155                 160

Ala Thr Glu Thr Cys Phe Leu Gln Asp Tyr Met Gly Val Thr Asp Thr
                165                 170                 175

Gly Ser Ser Ser Gln Trp Pro Arg Phe Ser Ser Ser Asp Thr Ile Met
                180                 185                 190

Ala Ala Ala Ala Arg Ala Ala Thr Thr Arg Ala Pro Glu Thr Leu
            195                 200                 205

Pro Leu Phe Pro Thr Cys Gly Asp Asp Gly Ser Gly Ser Ser Ser
210                 215                 220

Tyr Leu Pro Phe Trp Gly Ala Ala Ser Thr Thr Ala Gly Ala Thr Ser
225                 230                 235                 240

Ser Val Ala Ile Gln Gln His Gln Leu Gln Glu Gln Tyr Ser Phe
                245                 250                 255

Tyr Ser Asn Ser Asn Ser Thr Gln Leu Ala Gly Thr Gly Asn Gln Asp
                260                 265                 270

Val Ser Ala Thr Ala Ala Ala Ala Ala Leu Glu Leu Ser Leu Ser
            275                 280                 285

Ser Trp Cys Ser Pro Tyr Pro Ala Ala Gly Ser Met
    290                 295                 300

<210> SEQ ID NO 60
<211> LENGTH: 1368
<212> TYPE: DNA
<213> ORGANISM: Zea mays

<400> SEQUENCE: 60
gtccgagcta ggtcacagaa gcgctcagga aggccgctga gatagaggca tggcggccaa      60
tgcgggcggc ggtggagcgg gaggaggcag cggcagcgtg gctgcgccgg cggtgtgccg     120
ccccagcggc tcgcggtgga cgccgacgcc ggagcagatc aggatgctga aggagctcta     180
ctacggctgc ggcatccggt cgcccagctc ggagcagatc cagcgcatca ccgccatgct     240
gcggcagcac ggcaagatcg agggcaagaa cgtcttctac tggttccaga accacaaggc     300
ccgcgagcgc cagaagcgcc gcctcaccag cctcgacgtc aacgtgcccg ccgccggcgc     360
ggccgacgcc accaccagcc aactcggcgt cctctcgctg tcgtcgccgc cgccttcagg     420
cgcggcgcct ccctcgccca ccctcggctt ctacgccgcc ggcaatggcg gcggatcggc     480
tgtgctgctg gacacgagtt ccgactgggg cagcagcggc gctgccatgg ccaccgagac     540
atgcttcctg caggtacggc ggtgcgcgcc gcaggactac atgggcgtg acggacacgg     600
gcagctcgtc gcagtggcca cgcttctcgt cgtcggacac gataatggcg gcggccgcgg     660
cgcgggcggc gacgacgcgg gcgcccgaga cgctccctct cttcccgacc tgcggcgacg     720
acggcggcag cggtagcagc agctacttgc cgttctgggg tgccgcgtcc acaactgccg     780
gcgccacttc ttccgttgcg atccagcagc aacaccagct gcaggagcag tacagctttt     840
acagcaacag caacagcacc cagctggccg gcaccggcaa ccaagacgta tcggcaacag     900
cagcagcagc cgccgcccctg gagctgagcc tcagctcatg gtgctcccct accctgctg     960
cagggagtat gtgagagcaa cgcgagctgc cactgctctt cacttatgtc tctggaatgg    1020
aaggaggagg aagtgagcat agcgttggtg cgttgctgtc attgtcctag gttagtagct    1080
agtgccagtt actagtaagc atcaggcata ggagtatgta gtagaagcat gcacgttgcc    1140
ggccagccag gctttagacg ggaaaagaat ttggtgcagc cggctgcaaa acaggatgtt    1200
```

```
tacagccccc acacaaaaaa aaaagattga ccctacctgt aacaataata acacaactaa    1260
aatgttattt gatggaccta caagtgggat aaatccttct ttttgtgagg tgctgcaaac    1320
attctggttc atcaatttt ttcctttaga ctccagctac tgcatgcg                  1368
```

<210> SEQ ID NO 61
<211> LENGTH: 228
<212> TYPE: PRT
<213> ORGANISM: Zea mays

<400> SEQUENCE: 61

```
Met Ala Ala Asn Ala Gly Gly Gly Ala Gly Gly Ser Gly Ser
1               5                   10                  15

Val Ala Ala Pro Ala Val Cys Arg Pro Ser Gly Ser Arg Trp Thr Pro
                20                  25                  30

Thr Pro Glu Gln Ile Arg Met Leu Lys Glu Leu Tyr Tyr Gly Cys Gly
            35                  40                  45

Ile Arg Ser Pro Ser Ser Glu Gln Ile Gln Arg Ile Thr Ala Met Leu
        50                  55                  60

Arg Gln His Gly Lys Ile Glu Gly Lys Asn Val Phe Tyr Trp Phe Gln
65                  70                  75                  80

Asn His Lys Ala Arg Glu Arg Gln Lys Arg Arg Leu Thr Ser Leu Asp
                85                  90                  95

Val Asn Val Pro Ala Ala Gly Ala Ala Asp Ala Thr Thr Ser Gln Leu
            100                 105                 110

Gly Val Leu Ser Leu Ser Ser Pro Pro Ser Gly Ala Ala Pro Pro
        115                 120                 125

Ser Pro Thr Leu Gly Phe Tyr Ala Ala Gly Asn Gly Gly Ser Ala
    130                 135                 140

Val Leu Leu Asp Thr Ser Ser Asp Trp Gly Ser Ser Gly Ala Ala Met
145                 150                 155                 160

Ala Thr Glu Thr Cys Phe Leu Gln Val Arg Arg Cys Ala Pro Ala Gly
                165                 170                 175

Leu His Gly Arg Asp Gly His Gly Gln Leu Val Ala Val Ala Thr Leu
            180                 185                 190

Leu Val Val Gly His Asp Asn Gly Gly Arg Gly Ala Gly Gly Asp
        195                 200                 205

Asp Ala Gly Ala Arg Asp Ala Pro Ser Leu Pro Asp Leu Arg Arg Arg
    210                 215                 220

Arg Arg Gln Arg
225
```

<210> SEQ ID NO 62
<211> LENGTH: 1638
<212> TYPE: DNA
<213> ORGANISM: Zea mays

<400> SEQUENCE: 62

```
gtccgagcta ggtcacagaa gcgctcagga aggccgctga gatagaggca tggcggccaa     60
tgcgggcggc ggtggagcgg gaggaggcag cggcagcggc agcgtggctg cgccggcggt    120
gtgccgcccc agcggctcgc ggtggacgcc gacgccggag cagatcagga tgctgaagga    180
gctctactac ggctgcggca tccggtcgcc cagctcggag cagatccagc gcatcaccgc    240
catgctgcgg cagcacggca agatcgaggg caagaacgtc ttctactggt tccagaacca    300
caaggcccgc gagcgccaga agcgccgcct caccagcctc gacgtcaacg tgcccgccgc    360
```

```
cggcgcggcc gacgccacca ccagccaact cggcgtcctc tcgctgtcgt cgccgccgcc      420
ttcaggtacg tgcgtcagtg cgtgtggtgt gtgggtagta tatatggtct ctccttgcat      480
tggcacgcca atcggccatc gatccaatca tatcatcgtc caaacgtata tagtacatgt      540
gactgcaaac tgatgtgcac cgtcgtcatc actgatcagg cgcggcgcct ccctcgccca      600
ccctcggctt ctacgccgcc ggcaatggcg cggatcggc tgtgctgctg gacacgagtt       660
ccgactgggg cagcagcggc gctgccatgg ccaccgagac atgcttcctg caggtcggtg      720
ctgtagtacg ttcttttctt gggcattgcg cgcagtttca cgttcgtacg tacgagttga      780
tcgccgcgtc gttccatcca ccggtatata taactgttag gtacggcggt gcgcgcccgc      840
aggactacat gggcgtgacg gacacgggca gctcgtcgca gtggccacgc ttctcgtcgt      900
cggacacgat aatggcggcg gccgcggcgc gggcggcgac gacgcgggcg cccgagacgc      960
tccctctctt cccgacctgc ggcgacgacg gcggcagcgg tagcagcagc tacttgccgt     1020
tctggggtgc cgcgtccaca actgccggcg ccacttcttc cgttgcgatc cagcagcaac     1080
accagctgca ggagcagtac agcttttaca gcaacagcaa cagcacccag ctggccggca     1140
ccggcaacca agacgtatcg gcaacagcag cagcagccgc cgccctggag ctgagcctca     1200
gctcatggtg ctccccttac cctgctgcag ggagtatgtg agagcaacgc gagctgccac     1260
tgctcttcac ttatgtctct ggaatggaag gaggaggaag tgagcatagc gttggtgcgt     1320
tgctgtcatt gtcctaggtt agtagctagt gccagttact agtaagcatc aggcatagga     1380
gtatgtagta gaagcatgca cgttgccggc cagccaggct ttagacggga aaagaatttg     1440
gtgcagccgg ctgcaaaaca ggatgtttac agccccccac acaaaaaaaa aaagattgac     1500
cctacctgta acaataataa cacaactaaa atgttatttg atggatctac aagtgggata     1560
aatccttctt tttgtgaggt gctgcaaaca ttctggttca tcaattttt tcctttagac       1620 tccagctact gcatgcgt                                                    1638

<210> SEQ ID NO 63
<211> LENGTH: 1484
<212> TYPE: DNA
<213> ORGANISM: Zea mays

<400> SEQUENCE: 63
gtccgagcta ggtcacagaa gcgctcagga aggccgctga gatagaggca tggcggccaa       60
tgcgggcggc ggtggagcgg gaggaggcag cggcagcggc agcgtggctg cgccggcggt      120
gtgccgcccc agcggctcgc ggtggacgcc gacgccggag cagatcagga tgctgaagga      180
gctctactac ggctgcggca tccggtcgcc cagctcggag cagatccagc gcatcaccgc      240
catgctgcgg cagcacggca agatcgaggg caagaacgtc ttctactggt tccagaacca      300
caaggcccgc gagcgccaga agcgccgcct caccagcctc gacgtcaacg tgcccgccgc      360
cggcgcggcc gacgccacca ccagccaact cggcgtcctc tcgctgtcgt cgccgccgcc      420
ttcaggcgcg cgcctccct cgcccaccct cggcttctac gccgccggca atggcggcgg      480
atcggctgtg ctgctggaca cgagttccga ctggggcagc agcggcgctg ccatggccac      540
cgagacatgc ttcctgcagg tcggtgctgt agtacgttct tttcttgggc attgcgcgca     600
gtttcacgtt cgtacgtacg agttgatcgc cgcgtcgttc catccaccgg tatatataac     660
tgttaggtac ggcggtgcgc gcccgcagga ctacatgggc gtgacggaca cgggcagctc     720
gtcgcagtgg ccacgcttct cgtcgtcgga cacgataatg gcggcggccg cggcgcgggc     780
```

-continued

```
ggcgacgacg cgggcgcccg agacgctccc tctcttcccg acctgcggcg acgacggcgg     840
cagcggtagc agcagctact tgccgttctg gggtgccgcg tccacaactg ccggcgccac     900
ttcttccgtt gcgatccagc agcaacacca gctgcaggag cagtacagct tttacagcaa     960
cagcaacagc acccagctgg ccggcaccgg caaccaagac gtatcggcaa cagcagcagc    1020
agccgccgcc ctggagctga gcctcagctc atggtgctcc ccttaccctg ctgcagggag    1080
tatgtgagag caacgcgagc tgccactgct cttcacttat gtctctggaa tggaaggagg    1140
aggaagtgag catagcgttg gtgcgttgct gtcattgtcc taggttagta gctagtgcca    1200
gttactagta agcatcaggc ataggagtat gtagtagaag catgcacgtt gccggccagc    1260
caggctttag acgggaaaag aatttggtgc agccggctgc aaaacaggat gtttacagcc    1320
ccccacacaa aaaaaaaaag attgacccta cctgtaacaa taataacaca actaaaatgt    1380
tatttgatgg atctacaagt gggataaatc cttcttttg tgaggtgctg caaacattct    1440
ggttcatcaa ttttttcct ttagactcca gctactgcat gcgt                     1484
```

<210> SEQ ID NO 64
<211> LENGTH: 345
<212> TYPE: PRT
<213> ORGANISM: Zea mays

<400> SEQUENCE: 64

```
Met Ala Ala Asn Ala Gly Gly Gly Gly Ala Gly Gly Ser Gly Ser
 1               5                  10                  15

Gly Ser Val Ala Ala Pro Ala Val Cys Arg Pro Ser Gly Ser Arg Trp
            20                  25                  30

Thr Pro Thr Pro Glu Gln Ile Arg Met Leu Lys Glu Leu Tyr Tyr Gly
        35                  40                  45

Cys Gly Ile Arg Ser Pro Ser Ser Glu Gln Ile Gln Arg Ile Thr Ala
    50                  55                  60

Met Leu Arg Gln His Gly Lys Ile Glu Gly Lys Asn Val Phe Tyr Trp
65                  70                  75                  80

Phe Gln Asn His Lys Ala Arg Glu Arg Gln Lys Arg Arg Leu Thr Ser
                85                  90                  95

Leu Asp Val Asn Val Pro Ala Gly Ala Ala Asp Ala Thr Thr Ser
            100                 105                 110

Gln Leu Gly Val Leu Ser Leu Ser Pro Pro Ser Gly Ala Ala
        115                 120                 125

Pro Pro Ser Pro Thr Leu Gly Phe Tyr Ala Ala Gly Asn Gly Gly Gly
    130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Val Gly Ala Val Val Arg
                165                 170                 175

Ser Phe Leu Gly His Cys Ala Gln Phe His Val Arg Thr Tyr Glu Leu
            180                 185                 190

Ile Ala Ala Ser Phe His Pro Pro Val Tyr Ile Thr Val Arg Tyr Gly
        195                 200                 205

Gly Ala Arg Pro Gln Asp Tyr Met Gly Val Thr Asp Thr Gly Ser Ser
    210                 215                 220

Ser Gln Trp Pro Arg Phe Ser Ser Ser Asp Thr Ile Met Ala Ala Ala
225                 230                 235                 240

Ala Ala Arg Ala Ala Thr Thr Arg Ala Pro Glu Thr Leu Pro Leu Phe
                245                 250                 255
```

```
Pro Thr Cys Gly Asp Asp Gly Gly Ser Gly Ser Ser Ser Tyr Leu Pro
            260                 265                 270

Phe Trp Gly Ala Ala Ser Thr Thr Ala Gly Ala Thr Ser Ser Val Ala
        275                 280                 285

Ile Gln Gln Gln His Gln Leu Gln Glu Gln Tyr Ser Phe Tyr Ser Asn
    290                 295                 300

Ser Asn Ser Thr Gln Leu Ala Gly Thr Gly Asn Gln Asp Val Ser Ala
305                 310                 315                 320

Thr Ala Ala Ala Ala Ala Leu Glu Leu Ser Leu Ser Ser Trp Cys
                325                 330                 335

Ser Pro Tyr Pro Ala Ala Gly Ser Met
            340                 345

<210> SEQ ID NO 65
<211> LENGTH: 1355
<212> TYPE: DNA
<213> ORGANISM: Zea mays

<400> SEQUENCE: 65
```

| | | | | | |
|---|---|---|---|---|---|
| gtccgagcta | ggtcacagaa | gcgctcagga | aggccgctga | gatagaggca | tggcggccaa | 60 |
| tgcgggcggc | ggtggagcgg | gaggaggcag | cggcagcggc | agcgtggctg | cgccggcggt | 120 |
| gtgccgcccc | agcggctcgc | ggtggacgcc | gacgccggag | cagatcagga | tgctgaagga | 180 |
| gctctactac | ggctgcggca | tccggtcgcc | cagctcggag | cagatccagc | gcatcaccgc | 240 |
| catgctgcgg | cagcacggca | agatcgaggg | caagaacgtc | ttctactggt | tccagaacca | 300 |
| caaggcccgc | gagcgccaga | gcgccgcct | caccagcctc | gacgtcaacg | tgcccgccgc | 360 |
| cggcgcggcc | gacgccacca | ccagccaact | cggcgtcctc | tcgctgtcgt | cgccgccgcc | 420 |
| ttcaggcgcg | gcgcctccct | cgcccaccct | cggcttctac | gccgccggca | atggcggcgg | 480 |
| atcggctgtg | ctgctggaca | cgagttccga | ctggggcagc | agcggcgctg | ccatggccac | 540 |
| cgagacatgc | ttcctgcagg | actacatggg | cgtgacggac | acgggcagct | cgtcgcagtg | 600 |
| gccacgcttc | tcgtcgtcgg | acacgataat | ggcggcggcc | gcggcgcggg | cggcgacgac | 660 |
| gcgggcgccc | gagacgctcc | ctctcttccc | gacctgcggc | gacgacggcg | gcagcggtag | 720 |
| cagcagctac | ttgccgttct | ggggtgccgc | gtccacaact | gccggcgcca | cttcttccgt | 780 |
| tgcgatccag | cagcaacacc | agctgcagga | gcagtacagc | ttttacagca | acagcaacag | 840 |
| cacccagctg | gccggcaccg | gcaaccaaga | cgtatcggca | acagcagcag | cagccgccgc | 900 |
| cctggagctg | agcctcagct | catggtgctc | cccttaccct | gctgcaggga | gtatgtgaga | 960 |
| gcaacgcgag | ctgccactgc | tcttcactta | tgtctctgga | atggaaggag | gaggaagtga | 1020 |
| gcatagcgtt | ggtgcgttgc | tgtcattgtc | ctaggttagt | agctagtgcc | agttactagt | 1080 |
| aagcatcagg | cataggagta | tgtagtagaa | gcatgcacgt | tgccggccag | ccaggcttta | 1140 |
| gacgggaaaa | gaatttggtg | cagccggctg | caaaacagga | tgtttacagc | ccccacaca | 1200 |
| aaaaaaaaaa | gattgaccct | acctgtaaca | ataataacac | aactaaaatg | ttatttgatg | 1260 |
| gatctacaag | tgggataaat | ccttcttttt | gtgaggtgct | gcaaacattc | tggttcatca | 1320 |
| atttttttcc | tttagactcc | agctactgca | tgcgt | | | 1355 |

```
<210> SEQ ID NO 66
<211> LENGTH: 302
<212> TYPE: PRT
<213> ORGANISM: Zea mays
```

<400> SEQUENCE: 66

```
Met Ala Asn Ala Gly Gly Gly Ala Gly Gly Ser Gly Ser
  1               5                  10                  15
Gly Ser Val Ala Ala Pro Ala Val Cys Arg Pro Ser Gly Ser Arg Trp
             20                  25                  30
Thr Pro Thr Pro Glu Gln Ile Arg Met Leu Lys Glu Leu Tyr Tyr Gly
         35                  40                  45
Cys Gly Ile Arg Ser Pro Ser Ser Glu Gln Ile Gln Arg Ile Thr Ala
     50                  55                  60
Met Leu Arg Gln His Gly Lys Ile Glu Gly Lys Asn Val Phe Tyr Trp
 65                  70                  75                  80
Phe Gln Asn His Lys Ala Arg Glu Arg Gln Lys Arg Arg Leu Thr Ser
                 85                  90                  95
Leu Asp Val Asn Val Pro Ala Ala Gly Ala Ala Asp Ala Thr Thr Ser
            100                 105                 110
Gln Leu Gly Val Leu Ser Leu Ser Ser Pro Pro Ser Gly Ala Ala
        115                 120                 125
Pro Pro Ser Pro Thr Leu Gly Phe Tyr Ala Ala Gly Asn Gly Gly Gly
    130                 135                 140
Ser Ala Val Leu Leu Asp Thr Ser Ser Asp Trp Gly Ser Ser Gly Ala
145                 150                 155                 160
Ala Met Ala Thr Glu Thr Cys Phe Leu Gln Asp Tyr Met Gly Val Thr
                165                 170                 175
Asp Thr Gly Ser Ser Ser Gln Trp Pro Arg Phe Ser Ser Ser Asp Thr
            180                 185                 190
Ile Met Ala Ala Ala Ala Arg Ala Ala Thr Thr Arg Ala Pro Glu
        195                 200                 205
Thr Leu Pro Leu Phe Pro Thr Cys Gly Asp Asp Gly Gly Ser Gly Ser
    210                 215                 220
Ser Ser Tyr Leu Pro Phe Trp Gly Ala Ala Ser Thr Thr Ala Gly Ala
225                 230                 235                 240
Thr Ser Ser Val Ala Ile Gln Gln Gln His Gln Leu Gln Glu Gln Tyr
                245                 250                 255
Ser Phe Tyr Ser Asn Ser Asn Ser Thr Gln Leu Ala Gly Thr Gly Asn
            260                 265                 270
Gln Asp Val Ser Ala Thr Ala Ala Ala Ala Leu Glu Leu Ser
        275                 280                 285
Leu Ser Ser Trp Cys Ser Pro Tyr Pro Ala Ala Gly Ser Met
    290                 295                 300
```

<210> SEQ ID NO 67
<211> LENGTH: 1377
<212> TYPE: DNA
<213> ORGANISM: Zea mays

<400> SEQUENCE: 67

```
gtccgagcta ggtcacagaa gcgctcagga aggccgctga gatagaggca tggcggccaa      60
tgcgggcggc ggtggagcgg gaggaggcag cggcagcggc agcgtggctg cgccggcggt     120
gtgccgcccc agcggctcgc ggtggacgcc gacgccggag cagatcagga tgctgaagga     180
gctctactac ggctgcggca tccggtcgcc cagctcggag cagatccagc gcatcaccgc     240
catgctgcgg cagcacggca agatcgaggg caagaacgtc ttctactggt tccagaacca     300
caaggcccgc gagcgccaga agcgccgcct caccagcctc gacgtcaacg tgcccgccgc     360
```

-continued

```
cggcgcggcc gacgccacca ccagccaact cggcgtcctc tcgctgtcgt cgccgccgcc    420
ttcaggcgcg gcgcctccct cgcccaccct cggcttctac gccgcggca atggcggcgg     480 atcggctgtg ctgctggaca cgagttccga ctggggcagc agcggcgctg ccatggccac    540
cgagacatgc ttcctgcagg tacggcggtg cgcgcccgca ggactacatg ggcgtgacgg    600
acacgggcag ctcgtcgcag tggccacgct tctcgtcgtc ggacacgata atggcggcgg    660
ccgcggcgcg ggcggcgacg acgcgggcgc ccgagacgct ccctctcttc ccgacctgcg    720
gcgacgacgg cggcagcggt agcagcagct acttgccgtt ctgggtgcc gcgtccacaa     780 ctgccggcgc cacttcttcc gttgcgatcc agcagcaaca ccagctgcag gagcagtaca    840
gcttttacag caacagcaac agcacccagc tggccggcac cggcaaccaa gacgtatcgg    900
caacagcagc agcagccgcc gccctggagc tgagcctcag ctcatggtgc tccccttacc    960
ctgctgcagg gagtatgtga gagcaacgcg agctgccact gctcttcact tatgtctctg   1020
gaatggaagg aggaggaagt gagcatagcg ttggtgcgtt gctgtcattg tcctaggtta   1080
gtagctagtg ccagttacta gtaagcatca ggcataggag tatgtagtag aagcatgcac   1140
gttgccggcc agccaggctt tagacgggaa aagaatttgg tgcagccggc tgcaaaacag   1200
gatgtttaca gccccccaca caaaaaaaaa aagattgacc ctacctgtaa caataataac   1260
acaactaaaa tgttatttga tggatctaca agtgggataa atccttcttt ttgtgaggtg   1320
ctgcaaacat tctggttcat caatttttt cctttagact ccagctactg catgcgt       1377
```

<210> SEQ ID NO 68
<211> LENGTH: 230
<212> TYPE: PRT
<213> ORGANISM: Zea mays

<400> SEQUENCE: 68

```
Met Ala Ala Asn Ala Gly Gly Gly Ala Gly Gly Gly Ser Gly Ser
 1               5                  10                  15

Gly Ser Val Ala Ala Pro Ala Val Cys Arg Pro Ser Gly Ser Arg Trp
                20                  25                  30

Thr Pro Thr Pro Glu Gln Ile Arg Met Leu Lys Glu Leu Tyr Tyr Gly
             35                  40                  45

Cys Gly Ile Arg Ser Pro Ser Ser Glu Gln Ile Gln Arg Ile Thr Ala
         50                  55                  60

Met Leu Arg Gln His Gly Lys Ile Glu Gly Lys Asn Val Phe Tyr Trp
 65                  70                  75                  80

Phe Gln Asn His Lys Ala Arg Glu Arg Gln Lys Arg Arg Leu Thr Ser
                 85                  90                  95

Leu Asp Val Asn Val Pro Ala Ala Gly Ala Ala Asp Ala Thr Thr Ser
            100                 105                 110

Gln Leu Gly Val Leu Ser Leu Ser Pro Pro Ser Gly Ala Ala
        115                 120                 125

Pro Pro Ser Pro Thr Leu Gly Phe Tyr Ala Ala Gly Asn Gly Gly
    130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Val Arg Arg Cys Ala Pro
                165                 170                 175

Ala Gly Leu His Gly Arg Asp Gly His Gly Gln Leu Val Ala Val Ala
            180                 185                 190

Thr Leu Leu Val Val Gly His Asp Asn Gly Gly Gly Arg Gly Ala Gly
```

195                 200                 205
Gly Asp Asp Ala Gly Ala Arg Asp Ala Pro Ser Leu Pro Asp Leu Arg
    210                 215                 220

Arg Arg Arg Arg Gln Arg
225                 230

<210> SEQ ID NO 69
<211> LENGTH: 1479
<212> TYPE: DNA
<213> ORGANISM: Zea mays

<400> SEQUENCE: 69
gtccgagcta ggtcacagaa gcgctcagga aggccgctga gatagaggca tggcggccaa      60
tgcgggcggc ggtggagcgg gaggaggcag cggcagcggc agcgtggctg cgccggcggt     120
gtgccgcccc agcggctcgc ggtggacgcc gacgccggag cagatcagga tgctgaagga     180
gctctactac ggctgcggca tccggtcgcc cagctcggag cagatccagc gcatcaccgc     240
catgctgcgg cagcacggca agatcgaggg caagaacgtc ttctactggt tccagaacca     300
caaggcccgc gagcgccaga gcgccgcct caccagcctc gacgtcaacg tgcccgccgc     360
cggcgcggcc gacgccacca ccagccaact cggcgtcctc tcgctgtcgt cgccgccgcc     420
ttcaggtacg tgcgtcagtg cgtgtggtgt gtgggtagta tatatggtct ctccttgcat     480
tggcacgcca atcggccatc gatccaatca tatcatcgtc caaacgtata tagtacatgt     540
gactgcaaac tgatgtgcac cgtcgtcatc actgatcagg cgcggcgcct ccctcgccca     600
ccctcggctt ctacgccgcc ggcaatggcg gcggatcggc tgtgctgctg acacgagtt     660
ccgactgggg cagcagcggc gctgccatgg ccaccgagac atgcttcctg caggtcggtg     720
ctgtagtacg ttcttttctt gggcattgcg cgcagtttca cgttcgtacg tacgagttga     780
tcgccgcgtc gttccatcca ccggtatata taactgttag gtacggcggt gcgcgccccgc     840
aggactacat gggcgtgacg gacacgggca gctcgtcgca gtggccacgc ttctcgtcgt     900
cggacacgat aatggcggcg gccgcggcgc gggcggcgac gacgcgggcg cccgagacgc     960
tccctctctt cccgacctgc ggcgacgacg gcggcagcgg tagcagcagc tacttgccgt    1020
tctggggtgc cgcgtccaca actgccggcg ccacttcttc cgttgcgatc cagcagcaac    1080
accagctgca ggagcagtac agcttttaca gcaacagcaa cagcacccag ctggccggca    1140
ccggcaacca agacgtatcg caacagcag cagcagccgc cgccctggag ctgagcctca    1200
gctcatggtg ctccccttac cctgctgcag ggagtatgtg agagcaacgc gagctgccac    1260
tgctcttcac ttatgtctct ggaatggaag gaggaggaag tgagcatagc gttggtgcgt    1320
tgctgtcatt gtcctaggtt agtagctagt gccagttact agtaagcatc aggcatagga    1380
gtatgtagta gaagcatgca cgttgccggc cagccaggct ttagacggga aaagaatttg    1440
gtgcagccgg ctgcaaaaca ggatgtttac agccccccc                           1479

<210> SEQ ID NO 70
<211> LENGTH: 1325
<212> TYPE: DNA
<213> ORGANISM: Zea mays

<400> SEQUENCE: 70
gtccgagcta ggtcacagaa gcgctcagga aggccgctga gatagaggca tggcggccaa      60
tgcgggcggc ggtggagcgg gaggaggcag cggcagcggc agcgtggctg cgccggcggt     120
gtgccgcccc agcggctcgc ggtggacgcc gacgccggag cagatcagga tgctgaagga     180

-continued

```
gctctactac ggctgcggca tccggtcgcc cagctcggag cagatccagc gcatcaccgc    240
catgctgcgg cagcacggca agatcgaggg caagaacgtc ttctactggt tccagaacca    300
caaggcccgc gagcgccaga agcgccgcct caccagcctc gacgtcaacg tgcccgccgc    360
cggcgcggcc gacgccacca ccagccaact cggcgtcctc tcgctgtcgt cgccgccgcc    420
ttcaggcgcg cgcctccct cgcccaccct cggcttctac gccgccggca atggcggcgg    480
atcggctgtg ctgctggaca cgagttccga ctggggcagc agcggcgctg ccatggccac    540
cgagacatgc ttcctgcagg tcggtgctgt agtacgttct tttcttgggc attgcgcgca    600
gtttcacgtt cgtacgtacg agttgatcgc cgcgtcgttc catccaccgg tatatataac    660
tgttaggtac ggcggtgcgc gcccgcagga ctacatgggc gtgacggaca cgggcagctc    720
gtcgcagtgg ccacgcttct cgtcgtcgga cacgataatg gcggcggccg cggcgcgggc    780
ggcgacgacg cgggcgcccg agacgctccc tctcttcccg acctgcggcg acgacgcgg    840 cagcggtagc agcagctact tgccgttctg gggtgccgcg tccacaactg ccggcgccac    900
ttcttccgtt gcgatccagc agcaacacca gctgcaggag cagtacagct tttacagcaa    960
cagcaacagc acccagctgg ccggcaccgg caaccaagac gtatcggcaa cagcagcagc   1020
agccgccgcc ctggagctga gcctcagctc atggtgctcc ccttaccctg ctgcagggag   1080
tatgtgagag caacgcgagc tgccactgct cttcacttat gtctctggaa tggaaggagg   1140
aggaagtgag catagcgttg gtgcgttgct gtcattgtcc taggttagta gctagtgcca   1200
gttactagta agcatcaggc ataggagtat gtagtagaag catgcacgtt gccgccagc   1260 caggctttag acgggaaaag aatttggtgc agccggctgc aaaacaggat gtttacagcc   1320
ccccc                                                                1325
```

<210> SEQ ID NO 71
<211> LENGTH: 345
<212> TYPE: PRT
<213> ORGANISM: Zea mays

<400> SEQUENCE: 71

```
Met Ala Ala Asn Ala Gly Gly Gly Ala Gly Gly Ser Gly Ser
  1               5                  10                  15

Gly Ser Val Ala Ala Pro Ala Val Cys Arg Pro Ser Gly Ser Arg Trp
                 20                  25                  30

Thr Pro Thr Pro Glu Gln Ile Arg Met Leu Lys Glu Leu Tyr Tyr Gly
             35                  40                  45

Cys Gly Ile Arg Ser Pro Ser Ser Glu Gln Ile Gln Arg Ile Thr Ala
         50                  55                  60

Met Leu Arg Gln His Gly Lys Ile Glu Gly Lys Asn Val Phe Tyr Trp
 65                  70                  75                  80

Phe Gln Asn His Lys Ala Arg Glu Arg Gln Lys Arg Arg Leu Thr Ser
                 85                  90                  95

Leu Asp Val Asn Val Pro Ala Ala Gly Ala Ala Asp Ala Thr Thr Ser
            100                 105                 110

Gln Leu Gly Val Leu Ser Leu Ser Ser Pro Pro Ser Gly Ala Ala
            115                 120                 125

Pro Pro Ser Pro Thr Leu Gly Phe Tyr Ala Ala Gly Asn Gly Gly Gly
        130                 135                 140

Ser Ala Val Leu Leu Asp Thr Ser Ser Asp Trp Gly Ser Ser Gly Ala
145                 150                 155                 160
```

```
Ala Met Ala Thr Glu Thr Cys Phe Leu Gln Val Gly Ala Val Val Arg
                165                 170                 175

Ser Phe Leu Gly His Cys Ala Gln Phe His Val Arg Thr Tyr Glu Leu
            180                 185                 190

Ile Ala Ala Ser Phe His Pro Pro Val Tyr Ile Thr Val Arg Tyr Gly
        195                 200                 205

Gly Ala Arg Pro Gln Asp Tyr Met Gly Val Thr Asp Thr Gly Ser Ser
    210                 215                 220

Ser Gln Trp Pro Arg Phe Ser Ser Asp Thr Ile Met Ala Ala Ala
225                 230                 235                 240

Ala Ala Arg Ala Ala Thr Thr Arg Ala Pro Glu Thr Leu Pro Leu Phe
                245                 250                 255

Pro Thr Cys Gly Asp Asp Gly Gly Ser Gly Ser Ser Tyr Leu Pro
            260                 265                 270

Phe Trp Gly Ala Ala Ser Thr Thr Ala Gly Ala Thr Ser Ser Val Ala
        275                 280                 285

Ile Gln Gln Gln His Gln Leu Gln Glu Gln Tyr Ser Phe Tyr Ser Asn
    290                 295                 300

Ser Asn Ser Thr Gln Leu Ala Gly Thr Gly Asn Gln Asp Val Ser Ala
305                 310                 315                 320

Thr Ala Ala Ala Ala Ala Leu Glu Leu Ser Leu Ser Ser Trp Cys
                325                 330                 335

Ser Pro Tyr Pro Ala Ala Gly Ser Met
            340                 345

<210> SEQ ID NO 72
<211> LENGTH: 1196
<212> TYPE: DNA
<213> ORGANISM: Zea mays

<400> SEQUENCE: 72
gtccgagcta ggtcacagaa gcgctcagga aggccgctga gatagaggca tggcggccaa      60
tgcgggcggc ggtggagcgg gaggaggcag cggcagcggc agcgtggctg cgccggcggt     120
gtgccgcccc agcggctcgc ggtggacgcc gacgccggag cagatcagga tgctgaagga     180
gctctactac ggctgcggca tccggtcgcc cagctcggag cagatccagc gcatcaccgc     240
catgctgcgg cagcacggca agatcgaggg caagaacgtc ttctactggt ccagaaacca     300
caaggcccgc gagcgccaga gcgccgcct caccagcctc gacgtcaacg tgcccgccgc     360
cggcgcggcc gacgccacca ccagccaact cggcgtcctc tcgctgtcgt cgccgccgcc     420
ttcaggcgcg cgcctccct cgcccaccct cggcttctac gccgccggca atggcggcgg     480
atcggctgtg ctgctggaca cgagttccga ctggggcagc agcggcgctg ccatggccac     540
cgagacatgc ttcctgcagg actacatggg cgtgacggac acgggcagct cgtcgcagtg     600
gccacgcttc tcgtcgtcgg acacgataat ggcggcggcc gcggcgcggg cggcgacgac     660
gcgggcgccc gagacgctcc ctctcttccc gacctgcggc gacgacggcg gcagcggtag     720
cagcagctac ttgccgttct ggggtgccgc gtccacaact gccggcgcca cttcttccgt     780
tgcgatccag cagcaacacc agctgcagga gcagtacagc tttttacagca acagcaacag     840
cacccagctg gccggcaccg gcaaccaaga cgtatcggca acagcagcag cagccgccgc     900
cctggagctg agcctcagct catggtgctc cccttaccct gctgcaggga gtatgtgaga     960
gcaacgcgag ctgccactgc tcttcactta tgtctctgga atggaaggag gaggaagtga    1020
gcatagcgtt ggtgcgttgc tgtcattgtc ctaggttagt agctagtgcc agttactagt    1080
```

-continued aagcatcagg cataggagta tgtagtagaa gcatgcacgt tgccggccag ccaggcttta 1140
gacgggaaaa gaatttggtg cagccggctg caaaacagga tgtttacagc cccccc 1196

<210> SEQ ID NO 73
<211> LENGTH: 302
<212> TYPE: PRT
<213> ORGANISM: Zea mays

<400> SEQUENCE: 73

```
Met Ala Asn Ala Gly Gly Gly Ala Gly Gly Gly Ser Gly Ser
  1               5                  10                  15

Gly Ser Val Ala Ala Pro Ala Val Cys Arg Pro Ser Gly Ser Arg Trp
                 20                  25                  30

Thr Pro Thr Pro Glu Gln Ile Arg Met Leu Lys Glu Leu Tyr Tyr Gly
             35                  40                  45

Cys Gly Ile Arg Ser Pro Ser Ser Glu Gln Ile Gln Arg Ile Thr Ala
         50                  55                  60

Met Leu Arg Gln His Gly Lys Ile Glu Gly Lys Asn Val Phe Tyr Trp
 65                  70                  75                  80

Phe Gln Asn His Lys Ala Arg Glu Arg Gln Lys Arg Arg Leu Thr Ser
                 85                  90                  95

Leu Asp Val Asn Val Pro Ala Ala Gly Ala Ala Asp Ala Thr Thr Ser
            100                 105                 110

Gln Leu Gly Val Leu Ser Leu Ser Ser Pro Pro Ser Gly Ala Ala
            115                 120                 125

Pro Pro Ser Pro Thr Leu Gly Phe Tyr Ala Ala Gly Asn Gly Gly Gly
        130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Asp Tyr Met Gly Val Thr
                165                 170                 175

Asp Thr Gly Ser Ser Ser Gln Trp Pro Arg Phe Ser Ser Ser Asp Thr
            180                 185                 190

Ile Met Ala Ala Ala Ala Arg Ala Ala Thr Thr Arg Ala Pro Glu
        195                 200                 205

Thr Leu Pro Leu Phe Pro Thr Cys Gly Asp Asp Gly Gly Ser Gly Ser
    210                 215                 220

Ser Ser Tyr Leu Pro Phe Trp Gly Ala Ala Ser Thr Thr Ala Gly Ala
225                 230                 235                 240

Thr Ser Ser Val Ala Ile Gln Gln Gln His Gln Leu Gln Glu Gln Tyr
                245                 250                 255

Ser Phe Tyr Ser Asn Ser Asn Ser Thr Gln Leu Ala Gly Thr Gly Asn
            260                 265                 270

Gln Asp Val Ser Ala Thr Ala Ala Ala Ala Ala Leu Glu Leu Ser
        275                 280                 285

Leu Ser Ser Trp Cys Ser Pro Tyr Pro Ala Ala Gly Ser Met
    290                 295                 300
```

<210> SEQ ID NO 74
<211> LENGTH: 1218
<212> TYPE: DNA
<213> ORGANISM: Zea mays

<400> SEQUENCE: 74
gtccgagcta ggtcacagaa gcgctcagga aggccgctga gatagaggca tggcggccaa 60

-continued

```
tgcgggcggc ggtggagcgg gaggaggcag cggcagcggc agcgtggctg cgccggcggt    120
gtgccgcccc agcggctcgc ggtggacgcc gacgccggag cagatcagga tgctgaagga    180
gctctactac ggctgcggca tccggtcgcc cagctcggag cagatccagc gcatcaccgc    240
catgctgcgg cagcacggca agatcgaggg caagaacgtc ttctactggt tccagaacca    300
caaggcccgc gagcgccaga agcgccgcct caccagcctc gacgtcaacg tgcccgccgc    360
cggcgcggcc gacgccacca ccagccaact cggcgtcctc tcgctgtcgt cgccgccgcc    420
ttcaggcgcg gcgcctccct cgcccaccct cggcttctac gccgccggca atggcggcgg    480
atcggctgtg ctgctggaca cgagttccga ctggggcagc agcggcgctg ccatggccac    540
cgagacatgc ttcctgcagg tacgcggtg cgcgcccgca ggactacatg gcgtgacgg     600 acacgggcag ctcgtcgcag tggccacgct ctcgtcgtc ggacacgata atggcggcgg    660
ccgcggcgcg ggcggcgacg acgcgggcgc ccgagacgct ccctctcttc ccgacctgcg    720
gcgacgacgg cggcagcggt agcagcagct acttgccgtt ctggggtgcc gcgtccacaa    780
ctgccggcgc cacttcttcc gttgcgatcc agcagcaaca ccagctgcag gagcagtaca    840
gcttttacag caacagcaac agcacccagc tggccggcac cggcaaccaa gacgtatcgg    900
caacagcagc agcagccgcc gccctggagc tgagcctcag ctcatggtgc tccccttacc    960
ctgctgcagg gagtatgtga gagcaacgcg agctgccact gctcttcact tatgtctctg   1020
gaatggaagg aggaggaagt gagcatagcg ttggtgcgtt gctgtcattg tcctaggtta   1080
gtagctagtg ccagttacta gtaagcatca ggcataggaa tatgtagtag aagcatgcac   1140
gttgccggcc agccaggctt tagacgggaa aagaatttgg tgcagccggc tgcaaaacag   1200
gatgtttaca gccccccc                                                 1218
```

<210> SEQ ID NO 75
<211> LENGTH: 230
<212> TYPE: PRT
<213> ORGANISM: Zea mays

<400> SEQUENCE: 75

```
Met Ala Ala Asn Ala Gly Gly Gly Ala Gly Gly Ser Gly Ser
  1               5                  10                  15

Gly Ser Val Ala Ala Pro Ala Val Cys Arg Pro Ser Gly Ser Arg Trp
                 20                  25                  30

Thr Pro Thr Pro Glu Gln Ile Arg Met Leu Lys Glu Leu Tyr Tyr Gly
             35                  40                  45

Cys Gly Ile Arg Ser Pro Ser Ser Glu Gln Ile Gln Arg Ile Thr Ala
         50                  55                  60

Met Leu Arg Gln His Gly Lys Ile Glu Gly Lys Asn Val Phe Tyr Trp
 65                  70                  75                  80

Phe Gln Asn His Lys Ala Arg Glu Arg Gln Lys Arg Arg Leu Thr Ser
                 85                  90                  95

Leu Asp Val Asn Val Pro Ala Ala Gly Ala Ala Asp Ala Thr Thr Ser
            100                 105                 110

Gln Leu Gly Val Leu Ser Leu Ser Ser Pro Pro Ser Gly Ala Ala
            115                 120                 125

Pro Pro Ser Pro Thr Leu Gly Phe Tyr Ala Ala Gly Asn Gly Gly Gly
        130                 135                 140

Ser Ala Val Leu Leu Asp Thr Ser Ser Asp Trp Gly Ser Ser Gly Ala
145                 150                 155                 160
```

```
Ala Met Ala Thr Glu Thr Cys Phe Leu Gln Val Arg Arg Cys Ala Pro
            165                 170                 175
Ala Gly Leu His Gly Arg Asp Gly His Gly Gln Leu Val Ala Val Ala
        180                 185                 190
Thr Leu Leu Val Val Gly His Asp Asn Gly Gly Arg Gly Ala Gly
        195                 200                 205
Gly Asp Asp Ala Gly Ala Arg Asp Ala Pro Ser Leu Pro Asp Leu Arg
    210                 215                 220
Arg Arg Arg Arg Gln Arg
225                 230

<210> SEQ ID NO 76
<211> LENGTH: 2325
<212> TYPE: DNA
<213> ORGANISM: Zea mays

<400> SEQUENCE: 76
```

| | | | | |
|---|---|---|---|---|
| ctcccaagac ggcaaaagtt agcaacccca tatatatgta acgacatgca ttttttttct | 60 |
| ctcctcgcaa atatgtatta acctgttaaa aaatgtatta acactttttt cacagctagt | 120 |
| agctagccac gcttttactt gtggcagagc ttgtgcgcga ccaccgccaa tttatttccc | 180 |
| atggacagta gcaagcactg tggtgccgtt ggtcaaaaag gatcactgcg aagctctctg | 240 |
| gctgttttga tgtgcaccaa tttgtctcac gcacacgctg cctagctcgc tagccttctt | 300 |
| ttctctgtca gcccggccgc cttcattcat ctctcgttca ttactgcatg catatatgcg | 360 |
| ttgttgcttt cacatacgat cgaccattgg atcggcatcg gcatggctgg tggccatgct | 420 |
| ctcgtgccct agctaaccct agcagctagc tagctagctc tatataactg gaggatctac | 480 |
| caggccagct tcgtccatgc cagtgccatc ctcatcctat agcgaaccgc aaaggcatag | 540 |
| tcacatagac taggaacgca cggcattctg cagatcgatt tgagttgtgt gtgtgtgcgc | 600 |
| gtgcgtgtgt gggaggttgc acttaccaca cacacacata accaagctac ctagggtagg | 660 |
| cgttgaatcc gagcgctagc agtagcaata gcatcgtcgt cctccatgcc gcagacacct | 720 |
| tcgactcgct ggtgcccgac gccggagcag ctgatgatcc tggaggagat gtaccggagc | 780 |
| ggcgtgagga cgcccaacgc ggcggagatc cagcagatca cggcgcacct ggcctactac | 840 |
| ggccgcatcg agggcaagaa cgtcttctac tggttccaga accacaaggc ccgcgagcgc | 900 |
| cagcggctcc gccgtcgcct ctgcgcccgg caccagcagc agtacgcgca gcagcaggcc | 960 |
| accgcggcgg ccccggcttc gagccctaac agcagcgcca ccgttccgtc cctcgcagca | 1020 |
| ggtggcagca gcgccggtgt gcatccggcg gtgatgcagc tgcaccatca ccagcacccg | 1080 |
| tacgcaacca acttcatgcc acaccagctg gtaggcatga ttgcatgact tgtagttaat | 1140 |
| tttacatttg cttgctagcg catgcctgat aataatgtat ctatattatg tacatgcgtg | 1200 |
| ttcatcactt gattgtatac tagggctaca tgggacagca ggtggcgact gttccgccag | 1260 |
| tgctgaaccc agctgctgcc ggcatggtgg accttgcagc tgcaagagca ggaggaggaa | 1320 |
| ataaggctac tgctgcaggt agtggtgcct atggaggtgg agctgggtta tacaacagct | 1380 |
| gcagcagcaa tcagctggag gagtgggagg ccacagatgc aatggagcac tgcgacgcca | 1440 |
| gctgcggtgc ggcatcgggc agctctgacg agggtggcgc gctccagctg ccgccatgct | 1500 |
| gccgccgtcc tctaaagacc ttggacctct tccccactaa gagcactgga ctcaaggacg | 1560 |
| agtgcagcag ctccaagtcc tcctcttgct ccacatccac caactaatta atcgttatta | 1620 |
| ccaaatcgct ctagtttcta catatattgc ttctagtagt tcttcgattt gctggctagc | 1680 |

-continued

```
tagtagctag attcgatcat ctcaagtgtg ccattatatt gttgtgttgt gtttgtgtgt    1740
gacgctacct gttttcattt gttataataa ctacgtttaa gttcagtac tcgaactcaa     1800 tctatgtata tctatcctgg tgtaatggat ttattgtttt atcacactgc aatttacact    1860
cgatcacgga agggatgact tagtgctaca tataatttga cttcttccct cttctatagt    1920
gatgcttcca ttatggagtt aatcaagtca agtatctatc ttgccctata gttaattgca    1980
ttgtgaaggc aaagaactta cctcattgtc ccaaactctt catgcaactt aatgataagc    2040
atccgcaaga cagtatttta agagtgtatg tgaataaacc ccacgacgac aacatttcaa    2100
aatgaaaaaa acacatgcca cttgcatggg atttctcacc attctttgga attaaaacgc    2160 cttgtctttta ttatattaaa tyatcagttt caacggtcgc cccgcgtcat ttttttttaca   2220 aagaacctct tgtattttc aaattcaacc cgcggtctca gatcatatca ctatcatatt    2280
tgttcgcaca tcagcatttt cgtagtttca ctctagcaac aaaac                    2325
```

<210> SEQ ID NO 77
<211> LENGTH: 2212
<212> TYPE: DNA
<213> ORGANISM: Zea mays

<400> SEQUENCE: 77

```
ctcccaagac ggcaaaagtt agcaacccca tatatatgta acgacatgca tttttttct     60 ctcctcgcaa atatgtatta acctgttaaa aaatgtatta acacttttt cacagctagt    120 agctagccac gcttttactt gtggcagagc ttgtgcgcga ccaccgccaa tttatttccc    180
atggacagta gcaagcactg tggtgccgtt ggtcaaaaag gatcactgcg aagctctctg    240
gctgttttga tgtgcaccaa tttgtctcac gcacacgctg cctagctcgc tagccttctt    300
ttctctgtca gcccggccgc cttcattcat ctctcgttca ttactgcatg catatatgcg    360
ttgttgcttt cacatacgat cgaccattgg atcggcatcg gcatggctgg tggccatgct    420
ctcgtgccct agctaaccct agcagctagc tagctagctc tatataactg gaggatctac    480
caggccagct tcgtccatgc cagtgccatc ctcatcctat agcgaaccgc aaaggcatag    540
tcacatagac taggaacgca cggcattctg cagatcgatt tgagttgtgt gtgtgtgcgc    600
gtgcgtgtgt gggaggttgc acttaccaca cacacacata accaagctac ctagggtagg    660
cgttgaatcc gagcgctagc agtagcaata gcatcgtcgt cctccatgcc gcagacacct    720
tcgactcgct ggtgcccgac gccggagcag ctgatgatcc tggaggagat gtaccggagc    780
ggcgtgagga cgcccaacgc ggcggagatc cagcagatca cggcgcacct ggcctactac    840
ggccgcatcg agggcaagaa cgtcttctac tggttccaga accacaaggc ccgcgagcgc    900
cagcggctcc gccgtcgcct ctgcgcccgg caccagcagc agtacgcgca gcagcaggcc    960
accgcggcgg ccccggcttc gagccctaac agcagcgcca ccgttccgtc cctcgcagca   1020
ggtggcagca gcgccggtgt gcatccggcg gtgatgcagc tgcaccatca ccagcacccg   1080
tacgcaacca acttcatgcc acaccagctg ggctacatgg acagcaggt ggcgactgtt    1140 ccgccagtgc tgaacccagc tgctgccggc atggtgacc ttgcagctgc aagagcagga    1200
ggaggaaata aggctactgc tgcaggtagt ggtgcctatg gaggtggagc tgggttatac   1260
aacagctgca gcagcaatca gctggaggag tgggaggcca cagatgcaat ggagcactgc    1320
gacgccagct gcggtgcggc atcgggcagc tctgacgagg gtggcgcgct ccagctgccg    1380
ccatgctgcc gccgtcctct aaagaccttg gacctcttcc ccactaagag cactggactc    1440
aaggacgagt gcagcagctc caagtcctcc tcttgctcca catccaccaa ctaattaatc    1500
```

-continued

```
gttattacca aatcgctcta gtttctacat atattgcttc tagtagttct tcgatttgct    1560
ggctagctag tagctagatt cgatcatctc aagtgtgcca ttatattgtt gtgttgtgtt    1620
tgtgtgtgac gctacctgtt ttcatttgtt ataataacta cgtttaagtt tcagtactcg    1680
aactcaatct atgtatatct atcctggtgt aatggattta ttgttttatc acactgcaat    1740
ttacactcga tcacggaagg gatgacttag tgctacatat aatttgactt cttccctctt    1800
ctatagtgat gcttccatta tggagttaat caagtcaagt atctatcttg ccctatagtt    1860
aattgcattg tgaaggcaaa gaacttacct cattgtccca aactcttcat gcaacttaat    1920
gataagcatc cgcaagacag tattttaaga gtgtatgtga ataaaccccs cgacgacaac    1980
atttcaaaat gaaaaaaaca catgccactt gcatgggatt tctcaccatt ctttggaatt    2040
aaaacgcctt gtctttatta tattaaatya tcagtttcaa cggtcgcccc gcgtcatttt    2100
ttttacaaag aacctcttgt atttttcaaa ttcaacccgc ggtctcagat catatcacta    2160
tcatatttgt tcgcacatca gcattttcgt agtttcactc tagcaacaaa ac            2212
```

<210> SEQ ID NO 78
<211> LENGTH: 262
<212> TYPE: PRT
<213> ORGANISM: Zea mays

<400> SEQUENCE: 78

```
Met Pro Gln Thr Pro Ser Thr Arg Trp Cys Pro Thr Pro Glu Gln Leu
1               5                   10                  15

Met Ile Leu Glu Glu Met Tyr Arg Ser Gly Val Arg Thr Pro Asn Ala
            20                  25                  30

Ala Glu Ile Gln Gln Ile Thr Ala His Leu Ala Tyr Tyr Gly Arg Ile
        35                  40                  45

Glu Gly Lys Asn Val Phe Tyr Trp Phe Gln Asn His Lys Ala Arg Glu
    50                  55                  60

Arg Gln Arg Leu Arg Arg Arg Leu Cys Ala Arg His Gln Gln Gln Tyr
65                  70                  75                  80

Ala Gln Gln Gln Ala Thr Ala Ala Ala Pro Ala Ser Ser Pro Asn Ser
                85                  90                  95

Ser Ala Thr Val Pro Ser Leu Ala Gly Gly Ser Ser Ala Gly Val
            100                 105                 110

His Pro Ala Val Met Gln Leu His His Gln His Pro Tyr Ala Thr
        115                 120                 125

Asn Phe Met Pro His Gln Leu Gly Tyr Met Gly Gln Gln Val Ala Thr
    130                 135                 140

Val Pro Pro Val Leu Asn Pro Ala Ala Gly Met Val Asp Leu Ala
145                 150                 155                 160

Ala Ala Arg Ala Gly Gly Gly Asn Lys Ala Thr Ala Ala Gly Ser Gly
                165                 170                 175

Ala Tyr Gly Gly Gly Ala Gly Leu Tyr Asn Ser Cys Ser Ser Asn Gln
            180                 185                 190

Leu Glu Glu Trp Glu Ala Thr Asp Ala Met Glu His Cys Asp Ala Ser
        195                 200                 205

Cys Gly Ala Ala Ser Gly Ser Ser Asp Glu Gly Ala Leu Gln Leu
    210                 215                 220

Pro Pro Cys Cys Arg Arg Pro Leu Lys Thr Leu Asp Leu Phe Pro Thr
225                 230                 235                 240

Lys Ser Thr Gly Leu Lys Asp Glu Cys Ser Ser Ser Lys Ser Ser Ser
```

```
                245                 250                 255
Cys Ser Thr Ser Thr Asn
            260

<210> SEQ ID NO 79
<211> LENGTH: 1567
<212> TYPE: DNA
<213> ORGANISM: Zea mays

<400> SEQUENCE: 79
atggtcgtct cggtcgatcg cacaacactc aaaccctcgc tacggctacg tacagcaccg      60
gccttcttag ctttctttct ccagcgatcg atcgtctccg gccggccggc cggtctcccc     120
atatataaac tcgcgaggac gctcgatccc ttctcgtcta gtagtcgtta gcatagccct     180
agccctcagc tttccgtttt tacatatagt acgcactctc tcgctcgatc cgctacatcg     240
gtcgcgcgcc tagctctaca aagtttgaag ctttgtagct ctacatctac agagttcatt     300
agcatgaggc ttcaccattt ccatgtggct tacttggata aagcggcagg ctcgccgccg     360
ccgtcgtcgt caccaccatc catctcacca gcatctcaca gtcacagctc gtcgtctgct     420
gccaccatcg tccctctggc cctccagcaa tactgtctac gcccgcttgc gcccaagatc     480
tccttccctg aggcgaggaa gatggtcgtc cttcctgagt cgctcgcgt caggaatgct     540 tcttcgaggc tgctaaactg cacggttagg ctataaacca agagagagc ccatgtacta     600 gctagctagg aggacagtag tagaaacaca tatctctagc atgcatggtg tacgtacgta     660
tctcttaatt ttcattgtat caaagctgca ggtgcaagtg ccgccgacga cgacgacggt     720
gggtggcacg acgcggtgga acccgtcgcc ggaccagata agggtgctgg agatgctgta     780
ccgcgggggg atgcgcacgc ccaactcgtt ccagatcgag cagatcacgg aggagctcgg     840
caagtacggc cggatcgagg caagaacgt cttctactgg ttccagaacc acaaggcccg     900
cgagcgccag aagcagaagc gagctgccct cctcaccctc agcaccacca ccactgcttc     960
cacgctgcta ccaccagctg ctgaaaccaa ggtatataac tatatatgca ttgcagcagc    1020
ttgcgttatg tatatatgca ttgcatgcat aaatttaaat gcagtgaaca gctagcagta    1080
tcatcatatg tacgtacgta tgcatgcatg caggagggag tggagacgaa aaagaagaa    1140 gcgtgtgaag atgcatcgag ccgcaagcgg aggtgcaggg cctgggaaga tgtcgtcgtc    1200
catggtggcg gcgacgatgc cggtacggag gtagctgacg actactacac cgacgacgat    1260
gtgaccctgg agctcttccc gctgcgtcct gatcagggga aataaagcta gctagcagc    1320 tagctaacta attaagtaag gcggacaagc gtacgtatat gcgtaaagta tatgcccgat    1380
ccatgtctat gtcctctcgg tcgttccatg catgcatgtt ccctggatc gggctgctgt    1440 tcgtgcgaac actaaacact ttggtcattg gcgcgttgca tccacgtgtg tgctttgtat    1500
ggtaatagtg tggactaatg gacatgcttg gattgctcaa acgtacgctt ctagtgacag    1560
tgagtgg                                                              1567

<210> SEQ ID NO 80
<211> LENGTH: 1318
<212> TYPE: DNA
<213> ORGANISM: Zea mays

<400> SEQUENCE: 80
atggtcgtct cggtcgatcg cacaacactc aaaccctcgc tacggctacg tacagcaccg      60
gccttcttag ctttctttct ccagcgatcg atcgtctccg gccggccggc cggtctcccc     120
```

-continued

| | |
|---|---|
| atatataaac tcgcgaggac gctcgatccc ttctcgtcta gtagtcgtta gcatagccct | 180 |
| agccctcagc tttccgtttt tacatatagt acgcactctc tcgctcgatc cgctacatcg | 240 |
| gtcgcgcgcc tagctctaca aagtttgaag ctttgtagct ctacatctac agagttcatt | 300 |
| agcatgaggc ttcaccattt ccatgtggct tacttggata aagcggcagg ctcgccgccg | 360 |
| ccgtcgtcgt caccaccatc catctcacca gcatctcaca gtcacagctc gtcgtctgct | 420 |
| gccaccatcg tccctctggc cctccagcaa tactgtctac gcccgcttgc gcccaagatc | 480 |
| tccttccctg aggcgaggaa gatggtcgtc cttcctgagt tcgctcgcgt caggaatgct | 540 |
| tcttcgaggc tgctaaactg cacggtgcaa gtgccgccga cgacgacgac ggtgggtggc | 600 |
| acgacgcggt ggaacccgtc gccggaccag ataagggtgc tggagatgct gtaccgcggg | 660 |
| gggatgcgca cgcccaactc gttccagatc gagcagatca cggaggagct cggcaagtac | 720 |
| ggccggatcg agggcaagaa cgtcttctac tggttccaga accacaaggc ccgcgagcgc | 780 |
| cagaagcaga agcgagctgc cctcctcacc ctcagcacca ccaccactgc ttccacgctg | 840 |
| ctaccaccag ctgctgaaac caaggaggga gtggagacga aaaagaaga agcgtgtgaa | 900 |
| gatgcatcga gccgcaagcg gaggtgcagg gcctgggaag atgtcgtcgt ccatggtggc | 960 |
| ggcgacgatg ccggtacgga ggtagctgac gactactaca ccgacgacga tgtgaccctg | 1020 |
| gagctcttcc cgctgcgtcc tgatcagggg aaataaagct agctagctag ctagctaact | 1080 |
| aattaagtaa ggcggacaag cgtacgtata tgcgtaaagt atatgcccga tccatgtcta | 1140 |
| tgtcctctcg gtcgttccat gcatgcatgt tcccctggat cgggctgctg ttcgtgcgaa | 1200 |
| cactaaacac tttggtcatt ggcgcgttgc atccacgtgt gtgctttgta tggtaatagt | 1260 |
| gtggactaat ggacatgctt ggattgctca aacgtacgct tctagtgaca gtgagtgg | 1318 |

<210> SEQ ID NO 81
<211> LENGTH: 250
<212> TYPE: PRT
<213> ORGANISM: Zea mays

<400> SEQUENCE: 81

Met Arg Leu His His Phe His Val Ala Tyr Leu Asp Lys Ala Ala Gly
1               5                   10                  15

Ser Pro Pro Ser Ser Ser Pro Ser Ile Ser Pro Ala Ser His
            20                  25                  30

Ser His Ser Ser Ser Ala Ala Thr Ile Val Pro Leu Ala Leu Gln
        35                  40                  45

Gln Tyr Cys Leu Arg Pro Leu Ala Pro Lys Ile Ser Phe Pro Glu Ala
    50                  55                  60

Arg Lys Met Val Val Leu Pro Glu Phe Ala Arg Val Arg Asn Ala Ser
65                  70                  75                  80

Ser Arg Leu Leu Asn Cys Thr Val Gln Val Pro Pro Thr Thr Thr Thr
                85                  90                  95

Val Gly Gly Thr Thr Arg Trp Asn Pro Ser Pro Asp Gln Ile Arg Val
            100                 105                 110

Leu Glu Met Leu Tyr Arg Gly Gly Met Arg Thr Pro Asn Ser Phe Gln
        115                 120                 125

Ile Glu Gln Ile Thr Glu Glu Leu Gly Lys Tyr Gly Arg Ile Glu Gly
    130                 135                 140

Lys Asn Val Phe Tyr Trp Phe Gln Asn His Lys Ala Arg Glu Arg Gln
145                 150                 155                 160

Lys Gln Lys Arg Ala Ala Leu Leu Thr Leu Ser Thr Thr Thr Thr Ala

```
              165                 170                 175
Ser Thr Leu Leu Pro Pro Ala Ala Glu Thr Lys Glu Gly Val Glu Thr
            180                 185                 190

Lys Lys Glu Glu Ala Cys Glu Asp Ala Ser Ser Arg Lys Arg Arg Cys
            195                 200                 205

Arg Ala Trp Glu Asp Val Val Val His Gly Gly Gly Asp Asp Ala Gly
            210                 215                 220

Thr Glu Val Ala Asp Asp Tyr Tyr Thr Asp Asp Val Thr Leu Glu
225                 230                 235                 240

Leu Phe Pro Leu Arg Pro Asp Gln Gly Lys
                245                 250

<210> SEQ ID NO 82
<211> LENGTH: 28
<212> TYPE: DNA
<213> ORGANISM: Artificial Sequence
<220> FEATURE:
<223> OTHER INFORMATION: PCR primer 65505 directed to WUS

<400> SEQUENCE: 82
gtccgagcta ggtcacagaa gcgctcag                                        28

<210> SEQ ID NO 83
<211> LENGTH: 25
<212> TYPE: DNA
<213> ORGANISM: Artificial Sequence
<220> FEATURE:
<223> OTHER INFORMATION: PCR primer 65506 directed to WUS

<400> SEQUENCE: 83
tatcgtgtcc gacgacgcga agcgt                                           25

<210> SEQ ID NO 84
<211> LENGTH: 19
<212> TYPE: DNA
<213> ORGANISM: Artificial Sequence
<220> FEATURE:
<223> OTHER INFORMATION: PCR primer 66571 directed to WUS

<400> SEQUENCE: 84
ccaccctcgg cttctacgc                                                  19

<210> SEQ ID NO 85
<211> LENGTH: 27
<212> TYPE: DNA
<213> ORGANISM: Artificial Sequence
<220> FEATURE:
<223> OTHER INFORMATION: PCR primer 65507 directed to WUS

<400> SEQUENCE: 85
accccagaac ggcaagtagc tgctgct                                         27

<210> SEQ ID NO 86
<211> LENGTH: 15
<212> TYPE: DNA
<213> ORGANISM: Artificial Sequence
<220> FEATURE:
<223> OTHER INFORMATION: PCR primer 66577 directed to WUS

<400> SEQUENCE: 86
gcattgcgcg cagtt                                                      15

<210> SEQ ID NO 87
```

```
<211> LENGTH: 24
<212> TYPE: DNA
<213> ORGANISM: Artificial Sequence
<220> FEATURE:
<223> OTHER INFORMATION: PCR primer 67447 directed to WUS

<400> SEQUENCE: 87
acgcatgcag tagctggagt ctaa                                              24

<210> SEQ ID NO 88
<211> LENGTH: 343
<212> TYPE: PRT
<213> ORGANISM: Artificial Sequence
<220> FEATURE:
<223> OTHER INFORMATION: Consensus Sequence WUS2, 1st intron spliced

<400> SEQUENCE: 88
```

Met Ala Ala Asn Ala Gly Gly Gly Ala Gly Gly Ser Gly Ser
 1               5                  10                  15

Val Ala Ala Pro Ala Val Cys Arg Pro Ser Gly Ser Arg Trp Thr Pro
            20                  25                  30

Thr Pro Glu Gln Ile Arg Met Leu Lys Glu Leu Tyr Tyr Gly Cys Gly
        35                  40                  45

Ile Arg Ser Pro Ser Ser Glu Gln Ile Gln Arg Ile Thr Ala Met Leu
    50                  55                  60

Arg Gln His Gly Lys Ile Glu Gly Lys Asn Val Phe Tyr Trp Phe Gln
65                  70                  75                  80

Asn His Lys Ala Arg Glu Arg Gln Lys Arg Arg Leu Thr Ser Leu Asp
                85                  90                  95

Val Asn Val Pro Ala Ala Gly Ala Ala Asp Ala Thr Thr Ser Gln Leu
            100                 105                 110

Gly Val Leu Ser Leu Ser Ser Pro Pro Ser Gly Ala Ala Pro Pro
        115                 120                 125

Ser Pro Thr Leu Gly Phe Tyr Ala Ala Gly Asn Gly Gly Ser Ala
    130                 135                 140

Val Leu Leu Asp Thr Ser Ser Asp Trp Gly Ser Ser Gly Ala Ala Met
145                 150                 155                 160

Ala Thr Glu Thr Cys Phe Leu Gln Val Gly Ala Val Arg Ser Phe
                165                 170                 175

Leu Gly His Cys Ala Gln Phe His Val Arg Thr Tyr Glu Leu Ile Ala
            180                 185                 190

Ala Ser Phe His Pro Val Tyr Ile Thr Val Arg Tyr Gly Gly Ala
        195                 200                 205

Arg Pro Gln Asp Tyr Met Gly Val Thr Asp Thr Gly Ser Ser Ser Gln
    210                 215                 220

Trp Pro Arg Phe Ser Ser Ser Asp Thr Ile Met Ala Ala Ala Ala
225                 230                 235                 240

Arg Ala Ala Thr Thr Arg Ala Pro Glu Thr Leu Pro Leu Phe Pro Thr
                245                 250                 255

Cys Gly Asp Asp Gly Gly Ser Gly Ser Ser Ser Tyr Leu Pro Phe Trp
            260                 265                 270

Gly Ala Ala Ser Thr Thr Ala Gly Ala Thr Ser Ser Val Ala Ile Gln
        275                 280                 285

Gln Gln His Gln Leu Gln Glu Gln Tyr Ser Phe Tyr Ser Asn Ser Asn
    290                 295                 300

Ser Thr Gln Leu Ala Gly Thr Gly Asn Gln Asp Val Ser Ala Thr Ala
305                 310                 315                 320

```
Ala Ala Ala Ala Ala Leu Glu Leu Ser Leu Ser Ser Trp Cys Ser Pro
                325                 330                 335

Tyr Pro Ala Ala Gly Ser Met
            340

<210> SEQ ID NO 89
<211> LENGTH: 300
<212> TYPE: PRT
<213> ORGANISM: Artificial Sequence
<220> FEATURE:
<223> OTHER INFORMATION: Consensus Sequence WUS2, 1st & 2nd complete
      intron spliced

<400> SEQUENCE: 89

Met Ala Ala Asn Ala Gly Gly Gly Ala Gly Gly Gly Ser Gly Ser
 1               5                  10                  15

Val Ala Ala Pro Ala Val Cys Arg Pro Ser Gly Ser Arg Trp Thr Pro
                20                  25                  30

Thr Pro Glu Gln Ile Arg Met Leu Lys Glu Leu Tyr Tyr Gly Cys Gly
            35                  40                  45

Ile Arg Ser Pro Ser Ser Glu Gln Ile Gln Arg Ile Thr Ala Met Leu
     50                  55                  60

Arg Gln His Gly Lys Ile Glu Gly Lys Asn Val Phe Tyr Trp Phe Gln
 65              70                  75                  80

Asn His Lys Ala Arg Glu Arg Gln Lys Arg Arg Leu Thr Ser Leu Asp
                85                  90                  95

Val Asn Val Pro Ala Ala Gly Ala Ala Asp Ala Thr Thr Ser Gln Leu
            100                 105                 110

Gly Val Leu Ser Leu Ser Ser Pro Pro Ser Gly Ala Ala Pro Pro
        115                 120                 125

Ser Pro Thr Leu Gly Phe Tyr Ala Ala Gly Asn Gly Gly Ser Ala
    130                 135                 140

Val Leu Leu Asp Thr Ser Ser Asp Trp Gly Ser Ser Gly Ala Ala Met
145                 150                 155                 160

Ala Thr Glu Thr Cys Phe Leu Gln Asp Tyr Met Gly Val Thr Asp Thr
                165                 170                 175

Gly Ser Ser Ser Gln Trp Pro Arg Phe Ser Ser Ser Asp Thr Ile Met
            180                 185                 190

Ala Ala Ala Ala Ala Arg Ala Ala Thr Thr Arg Ala Pro Glu Thr Leu
        195                 200                 205

Pro Leu Phe Pro Thr Cys Gly Asp Asp Gly Gly Ser Gly Ser Ser Ser
    210                 215                 220

Tyr Leu Pro Phe Trp Gly Ala Ala Ser Thr Thr Ala Gly Ala Thr Ser
225                 230                 235                 240

Ser Val Ala Ile Gln Gln Gln His Gln Leu Gln Glu Gln Tyr Ser Phe
                245                 250                 255

Tyr Ser Asn Ser Asn Ser Thr Gln Leu Ala Gly Thr Gly Asn Gln Asp
            260                 265                 270

Val Ser Ala Thr Ala Ala Ala Ala Ala Leu Glu Leu Ser Leu Ser
        275                 280                 285

Ser Trp Cys Ser Pro Tyr Pro Ala Ala Gly Ser Met
    290                 295                 300

<210> SEQ ID NO 90
<211> LENGTH: 228
<212> TYPE: PRT
```

<213> ORGANISM: Artificial Sequence
<220> FEATURE:
<223> OTHER INFORMATION: Consensus Sequence WUS2, 1st & 2nd alternate intron spliced

<400> SEQUENCE: 90

```
Met Ala Ala Asn Ala Gly Gly Gly Ala Gly Gly Ser Gly Ser
1               5                   10                  15

Val Ala Ala Pro Ala Val Cys Arg Pro Ser Gly Ser Arg Trp Thr Pro
                20                  25                  30

Thr Pro Glu Gln Ile Arg Met Leu Lys Glu Leu Tyr Tyr Gly Cys Gly
            35                  40                  45

Ile Arg Ser Pro Ser Ser Glu Gln Ile Gln Arg Ile Thr Ala Met Leu
    50                  55                  60

Arg Gln His Gly Lys Ile Glu Gly Lys Asn Val Phe Tyr Trp Phe Gln
65                  70                  75                  80

Asn His Lys Ala Arg Glu Arg Gln Lys Arg Arg Leu Thr Ser Leu Asp
                85                  90                  95

Val Asn Val Pro Ala Ala Gly Ala Ala Asp Ala Thr Thr Ser Gln Leu
            100                 105                 110

Gly Val Leu Ser Leu Ser Ser Pro Pro Ser Gly Ala Ala Pro Pro
        115                 120                 125

Ser Pro Thr Leu Gly Phe Tyr Ala Ala Gly Asn Gly Gly Gly Ser Ala
    130                 135                 140

Val Leu Leu Asp Thr Ser Ser Asp Trp Gly Ser Ser Gly Ala Ala Met
145                 150                 155                 160

Ala Thr Glu Thr Cys Phe Leu Gln Val Arg Arg Cys Ala Pro Ala Gly
                165                 170                 175

Leu His Gly Arg Asp Gly His Gly Gln Leu Val Ala Val Ala Thr Leu
            180                 185                 190

Leu Val Val Gly His Asp Asn Gly Gly Arg Gly Ala Gly Gly Asp
        195                 200                 205

Asp Ala Gly Ala Arg Asp Ala Pro Ser Leu Pro Asp Leu Arg Arg Arg
    210                 215                 220

Arg Arg Gln Arg
225
```

<210> SEQ ID NO 91
<211> LENGTH: 25
<212> TYPE: PRT
<213> ORGANISM: Artificial Sequence
<220> FEATURE:
<223> OTHER INFORMATION: 25 amino acid sequence motif
<220> FEATURE:
<221> NAME/KEY: VARIANT
<222> LOCATION: (4)...(4)
<223> OTHER INFORMATION: Xaa = Pro(P) or Ser(S)
<220> FEATURE:
<221> NAME/KEY: VARIANT
<222> LOCATION: (17)...(17)
<223> OTHER INFORMATION: Xaa = Thr(T) or Pro(P)
<220> FEATURE:
<221> NAME/KEY: VARIANT
<222> LOCATION: (20)...(20)
<223> OTHER INFORMATION: Xaa = Gly(G) or Val(V)
<220> FEATURE:
<221> NAME/KEY: VARIANT
<222> LOCATION: (24)...(24)
<223> OTHER INFORMATION: Xaa = Ser(S) or Gly(G)

```
<400> SEQUENCE: 91

Gln Pro Pro Xaa Arg Pro Arg His Ala Val Pro Val Pro Ala Gly Glu
1               5                   10                  15

Xaa Ile Arg Xaa Gly Gly Gly Xaa Ser
            20              25
```

WUSCHEL (WUS) GENE HOMOLOGS

This application is a Continuation-In-Part of U.S. application Ser. No. 09/807,946, filed Apr. 20, 2001, pending, which is a national application that claims the benefit of PCT International Application No. PCT/US00/26648, filed Sep. 28, 2000, which in turn claims the benefit of U.S. Provisional Application No. 60/157,216, filed Oct. 1, 1999. The entire contents of the above applications are herein incorporated by reference.

FIELD OF THE INVENTION

This invention is in the field of plant molecular biology. More specifically, this invention pertains to nucleic acid fragments encoding Wuschel (WUS) proteins in plants and seeds.

BACKGROUND OF THE INVENTION

Organ formation in plants occurs via the activity of apical meristems. Plant meristems contain a pool of stem cells, which are able to self-maintain, and give rise to a variety of cell types including cells required for organ initiation. The initiation and maintenance of stem cells and their integration into organ-forming meristems are thus the basis for continuous plant development.

The Wuschel protein, designated hereafter as WUS, plays a key role in the initiation and maintenance of the apical meristem, which contains a pool of pluripotent stem cells (Endrizzi et al., 1996, Plant Journal 10:967-979; Laux et al., 1996, Development 122:87-96; and Mayer et al., 1998, Cell 95:805-815). *Arabidopsis* plants mutant for the WUS gene contain stem cells that are misspecified and that appear to undergo differentiation. WUS encodes a novel homeodomain protein, which presumably functions as a transcriptional regulator (Mayer et al., 1998, Cell 95:805-815). The stem cell population of Arabidopsis shoot meristems is believed to be maintained by a regulatory loop between the CLAVATA (CLV) genes which promote organ initiation and the WUS gene which is required for stem cell identity, with the CLV genes repressing WUS at the transcript level, and WUS expression being sufficient to induce meristem cell identity and the expression of the stem cell marker CLV3 (Brand et al. (2000) Science 289:617-619; Schoof et al. (2000) Cell 100:635-644). Constitutive expression of WUS in *Arabidopsis* has been recently shown to lead to adventitious shoot proliferation from leaves (in planta) (Laux, T., Talk Presented at the XVI International Botanical Congress Meeting, Aug. 1-7, 1999, St. Louis, Mo.).

There is a great deal of interest in identifying the genes that encode proteins involved in development in plants, generally toward the objective of altering plant growth and architecture. WUS represents one such gene. However, the WUS gene can also be used for the novel application of stimulating in vitro growth of plant tissue and improving transformation. In this manner, this gene can expand the range of tissues types targeted for transformation. Specifically, the WUS gene may be used to improve meristem transformation frequencies and could result in genotype independent transformation of many important crops such as maize, soybean and sunflower. Furthermore, transformation into meristems would stimulate the formation of new apical initials reducing the chimeric nature of the transgenic events. Lastly, ectopic expression into non-meristematic cells would stimulate adventive meristem formation. This could lead to transformation of non-traditional tissues such as leaves, leaf bases, stem tissue, etc. Alternatively, transformation of a more traditional target such as callus or the scutellum of immature embryos could promote a "non-traditional" growth response, i.e. meristems in place of somatic embryos. In addition, WUS may also be used as a genetic marker for meristems.

Modulation of WUS is expected to modulate plant and/or plant tissue phenotype including cell growth stimulation, organogenesis, and somatic embryogenesis. WUS may also be used to improve transformation via somatic embryogenesis. Expression of *Arabidopsis* WUS can induce stem cells in vegetative tissues, which can differentiate into somatic embryos (Zuo, et al. (2002) Plant J 30:349-359). The ability to stimulate organogenesis and/or somatic embryogenesis may be used to generate an apomictic plant. Apomixis has economic potential because it can cause any genotype, regardless of how heterozygous, to breed true. It is a reproductive process that bypasses female meiosis and syngamy to produce embryos genetically identical to the maternal parent. With apomictic reproduction, progeny of specially adaptive or hybrid genotypes would maintain their genetic fidelity throughout repeated life cycles. In addition to fixing hybrid vigor, apomixis can make possible commercial hybrid production in crops where efficient male sterility or fertility restoration systems for producing hybrids are not available. Apomixis can make hybrid development more efficient. It also simplifies hybrid production and increases genetic diversity in plant species with good male sterility.

Accordingly, the availability of nucleic acid sequences encoding all or a portion of a WUS protein would facilitate studies to better understand programmed development in plants, provide genetic tools to enhance the efficiency of gene transfer into meristem tissue and help provide alternative transformation methods in several important crops.

SUMMARY OF THE INVENTION

This invention relates to isolated polynucleotides encoding WUS polypeptides. The invention further provides isolated WUS polypeptides. The invention also provides methods of using the polynucleotides to modulate the level of WUS, improve transformation efficiency, to stimulate plant cell growth, including stem cells, to stimulate organogenesis, to stimulate somatic embryogenesis, to induce apomixis, and to provide a positive selection for cells comprising the polynucleotide. The invention also relates to cells, plants and seeds comprising the polynucleotides of the invention or produced by the methods of the invention.

BRIEF DESCRIPTION OF THE DRAWING AND SEQUENCE LISTINGS

The invention can be more fully understood from the following detailed description and the accompanying drawing and Sequence Listing, which form a part of this application.

FIG. 1, parts A & B, shows an alignment of the amino acid sequences of WUS protein encoded by the nucleotide sequences derived from corn clone cpi1c.pk012.p19 (SEQ ID NO: 4), corn clone p0058.chpab57r (SEQ ID NO: 10), soybean clone ses4d.pk0033.c8 (SEQ ID NO: 20), soybean clone sgs5c.pk0002.f2 (SEQ ID NO: 22), and a contig assembled using soybean clone ssm.pk0060.h4 and NCBI GenBank Identifier (GI) No. 4395781 (SEQ ID NO: 24), and the WUS protein from *Arabidopsis thaliana* (NCBI GI No. 4090200; SEQ ID NO: 25). Amino acids which are conserved among all and at least two sequences with an amino acid at that position are indicated with an asterisk (*). Dashes are used by the program to maximize alignment of the sequences.

FIG. 2, parts A & B, shows the stimulation of organogenesis by Wuschel. Epifluorescence microscopy shows the pattern of YFP expression and culture morphology in (A) maize embryo culture co-bombarded with Ubi:YFP and ubi:uidA control plasmids; and (B) maize embryo culture co-bombarded with Ubi:YFP and Ole:WUS2 plasmids. The control in panel (A) shows YFP expressing spots in tissue culture showing no developing projections, while panel (B) shows YFP expressing spots in the apices of outgrowths of tissue. Panel A—magnification=40×; Panel B—magnification=200×.

DETAILED DESCRIPTION OF THE INVENTION

The present invention concerns isolated polynucleotides comprising nucleotide sequences which encode polypeptides involved in the initiation and maintenance of stem cells in plants, i.e., polypeptides having Wuschel activity. The invention also provides isolated polypeptides having Wuschel activity.

The present invention concerns an isolated polynucleotide comprising a nucleotide sequence selected from the group consisting of: (a) a first nucleotide sequence encoding a polypeptide of at least 50 amino acids having at least 70% identity based on the Clustal method of alignment when compared to a polypeptide selected from the group consisting of SEQ ID NOs: 2, 4, and 12, (b) a second nucleotide sequence encoding a polypeptide of at least 100 amino acids having at least 70% identity based on the Clustal method of alignment when compared to a polypeptide selected from the group consisting of SEQ ID NOs:14, 16, 18, and 20, (c) a third nucleotide sequence encoding a polypeptide of at least 180 amino acids having at least 70% identity based on the Clustal method of alignment when compared to a polypeptide of SEQ ID NO:24, (d) a fourth nucleotide sequence encoding a polypeptide of at least 230 amino acids having at least 70% identity based on the Clustal method of alignment when compared to a polypeptide of SEQ ID NO:22, (e) a fifth nucleotide sequence encoding a polypeptide of at least 100 amino acids having at least 80% identity based on the Clustal method of alignment when compared to a polypeptide selected from the group consisting of SEQ ID NOs:6, 8, and 10, and (f) a sixth nucleotide sequence comprising the complement of (a), (b), (c), (d), or (e).

In a second embodiment, it is preferred that the isolated polynucleotide of the claimed invention comprises a first nucleotide sequence which comprises a nucleic acid sequence selected from the group consisting of SEQ ID NOs: 1, 3, 5, 7, 9, 11, 13, 15, 17, 19, 21, and 23 that codes for the polypeptide selected from the group consisting of SEQ ID NOs: 2, 4, 6, 8, 10, 12, 14, 16, 18, 20, 22, and 24.

In a third embodiment, this invention concerns an isolated polynucleotide comprising a nucleotide sequence of at least one of 60 (or at least one of 40, or at least one of 30) contiguous nucleotides derived from a nucleotide sequence selected from the group consisting of SEQ ID NOs: 1, 3, 5, 7, 9, 11, 13, 15, 17, 19, 21, and 23 and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, for example a baculovirus or a plant virus, comprising an isolated polynucleotide of the present invention or a chimeric gene of the present invention.

In a sixth embodiment, the invention also relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

In a seventh embodiment, the invention concerns an isolated WUS polypeptide selected from the group consisting of: (a) a polypeptide of at least 50 amino acids having at least 70% identity based on the Clustal method of alignment when compared to a polypeptide selected from the group consisting of SEQ ID NOs: 2, 4, and 12, (b) a polypeptide of at least 100 amino acids having at least 70% identity based on the Clustal method of alignment when compared to a polypeptide selected from the group consisting of SEQ ID NOs: 14, 16, 18, and 20, (c) a polypeptide of at least 180 amino acids having at least 70% identity based on the Clustal method of alignment when compared to a polypeptide of SEQ ID NO: 24, (d) a polypeptide of at least 230 amino acids having at least 70% identity based on the Clustal method of alignment when compared to a polypeptide of SEQ ID NO: 22, and (e) a polypeptide of at least 100 amino acids having at least 80% identity based on the Clustal method of alignment when compared to a polypeptide selected from the group consisting of SEQ ID NOs:6, 8, and 10.

In an eighth embodiment, the invention relates to a method of selecting an isolated polynucleotide that affects the level of expression of a WUS polypeptide or enzyme activity in a host cell, for example a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the WUS polypeptide or enzyme activity in the host cell containing the isolated polynucleotide; and (d) comparing the level of the WUS polypeptide or enzyme activity in the host cell containing the isolated polynucleotide with the level of the WUS polypeptide or enzyme activity in the host cell that does not contain the isolated polynucleotide.

In a ninth embodiment, the invention concerns a method of obtaining a nucleic acid fragment encoding a substantial portion of a WUS polypeptide, such as a plant WUS polypeptide, comprising the steps of: synthesizing an oligonucleotide primer comprising a nucleotide sequence of at least one of 60 (or at least one of 40, or at least one of 30) contiguous nucleotides derived from a nucleotide sequence selected from the group consisting of SEQ ID NOs: 1, 3, 5, 7, 9, 11, 13, 15, 17, 19, 21, and 23, and the complement of such nucleotide sequences; and amplifying a nucleic acid fragment (for example, a cDNA inserted in a cloning vector) using the oligonucleotide primer. Optionally, the amplified nucleic acid fragment will encode a substantial portion of a WUS amino acid sequence.

In a tenth embodiment, this invention relates to a method of obtaining a nucleic acid fragment encoding all or a substantial portion of the amino acid sequence encoding a WUS polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide of the present invention.

In a twelfth embodiment, this invention concerns a method for positive selection of a transformed cell comprising: (a) transforming a host cell with the chimeric gene of the present invention or an expression cassette of the present invention; and (b) growing the transformed host cell, for example a plant cell, such as a monocot or a dicot, under conditions which allow expression of the WUS polynucleotide, and identifying transformed cells.

In a thirteenth embodiment, this invention relates to a method of altering the level of expression of a WUS protein in a host cell comprising: (a) transforming a host cell with a chimeric gene of the present invention; and (b) growing the transformed host cell under conditions that are suitable for expression of the chimeric gene wherein expression of the chimeric gene results in production of altered levels of the WUS protein in the transformed host cell.

In another embodiment, the invention relates to isolated polynucleotides, having at least 70%, 75%, 80%, 85%, 90%, 95%, 97% or up to and including 100% identity over their entire length to at least one of the nucleic acid sequences selected from the group consisting of SEQ ID NOS: 26, 28, 30, 32, 34, 35, 37, 39, 41, 42, 44, 46, 48, 49, 51, 53, 55, 56, 58, 60, 62, 63, 65, 67, 69, 70, 72, 74, 76, 77, 79, and 80, which encode polypeptides having WUS activity. The invention also relates to isolated polynucleotides which are fully complementary to the nucleic acid sequences of this embodiment.

In another embodiment, the invention relates to isolated polynucleotides comprising at least a minimum whole integer number of contiguous nucleotides ranging from at least 30 contiguous nucleotides up to and including the full-length of the sequence. For example, the isolated polynucleotide comprises at least 30, 40, 50, 60, 75, 100, 150, 300, 500, 1000 contiguous nucleotides, up to and including the full-length of a nucleic acid sequence selected from the group consisting of SEQ ID NOS: 26, 28, 30, 32, 34, 35, 37, 39, 41, 42, 44, 46, 48, 49, 51, 53, 55, 56, 58, 60, 62, 63, 65, 67, 69, 70, 72, 74, 76, 77, 79, and 80. Optionally, the isolated polynucleotide is a full-length polynucleotide encoding a polypeptide having WUS activity, which comprises at least 30, 40, 50, 60, 75, 100, 150, 300, 500, 1000 contiguous nucleotides, up to and including the full-length of a nucleic acid sequence selected from the group consisting of SEQ ID NOS: 26, 28, 30, 32, 34, 35, 37, 39, 41, 42, 44, 46, 48, 49, 51, 53, 55, 56, 58, 60, 62, 63, 65, 67, 69, 70, 72, 74, 76, 77, 79, and 80. The invention also relates to isolated polynucleotides which are fully complementary to the nucleic acid sequences of this embodiment.

In another embodiment, the invention relates to isolated polynucleotides, or the complement thereof, which encode a polypeptide having WUS activity, wherein the encoded polypeptide has at least 70%, 75%, 80%, 85%, 90%, 95%, 97% or up to and including 100% identity to at least one of the amino acid sequences selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. The invention also relates to isolated polynucleotides which are fully complementary to the nucleic acid sequences of this embodiment.

In another embodiment, the invention relates to isolated polynucleotides which encode a polypeptide comprising a minimum whole integer number of contigous amino acids from at least one polypeptide selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81, wherein the number of contiguous amino acids is selected from the range of 20 amino acids up to and including the full length of the polypeptide. For example, the isolated polynucleotide encodes a polypeptide comprising at least 20, 25, 30, 40, 50, 75, 100, 200 contiguous amino acids, up to and including the full-length of at least one amino acid sequence selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. The invention also relates to isolated polynucleotides which are fully complementary to the nucleic acid sequences of this embodiment.

In another embodiment, the invention relates to isolated polynucleotides comprising primers capable of amplifying WUS polynucleotides from a nucleic acid library. In some embodiments, isolated polynucleotide amplification primers are selected from the group consisting of SEQ ID NOS: 82, 83, 84, 85, 86 and 87.

In another embodiment, the invention relates to DNA constructs, host cells, plants, and seeds comprising the isolated polynucleotides of the invention, or the complement thereof, particularly isolated polynucleotides having a certain percent identity to at least one nucleic acid sequence selected from the group consisting of SEQ ID NOS: 26, 28, 30, 32, 34, 35, 37, 39, 41, 42, 44, 46, 48, 49, 51, 53, 55, 56, 58, 60, 62, 63, 65, 67, 69, 70, 72, 74, 76, 77, 79, and 80, or encoding a polypeptide having a certain percent identity to at least one amino acid sequence selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. Also included are isolated polynucleotides comprising at least a minimum whole integer number of contiguous nucleotides, or encoding a polypeptide comprising a minimum whole integer number of contiguous amino acids, as described above, of the sequences of the invention.

In another embodiment, the invention relates to isolated polynucleotides encoding polypeptides having WUS activity, which comprise conserved domains or consensus amino acid sequences. The isolated polynucleotides comprise nucleic acid sequences which encode a WUS polypeptide comprising at least one conserved polypeptide motif. The polypeptide motifs include the homeodomain motif, the (E/R)TLPLFP motif, and the A(A/S)LEL(ST)L motif. Amino acid variations within these motifs are known, and included in this embodiment. Also included is a 25 amino acid motif located between the (E/R)TLPLFP and the A(A/S)LEL(ST)L motifs. In some embodiments, the isolated polynucleotides have a certain percent sequence identity to the polynucleotides of the present invention, wherein the sequence identity in the region of the polynucleotide encoding a conserved motif may be less than 100%. In some embodiments, the isolated polynucleotides are selected from the group consisting of SEQ ID NOS: 26, 28, 30, 32, 34, 35, 37, 39, 41, 42, 44, 46, 48, 49, 51, 53, 55, 56, 58, 60, 62, 63, 65, 67, 69, 70, 72, 74, 76, 77, 79, and 80. Optionally, this embodiment includes polynucleotides which encode polypeptides in which a motif is absent, for example, polypeptides lacking the 25 amino acid motif (SEQ ID NO: 91 QPP(P/S)RPRHAVPVPAGE(T/P)IR(G/V)GGG(S/G)S), the (E/R)TLPLFP motif or the A(A/S)LEL(ST)L motif. In some embodiments, the isolated polynucleotides have a certain percent sequence identity to the polynucleotides of the present invention, wherein at least one amino acid motif is absent. In some embodiments, the isolated polynucleotide is selected from the group consisting of SEQ ID NO: 30, 32, 39, 46, 49, 51, 53, 56, 58, 60, 63, 65, 67, 70, 72, 74, 77, and 80.

In another embodiment, the invention relates to isolated polynucleotides, or the complement thereof, which encode a polypeptide having WUS activity, wherein the encoded polypeptide has at least 70%, 75%, 80%, 85%, 90%, 95%, 97% or up to and including 100% identity to at least one of the consensus amino acid sequences selected from the group consisting of SEQ ID NOS: 88, 89, and 90. The invention also relates to isolated polynucleotides which are fully complementary to the nucleic acid sequences of this embodiment.

In another embodiment, the invention relates to isolated polypeptides having WUS activity, which comprise conserved domains or consensus amino acid sequences. The isolated polypeptides comprise at least one conserved polypeptide motif. The polypeptide motifs include the homeodomain motif, the (E/R)TLPLFP motif, and the A(A/S)LEL(ST)L motif. Amino acid variations within these motifs are known, and included in this embodiment. Also included is a 25 amino acid motif located between the (E/R)TLPLFP and the A(A/S)LEL(ST)L motifs. In some embodiments, the isolated polypeptides have a certain percent sequence identity to the polypeptides of the present invention, wherein the sequence identity in the region of the polynucleotide encoding a conserved motif may be less than 100%. In some embodiments, the isolated polypeptides are selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. Optionally, this embodiment includes polypeptides in which at least one motif is absent. This embodiment includes, for example, polypeptides lacking the 25 amino acid motif (SEQ ID NO: 91), the (E/R) TLPLFP motif or the A(A/S)LEL(ST)L motif. In some embodiments, the isolated polypeptides have a certain percent sequence identity to the polypeptides of the present invention, wherein at least one motif is absent. In some embodiments, the isolated polypeptide is selected from the group consisting of SEQ ID NO: SEQ ID NO: 31, 33, 40, 47, 50, 52, 54, 57, 59, 61, 64, 66, 68, 71, 73, 75, 78, and 81.

In another embodiment, the invention relates to isolated polypeptides having WUS activity, wherein the encoded polypeptide has at least 70%, 75%, 80%, 85%, 90%, 95%, 97% or up to and including 100% identity to at least one of the consensus amino acid sequences selected from the group consisting of SEQ ID NOS: 88, 89, and 90.

In another embodiment, the invention relates to isolated polypeptides having WUS activity, wherein the polypeptide has at least 70%, 75%, 80%, 85%, 90%, 95%, 97% or up to and including 100% identity to at least one of the amino acid sequences selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81.

In another embodiment, the invention relates to isolated polypeptides having WUS activity, wherein the polypeptide comprises at least a minimum whole integer number of contiguous amino acids from at least one polypeptide selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81, wherein the number of contiguous amino acids is selected from the range of 20 amino acids up to and including the full length of the polypeptide. For example, the isolated polypeptide comprises at least 20, 25, 30, 40, 50, 75, 100, 200 contiguous amino acids, up to and including the full-length of at least one amino acid sequence selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81.

In another embodiment, the invention relates to a method to modulate the level of WUS in a cell, plant cell, or plant. The method comprises introducing into the cell an isolated polynucleotide of the invention, and expressing the polynucleotide in the cell, wherein the expression of the polynucleotide modulates the level of WUS in the cell. The introduced polynucleotide optionally comprises a DNA construct operably linked to a promoter active in the cell, in either sense or antisense orientation. In some embodiments, the isolated polynucleotide encodes a polypeptide selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. In some embodiments, the isolated polynucleotide encodes a polypeptide selected from the group consisting of SEQ ID NOs: 2, 4, 6, 8, 10, 12, 14, 16, 18, 20, 22, and 24. In some embodiments the isolated polynucleotide is selected from the group consisting of SEQ ID NOS: 26, 28, 30, 32, 34, 35, 37, 39, 41, 42, 44, 46, 48, 49, 51, 53, 55, 56, 58, 60, 62, 63, 65, 67, 69, 70, 72, 74, 76, 77, 79, and 80. The cell is optionally cultured under conditions in order to generate a plant wherein the level of WUS is modulated. In other embodiments, the introduced polynucleotide optionally comprises an RNA molecule, which is introduced into the cell, plant cell, or plant. In another embodiment, the method to modulate the level of WUS in a cell, plant cell, or plant comprises introducing an isolated WUS polypeptide of the invention into the cell, plant cell, or plant. In some embodiments the isolated polypeptide is selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. In some embodiments, the isolated polypeptide is selected from the group consisting of SEQ ID NOs: 2, 4, 6, 8, 10, 12, 14, 16, 18, 20, 22, and 24.

In another embodiment, the invention relates to a method to stimulate plant cell growth. In some embodiments, stimulation of plant cell growth can provide a positive selection selection means, stimulate organogenesis, stimulate embryogenesis, including the production of asexually derived embryos, such as somatic embryos, and/or apomictic embryos. The method comprises introducing into the cell an isolated polynucleotide of the invention, and expressing the polynucleotide in the cell, wherein the expression of the polynucleotide modulates the level of WUS in the cell, thereby stimulating plant cell growth. The introduced polynucleotide optionally comprises a DNA construct operably linked to a promoter active in the cell, in either sense or antisense orientation. In some embodiments, the isolated polynucleotide encodes a polypeptide selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. In some embodiments, the isolated polynucleotide encodes a polypeptide selected from the group consisting of SEQ ID NOs: 2, 4, 6, 8, 10, 12, 14, 16, 18, 20, 22, and 24. In some embodiments the isolated polynucleotide is selected from the group consisting of SEQ ID NOS: 26, 28, 30, 32, 34, 35, 37, 39, 41, 42, 44, 46, 48, 49, 51, 53, 55, 56, 58, 60, 62, 63, 65, 67, 69, 70, 72, 74, 76, 77, 79, and 80. In some embodiments the polynucleotide is selected from the group consisting of SEQ ID NOs: 1, 3, 5, 7, 9, 11, 13, 15, 17, 19, 21, and 23. The cell is optionally cultured under conditions in order to generate a plant. In other embodiments, the introduced polynucleotide optionally comprises an RNA molecule, which is introduced into the cell, plant cell, or plant, thereby stimulating cell growth. In another embodiment, the method to plant cell growth comprises introducing an isolated WUS polypeptide of the invention into the cell, plant cell, or plant. In some embodiments the isolated polypeptide is selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. In some embodiments the isolated polypeptide is selected from the group consisting of SEQ ID NOs: 2, 4, 6, 8, 10, 12, 14, 16, 18, 20, 22, and 24. In some embodiments, cells stimulated to proliferate by polynucleotides and/or polypeptides of the invention are subsequently transformed with another polynucleotide of interest. WUS stimulates growth in a non-cell autonomous manner, therefore in some embodiments proliferating cells stimulated by WUS, but not comprising stably incorporated WUS are used as the host cells for transformation with a polynucleotide of interest.

In another embodiment, the invention relates to a method of positive selection for transformed plant cells. The method comprises introducing into a plant cell an isolated polynucleotide which encodes a polypeptide having WUS activity, expressing the polynucleotide, and culturing the transformed cells under conditions which provide positive selection for cells comprising the polynucleotide. Optionally, the culture conditions comprise conditions in which neither exogenous plant hormones, nor chemical selection agents are provided. The conditions may also comprise the addition of exogenous plant hormones, in any range of lower concentration up to the normal plant cell culture concentration. If the plant cell comprises another selectable marker, the conditions may comprise the addition of the selecting agent or method. In some embodiments, the isolated polynucleotide encodes a polypeptide selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. In some embodiments the isolated polynucleotide is selected from the group consisting of SEQ ID NOS: 26, 28, 30, 32, 34, 35, 37, 39, 41, 42, 44, 46, 48, 49, 51, 53, 55, 56, 58, 60, 62, 63, 65, 67, 69, 70, 72, 74, 76, 77, 79, and 80. In some embodiments the polynucleotide is selected from the group consisting of SEQ ID NOs: 1, 3, 5, 7, 9, 11, 13, 15, 17, 19, 21, and 23.

In another embodiment, the invention relates to a method to produce asexually derived embryos. The method comprises introducing into the cell an isolated polynucleotide of the invention, and expressing the polynucleotide in the cell, wherein the expression of the polynucleotide produces an asexually derived embryo. The introduced polynucleotide optionally comprises a DNA construct operably linked to a promoter active in the cell, in either sense or antisense orientation. In some embodiments, the isolated polynucleotide encodes a polypeptide selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. In some embodiments, the isolated polynucleotide encodes a polypeptide selected from the group consisting of SEQ ID NOs: 2, 4, 6, 8, 10, 12, 14, 16, 18, 20, 22, and 24. In some embodiments the isolated polynucleotide is selected from the group consisting of SEQ ID NOS: 26, 28, 30, 32, 34, 35, 37, 39, 41, 42, 44, 46, 48, 49, 51, 53, 55, 56, 58, 60, 62, 63, 65, 67, 69, 70, 72, 74, 76, 77, 79, and 80. In some embodiments the polynucleotide is selected from the group consisting of SEQ ID NOs: 1, 3, 5, 7, 9, 11, 13, 15, 17, 19, 21, and 23. The produced embryo is optionally cultured under conditions in order to generate a plant. In other embodiments, the introduced polynucleotide optionally comprises an RNA molecule, which results in the production of an asexually derived embryo. In another embodiment, the method to produce asexually derived embryos comprises introducing an isolated WUS polypeptide of the invention into the cell, plant cell, or plant. In some embodiments the isolated polypeptide is selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. In some embodiments the isolated polypeptide is selected from the group consisting of SEQ ID NOs: 2, 4, 6, 8, 10, 12, 14, 16, 18, 20, 22, and 24. In some embodiments the asexually derived embryos are somatic embryos or apomictic embryos. In some embodiments, the plant regenerated from the embryo has an apomictic phenotype.

In another embodiment, the invention relates to a method to generate an apomictic plant. The method comprises introducing into a plant cell an isolated polynucleotide which encodes a polypeptide having WUS activity, regenerating a plant comprising the polynucleotide, wherein the plant has an apomictic phenotype. The introduced polynucleotide optionally comprises a DNA construct operably linked to a promoter active in the cell. Optionally, the promoter active in the cell is an inducible promoter, a tissue-preferred promoter, a developmentally regulated promoter, or a promoter, or combination of promoters, having more than one of these properties. In one embodiment, the promoter is a nucellus-preferred promoter, such as the barley nuc-1 promoter, or an inducible promoter, like In2. In some embodiments, WUS expression may be further regulated by having another gradient, temporal or spatial, super-imposed by separating the coding region or encoded polypeptide into at least two segments which are separably regulated. In some embodiments, the coding region is interrupted by a recombinase flanked spacer region, which is excised when the appropriate recombinase is provided in a controlled manner. In some embodiments, the isolated polynucleotide encodes a polypeptide selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. In some embodiments, the isolated polynucleotide encodes a polypeptide selected from the group consisting of SEQ ID NOs: 2, 4, 6, 8, 10, 12, 14, 16, 18, 20, 22, and 24. In some embodiments the isolated polynucleotide is selected from the group consisting of SEQ ID NOS: 26, 28, 30, 32, 34, 35, 37, 39, 41, 42, 44, 46, 48, 49, 51, 53, 55, 56, 58, 60, 62, 63, 65, 67, 69, 70, 72, 74, 76, 77, 79, and 80. In some embodiments the polynucleotide is selected from the group consisting of SEQ ID NOs: 1, 3, 5, 7, 9, 11, 13, 15, 17, 19, 21, and 23. In other embodiments a polypeptide having WUS activity is reconstituted via intein splicing. Only cells comprising both segments that have been expressed and combined will comprise a polypeptide having WUS activity.

In another embodiment, the invention relates to a method to increase transformation frequency. The method comprises introducing into a plant cell an isolated polynucleotide of the invention which encodes a polypeptide having WUS acivity, and expressing the polynucleotide in the cell, wherein the expression of the polynucleotide increases transformation frequency. Transformation frequency is measured relative to a wild-type or control plant cell that does not contain and/or express the polynucleotide of the invention. The introduced polynucleotide optionally comprises a promoter active in the cell operably linked to the isolated polynucleotide. In some embodiments, the introduced polynucleotide further comprises a polynucleotide of interest, which may be operably linked to a promoter active in the cell, or a polynucleotide of interest may be separately introduced. In some embodiments, the isolated polynucleotide encodes a polypeptide selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. In some embodiments, the isolated polynucleotide encodes a polypeptide selected from the group consisting of SEQ ID NOs: 2, 4, 6, 8, 10, 12, 14, 16, 18, 20, 22, and 24. In some embodiments the isolated polynucleotide is selected from the group consisting of SEQ ID NOS: 26, 28, 30, 32, 34, 35, 37, 39, 41, 42, 44, 46, 48, 49, 51, 53, 55, 56, 58, 60, 62, 63, 65, 67, 69, 70, 72, 74, 76, 77, 79, and 80. In some embodiments the polynucleotide is selected from the group consisting of SEQ ID NOs: 1, 3, 5, 7, 9, 11, 13, 15, 17, 19, 21, and 23. Optionally, a transformed cell produced by the method is further cultured under conditions in order to generate a plant. In other embodiments, the introduced polynucleotide optionally comprises an RNA molecule which is introduced into the cell, plant cell, or plant. In another embodiment, the method comprises introducing an isolated WUS polypeptide of the invention into the cell, plant cell, or plant. In some embodiments the isolated polypeptide is selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. In some embodiments the isolated polypeptide is selected from the group consisting of SEQ ID NOs: 2, 4, 6, 8, 10, 12, 14, 16, 18, 20, 22, and 24. In certain embodiments, the plant cell is a typically non-transformable and/or recalcitrant plant cell.

In another embodiment, the invention relates to a method to stimulate organogenesis in a plant. The method comprises introducing into a plant cell an isolated polynucleotide of the invention which encodes a polypeptide having WUS activity, and expressing the polynucleotide in the cell, wherein the expression of the polynucleotide stimulates organogenesis. The introduced polynucleotide optionally comprises a promoter active in the cell operably linked to the isolated polynucleotide. In some embodiments, the introduced polynucleotide further comprises a polynucleotide of interest, which may be operably linked to a promoter active in the cell, or a polynucleotide of interest may be separately introduced. In some embodiments, the isolated polynucleotide encodes a polypeptide selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. In some embodiments, the isolated polynucleotide encodes a polypeptide selected from the group consisting of SEQ ID NOs: 2, 4, 6, 8, 10, 12, 14, 16, 18, 20, 22, and 24. In some embodiments the isolated polynucleotide is selected from the group consisting of SEQ ID NOS: 26, 28, 30, 32, 34, 35, 37, 39, 41, 42, 44, 46, 48, 49, 51, 53, 55, 56, 58, 60, 62, 63, 65, 67, 69, 70, 72, 74, 76, 77, 79, and 80. In some embodiments the polynucleotide is selected from the group consisting of SEQ ID NOs: 1, 3, 5, 7, 9, 11, 13, 15, 17, 19, 21, and 23. Optionally, a transformed cell produced by the method is further cultured under conditions in order to generate a plant. In other embodiments, the introduced polynucleotide optionally comprises an RNA molecule which is introduced into the cell, plant cell, or plant. In another embodiment, the method comprises introducing an isolated WUS polypeptide of the invention into the cell, plant cell, or plant. In some embodiments the isolated polypeptide is selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. in some embodiments the isolated polypeptide is selected from the group consisting of SEQ ID NOs: 2, 4, 6, 8, 10, 12, 14, 16, 18, 20, 22, and 24.

In another embodiment, the invention relates to a method to stimulate somatic embryogenesis in a plant. The method comprises introducing into a plant cell an isolated polynucleotide of the invention which encodes a polypeptide having WUS activity, and expressing the polynucleotide in the cell, wherein the expression of the polynucleotide stimulates somatic embryogenesis. The introduced polynucleotide optionally comprises a promoter active in the cell operably linked to the isolated polynucleotide. In some embodiments, the introduced polynucleotide further comprises a polynucleotide of interest, which may be operably linked to a promoter active in the cell, or a polynucleotide of interest may be separately introduced. In some embodiments, the isolated polynucleotide encodes a polypeptide selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. In some embodiments, the isolated polynucleotide encodes a polypeptide selected from the group consisting of SEQ ID NOs: 2, 4, 6, 8, 10, 12, 14, 16, 18, 20, 22, and 24. In some embodiments the isolated polynucleotide is selected from the group consisting of SEQ ID NOS: 26, 28, 30, 32, 34, 35, 37, 39, 41, 42, 44, 46, 48, 49, 51, 53, 55, 56, 58, 60, 62, 63, 65, 67, 69, 70, 72, 74, 76, 77, 79, and 80. In some embodiments the polynucleotide is selected from the group consisting of SEQ ID NOs: 1, 3, 5, 7, 9, 11, 13, 15, 17, 19, 21, and 23. Optionally, a transformed cell produced by the method is further cultured under conditions in order to generate a plant. In other embodiments, the introduced polynucleotide optionally comprises an RNA molecule which is introduced into the cell, plant cell, or plant. In another embodiment, the method comprises introducing an isolated WUS polypeptide of the invention into the cell, plant cell, or plant. In some embodiments the isolated polypeptide is selected from the group consisting of SEQ ID NOS: 27, 29, 31, 33, 36, 38, 40, 43, 45, 47, 50, 52, 54, 57, 59, 61, 64, 66, 68, 71, 73, 75, 78, and 81. in some embodiments the isolated polypeptide is selected from the group consisting of SEQ ID NOs: 2, 4, 6, 8, 10, 12, 14, 16, 18, 20, 22, and 24.

In another embodiment, the invention relates to any transgenic host cell, plant cell, plant, and/or seed produced by the methods of the invention. This embodiment includes those instances wherein the host cell, plant cell, plant, and/or seed is transgenic and comprises a polynucleotide of the invention. This embodiment also includes those instances wherein a polynucleotide or polypeptide of the invention was used in a transient manner in order to generate host cells, plant cells, plants and/or seeds having the desired traits. In certain embodiments, the host cell, plant cell, plant, and/or seed produced by the methods of the invention may further comprise other polynucleotides of interest.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA insert comprising the indicated cDNA clone ("full insert sequence" or "FIS"), contigs assembled from two or more EST, FIS, and/or PCR sequences ("Contig"), or sequences encoding the entire protein derived from an EST, an FIS, a contig, or an FIS and PCR fragment sequence ("complete gene sequence" or "CGS"). Nucleotide SEQ ID NOs: 1, 5, 11, and 15 correspond to nucleotide SEQ ID NOs: 1, 3, 5, and 7, respectively, presented in U.S. Provisional Application No. 60/157,216, filed Oct. 1, 1999. Amino acid SEQ ID NOs: 2, 6, 12, and 16 correspond to amino acid SEQ ID NOs: 2, 4, 6, and 8, respectively, presented in U.S. Provisional Application No. 60/157,216, filed Oct. 1, 1999. Nucleotide SEQ ID NOS: 1, 3, 5, 7, 9, 11, 13, 15, 17, 19, 20, 21, and 23, and amino acid SEQ ID NOS: 2, 4, 6, 8, 10, 12, 14, 16, 18, 20, 22, 24 and 25 retain the same sequence identifiers as presented in PCT International Application No. PCT/US00/26648 filed Sep. 28, 2000. The sequence descriptions and Sequence Listing attached hereto comply with the rules governing nucleotide and/or amino acid sequence disclosures in patent applications as set forth in 37 C.F.R. §1.821-1.825.

TABLE 1

WUSCHEL Sequences

| Protein (Plant Source) | Clone Designation | Status | SEQ ID NO: (Nucleotide) | SEQ ID NO: (Amino Acid) |
|---|---|---|---|---|
| WUS (Corn) | Contig of cpg1c.pk006.b16 cpi1c.pk012.p19 | Contig | 1 | 2 |
| WUS (Corn) | cpi1c.pk012.p19 (FIS) | CGS | 3 | 4 |
| WUS (Corn) | p0016.ctsas50r | EST | 5 | 6 |
| WUS (Corn) | p0016.ctsas50r | FIS | 7 | 8 |
| WUS (Corn) | p0058.chpab57r (FIS) | CGS | 9 | 10 |
| WUS (Corn) | p0083.cldev71r | EST | 11 | 12 |
| WUS (Corn) | p0083.cldev71r | FIS | 13 | 14 |
| WUS (Soybean) | Contig of scr1c.pk001.d2 ses4d.pk0033.c8 | Contig | 15 | 16 |
| WUS (Soybean) | scr1c.pk001.d2 | FIS | 17 | 18 |
| WUS (Soybean) | ses4d.pk0033.c8 (FIS) | CGS | 19 | 20 |
| WUS (Soybean) | sgs5c.pk0002.f2 | CGS | 21 | 22 |
| WUS (Soybean) | Contig of ssm.pk0060.h4 (FIS) NCBI GI No. 4395781 | CGS | 23 | 24 |
| WUS (Corn) | Contig of p0016.ctsas50r (FIS) PCR fragments (1$^{st}$ intron spliced) | CGS | 26 | 27 |
| WUS (Corn) | p0016.ctsas50r, 1$^{st}$ & complete 2$^{nd}$ intron spliced | CGS | 28 | 29 |
| WUS (Corn) | p0016.ctsas50r, 1$^{st}$ & alternate 2$^{nd}$ intron spliced | CGS | 30 | 31 |
| WUS (Corn) | Contig of p0083.cldev71r (FIS) PCR fragments | CGS | 32 | 33 |
| WUS (Corn) | Genomic DNA from B73 corresponding to p0016.ctsas50r | CGS | 34 | |
| WUS (Corn) | Genomic DNA from B73 corresponding to p0016.ctsas50r, 1$^{st}$ intron spliced | CGS | 35 | 36 |
| WUS (Corn) | Genomic DNA from B73 corresponding to p0016.ctsas50r, 1$^{st}$ & 2$^{nd}$ complete intron spliced | CGS | 37 | 38 |
| WUS (Corn) | Genomic DNA from B73 corresponding to p0016.ctsas50r, 1$^{st}$ & alternate 2$^{nd}$ intron spliced | CGS | 39 | 40 |
| WUS (Corn) | Genomic DNA from Mo17 corresponding to p0016.ctsas50r | CGS | 41 | |
| WUS (Corn) | Genomic DNA from Mo17 corresponding to p0016.ctsas50r, 1$^{st}$ intron spliced | CGS | 42 | 43 |
| WUS (Corn) | Genomic DNA from Mo17 corresponding to p0016.ctsas50r, 1$^{st}$ & 2$^{nd}$ complete intron spliced | CGS | 44 | 45 |
| WUS (Corn) | Genomic DNA from Mo17 corresponding to p0016.ctsas50r, 1$^{st}$ & alternate 2$^{nd}$ intron spliced | CGS | 46 | 47 |

TABLE 1-continued

WUSCHEL Sequences

| Protein (Plant Source) | Clone Designation | Status | SEQ ID NO: (Nucleotide) | SEQ ID NO: (Amino Acid) |
|---|---|---|---|---|
| WUS (Corn) | Genomic DNA from 07D corresponding to p0016.ctsas50r | CGS | 48 | |
| WUS (Corn) | Genomic DNA from 07D corresponding to p0016.ctsas50r, 1st intron spliced | CGS | 49 | 50 |
| WUS (Corn) | Genomic DNA from 07D corresponding to p0016.ctsas50r, 1st & 2nd complete intron spliced | CGS | 51 | 52 |
| WUS (Corn) | Genomic DNA from 07D corresponding to p0016.ctsas50r, 1st & alternate 2nd intron spliced | CGS | 53 | 54 |
| WUS (Corn) | Genomic DNA from KW3 corresponding to p0016.ctsas50r | CGS | 55 | |
| WUS (Corn) | Genomic DNA from KW3 corresponding to p0016.ctsas50r, 1st intron spliced | CGS | 56 | 57 |
| WUS (Corn) | Genomic DNA from KW3 corresponding to p0016.ctsas50r, 1st & 2nd complete intron spliced | CGS | 58 | 59 |
| WUS (Corn) | Genomic DNA from KW3 corresponding to p0016.ctsas50r, 1st & alternate 2nd intron spliced | CGS | 60 | 61 |
| WUS (Corn) | Genomic DNA from 3DT corresponding to p0016.ctsas50r | CGS | 62 | |
| WUS (Corn) | Genomic DNA from 3DT corresponding to p0016.ctsas50r, 1st intron spliced | CGS | 63 | 64 |
| WUS (Corn) | Genomic DNA from 3DT corresponding to p0016.ctsas50r, 1st & 2nd complete intron spliced | CGS | 65 | 66 |
| WUS (Corn) | Genomic DNA from 3DT corresponding to p0016.ctsas50r, 1st & alternate 2nd intron spliced | CGS | 67 | 68 |
| WUS (Corn) | Genomic DNA from 09B corresponding to p0016.ctsas50r | CGS | 69 | |
| WUS (Corn) | Genomic DNA from 09B corresponding to p0016.ctsas50r, 1st intron spliced | CGS | 70 | 71 |
| WUS (Corn) | Genomic DNA from 09B corresponding to p0016.ctsas50r, 1st & 2nd complete intron spliced | CGS | 72 | 73 |
| WUS (Corn) | Genomic DNA from 09B corresponding to p0016.ctsas50r, 1st & alternate 2nd intron spliced | CGS | 74 | 75 |
| WUS (Corn) | Genomic WUS5, gss | CGS | 76 | |
| WUS (Corn) | Genomic WUS5 gss, single intron spliced | CGS | 77 | 78 |
| WUS (Corn) | Genomic WUS6, gss | CGS | 79 | |
| WUS (Corn) | Genomic WUS6, gss, 1st & 2nd intron spliced | CGS | 80 | 81 |
| WUS | Consensus WUS2, 1st intron spliced | | | 88 |

TABLE 1-continued

WUSCHEL Sequences

| Protein (Plant Source) | Clone Designation | Status | SEQ ID NO: (Nucleotide) | (Amino Acid) |
|---|---|---|---|---|
| WUS | Consensus WUS2, 1st & 2nd complete intron spliced | | | 89 |
| WUS | Consensus WUS2, 1st & alternate 2nd intron spliced | | | 90 |
| Motif | 25 amino acid motif | | | 91 |

The Sequence Listing contains the one letter code for nucleotide sequence characters and the three letter codes for amino acids as defined in conformity with the IUPAC-IUBMB standards described in Nucleic Acids Res. 13:3021-3030 (1985) and in the Biochemical J. 219(2):345-373 (1984) which are herein incorporated by reference. The symbols and format used for nucleotide and amino acid sequence data comply with the rules set forth in 37 C.F.R. §1.822.

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include a polynucleotide comprising at least 60 contiguous nucleotides, or at least 40 contiguous nucleotides, and optionally at least 30 contiguous nucleotides derived from SEQ ID NOS: 1, 3, 5, 7, 9, 11, 13, 15, 17, 19, 21, or 23, or the complement of such sequences.

The length of the polynucleotide is given as an integer selected from the group consisting of from at least 30 to the length of the nucleic acid sequence from which the polynucleotide is a subsequence of. Therefore, an isolated polynucleotide of the present invention also includes polynucleotides comprising contiguous nucleotides of at least 10, 20, 30, 40, 50, 60, 70, 80, 90, 100, 120, 150, 175, 200, 250, 300, 500 or up to and including the full-length of the polynucleotides of SEQ ID NOS: 1, 3, 5, 7, 9, 11, 13, 15, 17, 19, 21, or 23 and the polynucleotides of SEQ ID NOS: 26, 28, 30, 32, 34, 35, 37, 39, 41, 42, 44, 46, 48, 49, 51, 53, 55, 56, 58, 60, 62, 63, 65, 67, 69, 70, 72, 74, 76, 77, 79, or 80. Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides. The subsequences of the present invention can comprise structural characteristics of the sequence from which it is derived, for example including but not limited to, signal sequences, translational start sites, polyadenylation sites, conserved motifs, introns, exons, UTR's, and the like.

As used herein "fully complementary" refers to a nucleic acid sequence which is 100% complementary to a reference nucleic acid sequence.

The term "apomixis" is used to describe asexual reproduction that replaces or substitutes for sexual methods of reproduction. When apomixis occurs, embryos are produced from maternal tissue and use only the maternal genome, and are referred to as "apomictic embryos". A plant capable of producing embryos in the absence of fertilization is referred to as an "apomictic plant", or a plant that has an "apomictic phenotype".

As used herein, "Wuschel polynucleotide" or "WUS polynucleotide" means a polynucleotide encoding a polypeptide with Wuschel activity, or a polynucleotide capable of modulating the expression of mRNA or protein in a host cell. The term is also inclusive of fragments, variants, homologues, alleles or precursors with the any one of the above stated functions.

A "protein" or "polypeptide" is a chain of amino acids arranged in a specific order determined by the coding sequence in a polynucleotide encoding the polypeptide. Each protein or polypeptide has a unique function. As used herein, "polypeptide" means proteins, protein fragments, modified proteins (e.g., glycosylated, phosphorylated, or other modifications), amino acid sequences and synthetic amino acid sequences. The polypeptide can be modified or not.

As used herein, "Wuschel polypolypeptide" or "WUS polypeptide" means a polypeptide having Wuschel activity, i.e., involved in the initiation and maintenance of stem cells in plants. Wuschel activity stimulates cell growth, including stem cells. Wuschel is a plant homeodomain protein, comprising an 'atypical' (compared to the animal homeodomain motif) helix-loop-helix-turn-helix homeodomain motif comprising extra amino acid residues in the loop and/or turn of the domain. Wuschel proteins may further comprise other conserved motifs, such as the two conserved Wuschel C-terminal domains, the (E/R)TLPLFP and A(A/S)LEL(S/T)L domains. The term is also inclusive of fragments, variants, homologues, with the any one of the above stated functions.

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material. The term "isolated" polynucleotide refers to a polynucleotide that is substantially free from other nucleic acid sequences, such as other chromosomal and extrachromosomal DNA and RNA, that normally accompany or interact with it as found in its naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that silencing of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (or at least one of 40, or at least one of 30) contiguous nucleotides derived from a nucleotide sequence selected from the group consisting of SEQ ID NOs: 1, 3, 5, 7, 9, 11, 13, 15, 17, 19, 21, and 23, and the complement of such nucleotide sequences may be used in methods of selecting an isolated polynucleotide that affects the expression of a WUS polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, or to screen for highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. More stringent conditions may use higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, or at least about 80% identical to the amino acid sequences reported herein. Nucleic acid fragments that encode amino acid sequences that are about 85% identical to the amino acid sequences are reported herein. Nucleic acid fragments encode amino acid sequences that are at least about 90% identical to the amino acid sequences are also reported herein. Nucleic acid fragments that encode amino acid sequences that are at least about 95% identical to the amino acid sequences are reported herein. Suitable nucleic acid fragments not only have the above identities but typically encode a polypeptide having at least 50 amino acids, at least 100 amino acids, at least 150 or 180 amino acids, at least 200 or 230 amino acids, or at least 250 amino acids.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers & Miller (1988) CABIOS 4:11-17; the local alignment algorithm of Smith et al. (1981) Adv. Appl. Math. 2:482; the global alignment algorithm of Needleman & Wunsch (1970) J. Mol. Biol. 48:443-453; the search-for-local alignment method of Pearson & Lipman (1988) PNAS 85:2444-2448; the algorithm of Karlin & Altschul (1990) PNAS 87:2264-2268, modified as in Karlin & Altschul (1993) PNAS 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, PILEUP, PRETTY, BLAST, FASTA, and TFASTA in the GCG Wisconsin Genetics Software Package, Version 10 (Accelrys Inc., 9685 Scranton Road, San Diego, Calif., USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucl. Acids Res. 16:10881-90; Huang et al. (1992) CABIOS 8:155-65; and Pearson et al. (1994) Meth. Mol. Biol. 24:307-331.

Sequence alignments and percent identity calculations, particularly for sequences selected from the group consisting of SEQ ID NOS: 1-25, were performed using the Megalign program of the LASERGENE bioinformatics computing suite (DNASTAR Inc., Madison, Wis.). Percent sequence identity can also be calculated over the entire length of the sequences compared using the alignment algorithm of Needleman & Wunsch, J. Mol. Biol. 48:443 (1970), for example as implemented in the GAP algorithm in the GCG™ software package (Accelrys, San Diego, Calif.). GAP Version 10 uses the following default parameters: % identity for a nucleotide sequence using GAP Weight of 50 and Length Weight of 3; % identity for an amino acid sequence using the BLOSUM62 scoring matrix (Henikoff & Henikoff, PNAS 89:10915-10919 (1992)), GAP Weight of 8 and Length Weight of 2.

Multiple alignment of the sequences, particularly for sequences selected from the group consisting of SEQ ID NOS: 1-25, was performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Multiple alignments of polynucleotide and polypeptide sequences can also be generated using the PileUp program (Feng & Doolittle, J. Mol. Evol. 25:351-360 (1987)) in the GCG™ software package (Accelrys, San Diego, Calif.), which uses the following default parameters for amino acid sequences of the BLOSUM62 scoring matrix (Henikoff & Henikoff, PNAS 89:10915-10919 (1992)), GAP Weight=8 and Length Weight=2. For polynucleotide sequences, PILEUP uses the default parameters of GAP Weight=5, and Length Weight=1.

Optionally, one of skill can use the PRETTY program for alignment of polynucleotide and polypeptide sequences, as found in the GCG™ software package (Accelrys, San Diego, Calif.), which uses the following default parameters for amino acid sequences of the BLOSUM62 scoring matrix (Henikoff & Henikoff, PNAS 89:10915-10919 (1992)), GAP Weight=8 and Length Weight=2, and which also generates a consensus sequence for the alignment. For polynucleotide sequences, PRETTY uses the default parameters of GAP Weight=5, and Length Weight=1.

Substantially similar polynucleotides of the instant invention may also be characterized by the percent identity of the nucleic acid sequences to the polynucleotides disclosed herein, as determined by algorithms commonly employed by those skilled in this art. Isolated polynucleotides of the present invention comprise nucleic acids sequences that have at least 70%, 75%, 80%, 85%, 90%, 95%, 96%, 97%, 98% or 99% identity to the polynucleotides disclosed, e.g., SEQ ID NOS: 1, 3, 5, 7, 9, 11, 13, 15, 19, 21, or 23, or SEQ ID NOS: 26, 28, 30, 32, 34, 35, 37, 39, 41, 42, 44, 46, 48, 49, 51, 53, 55, 56, 58, 60, 62, 63, 65, 67, 69, 70, 72, 74, 76, 77, 79, or 80. Sequence alignments and percent identity calculations may performed using standard methods and algorithms, as described above.

As used herein, "substantially similar" in reference to polypeptides and amino acid sequences refers to polypeptides wherein changes (e.g., modification, substitution, deletion, insertion) in one or more amino acids do not affect the functional properties of the polypeptide, i.e., at least one activity of the polypeptide is retained, such as a protein-protein interaction, antibody binding, or enzymatic and/or biological activity. It is therefore understood that the invention encompasses more than the specific exemplary amino acid sequences and includes functional equivalents thereof. The terms "substantially similar" and "corresponding substantially" are used interchangeably herein. For these purposes, substantially similar polypeptides normally comprise amino acid sequences having a sequence identity of at least 60%, 70%, 75%, 80%, 85%, 90%, 95%, 97%, or greater.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) J. Mol. Biol. 215:403410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a polynucleotide that expresses a specific protein, including regulatory sequences preceding (5' non-coding sequences) and following (3' non-coding sequences) the coding sequence. "Native" refers to a polynucleotide as found in nature with its own regulatory sequences. "Chimeric" refers any polynucleotide that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) Biochemistry of Plants 15:1-82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) Mol. Biotechnol. 3:225-236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) Plant Cell 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation. The term is also inclusive of protein trans-splicing events (e.g. inteins) which produce a single functional polypeptide.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) Ann. Rev. Plant Phys. Plant Mol. Biol. 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100:1627-1632).

"Transformation" refers to the transfer of a nucleic acid fragment into the genome of a host organism. Host organisms containing the transformed nucleic acid fragments are referred to as "transgenic" organisms. Examples of methods of plant transformation include *Agrobacterium*-mediated transformation (De Blaere et al. (1987) Meth. Enzymol. 143:277) and particle-accelerated or "gene gun" transformation technology (Klein et al. (1987) Nature (London) 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. The term "transformation" as used herein refers to both stable transformation and transient transformation.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be used by itself or may be used in conjunction with a vector. If a vector is used, the choice of vector is dependent upon the method that will be used to transform host plants as is well known to those skilled in the art.

In reference to transformation, particularly stable transformation, a "recalcitrant" cell or line is a cell or line wherein introduction of a polynucleotide of interest into the cell generally does not result in the recovery of stably transformed tissue that can be regenerated to produce a transformed plant. The term is inclusive of known recalcitrant genotypes, as well as older tissues, or tissue sources which generally do not respond and/or proliferate in standard culture conditions.

As used herein "transient transformation" refers to the transfer of a nucleic acid fragment or protein into the nucleus (or DNA-containing organelle) of a host organism resulting in gene expression without, necessarily, resulting in integration and stable inheritance.

As used herein, the term "positive selection" refers to any means by which a selectable phenotype or growth advantage is produced relative to control cells in the absence of chemical selection. The term is inclusive of positive selection Standard recombinant DNA and molecular cloning techniques used herein are well known in the art and are described more fully in Sambrook et al. Molecular Cloning: A Laboratory Manual; Cold Spring Harbor Laboratory Press: Cold Spring Harbor, 1989 (hereinafter "Maniatis").

"Motifs" refers to short regions of conserved sequences of nucleic acids or amino acids that comprise part of a longer sequence. These conserved motifs may be associated with a specific function. These conserved motifs could be used to identify new homologues in plants. It is expected that some or all of the motifs may be found in a homologue. Also, it is expected that one or two of the conserved amino acids in any given motif may differ in a true homologue.

"PCR" or "polymerase chain reaction" is well known by those skilled in the art as a technique used for the amplification of specific DNA segments (U.S. Pat. Nos. 4,683,195 and 4,800,159).

As used herein, the term "plant" includes reference to whole plants, plant organs (e.g., leaves, stems, roots, etc.), plant tissue, seeds and plant cells, and progeny of the same. Plant cell, as used herein includes, without limitation, seeds, suspension cultures, embryos, meristematic regions, callus tissue, leaves, roots, shoots, gametophytes, sporophytes, pollen, and microspores.

As used herein, the term "organogenesis" refers to stem cell and/or meristematic activity that leads to the differentiation of organs.

As used herein, the term "asexually derived embryo" refers to any embryo generated in the absence of fertilization. The term is inclusive of apomictic and somatic embryos. As used herein, the term "somatic embryogenesis" refers to non-zygotic embryogenesis.

As used herein, the term "stem cells" refers to pleuripotent cells that give rise to both additional stem cells as well as cells that can differentiate into other cell types.

The present invention concerns isolated polynucleotides which encode polypeptides having WUS activity or that can modulate the level or activity of WUS in a cell, isolated polypeptides having WUS activity, and methods of using these sequences. Wuschel is involved in the initiation and maintenance of plant stem cells. Loss-of-function mutations in the WUS gene lead to shoot and floral meristems that fail to self-maintain. WUS mRNA expression is localized to a small group of cells in the central zone, below the L3 of the apical meristem, and affects stem cell fate in a non-cell autonomous manner (Mayer et al. (1998) Cell 95:805-815, herein incorporated by reference). Cells of the central zone divide relatively infrequently, while cells in the surrounding peripheral zone divide rapidly. Cell position in the meristem appears to regulate stem cell fate, via the interactions of many regulatory genes, including WUS, STM, CLV and the like (see, e.g., Byrne et al. (2003) Curr. Op. Gen. Dev. 13:551-557; Doerner (2000) Curr. Biol. 10:R826-R829; and Sharma, et al. (2003) PNAS 100:11823-11829, the contents of which are all herein incorporated by reference).

WUS encodes a homeodomain transcription factor polypeptide whose function is to bind a target DNA sequence and direct expression of the target gene. Binding of WUS to a DNA sequence was confirmed by Lohmann and co-workers (2001) Cell 105:793-803. The homeodomain region is approximately 61-64 amino acids with a substructure of alpha helix1-loop-alpha helix2-turn-alpha helix 3. Alpha helix3 makes the primary contact with the DNA sequence, although other substructures of the homeodomain polypeptide affect the level and specificity of interaction with the target DNA. The WUS homeodomain falls into a subcategory of homeodomain transcription factors depending on the presence and number of extra amino acids present in the loop and turn substructures relative to animal homeodomain transcription factors. One or two extra amino acids in the loop and four extra amino acids in the turn define the WUS family of transcription factors from other homeodomain transcription factors ("1+4" or "2+4" categories, Kamiya et al. (2003) Plant J 35:429441). For example, WUS2 (p0016.ctsas5 or) is in the "2+4" category of homeodomain factors, like the Arabidopsis protein, whereas the other WUS sequences of the present invention belong to the "1+4" category (e.g., p0083.cldev71r, represented in SEQ ID NO: 33). Two secondary protein motifs have been identified (Stuurman et al. (2002) Genes Dev. 16:2213-2218) and include a highly conserved (E/R)TLPLFP and less conserved A(A/S)LEL(S/T)L amino acid sequences near the C-terminal end of the polypeptide. The role of these secondary motifs are not clear, but such leucine-rich motifs are generally involved in protein-protein interactions. The A(A/S)LEL(S/T)L shows significant similarity to C-terminal motifs identified in zn-finger proteins and ERFs, which have been implicated to act as a repressor domain via protein-protein interaction (Ohta, et al. (2001) Plant Cell 13:1959-1968; and Dinkins et al. (2003) Plant Science 165:33-41; herein incorporated by reference).

The present invention concerns an isolated polynucleotide comprising a nucleotide sequence selected from the group consisting of: (a) a first nucleotide sequence encoding a polypeptide of at least 50 amino acids having at least 70% identity based on the Clustal method of alignment when compared to a polypeptide selected from the group consisting of SEQ ID NOs: 2, 4, and 12, (b) a second nucleotide sequence encoding a polypeptide of at least 100 amino acids having at least 70% identity based on the Clustal method of alignment when compared to a polypeptide selected from the group consisting of SEQ ID NOs: 14, 16, 18, and 20, (c) a third nucleotide sequence encoding a polypeptide of at least 180 amino acids having at least 70% identity based on the Clustal method of alignment when compared to a polypeptide of SEQ ID NO: 24, (d) a fourth nucleotide sequence encoding a polypeptide of at least 230 amino acids having at least 70% identity based on the Clustal method of alignment when compared to a polypeptide of SEQ ID NO: 22, (e) a fifth nucleotide sequence encoding a polypeptide of at least 100 amino acids having at least 80% identity based on the Clustal method of alignment when compared to a polypeptide selected from the group consisting of SEQ ID NOs: 6, 8, and 10, and (f) a sixth nucleotide sequence comprising the complement of (a), (b), (c), (d), or (e).

The first nucleotide sequence may comprise a nucleic acid sequence selected from the group consisting of SEQ ID NOS: 1, 3, 5, 7, 9, 11, 13, 15, 17, 19, 21, and 23, that codes for the polypeptide selected from the group consisting of SEQ ID NOS: 2, 4, 6, 8, 10, 12, 14, 16, 18, 20, 22, and 24.

Nucleic acid fragments encoding at least a portion of several WUS proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other WUS proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) Proc. Natl. Acad. Sci. USA 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) Proc. Natl. Acad. Sci. USA 86:5673-5677; Loh et al. (1989) Science 243:217-220). Products generated by the 3' and 5' RACE procedures can be combined to generate full-length cDNAs (Frohman and Martin (1989) Techniques 1:165). Consequently, a polynucleotide comprising a nucleotide sequence of at least one of 60 (or at least 40, or at least 30) contiguous nucleotides derived from a nucleotide sequence selected from the group consisting of SEQ ID NOs: 1, 3, 5, 7, 9, 11, 13, 15, 17, 19, 21, and 23 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a WUS polypeptide, optionally a substantial portion of a plant WUS polypeptide, comprising the steps of: synthesizing an oligonucleotide primer comprising a nucleotide sequence of at least one of 60 (or of at least 40, or at least one of 30) contiguous nucleotides derived from a nucleotide sequence selected from the group consisting of SEQ ID NOs: 1, 3, 5, 7, 9, 11, 13, 15, 17, 19, 21, and 23, and the complement of such nucleotide sequences; and amplifying a nucleic acid fragment (e.g., cDNA inserted in a cloning vector) using the oligonucleotide primer. Optionally, the amplified nucleic acid fragment will encode a portion of a WUS polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) Adv. Immunol. 36:1-34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering development (e.g., the initiation and maintenance of meristem apical initials) in those plants.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' non-coding sequences encoding transcription termination signals may also be provided. The instant chimeric gene may also comprise one or more introns in order to facilitate gene expression.

It is well known in the art that silencing of gene expression may be accomplished using nucleic acid fragments representing less than the entire coding region of a gene, and by using nucleic acid fragments that do not share 100% sequence identity with the gene to be suppressed.

Reduction of the activity of specific genes (also known as gene silencing, or gene suppression) is desirable for several aspects of genetic engineering in plants. Many techniques for gene silencing are well known to one of skill in the art, including but not limited to antisense technology (see, e.g., Sheehy et al. (1988) PNAS USA 85:8805-8809; and U.S.

Pat. Nos. 5,107,065; 5,453,566; and 5,759,829); cosuppression (e.g., Taylor (1997) Plant Cell 9:1245; Jorgensen (1990) Trends Biotech. 8(12):340-344; Flavell (1994) PNAS USA 91:3490-3496; Finnegan et al. (1994) Bio/Technology 12: 883-888; and Neuhuber et al. (1994) Mol. Gen. Genet. 244:230-241); RNA interference (Napoli et al. (1990) Plant Cell 2:279-289; U.S. Pat. No. 5,034,323; Sharp (1999) Genes Dev. 13:139-141; Zamore et al. (2000) Cell 101:25-33; and Montgomery et al. (1998) PNAS USA 95:15502-15507), virus-induced gene silencing (Burton et al. (2000) Plant Cell 12:691-705; and Baulcombe (1999) Curr. Op. Plant Bio. 2:109-113); target-RNA-specific ribozymes (Haseloff et al. (1988) Nature 334: 585-591); hairpin structures (Smith et al. (2000) Nature 407:319-320; WO 99/53050; WO 02/00904; and WO 98/53083); ribozymes (Steinecke et al. ((1992) EMBO J. 11:1525; and Perriman et al. ((1993) Antisense Res. Dev. 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art. The references cited above are herein incorporated by reference in their entirety.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will likely result in different levels and patterns of expression (Jones et al. (1985) EMBO J. 4:2411-2418; De Almeida et al. (1989) Mol. Gen. Genetics 218:78-86), and thus multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) Cell 56:247-253), signal sequences or sequences encoding endoplasmic reticulum localization (Chrispeels (1991) Ann. Rev. Plant Phys. Plant Mol. Biol. 42:21-53), or nuclear localization signals (Raikhel (1992) Plant Phys. 100:1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In certain embodiments the WUS nucleic acid sequences of the present invention can be stacked with any combination of polynucleotide sequences of interest in order to create plants with a desired phenotype. For example, the polynucleotides of the present invention may be stacked with any other polynucleotides of the present invention, such as any combination of WUS1 (SEQ ID NOS: 11, 13, and 32), WUS2 (SEQ ID NOS: 5, 7, 26, 28, 30, 34, 35, 37, 39, 41, 42, 44, 46, 48, 49, 51, 53, 55, 56, 58, 60, 62, 63, 65, 67, 69, 70, 72, and, 74), WUS3 (SEQ ID NO: 3), WUS5 (SEQ ID NOS: 76, and 77), WUS6 (SEQ ID NOS: 79, and 80), and other WUS sequences (SEQ ID NOS: 1, 9, 15, 17, 19, 21, 23, 88, 89, and 90). The WUS polynucleotides of the present invention can also be combined with other genes implicated in transcriptional regulation, homeotic gene regulation, stem cell maintenance and proliferation, cell division, and/or cell differentiation such as other WUS homologues (see, e.g, Mayer et al. (1998) Cell 95:805-815); clavata (e.g., CLV1, CVL2, CLV3) (see, e.g., WO 03/093450; Clark et al. (1997) Cell 89:575-585; Jeong et al. (1999) Plant Cell 11:1925-1934; Fletcher et al. (1999) Science 283:1911-1914); Clavata and Embryo Surround region genes (e.g., CLE) (see, e.g., Sharma et al. (2003) Plant Mol. Biol. 51:415-425; Hobe et al. (2003) Dev Genes Evol 213:371-381; Cock & McCormick (2001) Plant Physiol 126:939-942; and Casamitjana-Martinez et al. (2003) Curr Biol 13:1435-1441); baby boom (e.g., BNM3, BBM) (see, e.g., WO 00/75530; Boutileir et al. (2002) Plant Cell 14:1737-1749); Zwille (Lynn et al. (1999) Dev 126:469481); leafy cotyledon (e.g., Lec1, Lec2) (see, e.g., Lotan et al. (1998) Cell 93:1195-1205; WO 00/28058; Stone et al. (2001) PNAS 98:11806-11811; and U.S. Pat. No. 6,492,577); Shoot Meristem-less (STM) (Long et al. (1996) Nature 379:66-69); ultrapetala (ULT) (see, e.g., Fletcher (2001) Dev 128: 1323-1333); mitogen activated protein kinase (MAPK) (see, e.g., Jonak et al. (2002) Curr Opin Plant Biol 5:415); kinase associated protein phosphatase (KAPP) (see, e.g., Williams et al. (1997) PNAS 94:10467-10472; and Trotochaud et al. (1999) Plant Cell 11:393-406); ROP GTPase (see, e.g., Wu et al. (2001) Plant Cell 13:2841-2856; and Trotochaud et al. (1999) Plant Cell 11:393-406); fasciata (e.g., FAS1, FAS2) (see, e.g., Kaya et al. (2001) Cell 104:131-142); cell cycle genes (see, e.g., U.S. Pat. No. 6,518,487; WO 99/61619; and WO 02/074909), Shepherd (SHD) (see, e.g., Ishiguro et al. (2002) EMBO J. 21:898-908); Poltergeist (see, e.g., Yu et al. (2000) Dev 127:1661-1670; Yu et al. (2003) Curr Biol 13:179-188); Pickle (PKL) (see, e.g., Ogas et al. (1999) PNAS 96:13839-13844); knox genes (e.g., KN1, KNAT1) (see, e.g., Jackson et al. (1994) Dev 120:405-413; Lincoln et al. (1994) Plant Cell 6:1859-1876; Venglat et al. (2002) PNAS 99:4730-4735); fertilization independent endosperm (FIE) (e.g., Ohad, et al. (1999) Plant Cell 11:407-415), and the like, the disclosures of which are herein incorporated by reference. The combinations generated can also include multiple copies of any one of the polynucleotides of interest. The combinations may have any combination of up-regulating and down-regulating expression of the combined polynucleotides. The combinations may or may not be combined on one construct for transformation of the host cell, and therefore may be provided sequentially or simultaneously. The host cell may be a wild-type or mutant cell, in a normal or aneuploid state.

The polynucleotides of the present invention can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) Eur. J. Biochem. 165:99-106; and WO 98/20122); and high methionine proteins (Pedersen et al. (1986) J. Biol. Chem. 261:6279; Kirihara et al. (1988) Gene 71:359; and Musumura et al. (1989) Plant Mol. Biol. 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5723,756; 5,593, 881; Geiser et al. (1986) Gene 48:109); fumonisin detoxification genes (U.S. Pat. No. 5,792,931); avirulence and disease resistance genes (Jones et al. (1994) Science 266: 789; Martin et al. (1993) Science 262:1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)), the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combine with any combination of other suppression cassettes or overexpression cassettes to generate the desired combination of traits in the plant.

In another embodiment, the present invention concerns an isolated polypeptide selected from the group consisting of: (a) a polypeptide of at least 50 amino acids having at least 70% identity based on the Clustal method of alignment when compared to a polypeptide selected from the group consisting of SEQ ID NOs: 2, 4, and 12, (b) a polypeptide of at least 100 amino acids having at least 70% identity based on the Clustal method of alignment when compared to a polypeptide selected from the group consisting of SEQ ID NOs: 14, 16, 18, and 20, (c) a polypeptide of at least 180 amino acids having at least 70% identity based on the Clustal method of alignment when compared to a polypeptide of SEQ ID NO: 24, (d) a polypeptide of at least 230 amino acids having at least 70% identity based on the Clustal method of alignment when compared to a polypeptide of SEQ ID NO: 22, and (e) a polypeptide of at least 100 amino acids having at least 80% identity based on the Clustal method of alignment when compared to a polypeptide selected from the group consisting of SEQ ID NOs:6, 8, and 10.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded WUS protein. An example of a vector for high level expression of the instant polypeptides in a bacterial host is provided (Example 12).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) Genomics 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: Nonmammalian Genomic Analysis: A Practical Guide, Academic press 1996, pp. 319-346, and references cited therein).

In another embodiment, nucleic acid probes derived from the instant nucleic acid sequences may be used in direct fluorescence in situ hybridization (FISH) mapping (Trask (1991) Trends Genet. 7:149-154). Although current methods of FISH mapping favor use of large clones (several to several hundred KB; see Laan et al. (1995) Genome Res. 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) J. Lab. Clin. Med. 11:95 96), polymorphism of POR-amplified fragments (CAPS; Sheffield et al. (1993) Genomics 16:325 332), allele-specific ligation (Landegren et al. (1988) Science 241:1077 1080), nucleotide extension reactions (Sokolov (1990) Nucleic Acids Res. 18:3671), Radiation Hybrid Mapping (Walter et al. (1994) Nat. Genet. 7:22 28) and Happy Mapping (Dear and Cook (1989) Nucleic Acids Res. 17:6795 6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) Proc. Natl. Acad. Sci USA 86:9402-9406; Koes et al. (1995) Proc. Natl. Acad. Sci USA 92:8149-8153; Bensen et al. (1995) Plant Cell 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

Using a chemical-inducible activation-tagging, Zuo et al. showed that induced overexpression of WUS in Arabidopsis caused somatic embryo formation in all tissues and organs tested, without any external plant hormones (Zuo et al. (2002) Plant J. 30:349-359; U.S. Patent Application Publication No. US 2003/0082813 A1). Somatic embryogenesis is a unique pathway for asexual propagation or somatic cloning in plants. The developmental process of somatic embryogenesis is believed to share considerable similarity with that of zygotic embryogenesis (Mordhorst et al. (1997) Crit. Rev. Plant Sci. 16:535-576; Zimmerman (1993) Plant Cell 5:1411-1423).

In another embodiment of the invention, embryogenesis is induced in haploid cells, such as pollen cells, egg cells, or cells from a haploid line such as RWS, to produce haploid plants. This can be achieved by stably transforming a plant cell or tissue with a WUS gene under the control of a tissue specific promoter that is active in a haploid cell or tissue, and expressing the WUS gene therein, or by introducing the WUS gene into a plant tissue or cell under the control of an inducible promoter and applying the inducer to cause expression of the WUS gene therein. In one embodiment, the WUS gene is under the control of a promoter that is both haploid-tissue specific and inducible. In another embodiment, a promoter is used that is both inducible and tissue-specific, giving greater control over the process. In another embodiment, WUS is operably linked to an inducible egg-specific promoter and used to induce embryogenesis. In another embodiment, a WUS gene linked to an inducible pollen-specific promoter is used to induce somatic embryogenesis in pollen cells. Expression of WUS in the haploid tissue or cell (for example, by application of the inducer specific for the inducible promoter) results in the formation of haploid somatic embryos, which can be grown into haploid plants using standard techniques.

When an inducible promoter is used (whether tissue specific or not), one embodiment comprises exposing excised transgenic tissue containing the haploid cells (e.g., pollen or female gametophytic cell, such as an egg) to the inducer for a time sufficient to induce somatic embryo formation, withdrawing the inducer, and then growing the somatic embryo into a transgenic haploid plant in the absence of the inducer.

Diploidization of the haploid plants to form dihaploids, either spontaneously or by treatment with the appropriate chemical (e.g. colchicine) can significantly expedite the process of obtaining homozygous plants as compared to a method of conventional genetic segregation. Further, besides facilitating breeding, this finds use in studies of mutagenesis and other genetic studies, because dihaploids are homozygous, containing the duplicated copies of each gene, expected to be identical.

Additionally, WUS genes may be used to induce apomixis in plants. Apomixis and methods of conferring apomixis into plants are discussed in several patents (see, e.g., U.S. Pat. Nos. 5,710,367; 5,811,636; 6,028,185; 6,229,064; and 6,239,327 as well as WO 00/24914 which are incorporated herein by reference). Reproduction in plants is ordinarily classified as sexual or asexual. The term apomixis is generally accepted as the replacement of sexual reproduction by various forms of asexual reproduction (Rieger et al., IN Glossary of Genetics and Cytogenetics, Springer-Verlag, New York, N.Y., 1976). In general, the initiation of cell proliferation in the embryo and endosperm are uncoupled from fertilization. Apomixis is a genetically controlled method of reproduction in plants where the embryo is formed without union of an egg and a sperm. There are three basic types of apomictic reproduction:

1) apospory—embryo develops from a chromosomally unreduced egg in an embryo sac derived from a somatic cell in the nucellus,
2) diplospory—embryo develops from an unreduced egg in an embryo sac derived from the megaspore mother cell, and
3) adventitious embryony—embryo develops directly from a somatic cell. In most forms of apomixis, pseudogamy or fertilization of the polar nuclei to produce endosperm is necessary for seed viability.

These types of apomixis have economic potential because they can cause any genotype, regardless of how heterozygous, to breed true. It is a reproductive process that bypasses female meiosis and syngamy to produce embryos genetically identical to the maternal parent. With apomictic reproduction, progeny of specially adaptive or hybrid genotypes would maintain their genetic fidelity throughout repeated life cycles. In addition to fixing hybrid vigor, apomixis can make possible commercial hybrid production in crops where efficient male sterility or fertility restoration systems for producing hybrids are not available. Apomixis can make hybrid development more efficient. It also simplifies hybrid production and increases genetic diversity in plant species with good male sterility.

It would be ideal to find genes controlling obligate or a high level of apomixis in the cultivated species and be able to readily hybridize cross-compatible sexual x apomictic genotypes to produce true-breeding $F_1$ hybrids. To date, most desirable genes controlling apomixis are found in the wild species which are distantly related to the cultivated species. Although interspecific crosses may be possible between the cultivated and wild species, chromosome pairing between genomes is usually low or nonexistent.

Although apomixis is effectively used in *Citrus* to produce uniform and disease-and virus-free rootstock (Parleviiet et al. (1959) Citrus Proc. Am. Soc. Hort. Sci. 74:252-260) and in buffelgrass (Bashaw (1980) Crop Sci. 20:112) and Poa (Pepin et al. (1971) Crop Sci. 11:445-448) to produce improved cultivars, it has not been successfully transferred to a cultivated crop plant. The transfer of apomixis to important crops would make possible development of true-breeding hybrids and commercial production of hybrids without a need for cytoplasmic-nuclear male sterility and high cost, labor-intensive production processes. An obligately apomictic $F_1$ hybrid would breed true through the seed indefinitely and could be considered a vegetative or clonal method of reproduction through the seed. The development of apomictically reproducing cultivated crops would also provide a major contribution toward the food security in developing nations.

Examples of promoters under developmental control include promoters that preferentially initiate transcription in certain tissues, such as leaves, roots, seeds, fibers, xylem vessels, tracheids, or sclerenchyma. Such promoters are referred to as tissue-preferred. Promoters that initiate transcription only or primarily in certain tissues are referred to as tissue-specific or tissue-preferred. A cell type specific promoter primarily drives expression in certain cell types in one or more organs, for example, vascular cells in roots or leaves. An inducible promoter is a promoter that is under environmental control. Examples of environmental conditions that may effect transcription by inducible promoters include anaerobic conditions or the presence of light. Tissue-specific, tissue-preferred, cell type specific, and inducible promoters constitute the class of non-constitutive promoters. A constitutive promoter is a promoter that is active under most environmental conditions.

Constitutive promoters include, for example, the core promoter of the Rsyn7 promoter and other constitutive promoters disclosed in WO 99/43838 and U.S. Pat. No. 6,072,050; the core CaMV35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632; and Christensen et al. (1992)Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

In some embodiments it will be beneficial to express the gene from an inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) Neth. J. Plant Pathol. 89:245-254; Uknes et al. (1992) Plant Cell 4:645-656; and Van Loon (1985) Plant Mol. Virol. 4:111-116. See also WO 99/43819, herein incorporated by reference. Promoters that are expressed locally at or near the site of pathogen infection are also available. See, for example, Marineau et al. (1987) Plant Mol. Biol. 9:335-342; Matton et al. (1989) Molecular Plant-Microbe Interactions 2:325-331; Somsisch et al. (1986) PNAS USA 83:2427-2430; Somsisch et al. (1988) Mol. Gen. Genet. 2:93-98; and Yang (1996) PNAS USA 93:14972-14977. See also, Chen et al. (1996) Plant J. 10:955-966; Zhang et al. (1994) PNAS USA 91:2507-2511; Warner et al. (1993) Plant J. 3:191-201; Siebertz et al. (1989) Plant Cell 1:961-968; U.S. Pat. No. 5,750,386 (nematode-inducible); and the references cited therein. The inducible promoter for the maize PRms gene is induced by the pathogen *Fusarium moniliforme* (see, for example, Cordero et al. (1992) Physiol. Mol. Plant Path. 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) Ann. Rev. Phytopath. 28:425-449; Duan et al. (1996) Nature Biotech. 14:494-498); wun1 and wun2, U.S. Pat. No. 5,428,148; win1 and win2 (Stanford et al. (1989) Mol. Gen. Genet. 215:200-208); systemin (McGurl et al. (1992) Science 225:1570-1573); WIP1 (Rohmeier et al. (1993) Plant Mol. Biol. 22:783-792; Eckelkamp et al. (1993) FEBS Letts 323:73-76); MPI gene (Corderok et al. (1994) Plant J. 6:141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) PNAS USA 88:10421-10425 and McNellis et al. (1998) Plant J. 14:247-257) and tetracycline-inducible and tetracycline-repressible promoters (see, for example, Gatz et al. (1991) Mol. Gen. Genet. 227:229-237, and U.S. Pat. Nos. 5,814, 618 and 5,789,156), herein incorporated by reference.

Tissue-preferred promoters can be utilized to target enhanced expression of a sequence of interest within a particular plant tissue. Tissue-preferred promoters include those identified by Kawamata et al. (1997) Plant Cell Physiol. 38:792-803; Hansen et al. (1997) Mol. Gen Genet. 254:337-343; Russell et al. (1997) Transgenic Res. 6:157-168; Rinehart et al. (1996) Plant Physiol. 112:1331-1341; Van Camp et al. (1996) Plant Physiol. 112:525-535; Canevascini et al. (1996) Plant Physiol. 112:513-524; Yamamoto et al. (1994) Plant Cell Physiol. 35:773-778; Lam (1994) Results Probl. Cell Differ. 20:181-196; Orozco et al. (1993) Plant Mol. Biol. 23:1129-1138; Matsuoka et al. (1993) PNAS USA 90:9586-9590; and Guevara-Garcia et al. (1993) Plant J. 4:495-505. Such promoters can be modified, if necessary, for weak expression.

Leaf-preferred promoters are known in the art. See, for example, Yamamoto et al. (1997) Plant J. 12:255-265; Kwon et al. (1994) Plant Physiol. 105:357-67; Yamamoto et al. (1994) Plant Cell Physiol. 35:773-778; Gotor et al. (1993) Plant J 3:509-18; Orozco et al. (1993) Plant Mol. Biol. 23:1129-1138; and Matsuoka et al. (1993) PNAS USA 90:9586-9590. In addition, promoter of cab and ribisco can also be used. See, for example, Simpson et al. (1958) EMBO J. 4:2723-2729 and Timko et al. (1988) Nature 318:57-58.

Root-preferred promoters are known and can be selected from the many available from the literature or isolated de novo from various compatible species. See, for example, Hire et al. (1992) Plant Mol. Biol. 20(2):207-218 (soybean root-specific glutamine synthetase gene); Keller and Baumgartner (1991) Plant Cell 3(10):1051-1061 (root-specific control element in the GRP 1.8 gene of French bean); Sanger et al. (1990) Plant Mol. Biol. 14(3):433-443 (root-specific promoter of the mannopine synthase (MAS) gene of *Agrobacterium tumefaciens*); and Miao et al. (1991) Plant Cell 3(1):11-22 (full-length cDNA clone encoding cytosolic glutamine synthetase (GS), which is expressed in roots and root nodules of soybean). Additional root-preferred promoters include the VfENOD-GRP3 gene promoter (Kuster et al. (1995) Plant Mol. Biol. 29(4):759-772); and rolB promoter (Capana et al. (1994) Plant Mol. Biol. 25(4):681-691. See also U.S. Pat. Nos. 5,837,876; 5,750,386; 5,633,363; 5,459, 252; 5,401,836; 5,110,732; and 5,023,179.

Seed-preferred promoters include both promoters active during seed development such as promoters of seed storage proteins, as well as those promoters active during seed germination. See Thompson et al. (1989) BioEssays 10:108, herein incorporated by reference. Such seed-preferred promoters include, but are not limited to, Cim1 (cytokinin-induced message); cZ19B1 (maize 19 kDa zein); milps (myo-inositol-1-phosphate synthase) (WO 00/11177; and U.S. Pat. No. 6,225,529; herein incorporated by reference). Gamma-zein (27 kDa zein) is an exemplary endosperm-preferred promoter. Globulin-1 and oleosin are exemplary embryo-preferred promoters. The barley nucellus-preferred promoter, nuc1, is also of interest. For dicots, seed-specific promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma-zein, waxy, shrunken 1, shrunken 2, globulin 1, etc. See also WO 00/12733, where seed-preferred promoters from end1 and end2 genes are disclosed; herein incorporated by reference. Stalk-preferred promoter(s) include, for example, S2A (Abrahams et al. 1995 Plant Mol Biol 27:513-528).

Where low-level expression is desired, a weak promoter will be used, i.e., a promoter that drives expression of a coding sequence at a low level. Alternatively, it is recognized that weak promoters also encompasses promoters that are expressed in only a few cells and not in others to give a total low level of expression. Such weak constitutive promoters include, for example, the core promoter of the Rsyn7 promoter (WO 99/43838; and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

The isolated polynucleotides or polypeptides may be introduced into the plant by one or more techniques typically used for direct delivery into cells. Such protocols may vary depending on the type of organism, cell, plant or plant cell, i.e. monocot or dicot, targeted for gene modification. Suitable methods of transforming plant cells include microinjection (Crossway et al. (1986) Biotechniques 4:320-334; and U.S. Pat. No. 6,300,543), electroporation (Riggs et al. (1986) Proc. Natl. Acad. Sci. USA 83:5602-5606, direct gene transfer (Paszkowski et al. (1984) EMBO J. 3:2717-2722), and ballistic particle acceleration (see, for example, Sanford et al., U.S. Pat. No. 4,945,050; WO 91/10725; and McCabe et al. (1988) Biotechnology 6:923-926). Also see, Tomes et al., Direct DNA Transfer into Intact Plant Cells Via Microprojectile Bombardment. pp. 197-213 in Plant Cell, Tissue and Organ Culture, Fundamental Methods. eds. O. L. Gamborg & G. C. Phillips. Springer-Verlag Berlin Heidelberg New York, 1995; U.S. Pat. No. 5,736,369 (meristem); Weissinger et al. (1988) Ann. Rev. Genet. 22:421-477; Sanford et al. (1987) Particulate Science and Technology 5:27-37 (onion); Christou et al. (1988) Plant Physiol. 87:671-674 (soybean); Datta et al. (1990) Biotechnology 8:736-740 (rice); Klein et al. (1988) Proc. Natl. Acad. Sci. USA 85:43054309 (maize); Klein et al. (1988) Biotechnology 6:559-563 (maize); WO 91/10725 (maize); Klein et al. (1988) Plant Physiol. 91:440-444 (maize); Fromm et al. (1990) Biotechnology 8:833-839; and Gordon-Kamm et al. (1990) Plant Cell 2:603-618 (maize); Hooydaas-Van Slogteren & Hooykaas (1984) Nature (London) 311:763-764; Bytebier et al. (1987) Proc. Natl. Acad. Sci. USA 84:5345-5349 (Liliaceae); De Wet et al. (1985) In The Experimental Manipulation of Ovule Tissues, ed. G. P. Chapman et al., pp. 197-209. Longman, N.Y. (pollen); Kaeppler et al. (1990) Plant Cell Reports 9:415-418; and Kaeppler et al. (1992) Theor. Appl. Genet. 84:560-566 (whisker-mediated transformation); U.S. Pat. No. 5,693,512 (sonication); D'Halluin et al. (1992) Plant Cell 4:1495-1505 (electroporation); Li et al. (1993) Plant Cell Reports 12:250-255; and Christou & Ford (1995) Annals of Botany 75:407-413 (rice); Osjoda et al. (1996) Nature Biotech. 14:745-750; Agrobacterium mediated maize transformation (U.S. Pat. No. 5,981,840); silicon carbide whisker methods (Frame et al. (1994) Plant J. 6:941-948); laser methods (Guo et al. (1995) Physiologia Plantarum 93:19-24); sonication methods (Bao et al. (1997) Ultrasound in Medicine & Biology 23:953-959; Finer & Finer (2000) Lett Appl Microbiol. 30:406-10; Amoah et al. (2001) J Exp Bot 52:1135-42); polyethylene glycol methods (Krens et al. (1982) Nature 296:72-77); protoplasts of monocot and dicot cells can be transformed using electroporation (Fromm et al. (1985) Proc. Natl. Acad. Sci. USA 82:5824-5828) and microinjection (Crossway et al. (1986) Mol. Gen. Genet. 202:179-185); all of which are herein incorporated by reference.

The target for transformation could be in the form of plant cells, tissues, or organs such as embryo, callus, meristem, leaf, inflorescence, root, shoot or seed. In other methods plant gametes, microspores, pollen, mother cells, zygote, or nucellar cells can be used, or subcellular organelles such as chloroplasts and mitochondria.

Plants cells transformed with a plant expression vector can be regenerated, e.g., from single cells, callus tissue or leaf discs according to standard plant tissue culture techniques. Various cells, tissues, and organs from almost any plant can be successfully cultured to regenerate an entire plant. Plant regeneration from cultured protoplasts is described in Evans et al., Protoplasts Isolation and Culture, Handbook of Plant Cell Culture, Macmillan Publishing Company, New York, pp. 124-176 (1983); and Binding, Regeneration of Plants, Plant Protoplasts, CRC Press, Boca Raton, pp. 21-73 (1985), all of which are herein incorporated by reference.

The regeneration of plants containing the foreign gene introduced by *Agrobacterium* can be achieved as described by Horsch et al. (1985) *Science* 227:1229-1231, and Fraley et al. (1983) Proc. Natl. Acad. Sci. USA. 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al. (1987) Ann. Rev. Plant Phys. 38:467-486. The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, The Maize Handbook, Freeling and Walbot, Eds., Springer, New York (1994); Corn and Corn Improvement, 3rd edition, Sprague and Dudley Eds., American Society of Agronomy, Madison, Wis. (1988).

The cells, which have been altered by any targeted gene modification method, may also be grown into plants in accordance with conventional ways. See, for example, McCormick et al. (1986) Plant Cell Reports 5:81-84; Gruber et.al., 1993, "Vectors for Plant Transformation" In: Methods in Plant Molecular Biology and Biotechnology; Glick and Thompson, eds., CRC Press, Inc., Boca Raton, pages 89-119; and Gordon-Kamm et al. (1990) Plant Cell 2:603-618. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited.

The present invention may be used for transformation of any plant species of angiosperms and gymnosperms, particularly monocotyledonous and dicotyledonous plants including, but not limited to, corn (*Zea mays*), *Brassica* sp. (e.g., *B. napus, B. juncea*), particularly those Brassica species useful as sources of seed oil, alfalfa (*Medicago sativa*), rice (*Oryza sativa*), rye (*Secale cereale*), sorghum (*Sorghum bicolor, S. vulgare*), millet (e.g., pearl millet (*Pennisetum glaucum*), proso millet (*Pnaicum miliaceum*), foxtail millet (*Setaria italica*), and finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (e.g., *Gossypium barbadense*, and *G. hirsutum*), sweet potato (*Ipomoea batatus*), cassava (*Manihot esculenta*), coffee (*Coffea spp.*), coconut (*Cocos nucifera*), pineapple (*Ananas comosus*), citrus trees (*Citrus spp.*), cocoa (*Theobroma cacao*), tea (*Camellia sinensis*), banana (*Musa spp.*), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum spp.*), oats (*Avena*), barley (*Hordeum*), vegetables, ornamentals, turf grass, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus spp.*), and members of the genus Cucumis such as cucumber (*C. sativus*), cantaloupe (*C. cantalupensis*), and musk melon (*C. melo*). Ornamentals include azalea (*Rhododendron spp.*), hydrangea (*Macrophylla hydrangea*), hibiscus (*Hibiscus rosasanensis*), roses (*Rosa spp.*), tulips (*Tulipa spp.*), daffodils (*Narcissus spp.*), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of particular interest in the present invention include crop plants, for example, corn, alfalfa, sunflower, Brassica, soybean, cotton, safflower, peanut, sorghum, wheat, millet, tobacco, etc., particularly corn and soybean.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various corn (*Zea mays*) and soybean (*Glycine max*) tissues were prepared. The characteristics of the libraries are described below.

TABLE 2 cDNA Libraries from Corn and Soybean

| Library | Tissue | Clone |
|---|---|---|
| cpg1c | Corn Pooled BMS Treated with Chemicals Related to RNA, DNA Synthesis* | cpg1c.pk006.b16 |
| cpi1c | Corn Pooled BMS Treated with Chemicals Related to Biochemical Compound Synthesis** | cpi1c.pk012.p19 |
| p0016 | Corn Tassel Shoots, Pooled, 0.1-1.4 cm | p0016.ctsas50r |
| p0058 | Sweet Corn Hybrid (Honey N Pearl) Shoot Culture | p0058.chpab57r |
| p0083 | Corn Whole Kernels 7 Days After Pollination | p0083.cldev71r |
| scr1c | Soybean Embryogenic Suspension Culture Subjected to 4 Vacuum Cycles and Collected 12 Hrs Later | scr1c.pk001.d2 |
| ses4d | Soybean Embryogenic Suspension 4 Days After Subculture | ses4d.pk0033.c8 |
| sgs5c | Soybean Seeds 4 Days After Germination | sgs5c.pk0002.f2 |
| ssm | Soybean Shoot Meristem | ssm.pk0060.h4 |

*Chemicals used included hydroxyurea, aphidicolin, HC-toxin, actinomycin D, all of which are commercially available from Calbiochem-Novabiochem Corp. (1-800-628-8470)
**Chemicals used included sorbitol, egosterol, taxifolin, methotrexate, D-mannose, D-glactose, alpha-amino adipic acid, ancymidol, all of which are commercially available from Calbiochem-Novabiochem Corp. (1-800-628-8470)

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al. (1991) Science 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) Nucleic Acids Res. 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (dihydrofolate reductase (DHFR) Fling and Richards (1983) Nucleic Acids Res. 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA does not cover the entire open reading frame, typically the 5' region is absent. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries can be chosen based on previous knowledge that the specific gene should be found in a certain tissue, and/or can be randomly chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification, a nested set of primers is used for both methods. The resulting DNA fragment is ligated into a pBluescript vector using a commercial kit and following the manufacturer's protocol. This kit is selected from many available from several vendors including InVitrogen (Carlsbad, Calif.), Promega Biotech (Madison, Wis.), and Gibco-BRL (Gaithersburg, Md.). The plasmid DNA is isolated by the alkaline lysis method and submitted for sequencing and assembly using Phred/Phrap, as above.

Example 2

Identification of cDNA Clones cDNA clones encoding WUS protein were identified by conducting BLAST (Basic Local Alignment Search Tool; Altschul et al. (1993) J. Mol. Biol. 215:403-410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) Nat. Genet. 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous sequences.

ESTs submitted for analysis are compared to the GenBank database as described above. ESTs that contain sequences more 5- or 3-prime can be found by using the BLASTN algorithm (Altschul et al. (1997) Nucleic Acids Res. 25:3389-3402) against the DuPont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the TBLASTN algorithm. The TBLASTN algorithm searches an amino acid query against a nucleotide database that is translated in all 6 reading frames. This search allows for differences in nucleotide codon usage between different species, and for codon degeneracy.

Example 3

Characterization of cDNA Clones Encoding WUS Protein Homologs

The BLASTX search using the EST sequences from clones listed in Table 3 revealed similarity of the polypeptides encoded by the cDNAs to WUS proteins from *Arabidopsis thaliana* (NCBI GenBank Identifier (GI) No. 3785979) and *Arabidopsis thaliana* (NCBI GI No. 4090200; SEQ ID NO: 25). Shown in Table 3 are the BLAST results for individual ESTs ("EST"), the sequences of the entire cDNA inserts comprising the indicated cDNA clones ("FIS"), or contigs assembled from two or more ESTs ("Contig").

TABLE 3

BLAST Results for Sequences Encoding Polypeptides Homologous to *Arabidopsis thaliana* WUS Proteins

| Clone | Status | SEQ ID | BLAST pLog Score |
|---|---|---|---|
| Contig composed of: cpg1c.pk006.b16 cpi1c.pk012.p19 | Contig | 2 | 14.30 (NCBI GI No. 3785979) |
| p0016.ctsas50r | EST | 6 | 31.00 (NCBI GI No. 4090200) |
| p0083.cldev71r | EST | 12 | 17.40 (NCBI GI No. 3785979) |
| Contig composed of: scr1c.pk001.d2 ses4d.pk0033.c8 | Contig | 16 | 24.52 (NCBI GI No. 3785979) |

The data in Table 4 represents a calculation of the percent identity of the amino acid sequences set forth in SEQ ID NOs: 2, 6, 12 and 16 and the *Arabidopsis thaliana* (NCBI GI No. 3785979) and (NCBI GI No. 4090200; SEQ ID NO: 25) sequences. The percent identity between the amino acid sequences set forth in SEQ ID NOs: 2, 6, 12 and 16 as compared to the Arabidopsis sequences ranged from 37-45%.

TABLE 4

Percent Identity of Amino Acid Sequences Deduced From the Nucleotide Sequences of cDNA Clones Encoding Polypeptides Homologous to *Arabidopsis thaliana* WUS Proteins

| SEQ ID NO. | Percent Identity to |
|---|---|
| 2 | 43% (NCBI GI No. 3785979) |
| 6 | 45% (NCBI GI No. 4090200) |
| 12 | 37% (NCBI GI No. 3785979) |
| 16 | 37% (NCBI GI No. 3785979) |

The sequence of the entire cDNA insert in most of the clones listed in Table 3 was determined. Further sequencing and searching of the DuPont proprietary database allowed the identification of other corn and soybean clones encoding WUS protein. The BLASTX search using the EST sequences from clones listed in Table 5 revealed similarity of the polypeptides encoded by the cDNAs to WUS proteins from *Arabidopsis thaliana* (NCBI GI Nos. 3785979, 4090200, 4580396, 9294502 and 6091768) and *Oryza sativa* (NCBI GI No. 8099120). Shown in Table 5 are the BLAST results for individual ESTs ("EST"), the sequences of the entire cDNA inserts comprising the indicated cDNA clones ("FIS"), sequences of contigs assembled from two or more ESTs ("Contig"), sequences of contigs assembled from an FIS and one or more ESTs or PCR fragment sequence ("Contig*"), or sequences encoding the entire protein derived from an EST, an FIS, a contig, or an FIS and PCR fragment sequence ("CGS"):

TABLE 5

BLAST Results for Sequences Encoding Polypeptides Homologous to WUS Proteins

| Clone | Status | SEQ ID | NCBI GI No. | BLAST pLog Score |
|---|---|---|---|---|
| cpi1c.pk012.p19 (FIS) | CGS | 4 | 3785979 | 21.30 |
| p0016.ctsas50r | FIS | 8 | 4090200 | 27.00 |
| p0058.chpab57r (FIS) | CGS | 10 | 6091768 | 36.52 |
| p0083.cldev71r | FIS | 14 | 4580396 | 15.70 |
| scr1c.pk001.d2 | FIS | 18 | 3785979 | 20.04 |
| ses4d.pk0033.c8 (FIS) | CGS | 20 | 3785979 | 21.10 |
| sgs5c.pk0002.f2 (EST) | CGS | 22 | 8099120 | 23.70 |
| Contig of ssm.pk0060.h4 (FIS) NCBI GI No. 4395781 | CGS | 24 | 9294502 | 23.00 |

FIG. 1 (A & B) presents an alignment of the amino acid sequences set forth in SEQ ID NOs: 4, 10, 20, 22, and 24 and the *Arabidopsis thaliana* sequence (NCBI GI No. 4090200; SEQ ID NO: 25). The data in Table 6 represents a calculation of the percent identity of the amino acid sequences set forth in SEQ ID NOs: 4, 10, 20, 22, and 24 and the *Arabidopsis thaliana* sequence (NCBI GI No. 4090200; SEQ ID NO: 25).

TABLE 6

Percent Identity of Amino Acid Sequences Deduced From the Nucleotide Sequences of cDNA Clones Encoding Polypeptides Homologous to WUS Protein

| SEQ ID NO. | Percent Identity to NCBI GI No. 4090200; SEQ ID NO: 25 |
|---|---|
| 4 | 22.7 |
| 10 | 18.2 |
| 20 | 25.0 |
| 22 | 21.6 |
| 24 | 22.2 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a WUS protein. These sequences represent the first corn and soybean sequences encoding WUS proteins known to Applicant.

Example 4

Sunflower Meristem Transformation

There are a number of published examples of meristem transformation systems for dicot species including soybean (McCabe et al. (1988) BioTechnology 6:923-926), sunflower (Bidney et al. (1992) Plant Mol. Biol. 18:301-313), and cotton (Gould et al. (1998) Plant Mol. Biol. Rep. 16:283), where chimeric genes are delivered to cells of the meristem and then participate in formation of shoots, reproductive structures and ultimately seed. Transgene delivery is accomplished by both standard particle bombardment protocols as described for soybean or by T-DNA and *Agrobacterium* protocols as described for sunflower and cotton. The WUS gene could be delivered to dicot meristem targets for either stable or transient transformation to impact the transformation response. WUS could be delivered together with agronomic genes or be used as a conditioning treatment prior to or following the protocol for DNA delivery. The methods for sunflower meristem transformation follow.

Sunflower meristem transformation is achieved by a protocol for direct DNA delivery by particle bombardment or a protocol involving a combination of DNA-free particle bombardment followed by use of *Agrobacterium* inoculation for DNA delivery as described in Bidney et al. (supra). Sunflower line SMF3, described in Burrus et al. (1991, Plant Cell Rep. 10:161-166) is used. The explant source is dry sunflower seed that is imbibed and dissected into meristem explants. Seeds are dehulled and surface sterilized then placed in sterile petri plates on two layers of filter paper moistened with sterile distilled water for overnight imbibition in the dark at 26° C. in a Percival incubator. The next day, cotyledons and root radicle are removed and meristem explants transferred to 374E medium (MS salts, Shepard vitamins, 40 mg/l adenine sulfate, 3% sucrose, 0.5 mg/l 6-BAP, 0.25 mg/l IAA, 0.1 mg/l GA, pH 5.6, and 0.8% Phytagar). Explants are cultured for 24 hr on 374E medium in the dark at 26° C. Following this culture period, elongated primary leaves are removed to expose the apical meristem. The meristem explants are placed in the center of petri plates with 374M medium (374E with 1.2% Phytagar) in preparation for particle bombardment then back in the dark for another 24 hr period at 26° C.

Particle preparation for the *Agrobacterium* based protocol is done by suspending 18.8 mg of 1.8 μm tungsten particles or 21.6 mg of 2.0 μm gold particles in 200 μl absolute ethanol. Following particle resuspension by sonication and vigorous mixing, 10 μl of particle suspension is dropped on the center of the surface of macro-carrier. Plates of 374M medium containing sunflower meristem explants are shot twice by a DuPont Biolistics PDS1000 helium gun with vacuum drawn to 26 Hg, with 650 psi rupture discs, and at the top level in the gun. Following particle bombardment, explants are spread out on the 374M plates, inoculated with an *Agrobacterium* suspension and co-cultured in the light at 26° C. for 4d. The *Agrobacterium* inoculating suspension is prepared by first starting a 5 ml liquid culture in 60A medium with kanamycin (YEP medium—10 g/l Bactopeptone, 10 g/l yeast extract, 5 g/l sodium chloride, pH 7.0, and 50 mg/l kanamycin) grown to log phase (OD600 0.5-1.0).

The log phase growth *Agrobacterium* suspension is centrifuged at 6K for 5 min and the supernatant discarded. The bacterial pellet is resuspended in inoculation medium (IM) (IM—12.5 mM MES, 1 g/l ammonium chloride, 0.3 g/l magnesium sulfate, pH 5.7) to a final calculated OD600 vis of 4.0. The inoculating *Agrobacterium* suspension is applied twice using a micro-pipette and 0.5 μl of suspension per explant. After the 4d co-cultivation of sunflower meristem explants, the expanded bases of explants are trimmed off and they are transferred to 374C medium (374E which lacks hormones, but adds 250 mg/l cefotaxime) and cultured for two weeks in the light under 18 hr day length at 26° C.

Alternatively, a direct DNA delivery protocol can be applied to sunflower meristem explants prepared as described above. Particles are prepared as follows: to 50 μL of a 15 mg/mL 0.6 μm gold particle suspension is added (in order): 10 μL DNA (0.1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 500 μL 100% ethanol and resuspended in 30 μL of 100% ethanol. The DNA/particle suspension can be sonicated three times for one second each. Five μL of the DNA-coated gold particles are then loaded on each macro carrier disk. Meristem explants are bombarded as described in the previous paragraph, spread out on 374M medium, and cultured for 4d in a Percival incubator under 18 hr of daylength at 26° C. The expanded bases of the explant are then cut off and the explant transferred to 374C medium for 2 wk of culture under the long day conditions at 26° C.

After two weeks sunflower shoots emerge from the meristem explants on 374C medium. The shoots can be scored destructively or non-destructively for the frequency of transgenic sectors per experiment and the quality of sectors with longer, wider, and deeper transgenic sectors being more desirable. They can be scored and compared to control using scorable markers such as the GUS enzyme or green fluorescence protein (GFP). Transgenic plants and seed can be obtained by adding steps to the procedure as outlined below. An assay is required such as an enzyme assay or ELISA for an agronomic protein of interest. An example is provided using the enzyme oxalate oxidase as a scorable marker (see, for example, U.S. Pat. No. 6,166,291, herein incorporated by reference). Chemical selection is not required for this transformation process.

Primary shoots following two weeks of culture on 374C medium are screened using the oxalate oxidase enzyme assay. Oxalate oxidase enzyme assays are set up using fresh leaf or cotyledon tissue to identify transformants. The assay method is done according to the protocol of Suigura et al. (1979) Chem. Pharm. Bull. 27(9):2003-2007. The assay is a two step reaction in which hydrogen peroxide is generated by oxalate oxidase in the first step then detected quantitatively by a peroxidase linked color reaction in the second. The color reaction is then measured by spectrophotometer using visible light at 550 nm. The first step of the assay is initiated by grinding shoot derived leaf tissue, pooled leaf tips of 1 sample per shoot, in 0.1 M succinate buffer, pH 3.5. The extracts are centrifuged and supernatants are discarded because most of the enzyme activity is in the cell wall due to the signal peptide of oxalate oxidase. The pellet is resuspended in 0.1 M succinate buffer, pH 3.5, and 0.05 ml of an oxalic acid solution consisting of 10 mM oxalic acid dissolved in 0.1 M succinate buffer, pH 3.5. The oxalate oxidase enzyme reaction proceeds with mild agitation at room temperature (25° C.) for 4 hr. At the end of this time period the reactions are centrifuged and an aliquot of the supernatant removed and added to a volume of 1 M Tris, pH unadjusted, to adjust the samples to a final pH of 7.0 (Tris to 0.147 M) for the second reaction step of the assay. Color development is done by adding the following components in 0.2 M Tris HCl, pH 7.0, in a mixture such that listed final concentrations are achieved: horseradish peroxidase (20 μM), 4-aminoantipyrine (0.165 mM), and N,N-dimethylaniline (0.33 mM). Absorbance at 500 nm is read for samples of the color development reaction. Shoots positive for oxalate oxidase activity are moved into nodal culture for plant recovery and the negative shoots discarded.

Positive shoots are divided into nodal explants where each explant contains at least one node from which a shoot might be recovered. Nodal explants are cultured for 3d on 374G medium (374E plus 250 mg/l cefotaxime) in the light to release nodal meristems then transferred to 374C medium and cultured in the light at 26° C. for 4 weeks to allow nodal shoot development. Shoots derived from nodal culture are assayed for oxalate oxidase activity as described above. The oxalate oxidase positive shoots are moved to procedures for plant recovery in the greenhouse and the negatives discarded.

Assay positive shoots are recovered by grafting to Pioneer sunflower hybrid 6150 grown aseptically and in vitro on 48 P medium (½× MS salts, 0.5% sucrose, pH 5.0, 0.3% gelrite). Root-stock is prepared by surface sterilizing seed of 6150 as described above for SMF3 then imbibing in the light at 26° C. for 4 days. Following this initial germination step, seedlings are place in the dark on 48P medium for 4 d to elongate hypocotyls. The seedlings are then placed back into the light and can be used in the next 7-10 days for grafting. Grafting is done by first cutting the 6150 seedling in the hypocotyl region below the meristem, then slicing the hypocotyl longitudinally in half at the cut site. Transgenic shoots are cut at their base to separate from the originating explant and secured on the root-stock by using a Parafilm™ wrap. After about one week in vitro, the grafted plants are transferred to soil and maintained under humid conditions until they can survive in drier air in the greenhouse.

Transformed T0 plants are further characterized by oxalate oxidase activity assays to verify the continued presence of an active transgene and to determine if the transgene would be present in floral tissue. If there is a sector of transformation which does not develop into a new portion of the growing T0 plant, that plant portion is trimmed off to induce floral bud initiation from axillary meristems. T0 flowers are selfed, T1 seed is recovered, and the T1 seed is germinated for T1 transgenic plant identification. Cotyledon or leaf tissue of T1 seedlings is sampled and used to assay for the scorable transgene.

Example 5

Sunflower Leaf Explant Transformation Ectopic Expression of Soybean WUS to Induce Organogenesis In addition to testing WUS in meristem transformation, other tissue explants can be tested for the formation of adventive meristems following stable or transient transformation by WUS. The explant types are well known in the art of dicot transformation and might include hypocotyl explants, leaf explants, cotyledon explants, or immature tissues such as embryo or primary leaf as described here for sunflower. As described for meristem explants, the DNA delivery can be done by either the direct delivery of particle bombardment or by *Agrobacterium* delivery by T-DNA.

Using sunflower genotype SMF3 as an example, primary leaves are isolated from meristem explants prepared as described above. After the overnight culture of dissected seeds on 374E medium, the primary leaves have elongated. These are removed and placed in the center of sterile petri plates on filters moistened with 530 medium (MS salts, B5 vitamins, 3% sucrose, 4 mg/l p-chlorophenoxyacetic acid, pH 5.8) in preparation for particle bombardment. Primary leaf explants are spread out over the center of these plates such that none are overlapping others. Particle bombardment is done exactly as described above for direct DNA delivery to meristem explants except that a sterile 70 um nitex mesh is placed over the top of the explants to help prevent them from shifting during bombardment. The DNA delivered could include a chimeric gene, consisting of a constitutive promoter such as SCP1 combined with the selectable marker NPTII and the PINII 3' region, that allows for the preferential growth of transformed tissue. Alternatively, the WUS gene may provide a growth advantage to the tissue such that a selectable marker is not required. Following particle bombardment, the explants are cultured for 3d on filters continuously moistened with 530 medium by adding 0.5 mL of additional liquid medium per 24 hr. They are cultured in the Percival growth chamber in the light under 18 hr daylength and at 26° C. Primary leaf explants that show growth are then transferred to 374E medium containing 50 mg/l kanamycin if the selectable marker gene was used and cultured for 2 to 3 wk to allow transgenic callus and shoot formation. Cultures that do not respond are transferred every two weeks to 374E with 50 mg/l kanamycin until recoverable shoots are formed. Shoots are sampled, selected, and recovered to the greenhouse as described for meristem explants above.

Sunflower primary leaves can be transformed using *Agrobacterium* by slight modifications to the protocols above. The explants on 530 medium are bombarded as described for meristem explants in the *Agrobacterium* procedure above. An *Agrobacterium* suspension is produced exactly as described for meristem explants except that the liquid culture is 25 ml instead of 5 ml. The *Agrobacterium* cells are centrifuged, the growth medium supernatant discarded, and the cells resuspended to a calculated OD600 of 0.6 in inoculation medium. Primary leaf explants are inoculated in this suspension for 10 min, then placed back on 530 medium and co-cultivated for 3d under the growth chamber conditions described above. The explants are then transferred to 374D medium (374E, 50 mg/l kanamycin, 250 mg/l cefotaxime) and cultured for 2-3 weeks. Explants can be transferred every two weeks to fresh 374D medium until shoots can be recovered.

Example 6

Expression of Chimeric Genes in Monocot Cells

A chimeric gene comprising a cDNA encoding the instant polypeptide in sense orientation with respect to the maize 27 kD zein promoter that is located 5' to the cDNA, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described in Maniatis. The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene comprising, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the $^{35}$S promoter from Cauliflower Mosaic Virus (Odell et al. (1985) Nature 313:810-812) and the 3' region of the nopaline synthase (nos) gene from the T-DNA of the Ti plasmid of *Agrobacterium* tumefaciens.

The particle bombardment method (Klein et al. (1987) Nature 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialaphos (5 mg per liter) and lacks casein or proline. The tissue continues to grow slowly on this medium. After an additional 2 weeks the tissue can be transferred to fresh N6 medium containing bialaphos. After 6 weeks, areas of about 1 cm in diameter of actively growing callus can be identified on some of the plates containing the bialaphos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833-839).

Example 7

Transformation and Regeneration of Maize Embryos

Immature maize embryos from greenhouse donor plants are bombarded with a plasmid containing the gene of the invention operably linked to a promoter; this could be a weak promoter such as nos, a tissue-specific promoter, such as globulin-1, an inducible promoter such as In2, or a strong promoter such as ubiquitin plus a plasmid containing the selectable marker gene PAT (Wohlleben et al., 1988, Gene 70:25-37) that confers resistance to the herbicide Bialaphos. Transformation is performed as follows.

Maize ears are harvested 8-14 days after pollination and surface sterilized in 30% Chlorox bleach plus 0.5% Micro detergent for 20 minutes, and rinsed two times with sterile water. The immature embryos are excised and placed embryo axis side down (scutellum side up), 25 embryos per plate. These are cultured on 560L medium 4 days prior to bombardment in the dark. Medium 560L is an N6-based medium containing Eriksson's vitamins, thiamine, sucrose, 2,4-D, and silver nitrate. The day of bombardment, the embryos are transferred to 560Y medium for 4 hours and are arranged within the 2.5-cm target zone. Medium 560Y is a high osmoticum medium (560L with high sucrose concentration).

A plasmid vector comprising the gene of the invention operably linked to the selected promoter is constructed. This plasmid DNA plus plasmid DNA containing a PAT selectable marker is precipitated onto 1.1 μm (average diameter) tungsten pellets using a $CaCl_2$ precipitation procedure as follows: 100 μl prepared tungsten particles in water, 10 μl (1 μg) DNA in TrisEDTA buffer (1 μg total), 100 μl 2.5M $CaCl_2$, 10 μl 0.1M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 μl 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are positioned 2 levels below the stopping plate for bombardment in a DuPont Helium Particle Gun. All samples receive a single shot at 650 PSI, with a total of ten aliquots taken from each tube of prepared particles/DNA. As a control, embryos are bombarded with DNA containing the PAT selectable marker as described above without the gene of invention.

Following bombardment, the embryos are kept on 560Y medium, an N6 based medium, for 2 days, then transferred to 560R selection medium, an N6 based medium containing 3 mg/liter Bialaphos, and subcultured every 2 weeks. After approximately 10 weeks of selection, bialaphos-resistant callus clones are sampled for PCR and activity of the gene of interest. In treatments containing the WUS gene, it is expected that growth will be stimulated and transformation frequencies increased, relative to the control. Positive lines are transferred to 288J medium, an MS based medium with lower sucrose and hormone levels, to initiate plant regeneration. Following somatic embryo maturation (2-4 weeks), well-developed somatic embryos are transferred to medium for germination and transferred to the lighted culture room. Approximately 7-10 days later, developing plantlets are transferred to medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to Classic™ 600 pots (1.6 gallon) and grown to maturity. Plants are monitored for expression of the gene of interest.

Example 8

Ectopic Expression of Maize WUS to Induce Organogenesis

Using the genotype High type II as an example, embryos are isolated and cultured on 560P medium for 3-5 days. Twelve hours before bombardment these embryos are transferred to high osmotic 560Y medium. Expression cassettes containing the WUS cDNA are then co-introduced into the scutella of these embryos along with an expression cassette containing genes encoding selectable markers, such as Bar or Pat, or visual markers such as green fluorescent protein (GFP) or cyan fluorescent protein (CFP) using methods well described in the art for particle gun transformations. Twelve to 24 hours following bombardment, embryos are then transferred back to 560P culture medium and incubated in the dark at 26° C. After one week of culture these embryos are moved to 560R selection medium. Cultures are then transferred every two weeks until transformed colonies appear. It is expected that expression of WUS will stimulate adventive meristem (shoot) formation. This will be apparent when the cultures are compared to controls (transformed without the WUS cDNA or non-induced). Using either inducible expression cassettes, tissue specific promoters, or promoters of varying strengths it will be possible to control the levels of expression to maximize the formation of adventive meristems. Using either non-responsive genotypes or sub-optimal culture conditions with responsive genotypes, only the transformed cells expressing the WUS cDNA will form meristems and regenerate plants. For experiments in which WUS-induced shoot proliferation occurs via ectopic meristem formation, WUS can be used as a positive selective phenotype and no selection agent is required in the media. In this manner the WUS gene can be used as a positive selective marker (only the cells expressing the gene will form shoot meristems) and transformants can be recovered without a negative selective agent (i.e. bialaphos, basta, kanamycin, etc.).

Results

A. Ectopic Expression of Maize WUS1 to Stimulate Organogenesis.

Using the maize genotype High type II, immature embryos were isolated, cultured and transformed as described generally in Example 7 substituting 0.6 μm gold particles for tungsten and with the sample plate 7.5 cm below the stooping screen. DNA was delivered using co-transformation, a method where introduced DNA's are normally integrated in a single locus. As a control, embryos were shot with a 1:1 mixture of plasmids, the first plasmid containing a ubiquitin promoter-driven green fluorescence protein (GFP) and a second plasmid containing a ubiquitin driven uidA gene (GUS). In the WUSCHEL treatment, the embryos were bombarded with a 1:1 mixture of plasmids containing the ubiquitin promoter driving expression of GFP (Ubi:GFP) and a plasmid containing the WUS1 DNA (SEQ ID NO: 32) driven by the maize In2 promoter (In2:WUS1). The In2 promoter is induced by auxin-like compounds and is weakly expressed on callus maintenance medium. Each treatment contained 175 embryos. Embryos were allowed to callus on 560P medium without selection. After approximately 3 weeks, GFP-positive tissue was visually selected under a fluorescent microscope and transferred to fresh medium. After 8 weeks colony numbers and size were recorded. In the control, 4 small events (<1 cm$^2$) were recovered along with 1 medium event (1-2 cm$^2$) for a total of 5 events. In the WUS1 treatment, the colonies were both more numerous and larger. In this treatment 6 small events (<1 cm$^2$) were recovered along with 2 medium size events (1-2 cm$^2$) and 3 large events (>2 cm$^2$) for a total of 11 events. Plants were regenerated and some unusual phenotypes were observed during the plant regeneration process in the In2:WUS1 treatment, most notable were somatic embryos derived from root tips, a phenomenon observed with ectopic WUS expression in Arabidopsis (Zuo et al. (2002) Plant J. 30:349-359) One WUS1 event was observed with a highly unusual phenotype. In this event, ectopic earshoots and leaf-like structures were formed in a radial pattern on the abaxile side of the vegetative leaves. This is a highly unusual placement for meristems in angiosperms but a similar phenotype has been observed in *Arabidopsis* plants over-expressing WUSCHEL (Lohmann et al. (2001) Cell 105:793-803). All other regenerated plants were normal, as expected, since the In2 promoter is not on in the absence of auxin-like chemicals.

B. Ectopic Expression of Maize WUS in an Inbred to Stimulate Organogenesis.

Immature embryos were transformed as described in Example 7 with media alterations done to adapt the procedure for use with inbred germplasm and visual selection. Using the maize inbred 581, a tissue culture recalcitrant line, immature embryos from greenhouse grown plants were isolated 12 days after pollination and cultured on 605J medium (a medium containing both full strength MS salts (macro and micronutrient) and 0.6× N6 macronutrient salts plus additional B5 micronutrients, with a mixture of SH and Eriksson's vitamin, L-proline and casamino acids, silver nitrate, 0.3 mg/l 2,4-D and 1.2 mg/l Dicamba, 2% sucrose and 0.06% glucose, solidified with agar). The embryos were incubated in the dark at 28° C. overnight. The embryos were then transferred to a high osmoticum medium similar to 605J with the addition of 15% sucrose prior to particle bombardment. Embryos were shot in a method similar to that in Example 7 substituting 0.6 μm gold particles for tungsten. DNA was delivered using co-transformation, as noted above. As a control, embryos were shot with a 1:1 mixture of plasmid DNA's containing a Ubiquitin driven yellow fluorescence protein (YFP) and a plasmid containing a Ubiquitin driven uidA gene (GUS). In the WUSCHEL treatment the embryos were bombarded with a 1:1 mixture of plasmid DNA's containing the Ubiquitin promoter driving expression of YFP (Ubi:YFP) and a plasmid containing WUS2 (SEQ ID NO: 62) driven by the maize In2 promoter (In2:WUS2). Immediately following bombardment embryos were transferred back to low osmoticum 605J medium. Each treatment contained 90 embryos. Embryos were observed 3 days after bombardment and differences were observed between the treatments.

In the control treatment, hundreds of cells transiently expressing the YFP protein were visible under a fluorescent microscope, and in this population of fluorescing cells, cell division was very rare. Cells transiently expressing YFP were also apparent in the WUS2 treatment. However, in the WUS2 treatment, cell division was apparent in the cells surrounding the YFP positive cells, resulting in the appearance of a mound of cells with discrete YFP positive cells at the apex. Over the next few weeks these embryo/shoot-like outgrowths continued to elongate with the YFP expressing cells maintaining their position at the apex of projections or a few cells beneath the apex reminiscent of endogenous WUS expression in *Arabidopsis* apical meristems (Mayer et al. (1998) Cell 95:805-815). Embryos and embryogenic calli were transferred every two weeks. After approximately two months only YFP expressing calli were transferred. After 3 months, YFP tissue was transferred to regeneration medium lacking 2,4-D. No embryogenic YFP positive events were recovered from the control treatment. In contrast, over 24 YFP positive events with embryogenic callus were obtained from the WUS2 treatment. Plants were regenerated from the WUS2 treatment and sent to the greenhouse. This experiment was repeated with similar results, the control transformation frequency was 2%, while the transformation frequency in the In2:WUS2 treatment transformation frequency was 19%.

C. Ectopic Expression of Maize WUS2 is Sufficient to Stimulate Organogenesis/Embryogenesis in Recalicitrant Tissues There exists only a small developmental window in which maize embryos are amenable to tissue culture growth, a prerequisite for transformation. Normally this occurs between 9-12 days after pollination when the immature embryos are between 1.0-1.5 mm in length. Older, larger embryos fail to produce embryogenic callus and thus cannot be transformed. To demonstrate that WUS2 can be used to induce organogenesis/embryogenesis, embryos were isolated 17-18 days after pollination and used for transformation experiments. Using the maize inbreds 581, N46, and P38, immature embryos from greenhouse grown plants were isolated 17-18 days after pollination and cultured on 605J medium. Immature embryos were transformed and visually selected as described in Example 8B. DNA was delivered using co-transformation as described above. As a control, embryos were shot with a 1:1 mixture of plasmid DNA's containing a Ubiquitin driven YFP (Ubi:YFP) and a plasmid containing a Ubiquitin driven uidA gene (Ubi:uidA). In the WUSCHEL treatment the embryos were bombarded with a 1:1 mixture of plasmid DNA's containing the Ubiquitin promoter driving expression of the YFP (Ubi:YFP) and a plasmid containing the WUS2 DNA (SEQ ID NO: 62) driven by the maize Oleosin promoter (Ole:WUS2). Immediately following bombardment embryos were transferred back to low osmoticum 605J medium. Each bombarded plate contained 10 embryos. In the control, each genotype was represented by 2 plates. In the WUS2 treatment, 581 and N46 had 2 plates each while the P38 treatment had only 1 plate (10 embryos). Embryos were observed 5 days after bombardment and hundreds of YFP positive cells were seen in both treatments under the fluorescent microscope. When observed under visible light, embryo-like protuberances were visible in the WUS2 treatment. No embryo-like protuberances were observed in the control treatment. When observed under the fluorescent microscope each of the embryo-like protuberances in the WUS2 treatment was associated with YFP fluorescence demonstrating that WUS2 is sufficient to induce organogenesis from tissues that are normally unresponsive. These embryos are currently being cultured to obtain transformants. As observed in the WUS2 treatment in Example 8B, cell division was apparent in the cells surrounding the YFP positive cells, resulting in the appearance of a mound of cells with discrete YFP positive cells at the apex (SEE FIG. 2).

Example 9

Transient Expression of the WUS Gene Product to Induce Shoot Organogenesis

It may be desirable to "kick start" meristem formation by transiently expressing the WUS genes product. This can be done by delivering WUS 5' capped polyadenylated RNA, expression cassettes containing WUS DNA, or WUS protein. All of these molecules can be delivered using a biolistics particle gun. For example, 5' capped polyadenylated WUS RNA can easily be made in vitro using Ambion's mMessage mMachine kit. Following a delivery procedure outlined above, RNA is co-delivered along with DNA containing an agronomically useful expression cassette. It is expected that cells receiving WUS will form shoot meristems and a large portion of these will have integrated the agronomic gene. Plants regenerated from these embryos can then be screened for the presence of the agronomic gene.

Example 10

Maize Meristem Transformation

Meristem transformation protocols rely on the transformation of apical initials or cells that can become apical initials following reorganization due to injury or selective pressure. The progenitors of these apical initials differentiate to form the tissues and organs of the mature plant (i.e., leaves, stems, ears, tassels, etc.). The meristems of most angiosperms are layered with each layer having its own set of initials. Normally in the shoot apex these layers rarely mix. In maize the outer layer of the apical meristem, the L1, differentiates to form the epidermis while descendents of cells in the inner layer, the L2, give rise to internal plant parts including the gametes. The initials in each of these layers are defined solely by position and can be replaced by adjacent cells if they are killed or compromised. Meristem transformation frequently targets a subset of the population of apical initials and the resulting plants are chimeric. If for example, 1 of 4 initials in the L1 layer of the meristem are transformed only ¼ of epidermis would be transformed. Selective pressure can be used to enlarge sectors but this selection must be non-lethal since large groups of cells are required for meristem function and survival.

Transformation of a meristem cell with a WUS sequence under the expression of a promoter active in the apical meristem (either meristem-specific or constitutive) would allow the transformed cells to re-direct the initiation of new apical initials driving the meristem towards homogeneity and minimizing the chimeric nature of the plant body. To demonstrate this, the WUS sequence is cloned into a cassette with a promoter that is active within the meristem (i.e. either a strong constitutive maize promoter such as the ubiquitin promoter including the first ubiquitin intron, or a promoter active in meristematic cells such as the maize histone, cdc2 or actin promoter). Coleoptilar stage embryos are isolated and plated meristem-up on a high sucrose maturation medium (see Lowe et al., 1997, In *Genetic Biotechnology and Breeding of Maize and Sorghum, AS Tsaftaris*, ed., *Royal Society of Chemistry, Cambridge, UK, pp*94-97). The WUS expression cassette along with a reporter construct such as Ubi:GUS:pinII can then be co-delivered (preferably 24 hours after isolation) into the exposed apical dome using conventional particle gun transformation protocols. As a control, the WUS construct can be replaced with an equivalent amount of pUC plasmid DNA. After a week to 10 days of culture on maturation medium the embryos can be transferred to a low sucrose hormone-free germination medium. Leaves from developing plants can be sacrificed for GUS staining. Transient expression of the WUS sequence in meristem cells, through formation of new apical initials, will result in broader sectors or completely transformed meristems increasing the probability of germ-line transformation. Integration and expression of the WUS sequence will impart a competitive advantage to expressing cells resulting in a progressive enlargement of the transgenic sector. Due to the WUS-induced maintenance of apical initials and growth of their transformed derivatives, they will supplant wild-type meristem cells as the plant continues to grow. The result will be both enlargement of transgenic sectors within a given cell layer (i.e. periclinal expansion) and into adjacent cell layers (i.e. anticlinal invasions). As cells expressing the WUS gene occupy an increasingly large proportion of the meristem, the frequency of transgene germline inheritance goes up accordingly. Using WUS in this manner to target meristems will increase transformation rates, realtive to control treatments. Coleoptilar-stage embryos used as a source of meristems is used an example, but other meristem sources could be used as well, for example immature influorescences.

Example 11

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with fluorescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70-73; and U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810-812), the hygromycin phosphotransferase gene from plasmid pJR225 (from *E. coli*; Gritz et al. (1983) Gene 25:179-188) and the 3' region of the nopaline synthase (nos) gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 12

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) Gene 56:125-135) which employs the bacteriophage T7 RNA polymerase/T7 promoter system. Plasmid pBT430 was constructed by first destroying the EcoRI and Hind III sites in pET-3a at their original positions. An oligonucleotide adaptor containing EcoRI and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113-130). Cultures are grown in LB medium containing ampicillin (100 mg/L) at 25° C. At an optical density at 600 nm of approximately 1, IPTG (isopropylthio-α-galactoside, the inducer) can be added to a final concentration of 0.4 mM and incubation can be continued for 3 h at 25° C. Cells are then harvested by centrifugation and re-suspended in 50 µL of 50 mM Tris-HCl at pH 8.0 containing 0.1 mM DTT and 0.2 mM phenylmethylsulfonyl fluoride (PMSF). A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 13

Use of FLP/Frt System to Excise the WUS Cassette

In cases where the WUS gene has been integrated and WUS expression is useful in the recovery of maize transgenics (i.e. under conditions where continuous expression of WUS promotes adventive meristem formation), but is ultimately not desired in the final product, the WUS expression cassette (or any portion thereof that is flanked by appropriate FRT recombination sequences) can be excised using FLP-mediated recombination (see, for example, PCT Publication WO 99/25841; and WO 99/25821).

Example 14

Identification of WUS2 Haplotypes from Various Inbred Lines

Plant genomic DNA was isolated from 6 different inbred maize lines, 3DT, 09B, 07D, KW3, B73, and Mo17 using a standard CTAB extraction protocol (Doyle and Doyle, Focus, 1990). One gram of frozen immature leaf tissue was ground in liquid nitrogen using a pre-chilled mortar and pestle. The powdered tissue was transferred to a 50 mL Beckman centrifuge tube along with 100 mL of a pre-heated 60° C. CTAB isolation buffer (2% (w/v) cetyltrimethylammonium bromide; 1.4 M NaCl; 0.005% (v/v) 2-mercaptoethanol; 20 mM EDTA, pH 8.0; 100 mM Tris-HCl, pH 8.0).

The samples were incubated for 1 hour at 60° C. with gently swirling every 10 minutes. The samples were then extracted once with 24:1 (v/v) chloroform:isoamyl alcohol. In order to concentrate the phases, the samples were centrifuged at 3750 rpm (2800×g) at room temperature. The aqueous phase was removed with a wide bore pipette and transferred to a sterile 50 mL Beckman tube. Nucleic acids were precipitated by the addition of a 2/3 volume of ice cold 2-propanol and incubated overnight at −20° C. Following the ethanol precipitation of the DNA, the tubes were centrifuged for 30 minutes at 3750 rpm (2800×g) at 4° C. The resultant pellet was rinsed in 20 mL of a wash solution (80% (v/v) ethanol, 15 mM ammonium acetate) for 30 minutes before being centrifuged for 10 minutes at 4500 rpm (1600×g). Following centrifugation, the supernatant was removed and the DNA pellet was air dried overnight on the bench top. The following day, the DNA was resuspended in 0.75 mL TE (10 mM Tris-HCl, pH 8.0; 1 mM EDTA, pH 8.0).

Following genomic DNA isolation, gene specific primers were designed to amplify WUS2 (p0016.ctsas50r) genomic fragments from maize inbred lines, 3DT, 09B, 07D, KW3, B73, and Mo17 using a polymerase chain reaction (PCR) technique. Three sets of gene specific primers were used that generated overlapping WUS2 genomic DNA fragments that together spanned the entire WUS2 coding sequence. WUS2 primer pairs 65505 (SEQ ID NO: 82) (5'GTCCGAGCTAG-GTCACAGAAGCGCTCAGGA-3'); and 65506 (SEQ ID NO: 83) (5'TATCGTGTCCGACGACGCGAAGCGT-3'); 66571 (SEQ ID NO: 84) (5'-CCACCCTCGGCTTC-TACGC-3') and 65507 (SEQ ID NO: 85) (5'-ACCCCA-GAACGGCMGTAGCTGCTGCT-3'); 66577 (SEQ ID NO: 86) (5'-GCATTGCGCGCAGTT-3') and 67447 (SEQ ID NO: 87) (5'-ACGCATGCAGTAGCTGGAGTCTAA-3') amplified genomic DNA fragments that were approximately 757 bp, 512 bp, and 809 bp respectively. Amplified lengths should be taken as approximate since some variation within the WUS2 sequence between inbred lines was detected due to polymorphisms. PCR was performed using a three-step protocol that was preceded by an initial hotstart at 95° C. for 15 minutes: denaturation, 94° C. for 45 seconds; annealing, 60° C. for 45 seconds; extension, 72° C. for 1.5 minutes. Amplicons were separated on a 1% ethidium bromide stained agarose gel. Agarose gels were analyzed on a short wave (310 nm) UV transilluminator and captured using CCD imaging with the Quantity One image analysis/quantitation software from Bio-Rad (Hercules, Calif., USA). PCR products were gel purified, TA cloned into the pCR4.0 vector (InVitrogen, Carlsbad, Calif., USA), and submitted for sequencing. Consensus sequences for each inbred were generated using the Sequencher program version 4.1.4b7 (Gene Codes Corporation, Ann Arbor, Mich., USA). Approximately 1.4 kb of WUS2 sequence was derived from each inbred line and compared with one another. Any deviations between WUS2 sequence between the various inbred lines, such as insertion/deletions (indels) and/or single nucleotide polymorphisms (SNPs) were noted. Sequence ID numbers for genomic DNA sequences, and spliced products (see Example 18) that encompass the full-length WUS2 coding sequences are as follows:

3DT WUS2 nucleotide sequences, SEQ ID NOS: 62, 63, 65, and 67, and corresponding amino acid sequences, SEQ ID NO: 64, 66, and 68;

09B WUS2 nucleotide sequences, SEQ ID NOS: 69, 70, 72, and 74, and corresponding amino acid sequences, SEQ ID NOS: 71, 73, and 75;

07D WUS2 nucleotide sequences, SEQ ID NOS: 48, 49, 51, and 53, and corresponding amino acid sequences, SEQ ID NOS: 50, 52, and 54;

KW3 WUS2 nucleotide sequences, SEQ ID NOS: 55, 56, 58, and 60, and corresponding amino acid sequences, SEQ ID NOS: 57, 59, and 61;

B73 WUS2 nucleotide sequences, SEQ ID NOS: 34, 35, 37, and 39, and corresponding amino acid sequences, SEQ ID NOS: 36, 38, and 40; and Mo17 WUS2 nucleotide sequences, SEQ ID NOS: 41, 42, 44, and 46, and corresponding amino acid sequences, SEQ ID NOS: 43, 45, and 47.

Example 15

Placing WUS Genes Under the Control of a Tissue-Specific Promoter

The WUS gene can be placed under control of an inducible expression system, as described in Zuo et al. (2000) Plant J 24:265-273; and U.S. Patent Application Publication No. US 2003/0082813 A1, the entire contents of which are herein incorporated by reference. The G10-90 promoter in the XVE vector can be replaced with a tissue-specific promoter (e.g. a pollen-, root-stem- or leaf-specific promoter). A variety of tissue-specific promoters are well known to those of skill in the art. Because expression of a transgene is activated by the chimeric XVE gene which is controlled by a tissue-specific promoter in this Example, the $O^{lexA}$-46 promoter controlling the WUS transgene is therefore tissue-specific in an inducer-dependent manner. This means that WUS will be induced only in the presence of an inducer and only in the specific tissue corresponding to the tissue specific promoter. Appropriate tissues or cell types, can then be collected from the transgenic plants and used for induction of somatic embryos and regeneration of plants.

When pollen derived from transgenic plants carrying a pollen-specific promoter-XVE/$O^{lexA}$-46-WUS vector is used, progeny plants generated from pollen-derived somatic embryos should be haploid instead of diploid (see, e.g., Twell et al. (1989) Mol. Gen. Genet. 217(2-3):240-245; and Twell et al. (1990) Development 109(3):705-714 for pollen-specific promoters). In this embodiment of the invention, a transgenic plant having in its genome a WUS gene under the control of an inducible, pollen-specific promoter would not normally express the gene. Pollen from such a plant can be cultured in the presence of the inducer until somatic embryogenesis occurs, after which the inducer is removed and the haploid embryos are permitted to develop into haploid clones according to standard techniques.

Example 16

Generating an Apomictic Plant

Apomixis can be induced by introducing WUS into a plant cell in such a manner that the WUS gene is expressed in the appropriate tissues (e.g., nucellus tissue). This can be by means of, but is not limited to, placing the WUS gene under the control of a tissue-specific promoter (e.g., a nucellus-specific promoter), an inducible promoter, or a promoter that is both inducible and tissue-specific. Inducing expression of the WUS gene, e.g. in the nucellus, produces apomixis leading to an apomictic plant. This plant may then be used to establish a true-breeding plant line. Additionally, the vector utilized to transfer WUS into the plant cell can include any other desired heterologous gene in addition to WUS, including but not limited to, a marker gene or a gene to confer any desirable trait upon the plant, e.g., a gene resulting in larger plants, greater yield, stalk and/or root strength, cycle time, maturity zone, stress resistance(s), disease resistance(s), insect control and/or resistance(s), quality seed traits, added-value traits, etc. This would lead to the development of an apomictic line with the desired trait(s).

In a variation of the scheme, plant expression cassettes, including but not limited to monocot or dicot expression cassettes, directing WUS expression to the inner integument or nucellus can be constructed. An expression cassette directing expression of the WUS DNA sequences to the nucellus can be made using the barley Nuc1 promoter (Doan et al. (1996) Plant Mol. Biol. 31(4):877-886). Such an expression construct can be used for plant transformation. Other genes which confer desirable traits can also be included in the cassette, or provided on separate cassettes. For example, embryos can be co-bombarded with the selectable marker PAT fused to the GFP gene along with the nucellus specific WUS expression cassette.

It is anticipated that transgenic plants carrying the expression cassette will then be capable of producing de novo embryos from WUS expressing nucellar cells. In the case of maize, this is complemented by pollinating the ears to promote normal central cell fertilization and endosperm development. In another variation of this scheme, Nuc1:WUS transformations could be done using a FIE (fertility-independent endosperm)-null genetic background which would promote both de novo embryo development and endosperm development without fertilization (see Ohad et al. (1999) Plant Cell 11(3):407-415; and PCT publication WO 01/16325). Upon microscopic examination of the developing embryos it will be apparent that apomixis has occurred by the presence of embryos budding off the nucellus. In yet another variation of this scheme the WUS DNA sequences could be delivered as described above into a homozygous zygotic-embryo-lethal genotype, in this scenario, only the adventive embryos produced from somatic nucellus tissue would develop in the seed. Similarly, using Nuc1:WUS, to produce de novo embryos from the nucellus, in conjunction with a FIE suppression cassette would result in both embryo and endosperm development in the absence of fertilization.

WUS expression could be controlled by a simple tissue-specific promoter, in which case WUS would be expressed throughout the given tissue—for example throughout the nucellus in the case of the Nuc1 promoter. Or, WUS expression could be controlled in a way that confers a spatial gradient on top of the tissue specific localization, resulting in isolated pockets of expression. For example, using standard techniques as described above, plant tissue is transformed with the following:

Nuc1:FRT1-spacer—:nos term:FRT1::WUS::pinII+In2::FLP::pinII

When FLP expression is induced by the addition of safener during late ovule development, it results in sporadic, cell-autonomous excision of the FRT1-flanked spacer, thus activating expression of WUS in these scattered single cells, but only for the single cells located in the nucellus, as controlled by the Nuc1 promoter.

Of course, there are variations on this theme depending on which promoters are used. For example, Nuc1-driven FLP expression would activate WUS expression across a larger percentage of cells in the nucellus, and here you could use an inducible promoter (or even the nuc1 promoter again).

Another interesting variation on this theme that would confer a spatial gradient and a temporal gradient (a pulse) in a tissue-specific manner, by splitting the WUS coding region in two parts so the encoded products are made functional through intein splicing. Place the first half of the WUS gene in the nuc1/frt1-activated cassette and the second half of the WUS gene behind the In2 promoter. Upon adding a pulse of safener, for example through ear infusion, FLP activity would result in excision of the frt1-flanked spacer in scattered, single cells through the ear. However, only in the nucellus, where the first half of the WUS gene is being expressed, would intein splicing result in a functional WUS protein. Because the safener was added in a pulsed fashion, the second half of the WUS protein would only be encoded on a transient basis, resulting in pulsed expression of WUS in single cells within the nucellus.

Example 17

WUS Expression for Positive Selection

It is expected that transformants can be recovered using WUS expression to provide a positive selection means under reduced auxin levels or in the absence of auxins in the medium, and in the absence of herbicide or antibiotic selection.

To determine if WUS can be used in a positive selection scheme, transformation experiments, using any standard method including particle gun or *Agrobacterium*, can be performed. Transformants are selected on medium with normal auxin levels, or on medium with reduced or no auxin, or visually (using GFP) on medium without bialaphos. Transformation frequencies are based on numbers of embryos with one or more multicellular GFP positive cell clusters. For example, one can test this concept using two treatment variables. The first is that immature embryos are bombarded with a control plasmid (UBI:PAT~GFP) or with UBI:PAT~GFP+In2:WUS. The second variable is that the bombarded embryos are divided onto either normal bialaphos-containing selection medium (with normal auxin levels of 2 mg/L 2,4-D), or medium with no bialaphos and reduced 2,4-D levels (0.5 mg/L). It is expected from previous studies of positive selection that on bialaphos selection the WUS treatment will result in higher transformation frequency than the control. It is also anticipated that the low auxin medium (0.5 mg/L 2,4-D) will result in reduced growth rates. Consistent with this, it is expected that for the control plasmid treatment (UBI:PAT~GFP), recovery of GFP-expressing (fluorescent) colonies will be reduced relative to highly effective bialaphos selection treatment. In contrast, it is expected that WUS expression, through its stimulation of embryogenesis, may compensate for the low auxin environment, providing a growth advantage to the transgenic colonies, and maintaining the efficiency of transformant recovery at approximately the same range as the WUS/bialaphos-selected treatment.

On medium completely devoid of auxin, it is expected that colonies will only be observed in the WUS treatment. In this experiment, immature embryos are transformed with either the control plasmid (UBI:PAT~GFP) or with UBI:PAT~GFP+In2:WUS, and then plated either onto 3.0 mg/L bialaphos, 2.0 mg/L 2,4-D medium or onto no-bialaphos, no 2,4-D medium (in this latter treatment, wild-type maize callus will not exhibit embryonic growth). Again, it is expected that the WUS polynucleotide express will increase transformation significantly over the control plasmid value on normal auxin-containing, bialaphos selection medium. Also, it is expected that no transformants will be recovered with the control plasmid on medium devoid of exogenous auxin.

Even on auxin-containing medium, the WUS polynucleotide in combination with GFP+ expression can be used to recover transformants without chemical selection. For example, under these conditions it is expected that the recovery of transformants will be relatively efficient, but may require more diligence than the low-or no-auxin treatments above to separate the GFP-expressing colonies from the growing callus population.

Example 18

Splicing Variants of Genomic WUS Sequences

The polynucleotides generated in Example 14 are further evaluated and alternative splice sites are identified in the genomic sequences. Two introns are identified in the sequences, which can generate three alternately spliced products, a spliced sequence in which the first intron is spliced and the second intron remains, a spliced sequence in which the first and second introns are completely spliced, and a spliced sequence in which the first intron is spliced and the second intron is spliced in an alternate way. Of these products, the spliced sequence in which both introns are completely spliced is most likely to be the sequence which encodes the major protein product (Table 9). The polypeptides encoded by the alternatively spliced polynucleotide sequences are shown below, in Tables 7-9 in alignments generated using the CLUSTALW program under default parameters (VNTI software, Informax, Gaithersburg, Md.). Consensus sequences are also provided in the alignment. The consensus sequence generated by alignment of the WUS2 sequences with the $1^{st}$ intron spliced is presented as SEQ ID NO: 88. The consensus sequence generated by alignment of the WUS2 sequences with the $1^{st}$ intron and $2^{nd}$ intron spliced is presented as SEQ ID NO: 89. The consensus sequence generated by alignment of the WUS2 sequences with the $1^{st}$ intron and alternate splicing of the $2^{nd}$ intron is presented as SEQ ID NO: 90. Conserved amino acid motifs are shown in bold, the 25 amino acid motif is in italicized bold.

TABLE 7: Alignment of WUS2 amino acid sequences with 1st intron spliced:

```
                        1                                                50
    SEQ ID NO:27   (1)  MAANAGGGGAGGGSGSGSVAAPAVCRPSGSRWTPTPEQIRMLKELYYGCG
    SEQ ID NO:36   (1)  MAANAGGGGAGGGSGS--VAAPAVCCPSGSRWTPTPEQIRMLKELYYGCG
    SEQ ID NO:43   (1)  MAANAGGGGAGGGSGS--VAAPAVCRPSGSRWTPTPEQIRMLKELYYGCG
    SEQ ID NO:50   (1)  MAANAGGGGAGGGSGS--VAAPAVCRPSGSRWTPTPEQIRMLKELYYGCG
    SEQ ID NO:57   (1)  MAANAGGGGAGGGSGS--VAAPAVCRPSGSRWTPTPEQIRMLKELYYGCG
    SEQ ID NO:64   (1)  MAANAGGGGAGGGSGSGSVAAPAVCRPSGSRWTPTPEQIRMLKELYYGCG
    SEQ ID NO:71   (1)  MAANAGGGGAGGGSGSGSVAAPAVCRPSGSRWTPTPEQIRMLKELYYGCG
    SEQ ID NO:88   (1)  MAANAGGGGAGGGSGS  VAAPAVCRPSGSRWTPTPEQIRMLKELYYGCG 51                                               100
    SEQ ID NO:27  (51)  IRSPSSEQIQRITAMLRQHGKIEGKNVFYWFQNHKARERQKRRLTSLDVN
    SEQ ID NO:36  (49)  IRSPSSEQIQRITAMLRQHGKIEGKNVFYWFQNHEARERQKRRLTSLDVN
    SEQ ID NO:43  (49)  IRSPSSEQIQRITAMLRQHGKIEGKNVFYWFQNHKARERQKRRLTSLDVN
    SEQ ID NO:50  (49)  IRSPSSEQIQRITAMLRQHGKIEGKNVFYWFQNHKARERQKRRLTSLDVN
    SEQ ID NO:57  (49)  IRSPSSEQIQRITAMLRQHGKIEGKNVFYWFQNHKARERQKRRLTSLDVN
    SEQ ID NO:64  (51)  IRSPSSEQIQRITAMLRQHGKIEGKNVFYWFQNHKARERQKRRLTSLDVN
    SEQ ID NO:71  (51)  IRSPSSEQIQRITAMLRQHGKIEGKNVFYWFQNHKARERQKRRLTSLDVN
    SEQ ID NO:88  (51)  IRSPSSEQIQRITAMLRQHGKIEGKNVFYWFQNHKARERQKRRLTSLDVN 101                                              150
    SEQ ID NO:27 (101)  VPAAGAADATTSQLGVLSLSSPPPSGAAPPSPTLGFYAAGNGGGSAVLLD
    SEQ ID NO:36  (99)  VPAAGAADATTSQLGVLSLSSPPPSGAAPPSPTLGFYAAGNGGGSAVLLD
    SEQ ID NO:43  (99)  VPAAGAADATTSQLGVLSLSSPPPSGAAPPSPTLGFYAAGNGGGSAVLLD
    SEQ ID NO:50  (99)  VPAAGAADATTSQLGVLSLSSPPPSGAAPPSPTLGFYAAGNGGGSAVLLD
    SEQ ID NO:57  (99)  VPAAGAADATTSQLGVLSLSSPPPSGAAPPSPTLGFYAAGNGGGSAVLLD
    SEQ ID NO:64 (101)  VPAAGAADATTSQLGVLSLSSPPPSGAAPPSPTLGFYAAGNGGGSAVLLD
    SEQ ID NO:71 (101)  VPAAGAADATTSQLGVLSLSSPPPSGAAPPSPTLGFYAAGNGGGSAVLLD
    SEQ ID NO:88 (101)  VPAAGAADATTSQLGVLSLSSPPPSGAAPPSPTLGFYAAGNGGGSAVLLD 151                                              200
    SEQ ID NO:27 (151)  TSSDWGSSGAAMATETCFLQVGAVVRSFLGHCAQFHVRTYELIAASFHPP
    SEQ ID NO:36 (149)  TSSDWGSSGAAMATETCFLQVGAVVRSFLGHCAQFHVRTYELIAASFHPP
    SEQ ID NO:43 (149)  TSSDWGSSGAAMATETCFLQVGAVVRSFLGHCAQFHVRTYELIAASFHPP
    SEQ ID NO:50 (149)  TSSDWGSSGAAMATETCFLQVGAVVRSFLGHCAQFHVRTYELIAASFHPP
    SEQ ID NO:57 (149)  TSSDWGSSGAAMATETCFLQVGAVVRSFLGHCAQFHVRTYELIAASFHPP
```

```
SEQ ID NO:64  (151) TSSDWGSSGAAMATETCFLQVGAVVRSFLGHCAQFHVRTYELIAASFHPP
SEQ ID NO:71  (151) TSSDWGSSGAAMATETCFLQVGAVVRSFLGHCAQFHVRTYELIAASFHPP
SEQ ID NO:88  (151) TSSDWGSSGAAMATETCFLQVGAVVRSFLGHCAQFHVRTYELIAASFHPP 201                                               250
SEQ ID NO:27  (201) VYITVRYGGARPQDYMGVTDTGSSSQWPCFSSSDTIMAAAAAARVATTR
SEQ ID NO:36  (199) VYITVRYGGARPQDYMGVTDTGSSSQWPCLSSSDTIMAAAAARAP-TTR
SEQ ID NO:43  (199) VYITVRYGGARPQDYMGVTDTGSSSQWPCLSSSDTIMAAAAARAP-TTR
SEQ ID NO:50  (199) VYITVRYGGARPQDYMGVTDTGSSSQWPRFSSSDTIMAAAAARA--ATTR
SEQ ID NO:57  (199) VYITVRYGGARPQDYMGVTDTGSSSQWPRFSSSDTIMAAAAARA--ATTR
SEQ ID NO:64  (201) VYITVRYGGARPQDYMGVTDTGSSSQWPRFSSSDTIMAAAAARA--ATTR
SEQ ID NO:71  (201) VYITVRYGGARPQDYMGVTDTGSSSQWPRFSSSDTIMAAAAARA--ATTR
SEQ ID NO:88  (201) VYITVRYGGARPQDYMGVTDTGSSSQWPRFSSSDTIMAAAAARA  ATTR 251                                               300
SEQ ID NO:27  (251) APETLPLFPTCGDDDDDDSQPPPRPRHAVPVPAGETIRGGGGSSSSYLPF
SEQ ID NO:36  (248) PPETLPLFPTCGDDDDDDNQPPSRPRHAVPVPAGEPIRVGGGGSSSYLPF
SEQ ID NO:43  (248) PPETLPLFPTCGDDDDDDNQPPPRPRHAVPVPAGEPIRVGGGGSSSYLPF
SEQ ID NO:50  (247) APETLPLFPTCGDDGGSGS------------------------SSYLPF
SEQ ID NO:57  (247) APETLPLFPTCGDDGGSGS------------------------SSYLPF
SEQ ID NO:64  (249) APETLPLFPTCGDDGGSGS------------------------SSYLPF
SEQ ID NO:71  (249) APETLPLFPTCGDDGGSGS------------------------SSYLPF
SEQ ID NO:88  (251) APETLPLFPTCGDDGGSGS                        SSYLPF 301                                               350
SEQ ID NO:27  (301) WGAGAASTTAGATSSVAIQQQHQLQEQYSFYSN--STQLAGTGSQDVS--
SEQ ID NO:36  (298) WGA--ASTTAGATSSVAIQQQHQQQEQYIFYSN--STQLAGTGSQDVSAS
SEQ ID NO:43  (298) WGA--ASTTAGATSSVAIQQQHQLQEQYIFYSN--STQLAGTGSQDVSAS
SEQ ID NO:50  (272) WGA--ASTTAGATSSVAIQQQHQLQEQYSFYSNSNSTQLAGTGNQDVSAT
SEQ ID NO:57  (272) WGA--ASTTAGATSSVAIQQQHQLQEQYSFYSNSNSTQLAGTGNQDVSAT
SEQ ID NO:64  (274) WGA--ASTTAGATSSVAIQQQHQLQEQYSFYSNSNSTQLAGTGNQDVSAT
SEQ ID NO:71  (274) WGA--ASTTAGATSSVAIQQQHQLQEQYSFYSNSNSTQLAGTGNQDVSAT
SEQ ID NO:88  (301) WGA  ASTTAGATSSVAIQQQHQLQEQYSFYSNSNSTQLAGTGNQDVSAT 351            374
SEQ ID NO:27  (347) -ASAAALELSLSSWCSPYPAAGSM
SEQ ID NO:36  (344) AAAAAALELSLSSWCSPYPAAGSM
SEQ ID NO:43  (344) AAAAAALELSLSSWCSPYPAAGSM
```

```
SEQ ID NO:50  (320)  AAAAAALELSLSSWCSPYPAAGSM
SEQ ID NO:57  (320)  AAAAAALELSLSSWCSPYPAAGSM
SEQ ID NO:64  (322)  AAAAAALELSLSSWCSPYPAAGSM
SEQ ID NO:71  (322)  AAAAAALELSLSSWCSPYPAAGSM
SEQ ID NO:88  (351)  AAAAAALELSLSSWCSPYPAAGSM
```

TABLE 8: Alignment of WUS2 amino acid sequences with 1st & complete 2nd intron spliced (predicted to be most common protein product):

```
                          1                                                50
SEQ ID NO:29  (1)    MAANAGGGGAGGGSGSGSVAAPAVCRPSGSRWTPTPEQIRMLKELYYGCG
SEQ ID NO:38  (1)    MAANAGGGGAGGGSGS--VAAPAVCCPSGSRWTPTPEQIRMLKELYYGCG
SEQ ID NO:45  (1)    MAANAGGGGAGGGSGS--VAAPAVCRPSGSRWTPTPEQIRMLKELYYGCG
SEQ ID NO:52  (1)    MAANAGGGGAGGGSGS--VAAPAVCRPSGSRWTPTPEQIRMLKELYYGCG
SEQ ID NO:59  (1)    MAANAGGGGAGGGSGS--VAAPAVCRPSGSRWTPTPEQIRMLKELYYGCG
SEQ ID NO:66  (1)    MAANAGGGGAGGGSGSGSVAAPAVCRPSGSRWTPTPEQIRMLKELYYGCG
SEQ ID NO:73  (1)    MAANAGGGGAGGGSGSGSVAAPAVCRPSGSRWTPTPEQIRMLKELYYGCG
SEQ ID NO:89  (1)    MAANAGGGGAGGGSGS  VAAPAVCRPSGSRWTPTPEQIRMLKELYYGCG 51                                               100
SEQ ID NO:29  (51)   IRSPSSEQIQRITAMLRQHGKIEGKNVFYWFQNHKARERQKRRLTSLDVN
SEQ ID NO:38  (49)   IRSPSSEQIQRITAMLRQHGKIEGKNVFYWFQNHEARERQKRRLTSLDVN
SEQ ID NO:45  (49)   IRSPSSEQIQRITAMLRQHGKIEGKNVFYWFQNHKARERQKRRLTSLDVN
SEQ ID NO:52  (49)   IRSPSSEQIQRITAMLRQHGKIEGKNVFYWFQNHKARERQKRRLTSLDVN
SEQ ID NO:59  (49)   IRSPSSEQIQRITAMLRQHGKIEGKNVFYWFQNHKARERQKRRLTSLDVN
SEQ ID NO:66  (51)   IRSPSSEQIQRITAMLRQHGKIEGKNVFYWFQNHKARERQKRRLTSLDVN
SEQ ID NO:73  (51)   IRSPSSEQIQRITAMLRQHGKIEGKNVFYWFQNHKARERQKRRLTSLDVN
SEQ ID NO:89  (51)   IRSPSSEQIQRITAMLRQHGKIEGKNVFYWFQNHKARERQKRRLTSLDVN 101                                              150
SEQ ID NO:29  (101)  VPAAGAADATTSQLGVLSLSSPPPSGAAPPSPTLGFYAAGNGGGSAVLLD
SEQ ID NO:38  (99)   VPAAGAADATTSQLGVLSLSSPPPSGAAPPSPTLGFYAAGNGGGSAVLLD
SEQ ID NO:45  (99)   VPAAGAADATTSQLGVLSLSSPPPSGAAPPSPTLGFYAAGNGGGSAVLLD
SEQ ID NO:52  (99)   VPAAGAADATTSQLGVLSLSSPPPSGAAPPSPTLGFYAAGNGGGSAVLLD
SEQ ID NO:59  (99)   VPAAGAADATTSQLGVLSLSSPPPSGAAPPSPTLGFYAAGNGGGSAVLLD
SEQ ID NO:66  (101)  VPAAGAADATTSQLGVLSLSSPPPSGAAPPSPTLGFYAAGNGGGSAVLLD
SEQ ID NO:73  (101)  VPAAGAADATTSQLGVLSLSSPPPSGAAPPSPTLGFYAAGNGGGSAVLLD
SEQ ID NO:89  (101)  VPAAGAADATTSQLGVLSLSSPPPSGAAPPSPTLGFYAAGNGGGSAVLLD
```

```
                  151                                              200
SEQ ID NO:29 (151) TSSDWGSSGAAMATETCFLQDYMGVTDTGSSSQWPCFSSSDTIMAAAAAA
SEQ ID NO:38 (149) TSSDWGSSGAAMATETCFLQDYMGVTDTGSSSQWPCLSSSDTIMAAAAAR
SEQ ID NO:45 (149) TSSDWGSSGAAMATETCFLQDYMGVTDTGSSSQWPCLSSSDTIMAAAAAR
SEQ ID NO:52 (149) TSSDWGSSGAAMATETCFLQDYMGVTDTGSSSQWPRFSSSDTIMAAAAAR
SEQ ID NO:59 (149) TSSDWGSSGAAMATETCFLQDYMGVTDTGSSSQWPRFSSSDTIMAAAAAR
SEQ ID NO:66 (151) TSSDWGSSGAAMATETCFLQDYMGVTDTGSSSQWPRFSSSDTIMAAAAAR
SEQ ID NO:73 (151) TSSDWGSSGAAMATETCFLQDYMGVTDTGSSSQWPRFSSSDTIMAAAAAR
SEQ ID NO:89 (151) TSSDWGSSGAAMATETCFLQDYMGVTDTGSSSQWPRFSSSDTIMAAAAAR 201                                              250
SEQ ID NO:29 (201) ARVATTRAPETLPLFPTCGDDDDDDSQPPPRPRHAVPVPAGETIRGGGGS
SEQ ID NO:38 (199) AP-TTTRPPETLPLFPTCGDDDDDDNQPPSRPRHAVPVPAGEPIRVGGGG
SEQ ID NO:45 (199) AP-TTTRPPETLPLFPTCGDDDDDDNQPPPRPRHAVPVPAGEPIRVGGGG
SEQ ID NO:52 (199) A--ATTRAPETLPLFPTCGDDGGSGS-----------------------
SEQ ID NO:59 (199) A--ATTRAPETLPLFPTCGDDGGSGS-----------------------
SEQ ID NO:66 (201) A--ATTRAPETLPLFPTCGDDGGSGS-----------------------
SEQ ID NO:73 (201) A--ATTRAPETLPLFPTCGDDGGSGS-----------------------
SEQ ID NO:89 (201) A   ATTRAPETLPLFPTCGDDGGSGS 251                                              300
SEQ ID NO:29 (251) SSSYLPFWGAGAASTTAGATSSVAIQQQHQLQEQYSFYSN--STQLAGTG
SEQ ID NO:38 (248) SSSYLPFWGA--ASTTAGATSSVAIQQQHQQQEQYIFYSN--STQLAGTG
SEQ ID NO:45 (248) SSSYLPFWGA--ASTTAGATSSVAIQQQHQLQEQYIFYSN--STQLAGTG
SEQ ID NO:52 (223) -SSYLPFWGA--ASTTAGATSSVAIQQQHQLQEQYSFYSNSNSTQLAGTG
SEQ ID NO:59 (223) -SSYLPFWGA--ASTTAGATSSVAIQQQHQLQEQYSFYSNSNSTQLAGTG
SEQ ID NO:66 (225) -SSYLPFWGA--ASTTAGATSSVAIQQQHQLQEQYSFYSNSNSTQLAGTG
SEQ ID NO:73 (225) -SSYLPFWGA--ASTTAGATSSVAIQQQHQLQEQYSFYSNSNSTQLAGTG
SEQ ID NO:89 (251)  SSYLPFWGA   ASTTAGATSSVAIQQQHQLQEQYSFYSNSNSTQLAGTG 301               331
SEQ ID NO:29 (299) SQDVSAS---AAALELSLSSWCSPYPAAGSM
SEQ ID NO:38 (294) SQDVSASAAAAAALELSLSSWCSPYPAAGSM
SEQ ID NO:45 (294) SQDVSASAAAAAALELSLSSWCSPYPAAGSM
SEQ ID NO:52 (270) NQDVSATAAAAAALELSLSSWCSPYPAAGSM
SEQ ID NO:59 (270) NQDVSATAAAAAALELSLSSWCSPYPAAGSM
SEQ ID NO:66 (272) NQDVSATAAAAAALELSLSSWCSPYPAAGSM
```

SEQ ID NO:73 (272) NQDVSATAAAAAALELSLSSWCSPYPAAGSM
SEQ ID NO:89 (301) NQDVSATAAAAAALELSLSSWCSPYPAAGSM

TABLE 9: Alignment of WUS2 amino acid sequences with 1st and alternate 2nd intron spliced:

```
                    1                                                50
SEQ ID NO:31   (1)  MAANAGGGAGGGSGSGSVAAPAVCRPSGSRWTPTPEQIRMLKELYYGCG
SEQ ID NO:40   (1)  MAANAGGGAGGGSGS--VAAPAVCCPSGSRWTPTPEQIRMLKELYYGCG
SEQ ID NO:47   (1)  MAANAGGGAGGGSGS--VAAPAVCRPSGSRWTPTPEQIRMLKELYYGCG
SEQ ID NO:54   (1)  MAANAGGGAGGGSGS--VAAPAVCRPSGSRWTPTPEQIRMLKELYYGCG
SEQ ID NO:61   (1)  MAANAGGGAGGGSGS--VAAPAVCRPSGSRWTPTPEQIRMLKELYYGCG
SEQ ID NO:68   (1)  MAANAGGGAGGGSGSGSVAAPAVCRPSGSRWTPTPEQIRMLKELYYGCG
SEQ ID NO:75   (1)  MAANAGGGAGGGSGSGSVAAPAVCRPSGSRWTPTPEQIRMLKELYYGCG
SEQ ID NO:90   (1)  MAANAGGGAGGGSGS  VAAPAVCRPSGSRWTPTPEQIRMLKELYYGCG 51                                              100
SEQ ID NO:31  (51)  IRSPSSEQIQRITAMLRQHGKIEGKNVFYWFQNHKARERQKRRLTSLDVN
SEQ ID NO:40  (49)  IRSPSSEQIQRITAMLRQHGKIEGKNVFYWFQNHEARERQKRRLTSLDVN
SEQ ID NO:47  (49)  IRSPSSEQIQRITAMLRQHGKIEGKNVFYWFQNHKARERQKRRLTSLDVN
SEQ ID NO:54  (49)  IRSPSSEQIQRITAMLRQHGKIEGKNVFYWFQNHKARERQKRRLTSLDVN
SEQ ID NO:61  (49)  IRSPSSEQIQRITAMLRQHGKIEGKNVFYWFQNHKARERQKRRLTSLDVN
SEQ ID NO:68  (51)  IRSPSSEQIQRITAMLRQHGKIEGKNVFYWFQNHKARERQKRRLTSLDVN
SEQ ID NO:75  (51)  IRSPSSEQIQRITAMLRQHGKIEGKNVFYWFQNHKARERQKRRLTSLDVN
SEQ ID NO:90  (51)  IRSPSSEQIQRITAMLRQHGKIEGKNVFYWFQNHKARERQKRRLTSLDVN 101                                             150
SEQ ID NO:31 (101)  VPAAGAADATTSQLGVLSLSSPPPSGAAPPSPTLGFYAAGNGGGSAVLLD
SEQ ID NO:40  (99)  VPAAGAADATTSQLGVLSLSSPPPSGAAPPSPTLGFYAAGNGGGSAVLLD
SEQ ID NO:47  (99)  VPAAGAADATTSQLGVLSLSSPPPSGAAPPSPTLGFYAAGNGGGSAVLLD
SEQ ID NO:54  (99)  VPAAGAADATTSQLGVLSLSSPPPSGAAPPSPTLGFYAAGNGGGSAVLLD
SEQ ID NO:61  (99)  VPAAGAADATTSQLGVLSLSSPPPSGAAPPSPTLGFYAAGNGGGSAVLLD
SEQ ID NO:68 (101)  VPAAGAADATTSQLGVLSLSSPPPSGAAPPSPTLGFYAAGNGGGSAVLLD
SEQ ID NO:75 (101)  VPAAGAADATTSQLGVLSLSSPPPSGAAPPSPTLGFYAAGNGGGSAVLLD
SEQ ID NO:90 (101)  VPAAGAADATTSQLGVLSLSSPPPSGAAPPSPTLGFYAAGNGGGSAVLLD 151                                             200
```

```
SEQ ID NO:31  (151) TSSDWGSSGAAMATETCFLQVRRCAPAGLHGRDGHGQLVAVAMLLVVGHD
SEQ ID NO:40  (149) TSSDWGSSGAAMATETCFLQVRRCAPAGLHGRDGHGQLVAVAMLVVVRHD
SEQ ID NO:47  (149) TSSDWGSSGAAMATETCFLQVRRCAPAGLHGRDGHGQLVAVAMLVVVRHD
SEQ ID NO:54  (149) TSSDWGSSGAAMATETCFLQVRRCAPAGLHGRDGHGQLVAVATLLVVGHD
SEQ ID NO:61  (149) TSSDWGSSGAAMATETCFLQVRRCAPAGLHGRDGHGQLVAVATLLVVGHD
SEQ ID NO:68  (151) TSSDWGSSGAAMATETCFLQVRRCAPAGLHGRDGHGQLVAVATLLVVGHD
SEQ ID NO:75  (151) TSSDWGSSGAAMATETCFLQVRRCAPAGLHGRDGHGQLVAVATLLVVGHD
SEQ ID NO:90  (151) TSSDWGSSGAAMATETCFLQVRRCAPAGLHGRDGHGQLVAVATLLVVGHD 201                                             250
SEQ ID NO:31  (201) NGGGGGRGAGG-DDAGARDTPSLPDLRRRRRRQPAPAAAAARSPSPGRR
SEQ ID NO:40  (199) NGG--GRGAGADDDAAARDPPSLPDLRRRRRRQPAPVAAAARSPSPGRR
SEQ ID NO:47  (199) NGG--GRGAGADDDAAARDAPSLPDLRRRRRRQPAPAAAAARSPSPGRR
SEQ ID NO:54  (199) NGG--GRGAGG-DDAGARDAPSLPDLRRRRRQR----------------
SEQ ID NO:61  (199) NGG--GRGAGG-DDAGARDAPSLPDLRRRRRQR----------------
SEQ ID NO:68  (201) NGG--GRGAGG-DDAGARDAPSLPDLRRRRRQR----------------
SEQ ID NO:75  (201) NGG--GRGAGG-DDAGARDAPSLPDLRRRRRQR----------------
SEQ ID NO:90  (201) NGG   GRGAGG  DDAGARDAPSLPDLRRRRRQR 251                                             300
SEQ ID NO:31  (250) DHPRRRRQQQLLAVLGCRCRVHNCRRHFFRCDPAATPAAGAVQLLQQQH
SEQ ID NO:40  (247) AHPRRRWRQQQLLAVLG--CRVHNCRRHFFRCDPAATPAAGAVHLLQQQH
SEQ ID NO:47  (247) AHPRRRWRQQQLLAVLG--CRVHNCRRHFFRCDPAATPAAGAVHLLQQQH
SEQ ID NO:54  (229) -------------------------------------------------
SEQ ID NO:61  (229) -------------------------------------------------
SEQ ID NO:68  (231) -------------------------------------------------
SEQ ID NO:75  (231) -------------------------------------------------
SEQ ID NO:90  (251)

301                                             350
SEQ ID NO:31  (300) PAGRHRQPRRIGFSG---RPGAEPQLMVLPLPCCREHVRATRATTGTCVA
SEQ ID NO:40  (295) PAGRHRQPRRIGFSSSSRRPGAEPQLMVLPLPCCREHVTIALVRCCHCPR
SEQ ID NO:47  (295) PAGRHRQPRRIGFSSSSRRPGAEPQLMVLPLPCCREHVTIALVRCCHCPR
SEQ ID NO:54  (229) -------------------------------------------------
SEQ ID NO:61  (229) -------------------------------------------------
SEQ ID NO:68  (231) -------------------------------------------------
SEQ ID NO:75  (231) -------------------------------------------------
SEQ ID NO:90  (301)
```

```
                              351
SEQ ID NO:31  (347)  VIVLG--
SEQ ID NO:40  (345)  LVASASY
SEQ ID NO:47  (345)  LVASASY
SEQ ID NO:54  (229)  --------
SEQ ID NO:61  (229)  --------
SEQ ID NO:68  (231)  --------
SEQ ID NO:75  (231)  --------
SEQ ID NO:90  (351)
```

Example 19

Identification of Further Wuschel Qenomic Sequences

New full-length Wuschel sequences from *Zea mays* genomic sequences, denoted as WUS5 and WUS6, have been identified in the GSS database of NCBI GenBank, assembled, and analyzed using the fgenesh exon/intron prediction algorithm (Salamov & Solovyev (2000) Genome Res. 10:516), in a commercially available software implementation (Softberry, Mount Kisco, N.Y.). WUS5 genomic polynucleotide sequence is presented as SEQ ID NO: 76. Analysis using fgenesh predicts the presence of one intron, the spliced product is presented as SEQ ID NO: 77. The predicted WUS5 polypeptide is shown as SEQ ID NO: 78, as encoded by the polynucleotide of SEQ ID NO: 77. The WUS6 genomic polynucleotide sequence is presented as SEQ ID NO: 79. Analysis using fgenesh predicts the presence of two introns, the spliced product is presented as SEQ ID NO: 80. The predicted WUS6 polypeptide is shown as SEQ ID NO: 81, as encoded by SEQ ID NO: 80.

Example 20

Homeodomain and Conserved Domain Structure of Wuschel Polypeptides

Wuschel polypeptides typically comprise three conserved amino acid motifs, the N-terminal homeodomain region, and two two conserved Wuschel C-terminal domains, the (E/R)TLPFLP and A(A/S)LEL(S/T)L domains. The A(A/S)LEL(S/T)L shows significant similarity to C-terminal motifs identified in zn-finger proteins and ERFs, which have been implicated to act as a repressor domain via protein-protein interaction (Ohta et al. (2001) Plant Cell 13:1959-1968; and Dinkins et al. (2003) Plant Science 165:3341; herein incorporated by reference).

The homeodomain region of the Wuschel polypeptides is involved in making contact with target DNA. The homeodomain region consist of a helix1-loop-helix2-turn-helix3 structure where a fixed number of amino acids are present in the loop and turn regions in animal homeodomain polypetides. Plant homeodomain polypetides have extra amino acids in the loop, turn or both loop and turn regions of the homeodomain. Plant homeodomain polypeptides can be further classified into subgroups based on the number of extra amino acids present in the loop and turn regions. (Kamiya et al. (2003) Plant J 35:429441). The helix3 generally makes the contact with target DNA sequences. Differences in the number of amino acids in the loop and turn regions may affect target site specificities, therefore different subgroups would interact with unique DNA target sites. The Wuschel subgroup has one to two extra amino acids in the loop region and four extra amino acids in the turn region ("2+4"). WUS2 is the only one of the five maize Wuschel polypeptides that has two extra amino acids in the loop region ("2+4"). The other Wuschel polypeptides have one extra amino acid in the loop and four extra amino acids in the turn relative to animal homeodomain polypeptide sequences ("1+4"). Not to be limited to any particular theory, these subgroups are expected to have different functions controlling the meristems in the plant. It is expected that the "2+4" subgroup would influence embryo development and control shoot and floral meristem function whereas the "1+4" would impact both root and floral meristems.

A search of public domain sequences which give significant hits to the WUS sequences of the invention, and which comprise a homeodomain region yielded 64 sequences. Of these 64 sequences, only seven sequences, representing six plant species, have the 2+4 homeodomain. The 2+4 homeodomain structure appears to be unique in the homeodomain transcription factor family. Of the seven 2+4 sequences, two are from *Arabidopsis* (may represent landrace variants), and one each from *Petunia, Antirrhinum, Lycopersicon, Zea*, and *Oryza*. Also detected were 6 sequences with a homeodomain-ZIP structure, wherein the homeodomain has a 0+4 structure. The remaining sequences fall into the 1+4 homeodomain category, and are represented by sequences from wheat, sorghum, soybean, and Brassica. The top 25 hits have a (E/R)TLPFLP-like motif, and represent both 2+4 and 1+4 homeodomains. All seven sequences having the 2+4 homeodomain also comprise the A(A/S)LEL(S/T)L motif. WUS3 (SEQ ID NO: 4) and rice QHB (Kamiya et al. (2003) Plant J 35:429-441) both have a motif similar to A(A/S)LEL(S/T)L, therefore a total of nine sequences have all three identified motifs.

TABLE 10

Examples of Homeodomain Structure & Conserved Domains in Select Wuschel Polypeptides A. WUS2-SEQ ID NO: 27-1$^{st}$ intron spliced (2 + 4)

| | | | | |
|---|---|---|---|---|
| MAANAGGGA | GGGSGSGSVA | APAVCRPSGS | RWTPTPEQIR | MLKELYYGCG |
| IRSPSSEQIQ | RITAMLRQHG | KIEGKNVFYW | FQNHKARERQ | KRRLTSLDVN |
| VPAAGAADAT | TSQLGVLSLS | SPPPSGAAPP | SPTLGFYAAG | NGGGSAVLLD |
| TSSDWGSSGA | AMATETCFLQ | VGAVVRSFLG | HCAQFHVRTY | ELIAASFHPP |
| VYITVRYGGA | RPQDYMGVTD | TGSSSQWPCF | SSSDTIMAAA | AAAARVATTR |
| APETLPLFPT | CGDDDDDDSQ | PPPRPRHAVP | VPAGETIRGG | GGSSSSYLPF |

TABLE 10-continued

Examples of Homeodomain Structure & Conserved
Domains in Select Wuschel Polypeptides

```
WGAGAASTTA  GATSSVAIQQ  QHQLQEQYSF  YSNSTQLAGT  GSQDVSASAA

ALELSLSSWC  SPYPAAGSM
```

B. WUS2-SEQ ID NO: 29-1$^{st}$ and complete 2$^{nd}$ intron spliced (2 + 4)

```
MAANAGGGGA  GGGSGSGSVA  APAVCRPSGS  RWTPTPEQIR  MLKELYYGCG

IRSPSSEQIQ  RITAMLRQHG  KIEGKNVFYW  FQNHKARERQ  KRRLTSLDVN

VPAAGAADAT  TSQLGVLSLS  SPPPSGAAPP  SPTLGFYAAG  NGGGSAVLLD

TSSDWGSSGA  AMATETCFLQ  DYMGVTDTGS  SSQWPCFSSS  DTIMAAAAAA

ARVATTRAPE  TLPLFPTCGD  DDDDDSQPPP  RPRHAVPVPA  GETIRGGGGS

SSSYLPFWGA  GAASTTAGAT  SSVAIQQQHQ  LQEQYSFYSN  STQLAGTGSQ

DVSASAAALE  LSLSSWCSPY  PAAGSM
```

C. WUS2-SEQ ID NO: 31-1$^{st}$ and alternate 2$^{nd}$ intron spliced (2 + 4)

```
MAANAGGGGA  GGGSGSGSVA  APAVCRPSGS  RWTPTPEQIR  MLKELYYGCG

IRSPSSEQIQ  RITAMLRQHG  KIEGKNVFYW  FQNHKARERQ  KRRLTSLDVN

VPAAGAADAT  TSQLGVLSLS  SPPPSGAAPP  SPTLGFYAAG  NGGGSAVLLD

TSSDWGSSGA  AMATETCFLQ  VRRCAPAGLH  GRDGHGQLVA  VAMLLVVGHD

NGGGGGRGAG  GDDAGARDTP  SLPDLRRRRR  RRQPAPAAAA  ARSPSPGRRD

HPRRRRQQQQ  LLAVLGCRCR  VHNCRRHFFR  CDPAATPAAG  AVQLLQQQHP

AGRHRQPRRI  GFSGRPGAEP  QLMVLPLPCC  REHVRATRAT  TGTCVAVIVL

G
```

D. WUS1-SEQ ID NO: 33-p0083.cldev71r (1 + 4)

```
METPQQQSAA  AAAAAAHGQD  DGGSPPMSPA  SAAAAALANA  RWNPTKEQVA

VLEGLYEHGL  RTPSAEQIQQ  ITGRLREHGA  IEGKNVFYWF  QNHKARQRQR

QKQDSFAYFS  RLLRRPPPLP  VLSMPPAPPY  HHARVPAPPA  IPMPMAPPPP

AACNDNGGAR  VIYRNPFYVA  APQAPPANAA  YYYPQPQQQQ  QQQVTVMYQY

PRMEVAGQDK  MMTRAAAHQQ  QQHNGAGQQP  GRAGHPSRET  LQLFPLQPTF

VLRHDKGRAA  NGSNNDSLTS  TSTATATATA  TATASASISE  DSDGLESGSS

GKGVEEAPAL  PFYDFFGLQS  SGGR
```

Highlighted in bold are the protein sequence motifs that are conserved in WUS homologues. The second tyrosine (Y—shown in bold and italics) distinguishes WUS2 (p0016.ctsas50r) as being in the "2+4" category of homeodomain factors just like the *Arabidopsis* protein, whereas all of the other WUS sequences lack this tyrosine and thus belong to the "1+4" category (e.g., p0083.cldev71r represented in SEQ ID NO: 33); you will note that SEQ ID NO: 31 also lacks the second and third motifs due to the altered splicing event. (see Kamiya et al. (2003) Plant J 35:429-441 for homeodomain categorization).

TABLE 11

Positions of conserved motifs in Wuschel polypeptide sequences

| SEQ ID | Homeodomain | Type | (E/R)TLPFLP | A(A/S) LEL(S/T)L | 25 aa |
|---|---|---|---|---|---|
| 27 | 31-93 | 2 + 4 | 253-259 | 350-356 | 270-294 |
| 29 | 31-93 | 2 + 4 | 210-216 | 307-313 | 227-251 |
| 31 | 31-93 | 2 + 4 | — | — | — |
| 33 | 41-102 | 1 + 4 | 239-245 | — | — |
| 36 | 29-91 | 2 + 4 | 250-256 | 348-354 | 267-291 |

TABLE 11-continued

Positions of conserved motifs in Wuschel polypeptide sequences

| SEQ ID | Homeodomain | Type | (E/R)TLPFLP | A(A/S) LEL(S/T)L | 25 aa |
|---|---|---|---|---|---|
| 38 | 29-91 | 2 + 4 | 207-213 | 305-311 | 224-248 |
| 40 | 29-91 | 2 + 4 | — | — | — |
| 43 | 29-91 | 2 + 4 | 250-256 | 348-354 | 267-291 |
| 45 | 29-91 | 2 + 4 | 207-213 | 305-311 | 224-248 |
| 47 | 29-91 | 2 + 4 | — | — | — |
| 50 | 29-91 | 2 + 4 | 249-255 | 324-330 | — |
| 52 | 29-91 | 2 + 4 | 206-212 | 281-287 | — |
| 54 | 29-91 | 2 + 4 | — | — | — |
| 57 | 29-91 | 2 + 4 | 249-255 | 324-330 | — |
| 59 | 29-91 | 2 + 4 | 206-212 | 281-287 | — |
| 61 | 29-91 | 2 + 4 | — | — | — |
| 64 | 31-93 | 2 + 4 | 251-257 | 326-332 | — |
| 66 | 31-93 | 2 + 4 | 208-214 | 283-289 | — |
| 68 | 31-93 | 2 + 4 | — | — | — |
| 71 | 31-93 | 2 + 4 | 251-257 | 326-332 | — |
| 73 | 31-93 | 2 + 4 | 208-214 | 283-289 | — |
| 75 | 31-93 | 2 + 4 | — | — | — |
| 78 | 8-71 | 1 + 4 | 233-239 | — | — |
| 81 | 102-164 | 1 + 4 | 237-243 | — | — |
| 88 | 29-91 | 2 + 4 | 249-255 | 324-330 | — |
| 89 | 29-91 | 2 + 4 | 206-212 | 281-287 | — |
| 90 | 29-91 | 2 + 4 | — | — | — |

Example 21

Comparison of WUS2 from Public Inbred Lines and Elite Inbred Lines

Based on sequences for the ZmWUS2 sequences from several proprietary maize inbred lines and public lines (line B73, SEQ ID NOS: 34, 35, 37, and 39; line Mo17, SEQ ID NOS: 41, 42, 44, and 46; line 07D, SEQ ID NOS: 48, 49, 51, and 53; line KW3, SEQ ID NOS: 55, 56, 58, and 60; line 3DT, SEQ ID NOS: 62, 63, 65, and 67; and line 09B, SEQ ID NOS: 69, 70, 72, and 74), the public lines (B73 and Mo17) contain an extra 75 nucleotides that encode an extra 25 amino acids relative to the sequences of the proprietary lines (07D, KW3, 3DT, and 09B). This 25 amino acid difference resides in between two conserved Wuschel C-terminal domains, the (E/R)TLPFLP and A(A/S)LEL(S/T)L domains. The A(A/S)LEL(S/T)L shows significant similarity to C-terminal motifs identified in zn-finger proteins and ERFs, which have been implicated to act as a repressor domain via protein-protein interaction (Ohta et al. (2001) Plant Cell 13:1959-1968; and Dinkins et al. (2003) Plant Science 165:3341; herein incorporated by reference). The presence or absence of these 25 amino acids may change the orientation of these two domains in the mature polypeptide and thus may affect the interactive nature of these Wuschel polypeptides with other host factors. In other words, this sequence may function as a spacer that affects the relative orientation of these two motifs in the context of the whole protein structure. It is of note that the two public lines come from very different pedigrees, therefore the likelihood of inheriting this polymorphism from a common source is low. The inbred lines also represent different pedigrees, and different heterotic groups. The consistency of this difference is suggestive, possibly indicating that this polymorphism was somehow selected during the breeding of elite inbred lines. A Wuschel polynucleotide encoding a polypeptide from a proprietary maize inbred line noted above was used in transformation experiments, the results of which are shown in Example 8B.

Example 22

Comparison of Wuschel Polypeptide Sequences

The GCG (Accelrys, San Diego, Calif.) software implementation of the GAP algorithm (Needleman & Wunsch) was used to compare the polypeptides encoded by the full-length genomic or cDNA polynucleotides from maize to known Wuschel polypeptides from the model plant, *Arabidopsis thaliana*. Two *Arabidopsis* polypeptide sequences were used, represented by NCBI GI 4090200 (SEQ ID NO: 25); and NCBI GI 20197404 (which replaced GI 3785979 on Apr. 18, 2002). All comparisons were done using default parameters, namely the BLOSUM62 scoring matrix, Gap Creation Penalty=8, and Gap Extension Penalty=2. All percent sequence identities less than 70% have been rounded up to the nearest whole integer, all others are presented to the nearest tenth of a percent. Table 12 summarizes the results of these comparisons.

TABLE 12

GAP % Sequence Identity to Two Arabidopsis Wuschel Polypeptides

| SEQ ID NO: | GI 4090200 | GI 20197404 |
|---|---|---|
| 27 | 33% | 30% |
| 29 | 35% | 34% |
| 31 | 41% | 33% |
| 33 | 30% | 30% |
| 36 | 30% | 32% |
| 38 | 32% | 33% |
| 40 | 40% | 33% |
| 43 | 31% | 32% |
| 45 | 33% | 34% |
| 47 | 41% | 33% |
| 50 | 32% | 30% |
| 52 | 38% | 35% |
| 54 | 36% | 35% |
| 57 | 32% | 30% |
| 59 | 38% | 35% |
| 61 | 36% | 35% |
| 64 | 33% | 30% |
| 66 | 39% | 35% |
| 68 | 36% | 34% |
| 71 | 33% | 30% |
| 73 | 39% | 35% |
| 75 | 36% | 34% |
| 78 | 42% | 39% |
| 81 | 29% | 35% |
| 88 | 32% | 30% |
| 89 | 38% | 35% |
| 90 | 36% | 35% |

The GCG (Accelrys, San Diego, Calif.) software implementation of the GAP algorithm (Needleman & Wunsch) was further used to compare the polypeptides encoded by the full-length genomic, cDNA, or EST polynucleotides of the present invention. All comparisons were done using default parameters, namely the BLOSUM62 scoring matrix, Gap Creation Penalty=8, and Gap Extension Penalty=2. All percent sequence identities less than 70% have been rounded up to the nearest whole integer, all others are presented to the nearest tenth of a percent. Table 13 summarizes the results of these comparisons.

TABLE 13

GAP % Sequence Identity - Polypeptides

| SEQ ID NO: | 2 | 4 | 6 | 8 | 10 | 12 | 14 | 16 | 18 | 20 | 22 | 24 |
|---|---|---|---|---|---|---|---|---|---|---|---|---|
| 27 | 42 | 34 | 99.2 | 99.2 | 29 | 53 | 32 | 42 | 36 | 37 | 39 | 34 |
| 29 | 42 | 34 | 99.0 | 99.0 | 33 | 53 | 39 | 42 | 32 | 33 | 38 | 35 |
| 31 | 42 | 33 | 79.1 | 79.8 | 31 | 53 | 36 | 42 | 34 | 33 | 38 | 35 |
| 33 | 46 | 28 | 33 | 42 | 32 | 74.2 | 93.2 | 45 | 37 | 40 | 35 | 34 |
| 36 | 46 | 36 | 97.9 | 97.9 | 28 | 52 | 40 | 40 | 36 | 30 | 37 | 33 |
| 38 | 46 | 36 | 97.4 | 97.4 | 31 | 52 | 37 | 40 | 33 | 34 | 36 | 34 |
| 40 | 46 | 34 | 81.2 | 80.4 | 30 | 52 | 37 | 40 | 35 | 31 | 36 | 35 |
| 43 | 42 | 34 | 98.7 | 98.7 | 28 | 53 | 41 | 41 | 36 | 30 | 38 | 34 |
| 45 | 42 | 34 | 98.4 | 98.4 | 29 | 53 | 38 | 41 | 33 | 34 | 37 | 35 |
| 47 | 42 | 32 | 82.1 | 81.3 | 30 | 53 | 37 | 41 | 35 | 31 | 37 | 35 |
| 50 | 42 | 34 | 99.6 | 99.6 | 31 | 53 | 33 | 41 | 36 | 36 | 38 | 34 |
| 52 | 42 | 35 | 99.5 | 99.5 | 32 | 53 | 35 | 41 | 33 | 31 | 37 | 35 |
| 54 | 42 | 31 | 80.1 | 80.5 | 36 | 53 | 36 | 41 | 35 | 31 | 37 | 35 |
| 57 | 42 | 34 | 99.6 | 99.6 | 31 | 53 | 33 | 41 | 36 | 36 | 38 | 34 |
| 59 | 42 | 35 | 99.5 | 99.5 | 32 | 53 | 35 | 41 | 33 | 31 | 37 | 35 |
| 61 | 42 | 31 | 80.1 | 80.6 | 36 | 53 | 36 | 41 | 35 | 31 | 37 | 35 |
| 64 | 42 | 34 | 99.6 | 99.6 | 31 | 53 | 33 | 42 | 36 | 37 | 39 | 34 |
| 66 | 42 | 35 | 99.5 | 99.5 | 32 | 53 | 35 | 42 | 33 | 32 | 38 | 35 |
| 68 | 42 | 31 | 80.3 | 80.7 | 36 | 53 | 36 | 42 | 34 | 32 | 38 | 35 |
| 71 | 42 | 34 | 99.6 | 99.6 | 31 | 53 | 33 | 42 | 36 | 37 | 39 | 34 |
| 73 | 42 | 35 | 99.5 | 99.5 | 32 | 53 | 35 | 42 | 33 | 32 | 38 | 35 |
| 75 | 42 | 31 | 80.3 | 80.7 | 36 | 53 | 36 | 42 | 34 | 32 | 38 | 35 |
| 78 | 40 | 26 | 35 | 35 | 32 | 55 | 36 | 43 | 37 | 40 | 41 | 40 |
| 81 | 41 | 38 | 35 | 35 | 28 | 44 | 38 | 37 | 37 | 34 | 48 | 47 |
| 88 | 42 | 34 | 99.6 | 99.6 | 31 | 53 | 33 | 41 | 36 | 36 | 38 | 34 |
| 89 | 42 | 35 | 99.5 | 99.5 | 32 | 53 | 35 | 41 | 33 | 31 | 37 | 35 |
| 90 | 42 | 31 | 80.1 | 80.5 | 36 | 53 | 36 | 41 | 35 | 31 | 37 | 35 |

The GCG (Accelrys, San Diego, Calif.) software implementation of the GAP algorithm (Needleman & Wunsch) was further used to compare the full-length genomic, cDNA, or EST polynucleotides of the present invention. All comparisons were done using default parameters, namely Gap Creation Penalty=50, and Gap Extension Penalty=3. All percent sequence identities less than 70% have been rounded up to the nearest whole integer, all others are presented to the nearest tenth of a percent. Table 14 summarizes the results of these comparisons.

TABLE 14

GAP % Sequence Identity - Polynucleotides

| SEQ ID NO: | 1 | 3 | 5 | 7 | 9 | 11 | 13 | 15 | 17 | 19 | 21 | 23 |
|---|---|---|---|---|---|---|---|---|---|---|---|---|
| 26 | 42 | 45 | 99.3 | 99.7 | 44 | 53 | 49 | 50 | 42 | 44 | 44 | 45 |
| 28 | 41 | 47 | 81.8 | 84.4 | 44 | 53 | 48 | 50 | 42 | 42 | 37 | 43 |
| 30 | 38 | 47 | 81.8 | 84.8 | 45 | 53 | 47 | 50 | 43 | 42 | 36 | 45 |
| 32 | 47 | 45 | 54 | 53 | 43 | 87.4 | 98.8 | 47 | 40 | 40 | 43 | 43 |
| 34 | 41 | 45 | 98.9 | 99.2 | 42 | 52 | 46 | 48 | 41 | 44 | 38 | 43 |
| 35 | 41 | 47 | 98.9 | 99.2 | 44 | 53 | 48 | 49 | 41 | 43 | 44 | 45 |
| 37 | 46 | 45 | 79.7 | 82.6 | 48 | 53 | 48 | 49 | 43 | 47 | 37 | 39 |
| 39 | 39 | 45 | 81.5 | 84.4 | 44 | 52 | 49 | 49 | 42 | 42 | 38 | 36 |
| 41 | 43 | 43 | 99.2 | 99.5 | 42 | 52 | 46 | 47 | 41 | 45 | 38 | 43 |
| 42 | 43 | 47 | 99.2 | 99.5 | 43 | 53 | 49 | 48 | 41 | 44 | 44 | 45 |
| 44 | 46 | 45 | 80.3 | 83.2 | 47 | 53 | 49 | 48 | 43 | 46 | 37 | 39 |
| 46 | 39 | 45 | 82.1 | 84.9 | 44 | 53 | 50 | 48 | 41 | 42 | 38 | 36 |
| 48 | 39 | 43 | 99.6 | 99.9 | 43 | 52 | 46 | 47 | 41 | 45 | 39 | 43 |
| 49 | 39 | 46 | 99.6 | 99.9 | 45 | 53 | 49 | 48 | 42 | 44 | 43 | 45 |
| 51 | 47 | 47 | 82.5 | 82.6 | 44 | 51 | 47 | 48 | 40 | 44 | 39 | 38 |
| 53 | 41 | 48 | 99.5 | 83.7 | 45 | 53 | 49 | 48 | 43 | 44 | 40 | 38 |
| 55 | 39 | 43 | 99.6 | 99.9 | 43 | 52 | 46 | 47 | 41 | 45 | 39 | 43 |
| 56 | 39 | 46 | 99.6 | 99.9 | 45 | 53 | 49 | 48 | 42 | 44 | 43 | 45 |
| 58 | 47 | 47 | 82.5 | 82.6 | 44 | 51 | 47 | 48 | 40 | 44 | 39 | 38 |
| 60 | 41 | 48 | 99.5 | 83.7 | 45 | 53 | 49 | 48 | 43 | 44 | 40 | 38 |
| 62 | 39 | 43 | 99.6 | 99.9 | 43 | 52 | 46 | 49 | 41 | 45 | 40 | 45 |
| 63 | 39 | 46 | 99.6 | 99.9 | 42 | 53 | 49 | 50 | 42 | 44 | 39 | 46 |
| 65 | 47 | 46 | 82.7 | 82.8 | 43 | 51 | 46 | 50 | 40 | 44 | 40 | 38 |
| 67 | 41 | 47 | 99.5 | 83.8 | 44 | 53 | 50 | 50 | 43 | 45 | 40 | 38 |
| 69 | 39 | 43 | 99.6 | 99.9 | 41 | 52 | 46 | 49 | 41 | 45 | 38 | 45 |
| 70 | 39 | 46 | 99.6 | 99.9 | 45 | 53 | 47 | 50 | 42 | 44 | 44 | 46 |
| 72 | 47 | 45 | 82.7 | 82.8 | 43 | 51 | 48 | 50 | 40 | 44 | 38 | 38 |
| 74 | 41 | 46 | 99.5 | 83.8 | 45 | 53 | 50 | 50 | 43 | 45 | 36 | 38 |
| 76 | 47 | 45 | 50 | 49 | 42 | 56 | 45 | 49 | 43 | 44 | 41 | 44 |
| 77 | 47 | 47 | 55 | 51 | 44 | 53 | 47 | 46 | 41 | 43 | 41 | 41 |
| 79 | 47 | 40 | 46 | 47 | 39 | 49 | 40 | 49 | 41 | 42 | 45 | 45 |
| 80 | 47 | 38 | 50 | 51 | 39 | 50 | 40 | 47 | 42 | 43 | 48 | 48 |

The above examples are provided to illustrate the invention but not to limit its scope. Other variants of the invention will be readily apparent to one of ordinary skill in the art and are encompassed by the appended claims. All publications, patents, and patent applications cited herein are hereby incorporated in their entirety by reference.

What is claimed is:

1. An isolated polynucleotide comprising a nucleotide sequence encoding the WUSCHEL polypeptide of SEQ ID NO:14 which stimulates meristem proliferation of a plant cell.

2. The isolated polynucleotide of claim 1, wherein the nucleotide sequence comprises SEQ ID NO:13.

3. The complement of the polynucleotide of claim 1, wherein the complement and the polynucleotide consist of the same number of nucleotides and are 100% complementary.

4. A chimeric gene comprising the polynucleotide of claim 1, operably linked to a regulatory sequence functional in a host cell.

5. A transgenic plant comprising the chimeric gene of claim 4.

6. A seed from the transgenic plant of claim 5, wherein the seed comprises the chimeric gene.

7. A method for inducing meristem proliferation in a plant cell comprising:
   (a) transforming a plant cell with the polynucleotide of claim 1 operably linked to a regulatory sequence operable in the plant cell, and
   (b) expressing the polynucleotide to induce meristem proliferation.

8. The method of claim 7 wherein the polynucleotide is integrated into the plant cell genome to produce a transformed plant cell comprising the polynucleotide.

9. The method of claim 8 further comprising growing the transformed plant cell under plant growing conditions to produce a regenerated plant.

10. A plant produced by the method of claim 9.

11. A method for positive selection of a transformed cell, comprising:
   (a) transforming a plant cell with the polynucleotide of claim 1 operably linked to a regulatory sequence operable in the plant cell, and
   (b) expressing the polynucleotide for a time sufficient to induce organogenesis and provide a positive selection means.

12. A method for transforming a plant cell comprising introducing the polynucleotide of claim 1 into the cell.

13. A transformed plant cell produced by the method of claim 12 wherein the cell comprises the polynucleotide.

14. The method of claim 12 further comprising growing the transformed plant cell under plant growing conditions to produce a regenerated plant.

15. A plant produced by the method of claim 14, wherein the plant comprises the polynucleotide.

* * * * *